(12) United States Patent
Suh et al.

(10) Patent No.: US 9,745,280 B2
(45) Date of Patent: Aug. 29, 2017

(54) COMPOUND OR PHARMACEUTICALLY ACCEPTABLE SALT THEREOF, AND PHARMACEUTICAL COMPOSITION CONTAINING SAME AS ACTIVE INGREDIENT

(71) Applicant: SNU R&DB FOUNDATION, Seoul (KR)

(72) Inventors: Young-Ger Suh, Seoul (KR); Hongchan An, Seoul (KR); Seungbeom Lee, Seoul (KR); Kyu-Won Kim, Seoul (KR); Ho-Young Lee, Seoul (KR); Sang Geon Kim, Seoul (KR); Jeong Hun Kim, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 15/216,838

(22) Filed: Jul. 22, 2016

(65) Prior Publication Data
US 2016/0340331 A1 Nov. 24, 2016

Related U.S. Application Data

(63) Continuation-in-part of application No. 14/588,804, filed on Jan. 2, 2015, now abandoned, which is a continuation of application No. PCT/KR2012/005309, filed on Jul. 4, 2012.

(51) Int. Cl.
| | | |
|---|---|---|
| *C07D 407/06* | (2006.01) | |
| *C07D 311/74* | (2006.01) | |
| *C07D 311/58* | (2006.01) | |
| *C07D 493/12* | (2006.01) | |
| *C07D 493/04* | (2006.01) | |
| *C07D 493/14* | (2006.01) | |
| *C07D 407/10* | (2006.01) | |

(52) U.S. Cl.
CPC .......... *C07D 311/58* (2013.01); *C07D 311/74* (2013.01); *C07D 407/06* (2013.01); *C07D 407/10* (2013.01); *C07D 493/04* (2013.01); *C07D 493/12* (2013.01); *C07D 493/14* (2013.01)

(58) Field of Classification Search
CPC .. C07D 407/06; C07D 311/74; C07D 311/58; C07D 493/12; C07D 493/04; C07D 493/14
See application file for complete search history.

(56) References Cited

PUBLICATIONS

Vilain, 1977, caplus an 1977:439333.*
Hammes et al., 1996, https://www.ncbi.nlm.nih.gov/pubmed/8616710.*
Vilain et al., 1977, caplus an 1977:439333.*

* cited by examiner

*Primary Examiner* — Sun Jae Yoo
(74) *Attorney, Agent, or Firm* — Vorys, Sater, Seymour & Pease LLP; Min Suhn Koh

(57) ABSTRACT

A compound inhibiting Hsp90 and a pharmaceutical composition including the same as an active ingredient are described, which compound is represented by formula 2 and suppresses the expression of Hsp90, inhibits the accumulation of HIF-1α, the Hsp90 client protein, and efficiently inhibits the activation of VEGF. The compound displays low cytotoxicity and can be effectively used as an active ingredient of an anti-cancer agent, a diabetic retinopathy treating agent, and an anti-arthritic agent.

18 Claims, 18 Drawing Sheets

[Figure 1]
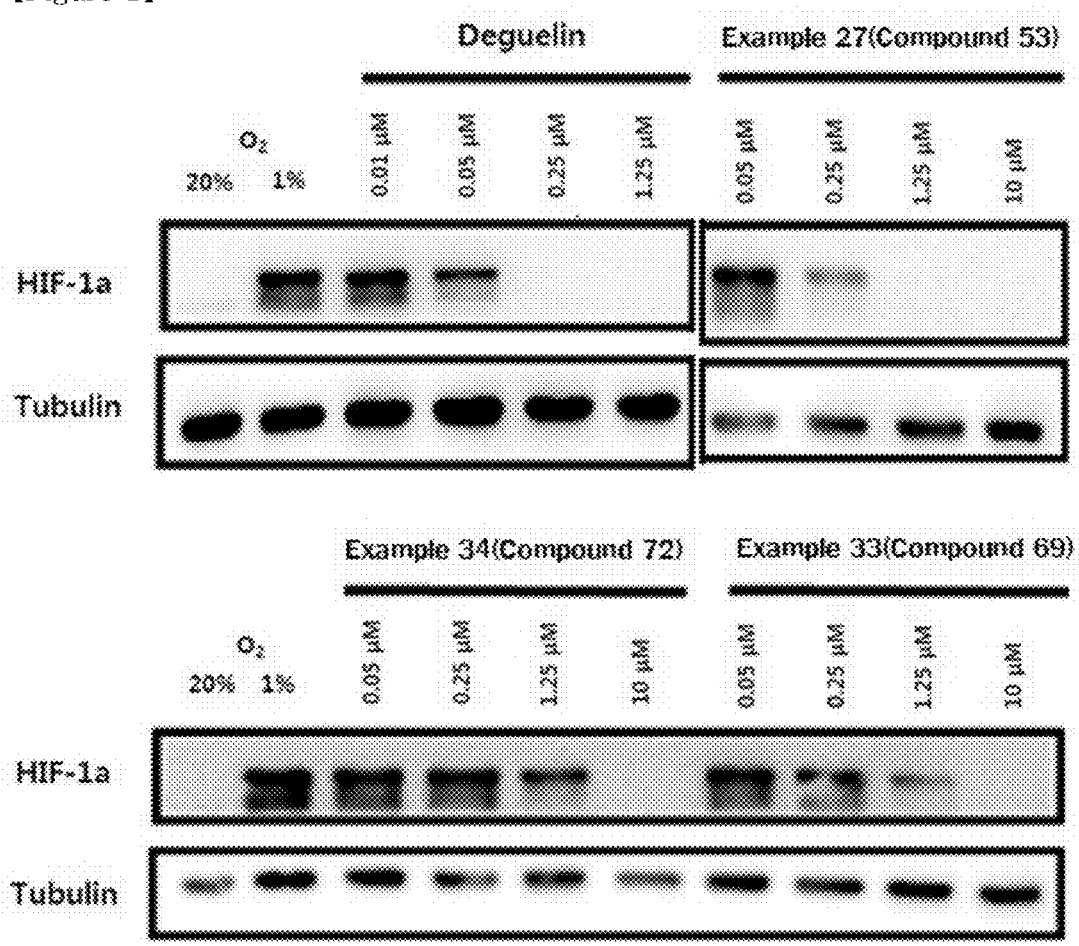

[Figure 2]
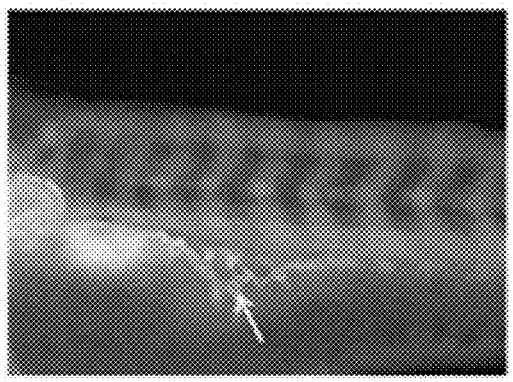
Example 27(Compound 53)
(50 nM)
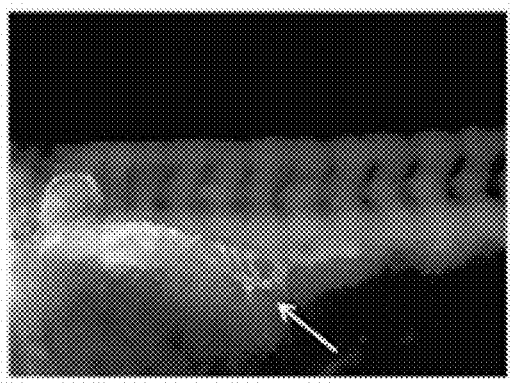
Example 27(Compound 53)
(250 nM)
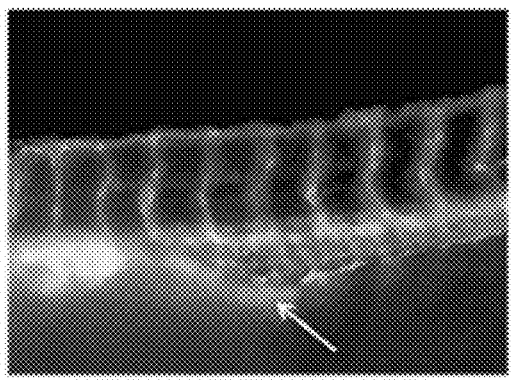
Example 27(Compound 53)
(1.25 µM)

[Figure 3]
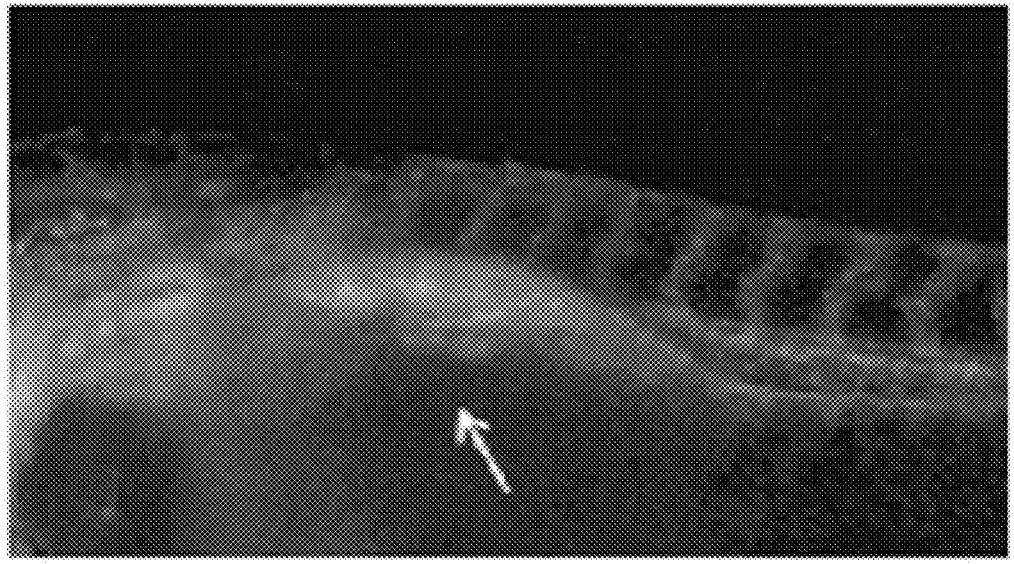
Example 33(Compound 69) (250 nM)
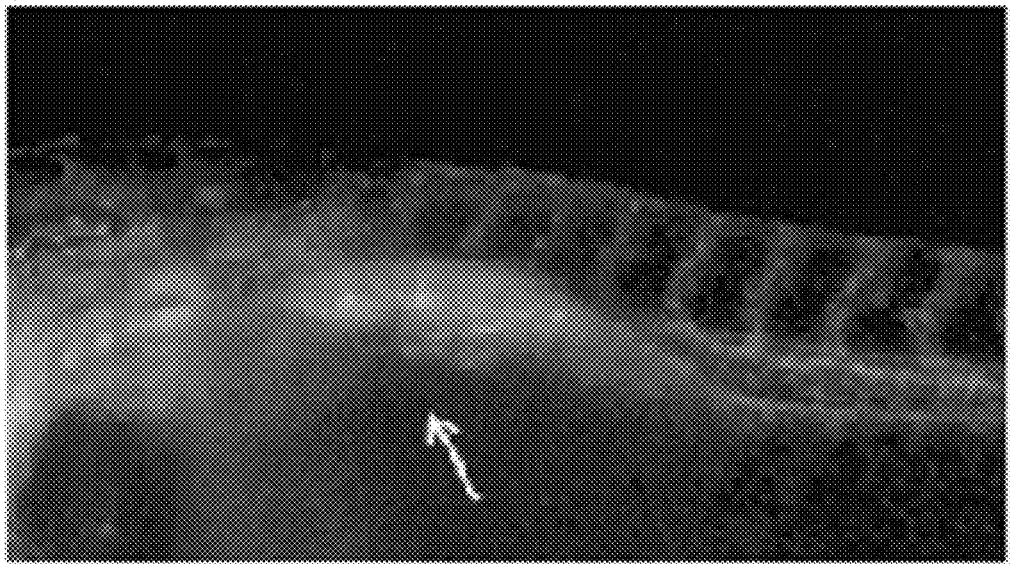
Example 33(Compound 69) (1.25 μM)

[Figure 4]
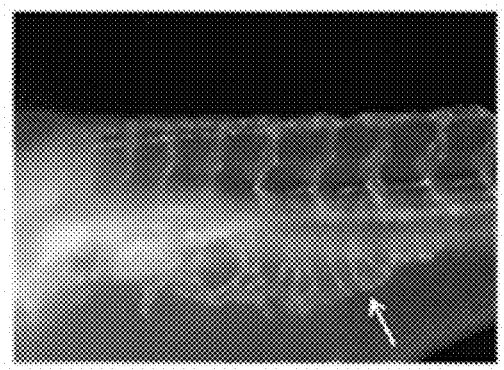
Example 34(Compound 72)
(50 nM)
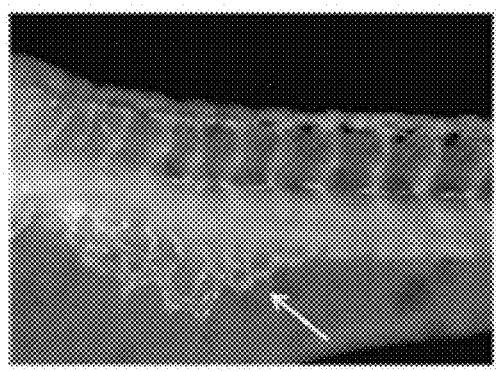
Example 34(Compound 72)
(250 nM)
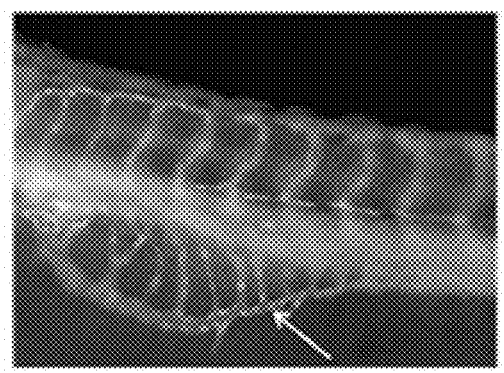
Example 34(Compound 72)
(1.25 μM)

[Figure 5]
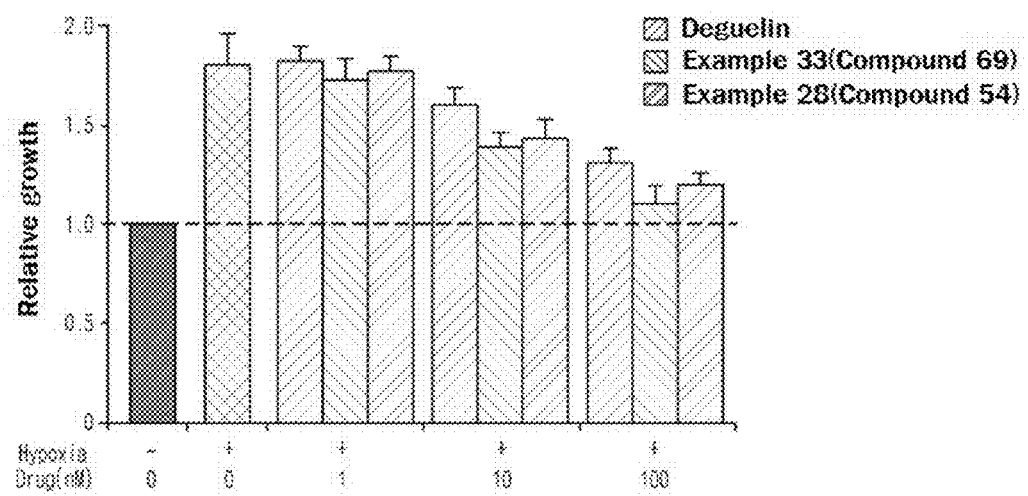

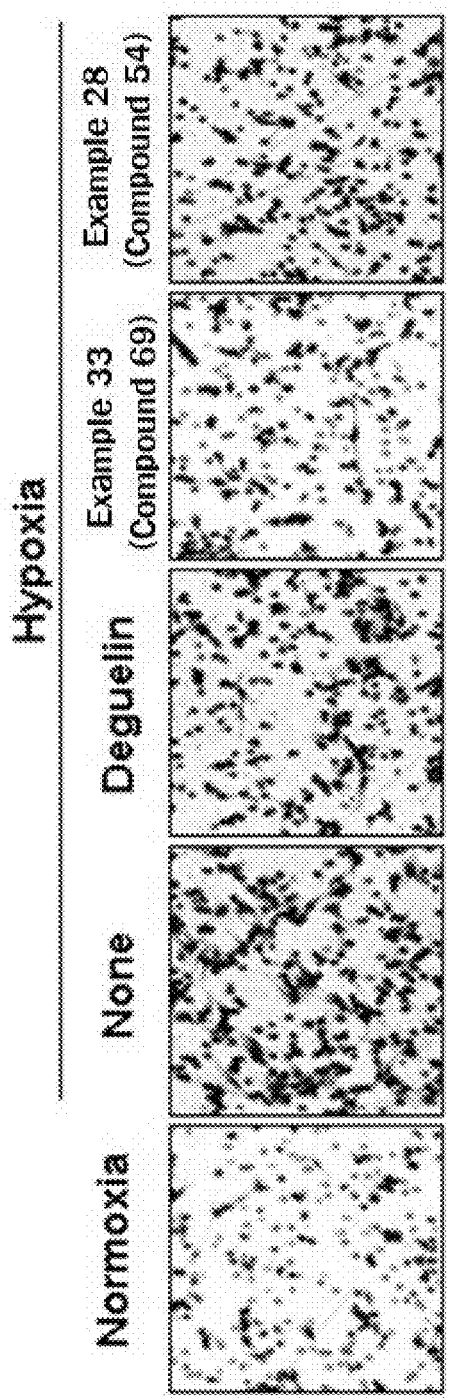
[Figure 6]

[Figure 7]
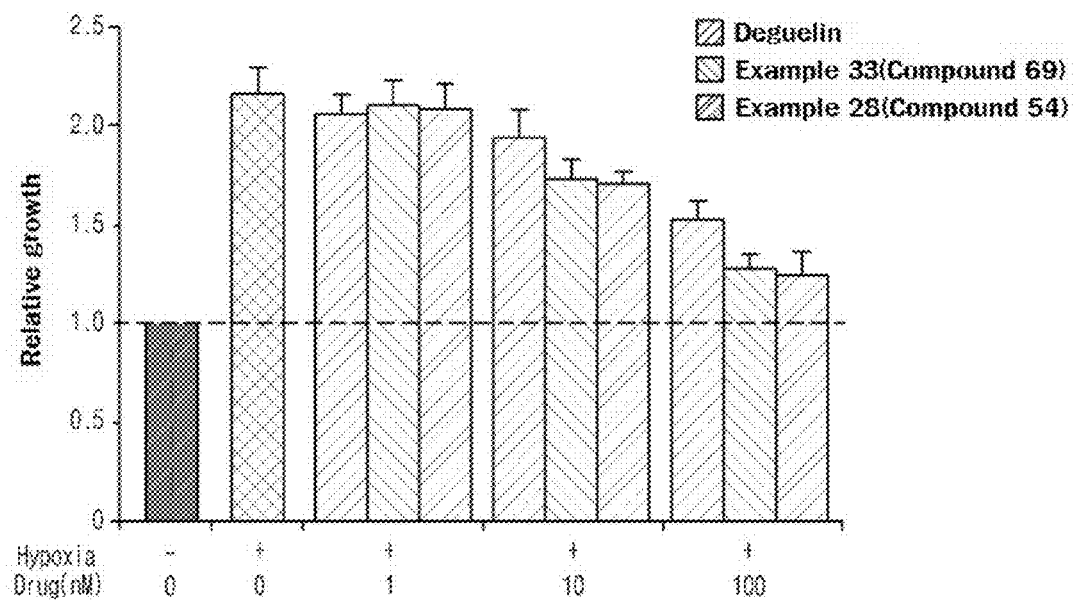

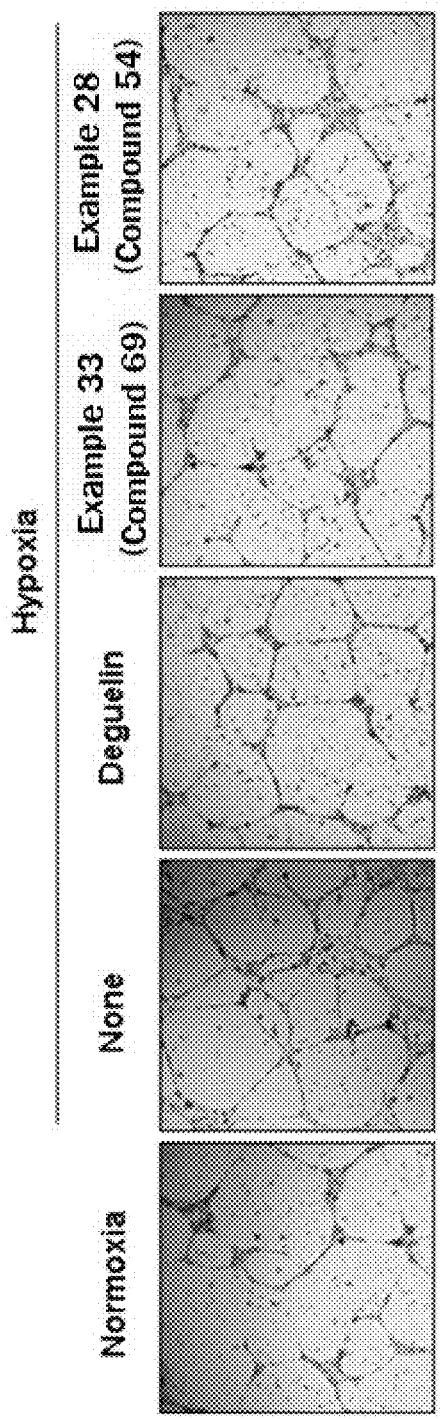
[Figure 8]

[Figure 9]
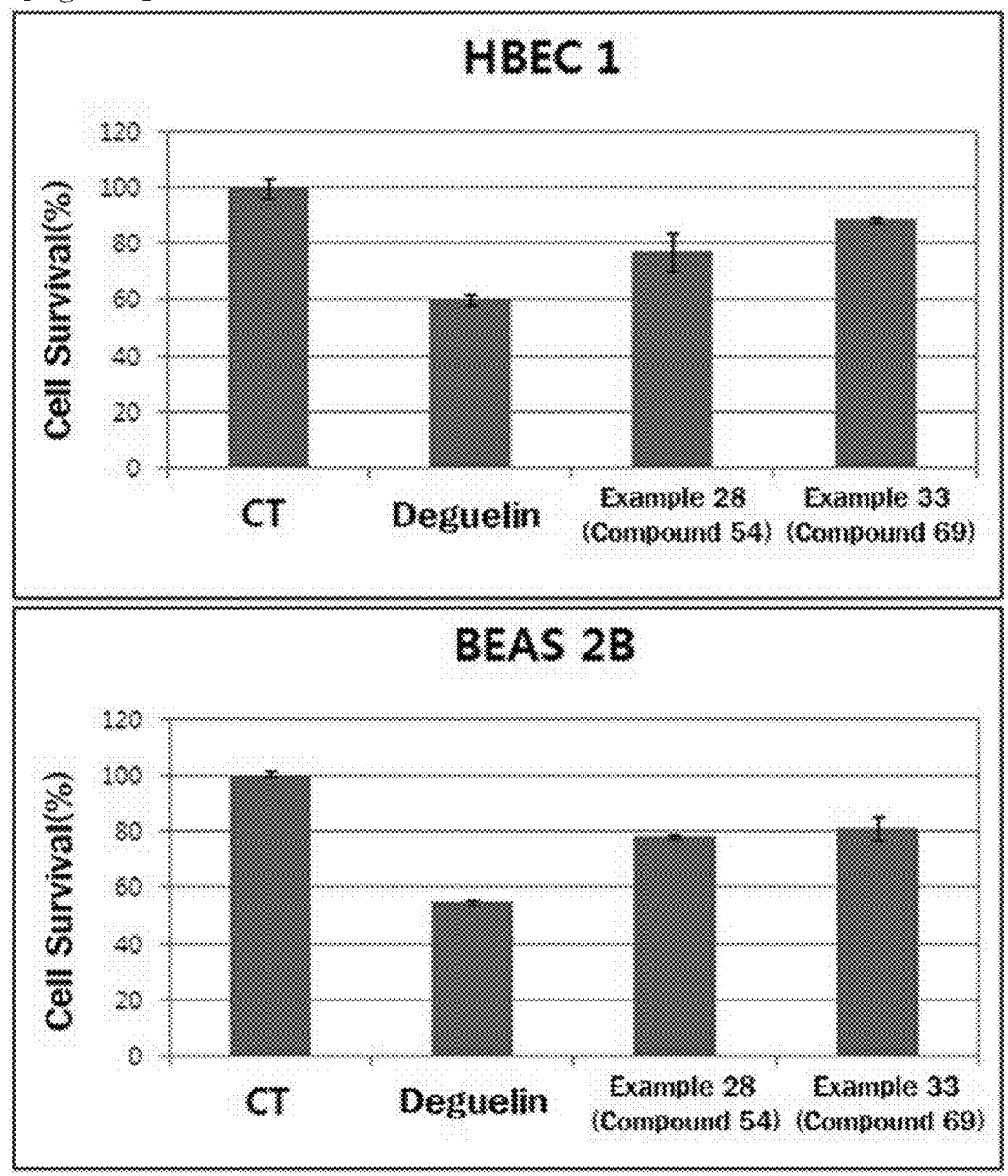

[Figure 10]
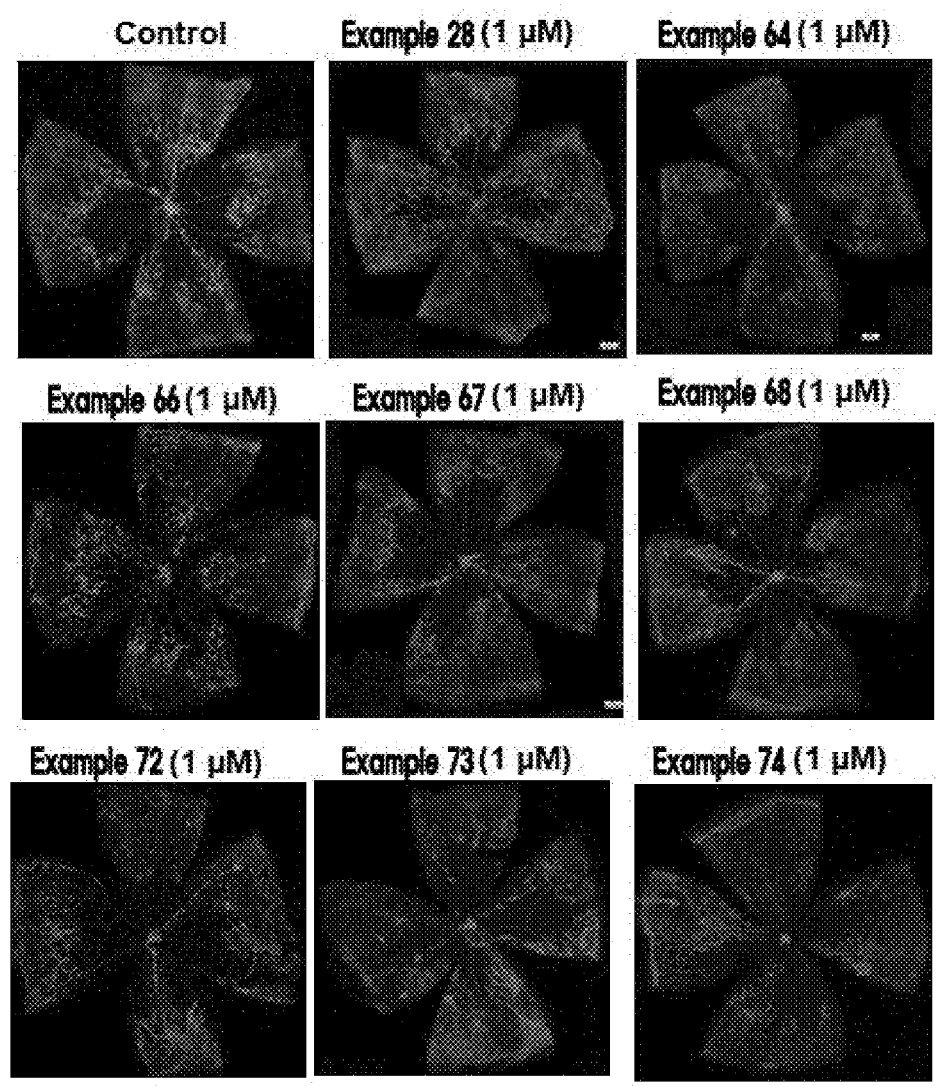

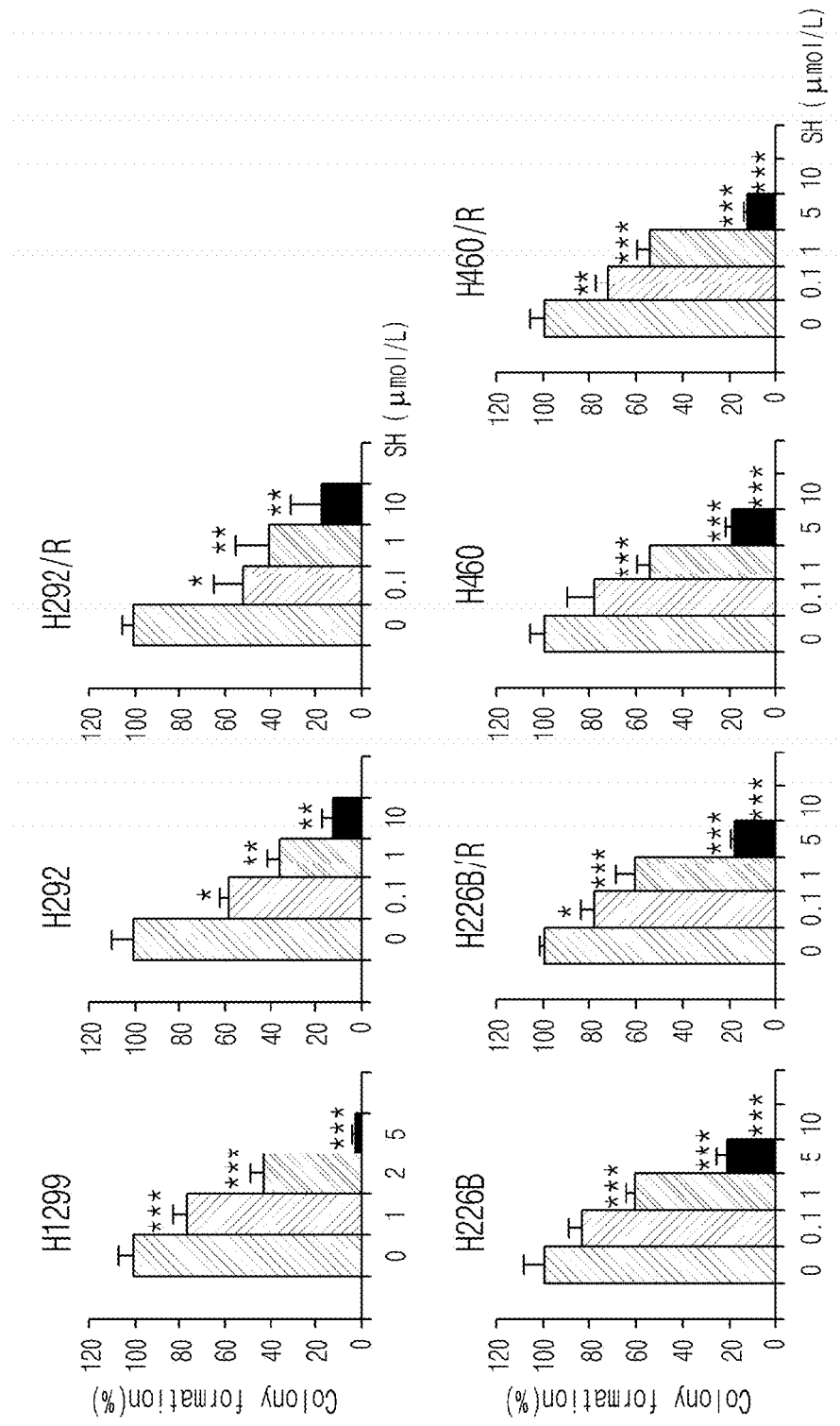
[Figure 11]

[Figure 12]
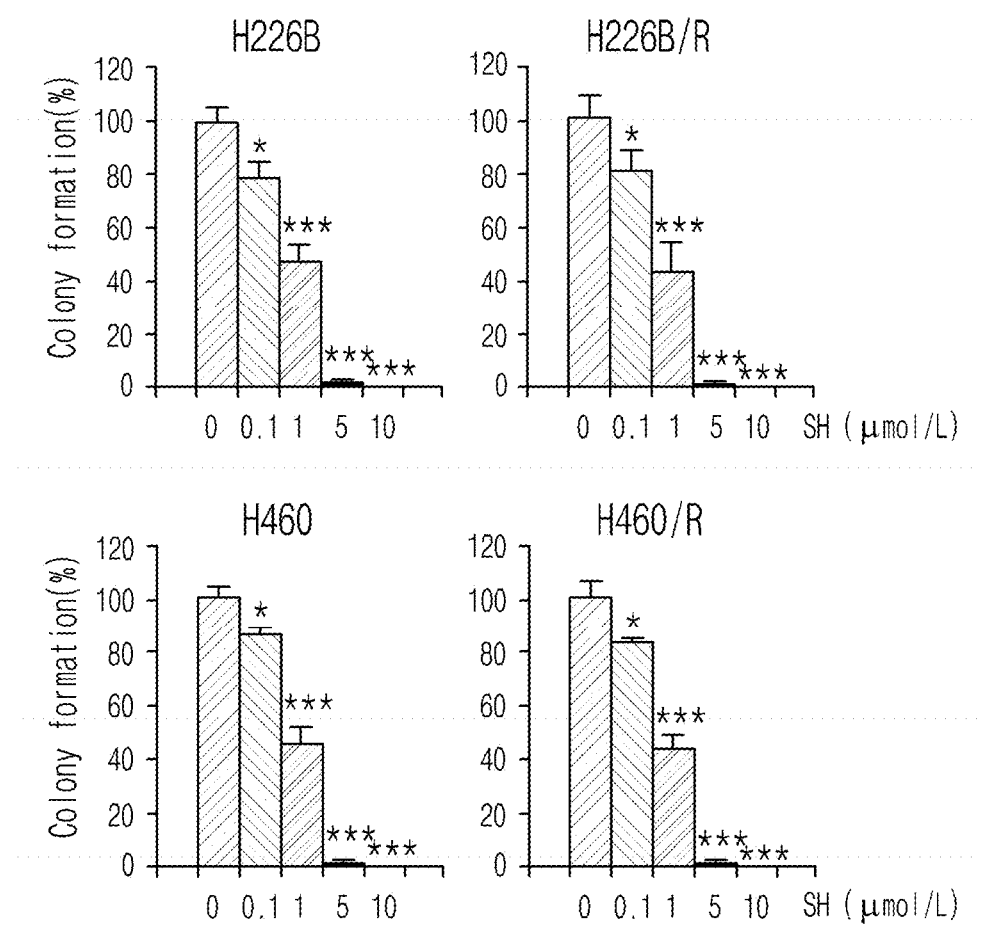

[Figure 13]
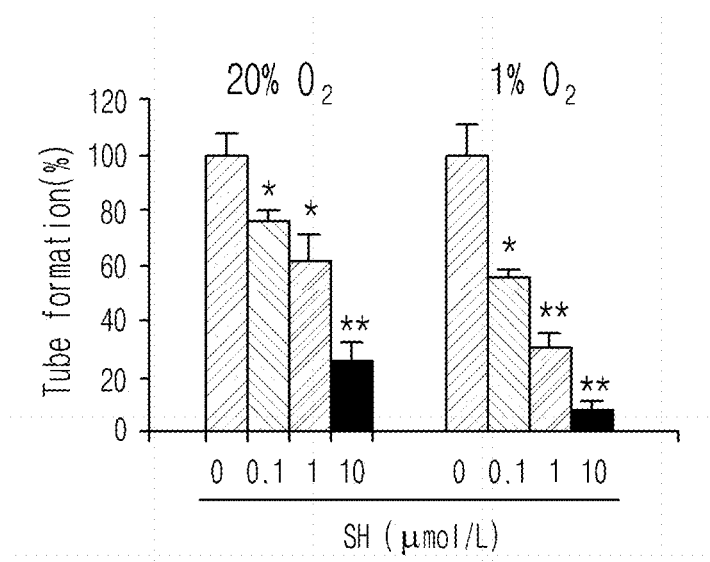

[Figure 14]
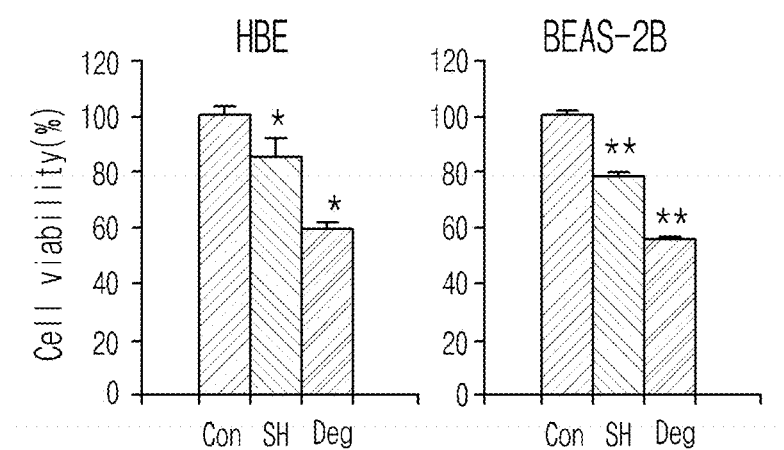

[Figure 15]
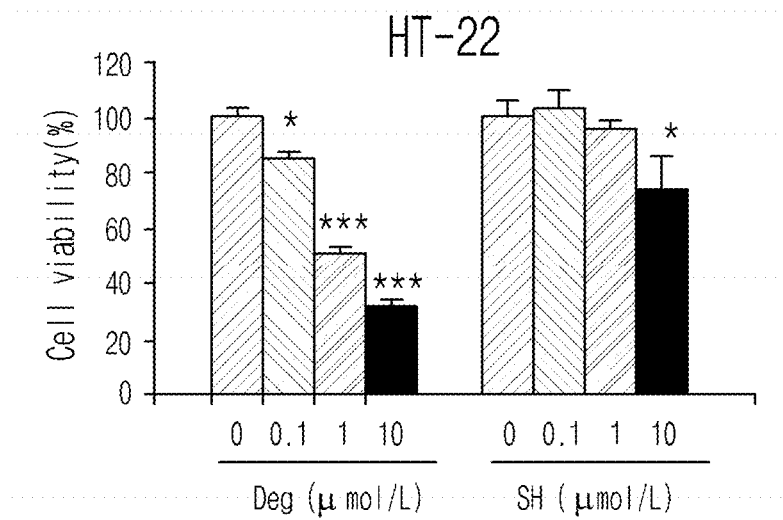

[Figure 16]
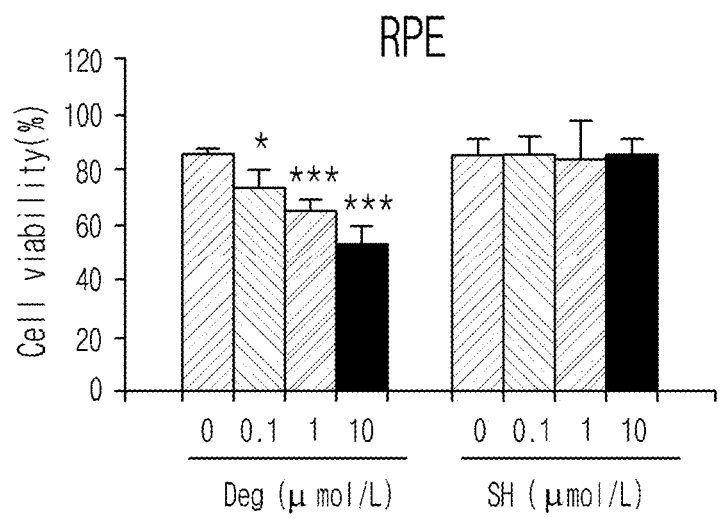

[Figure 17]
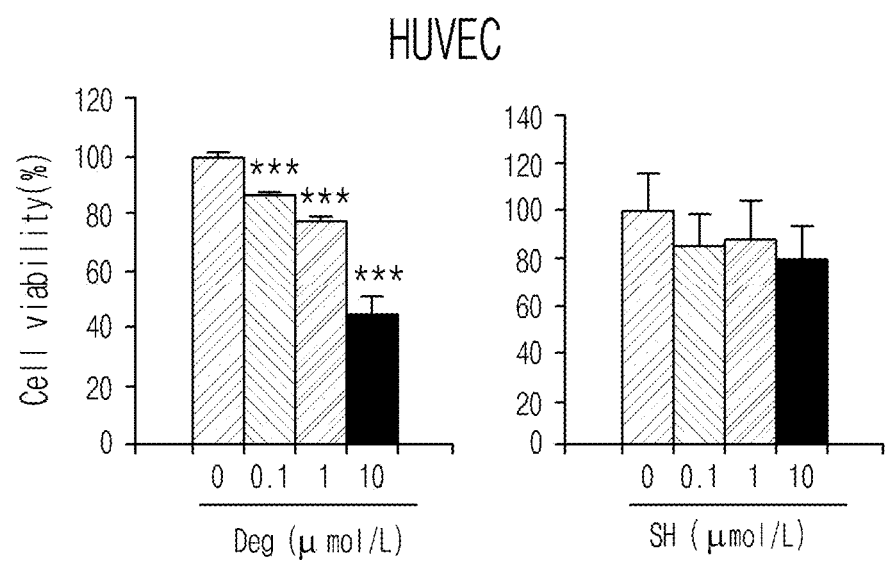

[Figure 18]
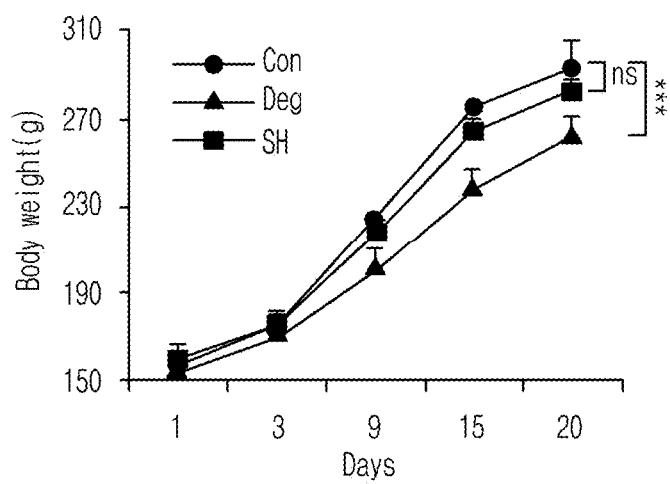

COMPOUND OR PHARMACEUTICALLY ACCEPTABLE SALT THEREOF, AND PHARMACEUTICAL COMPOSITION CONTAINING SAME AS ACTIVE INGREDIENT

BACKGROUND OF THE INVENTION

1. Field of the Invention

The present invention relates to a compound inhibiting Hsp90 and a pharmaceutical composition comprising the same as an active ingredient.

2. Description of the Related Art

Molecular chaperone such as heat-shock protein families (HSPs) is a protein that can activate nascent proteins and help refolding or decomposing a damaged protein by regulating the folding of a client protein through its activity of changing the ATP dependent structure. A client protein avoids aggregation by binding with such molecular chaperone. This binding can be a help for the intracellular deposition by membrane translocation of the client protein.

It has been known that the molecular chaperone functions of Hsp90, one of the heat-shock protein families, are necessary for the stabilization and activation of various client proteins involved in cell signaling pathway. The amount of Hsp90 takes 1~2% of the total intracellular proteins in the normal condition in the absence of external stimuli, but it becomes double the amount in the presence of external stimuli. Cancer inducible mutation of a client protein requires stronger and intensive Hsp90 functions, resulting in the over-expression of Hsp90. The over-expressed Hsp90 is commonly found in cancers [Bagatell, R.; Whitesell, L. Altered Hsp90 function in cancer: A unique therapeutic opportunity. *Mol. Cancer Ther.* 2004, 3, 1021-1030].

The Hsp90 client protein including ErbB2, Src, Met tyrosine kinase, MEK 1/2 (mitogen-activated protein kinase kinase), Akt, Raf-1, cyclin-dependent serine kinases, steroid hormone receptor, telomerase, metalloprotein-2 (MMP-2), and HIF-1α (hypoxia-inducible factor-1α) is found in various signaling pathways involved in cell survival, proliferation, invasion, metastasis, and angiogenesis, etc, and is contributed to the malignant phenotype [Eustace, B. K.; Sakurai, T.; Stewart, J. K.; Yimlamai, D.; Unger, C.; Zehetmeier, C.; Lain, B.; Torella, C.; Henning, S. W.; Beste, G.; Scroggins, B. T.; Neckers, L.; Ilag, L. L.; Jay, D. G. Functional proteomic screens reveal an essential extracellular role for hsp90 alpha in cancer cell invasiveness. *Nat. Cell Biol.* 2004, 6, 507-514].

In particular, HIF-1α, together with HIF-1β, is a subunit that composes HIF (hydroxia-inducible factor) and induces the expression of VEGF (vascular endothelial growth factor), the oxygen-instable transcriptional factor and one of the angiogenesis-regulating proteins, in order to control angiogenesis in the aspect of vascular destruction and vascular dysfunction. Angiogenesis is a process of generating a new blood vessel, which is necessary for the repair, regeneration, and development of blood vessels or metabolically activated tissues.

However, the pathological angiogenesis not only plays an important role in the growth and expansion of cancer via metastasis but also induces hemorrhage, endoleak, and tissue destruction by abnormally fast angiogenesis. So, the pathological angiogenesis causes not just cancer but also various angiogenesis-dependent diseases including diabetic retinopathy and age-related macular degeneration, and is also involved in chronic infectious diseases including psoriasis and rheumatoid arthritis.

Therefore, the inhibition of Hsp90 is expected to be a efficient treatment method for angiogenesis related diseases and thus the Hsp90 inhibitor can be a potential chemotherapeutic agent for angiogenesis related diseases [Eccles, S.; Massey, A.; Raynaud, F.; Sharp, S.; Box, G.; Valenti, M.; Patterson, L.; de Haven Brandon, A.; Gowan, S.; Boxall, F. NVP-AUY922: a heat shock protein 90 inhibitor active against xenograft tumor growth, angiogenesis, and metastasis. *Cancer Res.* 2008, 68, 2850].

Hsp90 exists mainly as a homodimer, which is composed of N-terminal, intermediate region, and C-terminal. Particularly, N-terminal contains adenine nucleotide-binding pocket in which a specific structural motif known as Bergerat fold is included, by which Hsp90 can harbor ATP-binding site, different from other kinases or Hsp70. This structural specificity provides a potential for the development of a selective Hsp90 inhibitor. In fact, followings are the examples of Hsp90 inhibitors so far.

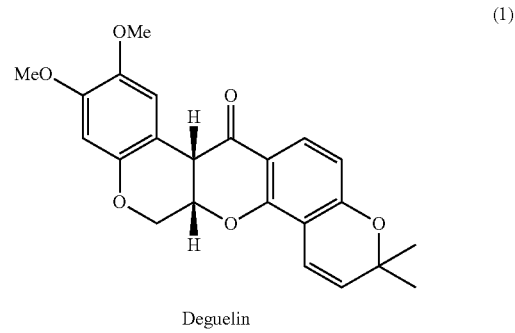

Deguelin (1)

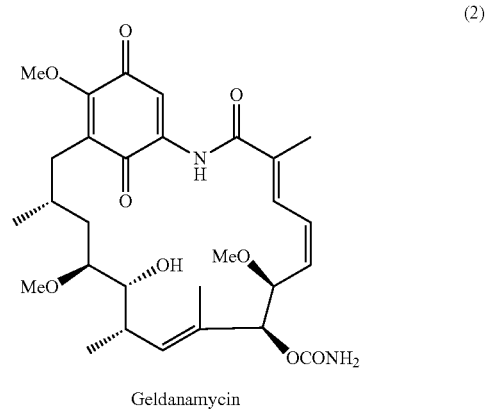

Geldanamycin (2)

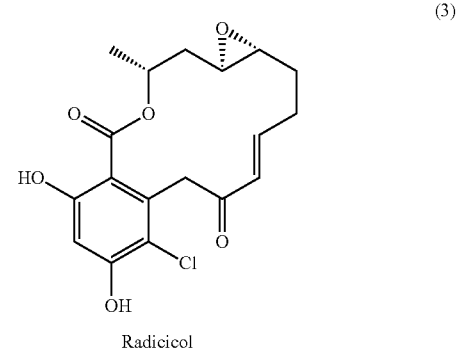

Radicicol (3)

-continued

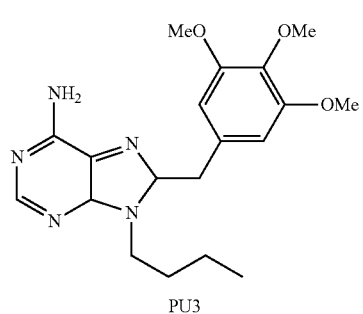

PU3

(4)

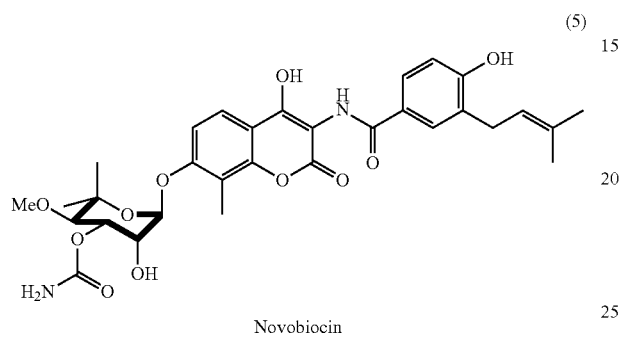

Novobiocin (5)

Most of Hsp90 inhibitors, which are exemplified by geldanamycin(2) and its derivative 17-AAG (17-arylamino-17-dimethoxy geldanamycin) having less toxicity, radicicol (3) and the more stable oxime derivative thereof, and the synthetic derivative PU3(4), are known to interact with ATP-binding pocket in N-terminal of Hsp90. In the meantime, the natural antibiotics novobiocin (5), known as a DNA gyrase inhibitor, displays an efficient Hsp90 inhibiting activity by interacting with ATP-binding pocket in C-terminal of Hsp90. Such Hsp90 inhibitors accelerate the degradation of various cancer inducing Hsp90 client proteins, so that they can bring a significant prevention effect in various cancer cell lines of preclinical models. Some of the Hsp90 inhibitors including 17-AAG are in clinical phase.

Deguelin(1) [Clark, E., A relation between rotenone, deguelin and tephrosin. 1931; Vol. 73, pp 17-18.] is a rotenoid compound isolated from Africa origin *Mundulea sericea*, which is known to have the effect of preventing the development of lung cancer induced by tobacco carcinogens by blocking Akt activation and also to display apoptotic effect and anti-angiogenesis effect in various transformed cell lines and cancer cell lines [Lee, H. Molecular mechanisms of deguelin-induced apoptosis in transformed human bronchial epithelial cells. *Biochem. Pharmacol.* 2004, 68, 1119-1124].

Even though the potential of deguelin as an anticancer agent or an anti-angiogenesis agent has been confirmed, the toxicity, low solubility, and chemical instability of deguelin draw a limit in its use as a drug.

The present inventors succeeded in synthesizing a compound showing the activity of deguelin but having less toxicity than deguelin and improved physicochemical properties and thereafter confirmed the Hsp90 inhibiting effect, anti-angiogenesis effect, and cytotoxicity of the compound, leading to the completion of this invention.

SUMMARY OF THE INVENTION

It is an object of the present invention to provide a compound inhibiting Hsp90.

It is another object of the present invention to provide a pharmaceutical composition for treating cancer comprising the compound as an active ingredient.

It is also an object of the present invention to provide a pharmaceutical composition for treating diabetic retinopathy comprising the compound as an active ingredient.

It is further an object of the present invention to provide a pharmaceutical composition for treating rheumatoid arthritis comprising the compound as an active ingredient.

To achieve the above objects, the present invention provides the compound represented by formula 1 or the pharmaceutically acceptable salt thereof:

[Formula 1]

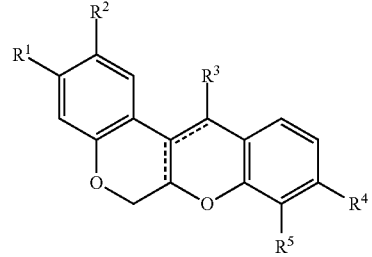

(In formula 1, $R^1$~$R^5$ are as defined in this description).

The present invention also provides the compound represented by formula 2 or the pharmaceutically acceptable salt thereof:

[Formula 2]

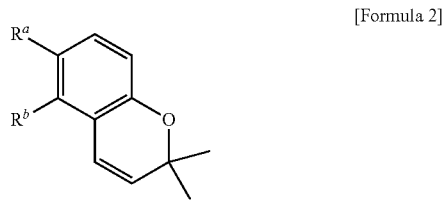

(In formula 2, $R^a$ and $R^b$ are as defined in this description).

The present invention also provides a pharmaceutical composition for preventing or treating cancer comprising the compound of formula 1 and/or the compound of formula 2 or the pharmaceutically acceptable salt thereof as an active ingredient.

The present invention also provides a pharmaceutical composition for preventing or treating diabetic retinopathy comprising the compound of formula 1 and/or the compound of formula 2 or the pharmaceutically acceptable salt thereof as an active ingredient.

In addition, the present invention provides a pharmaceutical composition for preventing or treating rheumatoid arthritis comprising the compound of formula 1 and/or the compound of formula 2 or the pharmaceutically acceptable salt thereof as an active ingredient.

Advantageous Effect

The compounds represented by formula 1 and formula 2 of the present invention suppress the expression of Hsp90 so that they can inhibit the accumulation of HIF-1α, the Hsp90 client protein, and also efficiently inhibit the activation of VEGF. In addition, these compounds display low toxicity, so that they can be effectively used as an active ingredient of an anti-cancer agent, a diabetic retinopathy treating agent, and an anti-arthritic agent.

BRIEF DESCRIPTION OF THE DRAWINGS

The application of the preferred embodiments of the present invention is best understood with reference to the accompanying drawings, wherein:

FIG. 1 is a diagram illustrating the result of Western blotting performed to measure the activity of the compounds of the present invention to inhibit the accumulation of HIF-1α.

FIG. 2 is a photograph illustrating the effect of the compound 53 of the present invention on angiogenesis.

FIG. 3 is a photograph illustrating the effect of the compound 69 of the present invention on angiogenesis.

FIG. 4 is a photograph illustrating the effect of the compound 72 of the present invention on angiogenesis.

FIG. 5 is a graph illustrating the inhibitory effect of the compound of the present invention on the proliferation of vascular endothelial cells.

FIG. 6 is a diagram illustrating the inhibitory effect of the compound of the present invention on the migration of vascular endothelial cells.

FIG. 7 is a graph illustrating the inhibitory effect of the compound of the present invention on the migration of vascular endothelial cells.

FIG. 8 is a diagram illustrating the inhibitory effect of the compound of the present invention on the tube formation of vascular endothelial cells.

FIG. 9 is a graph illustrating the cell survival rate (%) obtained by MTT assay performed to investigate the cytotoxicity of the compound of the present invention.

FIG. 10 is a photograph illustrating the inhibitory effect of the compound of the present invention on retinal neovascularization.

FIG. 11 is a graph illustrating the effect of the compound of the present invention on the anchorage-dependent colony formation of lung cancer cells with or without anticancer drug resistance.

FIG. 12 is a graph illustrating the effect of the compound of the present invention on the anchorage-independent growth of cells.

FIG. 13 is a graph illustrating the effect of the compound of the present invention on the tube formaion in the vascular endothelial cells.

FIG. 14 is a graph illustrating the cytotoxicity of the compound of the present invention on human normal lung epithelial cells.

FIG. 15 is a graph illustrating the cytotoxicity of the compound of the present invention on hippocampal cells.

FIG. 16 is a graph illustrating the cytotoxicity of the compound of the present invention on retinal pigment epithelial cells.

FIG. 17 is a graph illustrating the cytotoxicity of the compound of the present invention on endothelial cells.

FIG. 18 is a graph illustrating the effect of the compound of the present invention on the body weight of rats.

DESCRIPTION OF THE PREFERRED EMBODIMENTS

Hereinafter, the present invention is described in detail.

The present invention provides the compound represented by formula 1 or the pharmaceutically acceptable salt thereof:

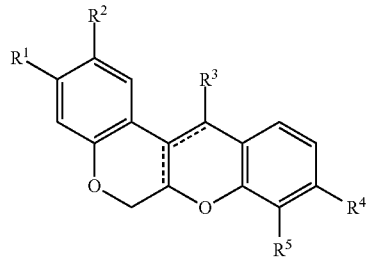

[Formula 1]

In formula 1, $R^1$ and $R^2$ are independently —H, —OH, $C_{1-4}$ straight or branched alkyl, or $C_{1-4}$ alkoxy;

$R^3$ is —H, —OH, =O, —$OR^6$, or =N—O—$R^7$;

$R^4$ is —H, —OH, $C_{1-4}$ alkoxy, acetate, benzyloxy, or phenylmethoxy;

$R^5$ is $C_{1-6}$ straight or branched alkyl or alkenyl;

Or $R^4$ and $R^5$ can form 5-8 atom saturated or unsaturated heterocycle containing one or more oxygen (O) atoms along with carbon atoms which are attached to the same, wherein the heterocycle can be substituted with one or more substituents independently selected from the group consisting of —OH and $C_{1-4}$ straight or branched alkyl;

$R^6$ is $C_{1-6}$ straight or branched alkyl or alkenyl, $C_{5-8}$ arylalkyl,

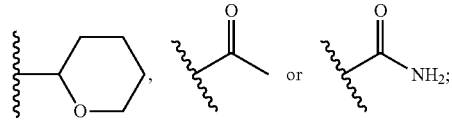

$R^7$ is —H, $C_{1-4}$ straight or branched alkyl, or $C_{5-8}$ arylalkyl;

--- is single bond or double bond; and

The compound of formula 1 is not the compound in which $R^1$ and $R^2$ are —OMe, $R^3$ is =O, and the ring formed by $R^4$ and $R^5$ is

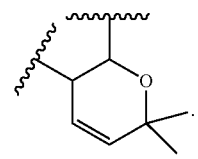 [SMILES: *C1C=CC(C)(C)OC1*]

Preferably, $R^1$ and $R^2$ are independently —OH or —OMe;

$R^3$ is —H, —OH, =O, —$OR^6$ or =N—O—$R^7$;

$R^4$ is —OH, $C_{1-3}$ alkoxy, acetate or phenylmethoxy;

$R^5$ is $C_{1-4}$ straight or branched alkyl or alkenyl;

Or $R^4$ and $R^5$ can form 5-6 atom saturated or unsaturated heterocycle containing one or more oxygen (O) atoms along with carbon atoms which are attached to the same, wherein the heterocycle can be substituted with —OH or $C_{1-2}$ alkyl;

$R^6$ is $C_{1-3}$ straight or branched alkyl or alkenyl, $C_{5-6}$ arylalkyl,

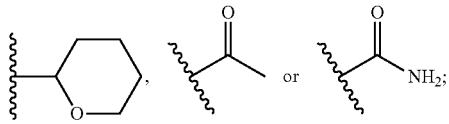

and

R[7] is —H, C$_{1-3}$ straight or branched alkyl, or C$_{5-6}$ arylalkyl.

More preferably,

R[3] is —H, —OH, ═O, methoxy, ethoxy, propoxy, 2-prophenoxy, benzyloxy,

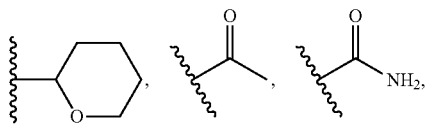

═N—OH, ═N—OMe or ═N—OBn,

R[4] is —OH, methoxy, 2-prophenoxy, benzyloxy or acetate,

R[5] is

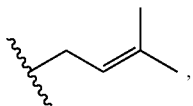 [SMILES: *CC=C(C)C]

Or R[4] and R[5] can form 6 atom heterocycle containing one or more oxygen (O) atoms, wherein the heterocycle can be substituted with —OH or C$_{1-2}$ alkyl. The heterocycle formed by R[4] and R[5] is

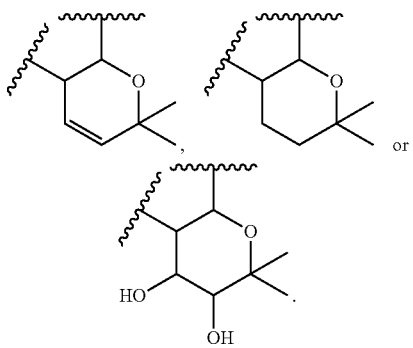

Specific examples of the compound represented by formula 1 of the present invention are as follows:

(6aS,12aS)-9-hydroxy-2,3-dimethoxy-8-(3-methyl-2-butenyl)-6a,12a-dihydrochromeno[3,4-b]chromen-12(6H)-one, (7aS,13aS)-9-hydroxy-13,13a-dihydro-10-methoxy-3,3-dimethyl-3H-chromeno[3,4-b]pyrano[2,3-h]chromen-7(7aH)-one, (7aS,13aS)-10-hydroxy-13,13a-dihydro-9-methoxy-3,3-dimethyl-3H-chromeno[3,4-b]pyrano[2,3-h]chromen-7(7aH)-one, (7aS,13aS)-13,13a-dihydro-9,10-dihydroxy-3,3-dimethyl-3H-chromeno[3,4-b]pyrano[2,3-h]chromen-7(7aH)-one, 9,10-dimethoxy-3,3-dimethyl-3H-chromeno[3,4-b]pyrano[2,3-h]chromen-7-(13H)-one, (7aS,13aS)-9,10-dimethoxy-3,3-dimethyl-7,7a,13,13a-tetrahydro-3H-chromeno[3,4-b]pyrano[2,3-h]chromene, (7S,7aR,3aS)-9,10-dimethoxy-3,3-dimethyl-7-ethoxy-7,7a,13,13a-tetrahydro-3H-chromeno[3,4-b]pyrano[2,3-h]chromene, (7S,7aR,3aS)-9,10-dimethoxy-3,3-dimethyl-7-propoxy-7,7a,13,13a-tetrahydro-3H-chromeno[3,4-b]pyrano[2,3-h]chromene, (7S,7aR,3aS)-7-benzyloxy-9,10-dimethoxy-3,3-dimethyl-7,7a,13,13a-tetrahydro-3H-chromeno[3,4-b]pyrano[2,3-h]chromene, (7S,7aS,13aS)-9,10-dimethoxy-3,3-dimethyl-7-(tetrahydro-2H-pyran-2-yloxy)-7,7a,13,13a-tetrahydro-3H-chromeno[3,4-b]pyrano[2,3-h]chromene, (7S,7aS,13aS)-9,10-dimethoxy-3,3-dimethyl-7,7a,13,13a-tetrahydro-3H-chromeno[3,4-b]pyrano[2,3,h]chromen-7-yl acetate, (13aS)-9,10-dimethoxy-3,3-dimethyl-13,13a-dihydro-3H-chromeno[3,4-b]pyrano[2,3-h]chromene, (7aR,13aS)-9,10-dimethoxy-3,3-dimethyl-13,13a-dihydro-3H-chromeno[3,4-b]pyrano[2,3-h]chromen-7(7aH)-one oxime, (7aR,13aS)-9,10-dimethoxy-3,3-dimethyl-13,13a-dihydro-3H-chromeno[3,4-b]pyrano[2,3-h]chromen-7(7aH)-one O-methyloxime, (7aR,13aS)-9,10-dimethoxy-3,3-dimethyl-13,13a-dihydro-3H-chromeno[3,4-b]pyrano[2,3-h]chromen-7(7aH)-one O-benzyloxime, (7aS,13aS)-1,2-dihydroxy-9,10-dimethoxy-3,3-dimethyl-2,3,13,13a-tetrahydro-1H-chromeno[3,4-b]pyrano[2,3-h]chromen-7 (7aH)-one, 2,3,9-trimethoxy-8-(3-methyl-but-2-enyl)-6a,12a-dihydro-6H-chromeno[3,4-b]chromen-12-one, 9-aryloxy-2,3-dimethoxy-8-(3-methyl-but-2-enyl)-6a,12a-dihydro-6H-chromeno[3,4-b]chromen-12-one, 9-benzyloxy-2,3-dimethoxy-8-(3-methyl-but-2-enyl)-6a,12a-dihydro-6H-chromeno[3,4-b]chromen-12-one, acetic acid 2,3-dimethoxy-8-(3-methyl-but-2-enyl)-12-oxo-6,6a,12,12a-tetrahydrochromeno[3,4-b]chromen-9-yl ester, and (7S,7aR,3aS)-9,10-dimethoxy-3,3-dimethyl-7-(prop-2-enoxy)-7,7a,13,13a-tetrahydro-3H-chromeno[3,4-b]pyrano[2,3-h]chromene.

The present invention also provides the compound represented by formula 2 or the pharmaceutically acceptable salt thereof:

[Formula 2]

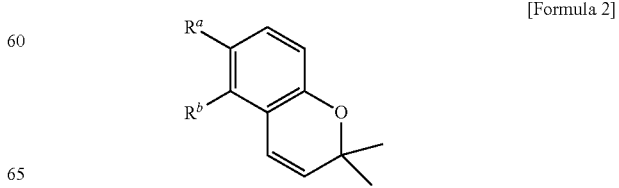

In formula 2,
R$^a$ is

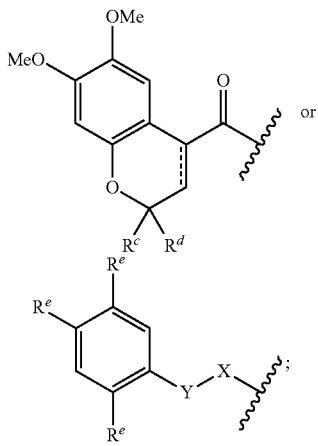

or

R$^b$ is —H, —OH or C$_{1-3}$ alkoxy;
Or R$^a$ and R$^b$ can form 5-8 atom heterocycle containing one or more oxygen (O) atoms along with carbon atoms which are attached to the same, wherein the heterocycle can be substituted with one or more substituents independently selected from the group consisting of =O and dimethoxyphenyl;

R$^c$ and R$^d$ are independently —H, C$_{1-3}$ straight or branched alkyl;

R$^e$ is independently —H or C$_{1-3}$ alkoxy;

X is

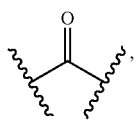 [SMILES: *C(*)=O]

—NH— or C$_{1-3}$ alkylene or alkenylene;
Y is C$_{1-3}$ alkylene or alkenylene,

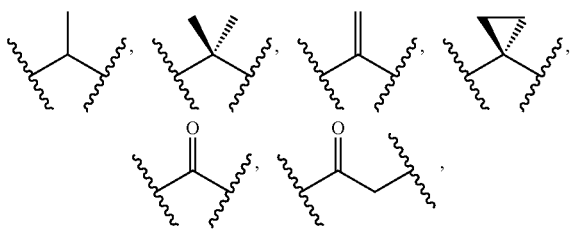

—NH—,

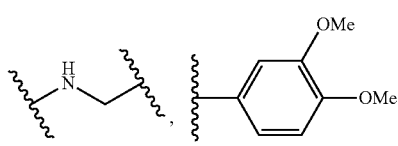

or —SO$_2$Ph; and
--- is single bond or double bond.

Preferably,
R$^a$ is

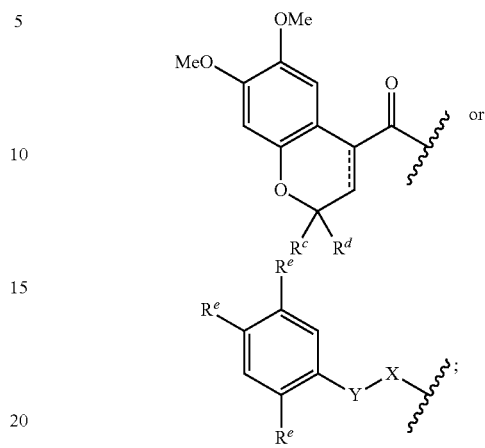

or

R$^b$ is —H, —OH or C$_{1-2}$ alkoxy;
Or R$^a$ and R$^b$ can form 5-6 atom heterocycle containing one or more oxygen (O) atoms along with carbon atoms which are attached to the same, wherein the heterocycle can be substituted with one or more substituents independently selected from the group consisting of =O and dimethoxyphenyl;

R$^c$ and R$^d$ are independently —H, C$_{1-2}$ straight or branched alkyl;

R$^e$ is independently —H or C$_{1-2}$ alkoxy;

X is

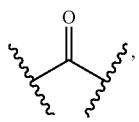

—NH— or C$_{1-2}$ alkylene or alkenylene; and
Y is —H, C$_{1-2}$ alkylene or alkenylene,

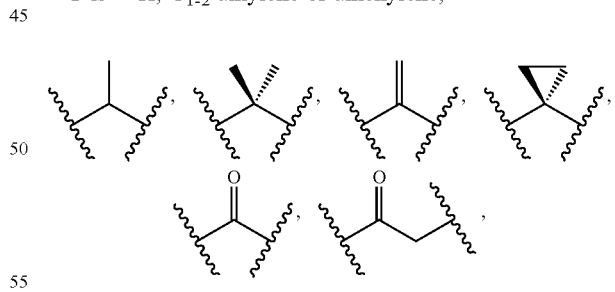

—NH—,

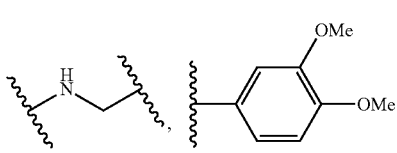

or —SO$_2$Ph.

More preferably,
R$^a$ is

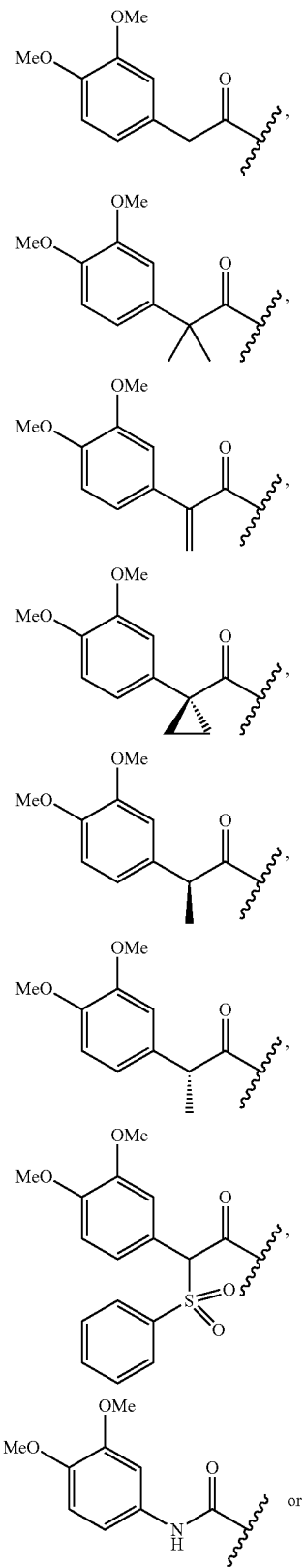

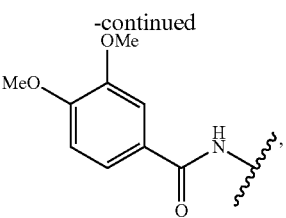

R$^b$ is —H, —OH or methoxy,

Or R$^a$ and R$^b$ can form 6 atom heterocycle containing an oxygen (O) atom along with carbon atoms which are attached to the same, wherein the heterocycle can be substituted with one or more substituents selected from the group consisting of =O and dimethoxyphenyl. At this time, the heterocycle is

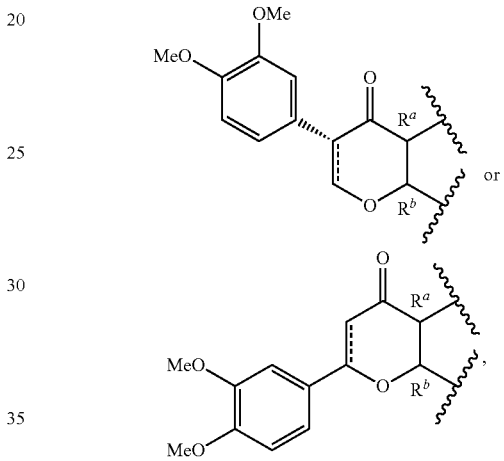

and

--- is single bond or double bond.

Alternatively, in Formula 2,

R$^a$ is

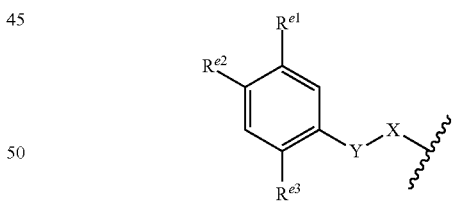

and R$^b$ is C$_{1-3}$ alkoxy, wherein R$^{e1}$, R$^{e2}$ and R$^{e3}$ are independently —H, C$_{1-3}$ alkoxy, —F, —O—CH$_2$—CH=CH$_2$, —CF$_3$, —NO$_2$ —CN, —OH, —NH$_2$, -Me, or R$^{e1}$ and R$^{e2}$ may be linked together to form

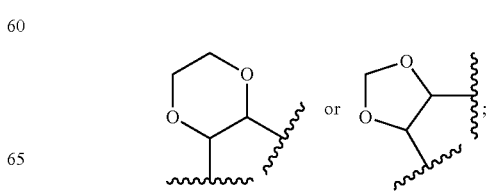

X is
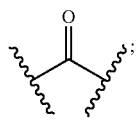 [SMILES: *C(*)=O];
Y is methylene,
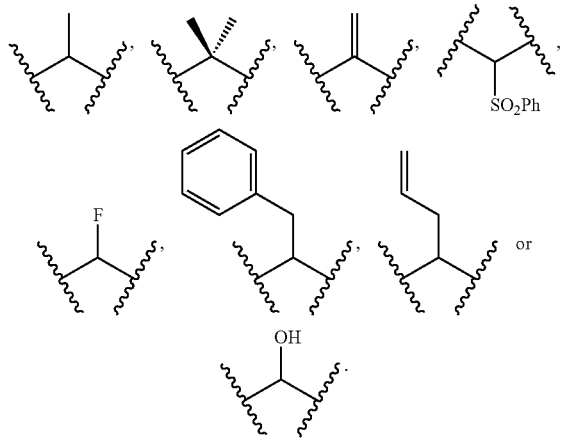
$R^b$ is preferably $C_{1-2}$ alkoxy, more preferably methoxy.
Preferably,
$R^a$ is
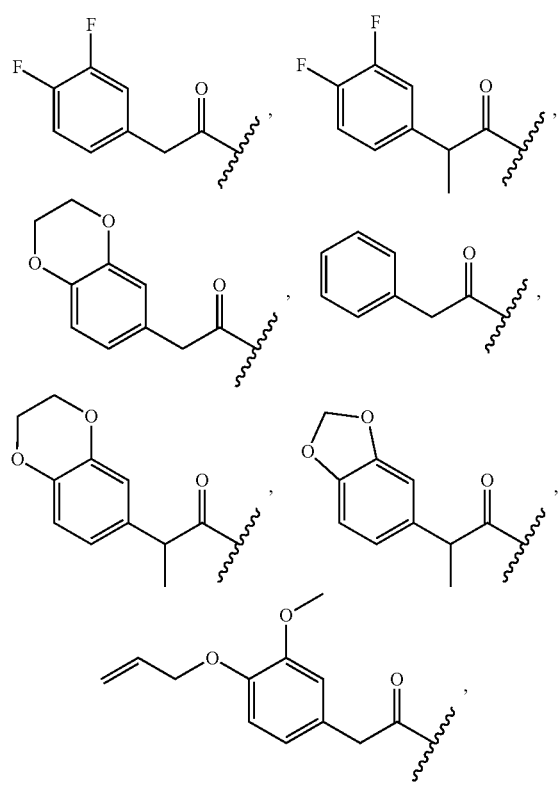
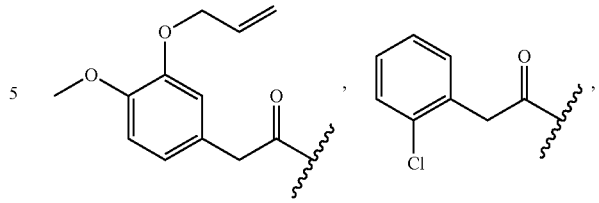
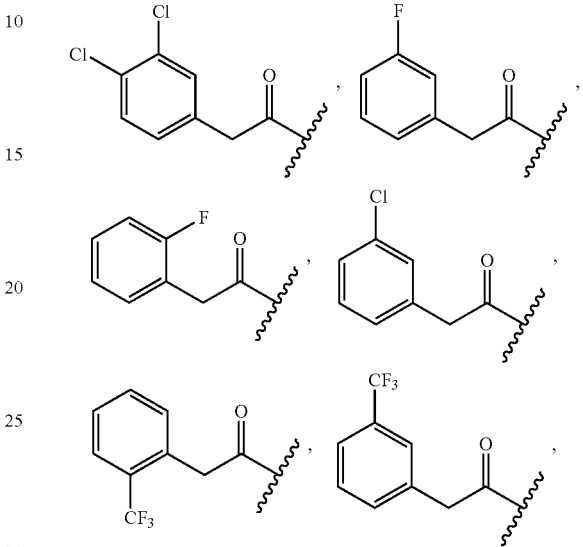
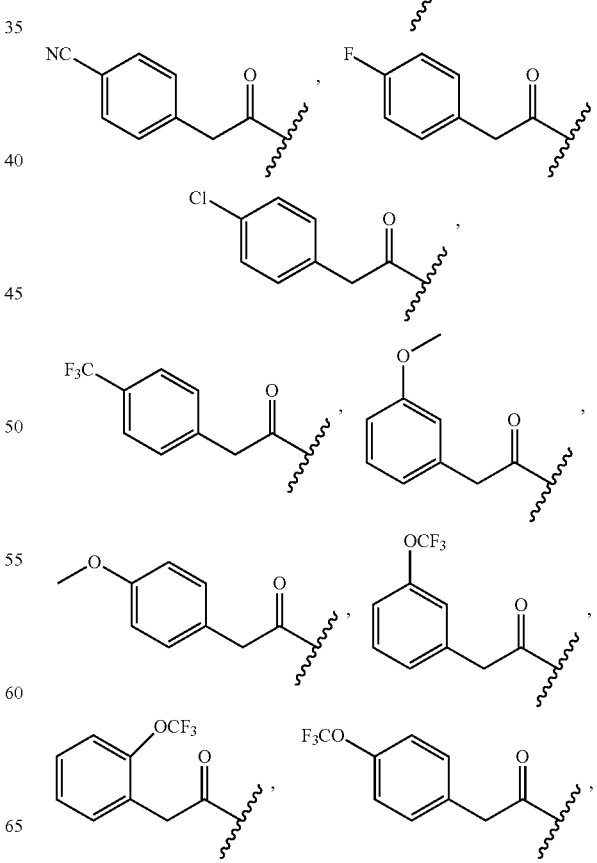

-continued

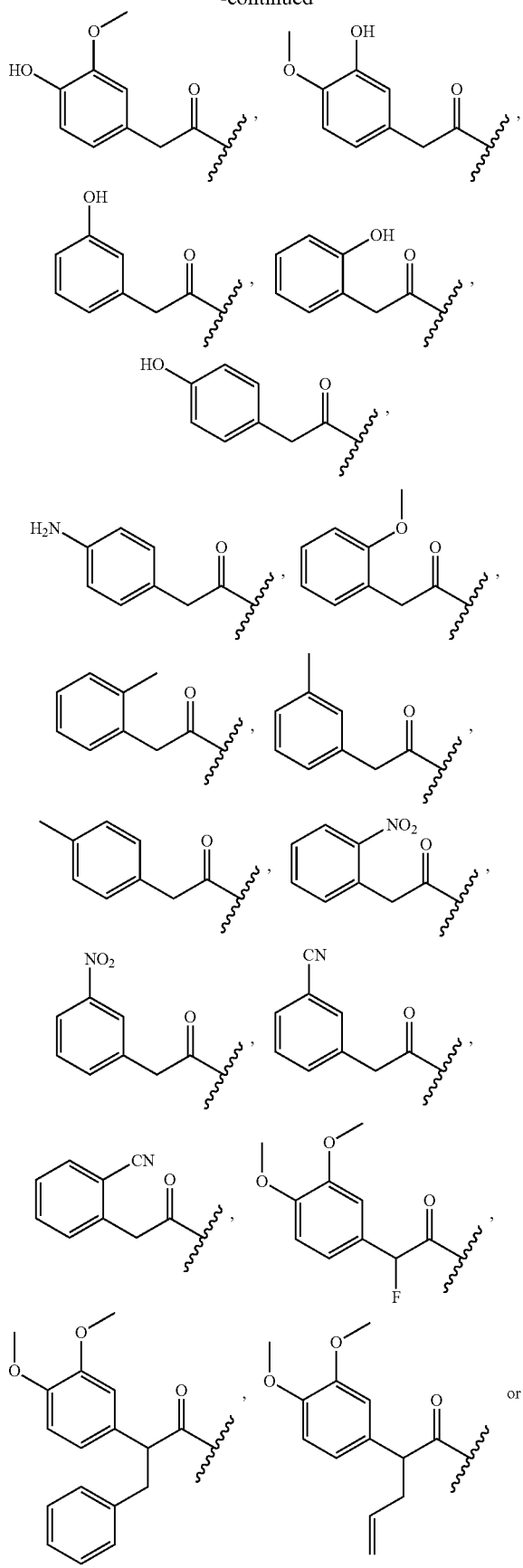

-continued

Specific examples of the compound represented by formula 2 of the present invention are as follows:
(3S)-3-(3,4-dimethoxyphenyl)-8,8-dimethyl-2,3-dihydro-4H,8H-pyrano[2,3-f]chromen-4-one,
(6,7-dimethoxychroman-4-yl) (2,2-dimethyl-2H-chromen-6-yl)methanone,
2-(3,4-dimethoxyphenyl)-1-(2,2-dimethyl-2H-chromen-6-yl)ethanone,
2-(3,4-dimethoxyphenyl)-1-(5-methoxy-2,2-dimethyl-2H-chromen-6-yl)ethanone,
2-(3,4-dimethoxyphenyl)-1-(5-methoxy-2,2-dimethyl-2H-chromen-6-yl)propan-1-one,
2-(3,4-dimethoxyphenyl)-1-(5-methoxy-2,2-dimethyl-2H-chromen-6-yl)-2-methylpropan-1-one,
2-(3,4-dimethoxyphenyl)-1-(5-methoxy-2,2-dimethyl-2H-chromen-6-yl)prop-2-en-1-one,
1-(3,4-dimethoxyphenyl)cyclopropyl) (5-methoxy-2,2-dimethyl-2H-chromen-6-yl)methanone,
(S)-2-(3,4-dimethoxyphenyl)-1-(5-methoxy-2,2-dimethyl-2H-chromen-6-yl)propan-1-one,
(R)-2-(3,4-dimethoxyphenyl)-1-(5-methoxy-2,2-dimethyl-2H-chromen-6-yl)propan-1-one,
3-(3,4-dimethoxyphenyl)-8,8-dimethyl-4H,8H-pyrano[2,3-f]chromen-4-one,
6,7-dimethoxy-2H-chromen-4-yl(2,2-dimethyl-2H-chromen-6-yl)methanone,
6,7-dimethoxy-2,2-dimethyl-2H-chromen-4-yl) (4-methoxy-2,2-dimethyl-2H-chromen-6-yl)methanone,
6,7-dimethoxy-2,2-dimethyl-2H-chromen-4-yl) (2,2-W dimethyl-2H-chromen-6-yl)methanone,
6,7-dimethoxy-2H-chromen-4-yl) (4-methoxy-2,2-dimethyl-2H-chromen-6-yl)methanone,
2-(3,4-dimethoxyphenyl)-1-(5-hydroxy-2,2-dimethyl-2H-chromen-6-yl)-2-(phenylsulfonyl)ethanone,
(3,4-dimethoxyphenyl) (2,2-dimethyl-2H-chromen-6-yl) methanone,
(E)-1-(3,4-dimethoxyphenyl)-3-(2,2-dimethyl-2H-chromen-6-yl)prop-2-en-1-one,
(E)-3-(3,4-dimethoxyphenyl)-1-(5-hydroxy-2,2-dimethyl-2H-chromen-6-yl)prop-2-en-1-one,
(E)-3-(3,4-dimethoxyphenyl)-1-(2,2-dimethyl-2H-chromen-6-yl)prop-2-en-1-one,
(E)-1-(5-hydroxy-2,2-dimethyl-2H-chromen-6-yl)-3-(2,4,5-trimethoxyphenyl)prop-2-en-1-one,
(E)-3-(3,4-dimethoxyphenyl)-1-(5-methoxy-2,2-dimethyl-2H-chromen-6-yl)prop-2-en-1-one,
(E)-1-(5-methoxy-2,2-dimethyl-2H-chromen-6-yl)-3-(2,4,5-trimethoxyphenyl)prop-2-en-1-one,
2-(3,4-dimethoxyphenyl)-8,8-dimethyl-4H,8H-pyrano[2,3-f]chromen-4-one,
2-(3,4-dimethoxyphenyl)-N-(5-methoxy-2,2-dimethyl-2H-chromen-6-yl)acet-amide,
N-(3,4-dimethoxybenzyl)-2,2-dimethyl-2H-chromen-6-carboxamide,
N-(3,4-dimethoxyphenyl)-2,2-dimethyl-2H-chromen-6-carboxamide, N-(2,2-dimethyl-2H-chromen-6-yl)-3,4-dimethoxybenzamide,
(R)-2-(3,4-dimethoxyphenyl)-1-(2,2-dimethyl-2H-chromen-6-yl)propan-1-one,
(S)-2-(3,4-dimethoxyphenyl)-1-(2,2-dimethyl-2H-chromen-6-yl)propan-1-one,
2-(3,4-difluorophenyl)-1-(5-methoxy-2,2-dimethyl-2H-chromen-6-yl)ethanone,
2-(3,4-difluorophenyl)-1-(5-methoxy-2,2-dimethyl-2H-chromen-6-yl)propan-1-one,
2-(2,3-dihydrobenzo[b][1,4]dioxin-6-yl)-1-(5-methoxy-2,2-dimethyl-2H-chromen-6-yl)ethanone,
1-(5-methoxy-2,2-dimethyl-2H-chromen-6-yl)-2-phenylethanone,
2-(2,3-dihydrobenzo[b][1,4]dioxin-6-yl)-1-(5-methoxy-2,2-dimethyl-2H-chromen-6-yl)propan-1-one,
2-(benzo[d][1,3]dioxol-5-yl)-1-(5-methoxy-2,2-dimethyl-2H-chromen-6-yl)propan-1-one,
2-(4-(allyloxy)-3-methoxyphenyl)-1-(5-methoxy-2,2-dimethyl-2H-chromen-6-yl)ethanone,
2-(3-(allyloxy)-4-methoxyphenyl)-1-(5-methoxy-2,2-dimethyl-2H-chromen-6-yl)ethanone,
2-(2-chlorophenyl)-1-(5-methoxy-2,2-dimethyl-2H-chromen-6-yl)ethanone,
2-(3,4-dichlorophenyl)-1-(5-methoxy-2,2-dimethyl-2H-chromen-6-yl)ethanone,
2-(3-fluorophenyl)-1-(5-methoxy-2,2-dimethyl-2H-chromen-6-yl)ethanone,
2-(2-fluorophenyl)-1-(5-methoxy-2,2-dimethyl-2H-chromen-6-yl)ethanone,
2-(3-chlorophenyl)-1-(5-methoxy-2,2-dimethyl-2H-chromen-6-yl)ethanone,
1-(5-methoxy-2,2-dimethyl-2H-chromen-6-yl)-2-(2-(trifluoromethyl)phenyl)ethanone,
1-(5-methoxy-2,2-dimethyl-2H-chromen-6-yl)-2-(3-(trifluoromethyl)phenyl)ethanone,
1-(5-methoxy-2,2-dimethyl-2H-chromen-6-yl)-2-(4-nitrophenyl)ethanone,
4-(2-(5-methoxy-2,2-dimethyl-2H-chromen-6-yl)-2-oxoethyl)benzonitrile,
2-(4-fluorophenyl)-1-(5-methoxy-2,2-dimethyl-2H-chromen-6-yl)ethanone,
2-(4-chlorophenyl)-1-(5-methoxy-2,2-dimethyl-2H-chromen-6-yl)ethanone,
1-(5-methoxy-2,2-dimethyl-2H-chromen-6-yl)-2-(4-(trifluoromethyl)phenyl)ethanone,
1-(5-methoxy-2,2-dimethyl-2H-chromen-6-yl)-2-(3-methoxyphenyl)ethanone,
1-(5-methoxy-2,2-dimethyl-2H-chromen-6-yl)-2-(4-methoxyphenyl)ethanone,
1-(5-methoxy-2,2-dimethyl-2H-chromen-6-yl)-2-(3-(trifluoromethoxy)phenyl)ethanone,
1-(5-methoxy-2,2-dimethyl-2H-chromen-6-yl)-2-(2-(trifluoromethoxy)phenyl)ethanone,
1-(5-methoxy-2,2-dimethyl-2H-chromen-6-yl)-2-(4-(trifluoromethoxy)phenyl)ethanone,
2-(4-hydroxy-3-methoxyphenyl)-1-(5-methoxy-2,2-dimethyl-2H-chromen-6-yl)ethanone,
2-(3-hydroxy-4-methoxyphenyl)-1-(5-methoxy-2,2-dimethyl-2H-chromen-6-yl)ethanone,
2-(3-hydroxyphenyl)-1-(5-methoxy-2,2-dimethyl-2H-chromen-6-yl)ethanone,
2-(2-hydroxyphenyl)-1-(5-methoxy-2,2-dimethyl-2H-chromen-6-yl)ethanone,
2-(4-hydroxyphenyl)-1-(5-methoxy-2,2-dimethyl-2H-chromen-6-yl)ethanone,
2-(4-aminophenyl)-1-(5-methoxy-2,2-dimethyl-2H-chromen-6-yl)ethanone,
1-(5-methoxy-2,2-dimethyl-2H-chromen-6-yl)-2-(2-methoxyphenyl)ethanone,
1-(5-methoxy-2,2-dimethyl-2H-chromen-6-yl)-2-o-tolylethanone,
1-(5-methoxy-2,2-dimethyl-2H-chromen-6-yl)-2-m-tolylethanone,
1-(5-methoxy-2,2-dimethyl-2H-chromen-6-yl)-2-p-tolylethanone,
1-(5-methoxy-2,2-dimethyl-2H-chromen-6-yl)-2-(2-nitrophenyl)ethanone,
1-(5-methoxy-2,2-dimethyl-2H-chromen-6-yl)-2-(3-nitrophenyl)ethanone,
3-(2-(5-methoxy-2,2-dimethyl-2H-chromen-6-yl)-2-oxoethyl)benzonitrile,
2-(2-(5-methoxy-2,2-dimethyl-2H-chromen-6-yl)-2-oxoethyl)benzonitrile,
2-(3,4-dimethoxyphenyl)-2-fluoro-1-(5-methoxy-2,2-dimethyl-2H-chromen-6-yl)ethanone,
2-(3,4-dimethoxyphenyl)-1-(5-methoxy-2,2-dimethyl-2H-chromen-6-yl)-3-phenylpropan-1-one,
2-(3,4-dimethoxyphenyl)-1-(5-methoxy-2,2-dimethyl-2H-chromen-6-yl)pent-4-en-1-one, and
2-(3,4-dimethoxyphenyl)-2-hydroxy-1-(5-methoxy-2,2-dimethyl-2H-chromen-6-yl)ethanone.

Specific examples of the compounds represented by formula 1 and formula 2 of the present invention are presented in Table 1.

TABLE 1

| Compound | Structure |
|---|---|
| Deguelin | 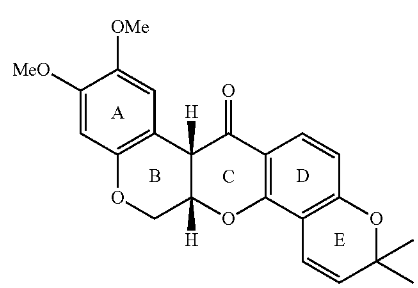 |

TABLE 1-continued

| Compound | Structure |
|---|---|
| Example 1 (Compound 8) | 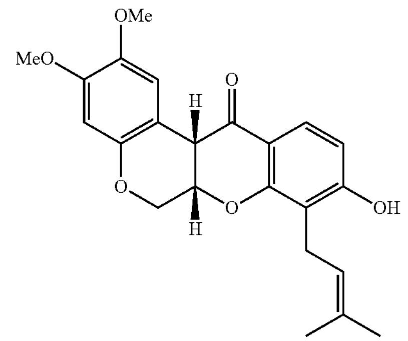 [SMILES: COc1cc2c(cc1OC)[C@@H]1C(=O)c3ccc(O)c(CC=C(C)C)c3O[C@@H]1CO2] |
| Example 2 (Compound 9) | 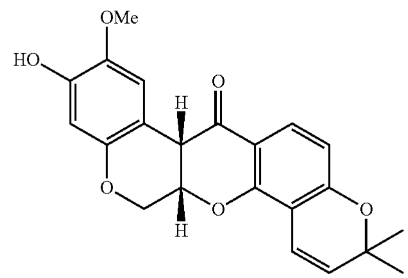 [SMILES: COc1cc2c(cc1O)OC[C@H]1Oc3c(ccc4c3C=CC(C)(C)O4)C(=O)[C@@H]21] |
| Example 3 (Compound 10) | 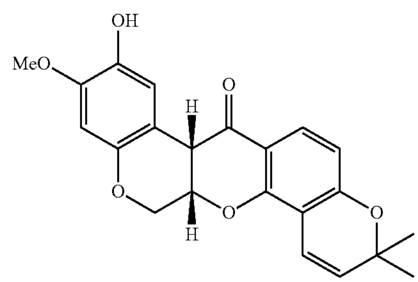 [SMILES: COc1cc2c(cc1O)[C@@H]1C(=O)c3ccc4c(c3O[C@@H]1CO2)C=CC(C)(C)O4] |
| Example 4 (Compound 11) | 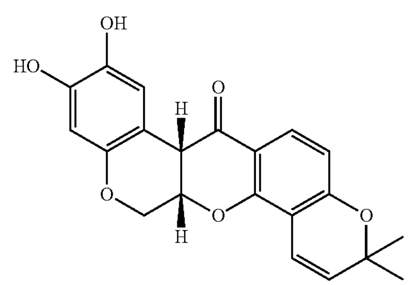 [SMILES: CC1(C)C=Cc2c(ccc3c2O[C@@H]2COc4cc(O)c(O)cc4[C@@H]2C3=O)O1] |
| Example 5 (Compound 12) | 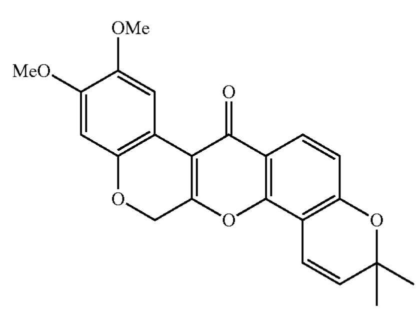 [SMILES: COc1cc2c(cc1OC)-c1c(oc3c4c(ccc3c1=O)OC(C)(C)C=C4)CO2] |

TABLE 1-continued

| Compound | Structure |
|---|---|
| Example 7 (Compound 13) | 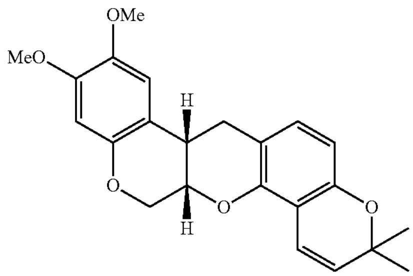 [SMILES: COc1cc2c(cc1OC)[C@@H]1Cc3ccc4c(c3O[C@@H]1CO2)C=CC(C)(C)O4] |
| Example 9 (Compound 16) | 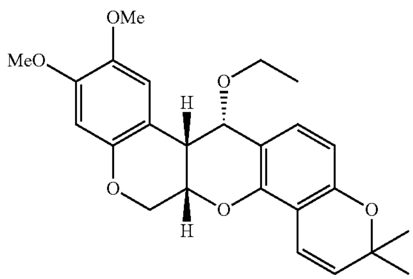 [SMILES: CCO[C@@H]1c2ccc3c(c2O[C@@H]2COc4cc(OC)c(OC)cc4[C@H]12)C=CC(C)(C)O3] |
| Example 10 (Compound 17) | 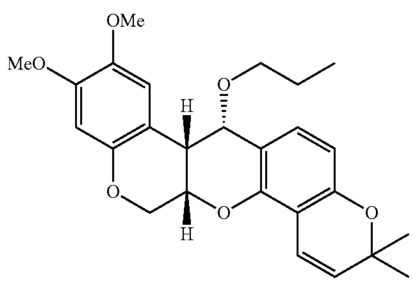 [SMILES: CCCO[C@@H]1c2ccc3c(c2O[C@@H]2COc4cc(OC)c(OC)cc4[C@H]12)C=CC(C)(C)O3] |
| Example 11 (Compound 18) | 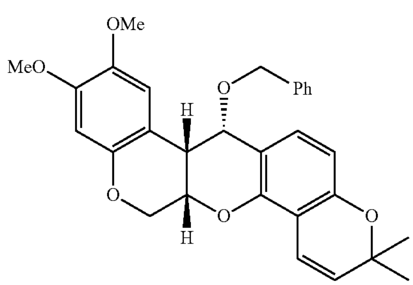 [SMILES: COc1cc2c(cc1OC)[C@@H]1[C@H](OCc3ccccc3)c3ccc4c(c3O[C@@H]1CO2)C=CC(C)(C)O4] |
| Example 12 (Compound 19) | 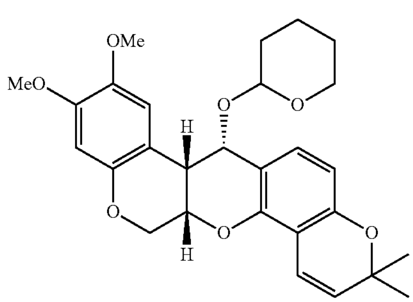 [SMILES: COc1cc2c(cc1OC)[C@@H]1[C@H](OC3CCCCO3)c3ccc4c(c3O[C@@H]1CO2)C=CC(C)(C)O4] |

TABLE 1-continued

| Compound | Structure |
|---|---|
| Example 13 (Compound 20) | 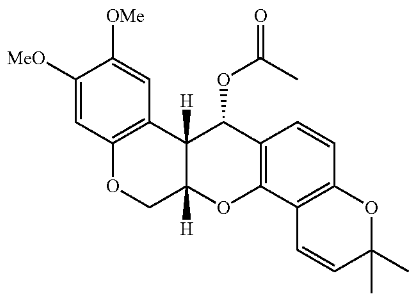 [SMILES: COc1cc2c(cc1OC)[C@@H]1[C@H](OC(C)=O)c3ccc4c(c3O[C@@H]1CO2)C=CC(C)(C)O4] |
| Example 15 (Compound 22) | 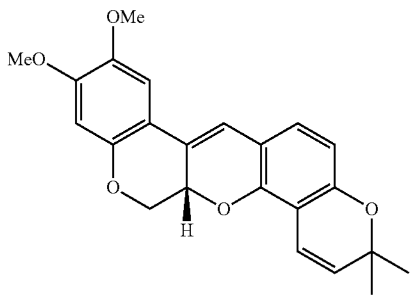 [SMILES: COc1cc2c(cc1OC)C1=Cc3ccc4c(c3O[C@@H]1CO2)C=CC(C)(C)O4] |
| Example 16 (Compound 23) | 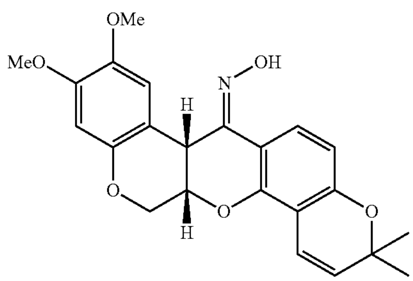 [SMILES: COc1cc2c(cc1OC)[C@@H]1/C(=N/O)c3ccc4c(c3O[C@@H]1CO2)C=CC(C)(C)O4] |
| Example 17 (Compound 24) | 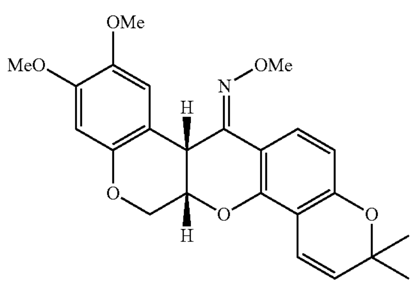 [SMILES: CO/N=C1\c2ccc3c(c2O[C@@H]2COc4cc(OC)c(OC)cc4[C@H]12)C=CC(C)(C)O3] |
| Example 18 (Compound 25) | 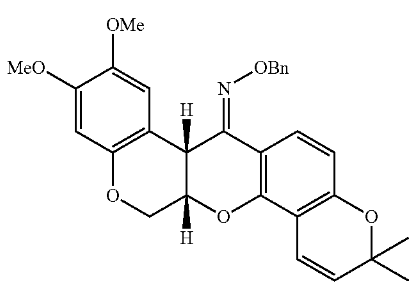 |

TABLE 1-continued

| Compound | Structure |
| --- | --- |
| Example 20 (Compound 27) | (structure) |
| Example 21 (Compound 28) | (structure) |
| Example 22 (Compound 29) | (structure) |
| Example 23 (Compound 30) | (structure) |

TABLE 1-continued

| Compound | Structure |
| --- | --- |
| Example 24 (Compound 31) | 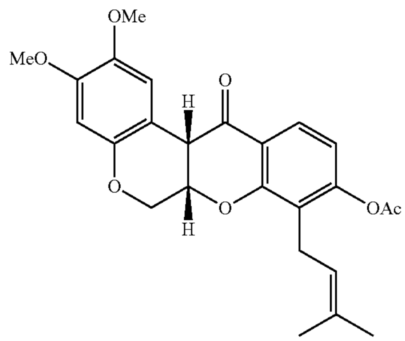 [SMILES: COc1cc2c(cc1OC)[C@@H]1C(=O)c3ccc(OC)c(CC=C(C)C)c3O[C@@H]1CO2] |
| Example 25 (Compound 37) | 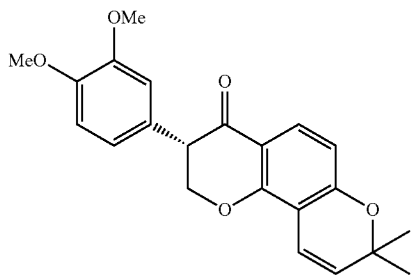 [SMILES: COc1ccc([C@H]2COc3c(ccc4c3C=CC(C)(C)O4)C2=O)cc1OC] |
| Example 26 (Compound 45) | 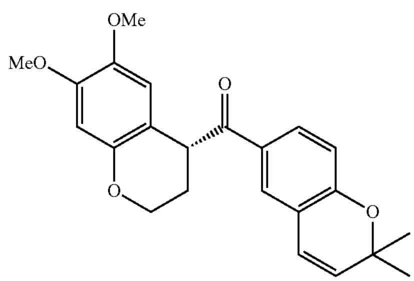 [SMILES: COc1cc2c(cc1OC)[C@H](C(=O)c1ccc3c(c1)C=CC(C)(C)O3)CCO2] |
| Example 27 (Compound 53) | 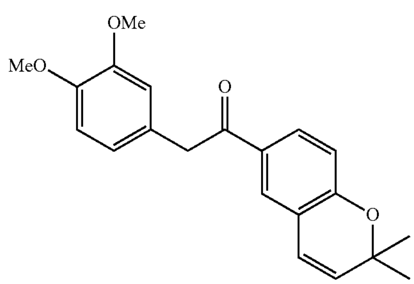 [SMILES: COc1ccc(CC(=O)c2ccc3c(c2)C=CC(C)(C)O3)cc1OC] |
| Example 28 (Compound 54) | 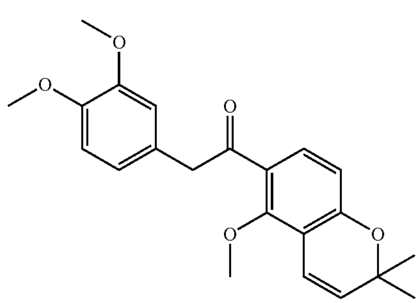 |

TABLE 1-continued

| Compound | Structure |
| --- | --- |
| Example 29 (Compound 56) | 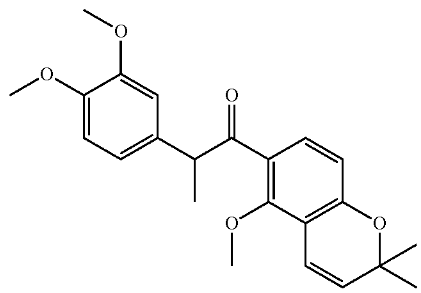 |
| Example 30 (Compound 57) | 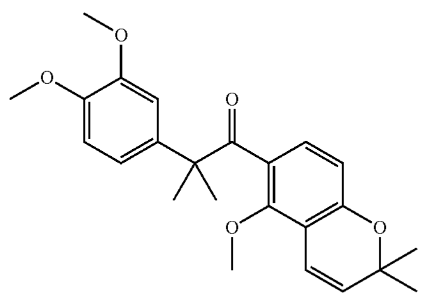 |
| Example 31 (Compound 58) | 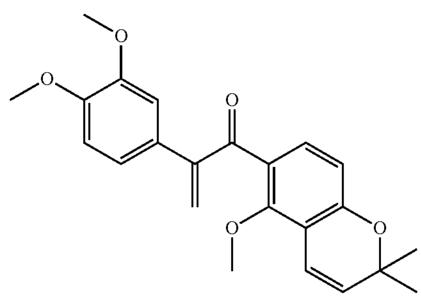 |
| Example 32 (Compound 59) | 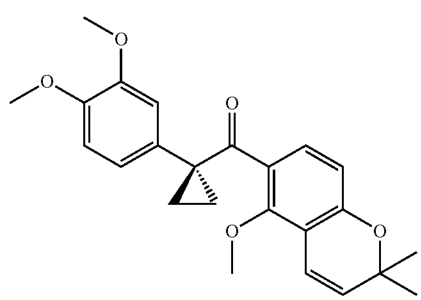 |
| Example 33 (Compound 69) | 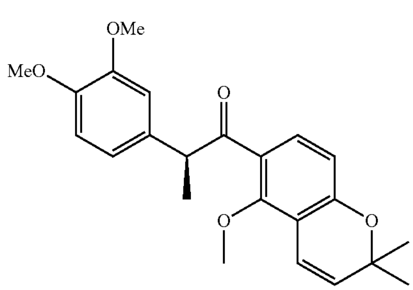 [SMILES: COc1ccc([C@H](C)C(=O)c2ccc3c(c2OC)C=CC(C)(C)O3)cc1OC] |

TABLE 1-continued

| Compound | Structure |
| --- | --- |
| Example 34 (Compound 72) | 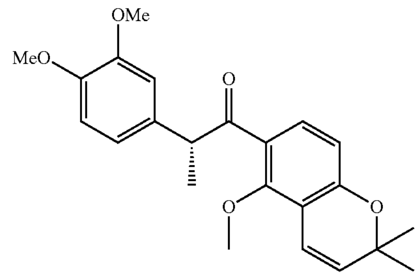 [SMILES: COc1ccc([C@@H](C)C(=O)c2ccc3c(c2OC)C=CC(C)(C)O3)cc1OC] |
| Example 35 (Compound 80) | 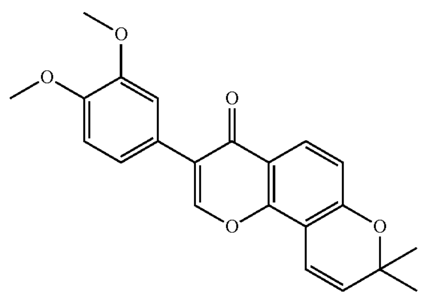 |
| Example 36 (Compound 81) | 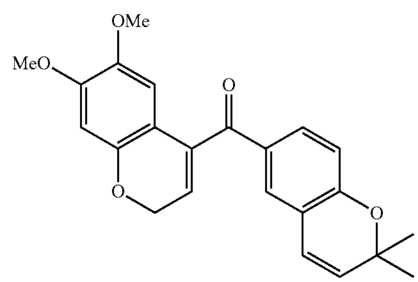 [SMILES: COc1cc2c(cc1OC)C(C(=O)c1ccc3c(c1)C=CC(C)(C)O3)=CCO2] |
| Example 37 (Compound 82) | 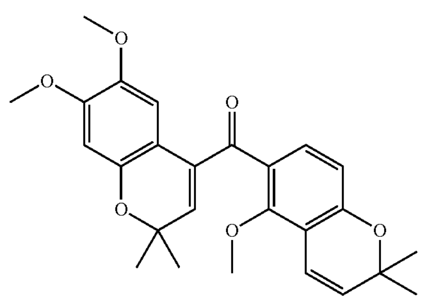 |
| Example 38 (Compound 83) | 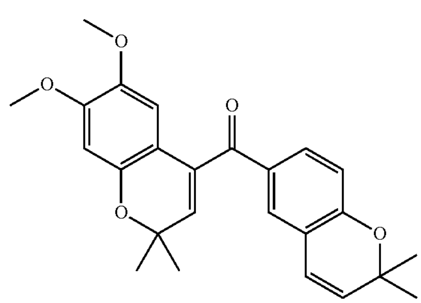 |

TABLE 1-continued

| Compound | Structure |
|---|---|
| Example 39 (Compound 84) | 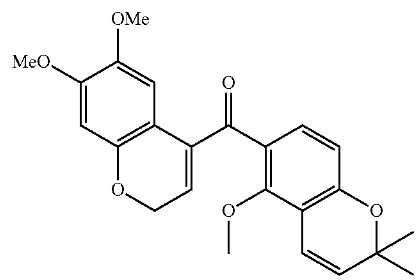 [SMILES: COc1cc2c(cc1OC)C(C(=O)c1ccc3c(c1OC)C=CC(C)(C)O3)=CCO2] |
| Example 40 (Compound 86) | 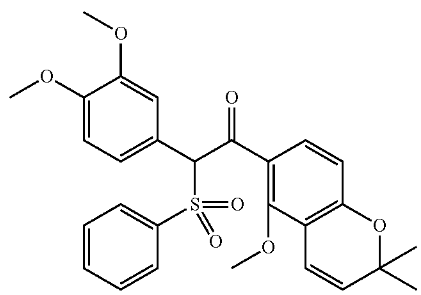 |
| Example 41 (Compound 87) | 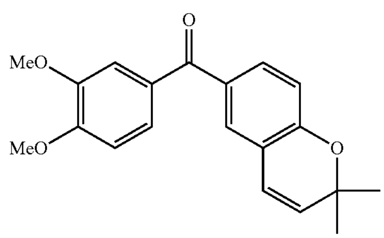 [SMILES: COc1ccc(C(=O)c2ccc3c(c2)C=CC(C)(C)O3)cc1OC] |
| Example 42 (Compound 88) | 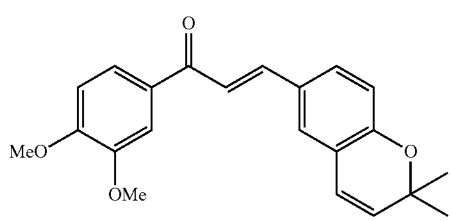 [SMILES: COc1ccc(C(=O)/C=C/c2ccc3c(c2)C=CC(C)(C)O3)cc1OC] |
| Example 43 (Compound 89) | 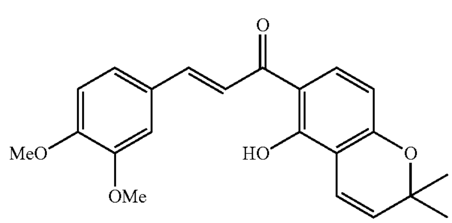 [SMILES: COc1ccc(/C=C/C(=O)c2ccc3c(c2O)C=CC(C)(C)O3)cc1OC] |
| Example 44 (Compound 90) | 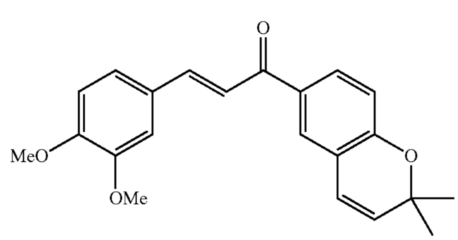 [SMILES: COc1ccc(/C=C/C(=O)c2ccc3c(c2)C=CC(C)(C)O3)cc1OC] |

TABLE 1-continued

| Compound | Structure |
|---|---|
| Example 45 (Compound 91) | 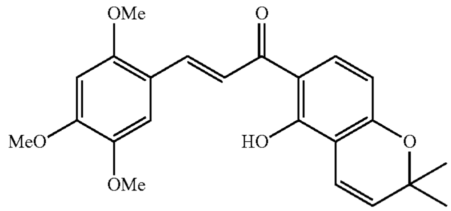 [SMILES: COc1cc(OC)c(OC)cc1/C=C/C(=O)c1ccc2c(c1O)C=CC(C)(C)O2] |
| Example 46 (Compound 92) | 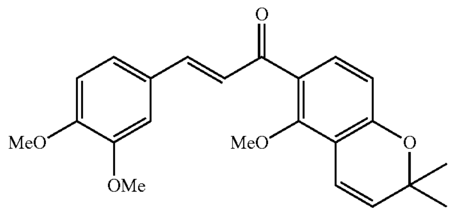 [SMILES: COc1ccc(/C=C/C(=O)c2ccc3c(c2OC)C=CC(C)(C)O3)cc1OC] |
| Example 47 (Compound 93) | 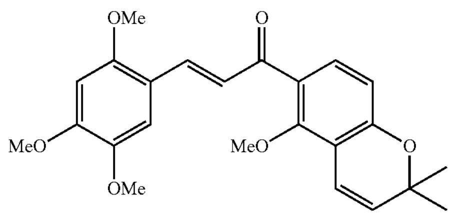 [SMILES: COc1cc(OC)c(OC)cc1/C=C/C(=O)c1ccc2c(c1OC)C=CC(C)(C)O2] |
| Example 48 (Compound 94) | 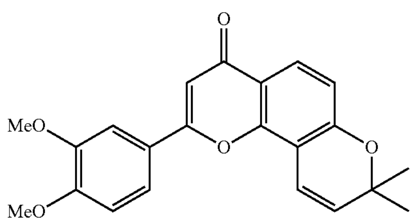 [SMILES: COc1ccc(-c2cc(=O)c3ccc4c(c3o2)C=CC(C)(C)O4)cc1OC] |
| Example 49 (Compound 95) | 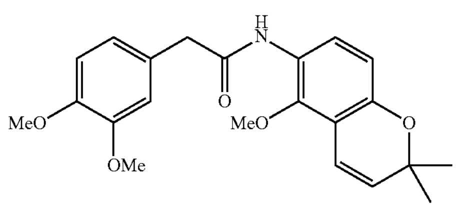 [SMILES: COc1ccc(CC(=O)Nc2ccc3c(c2OC)C=CC(C)(C)O3)cc1OC] |
| Example 50 (Compound 96) | 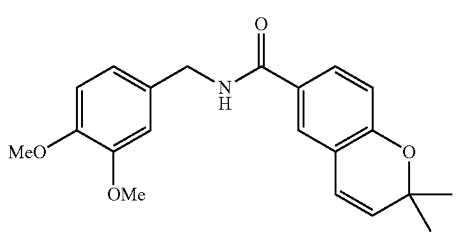 [SMILES: COc1ccc(CNC(=O)c2ccc3c(c2)C=CC(C)(C)O3)cc1OC] |
| Example 51 (Compound 97) | 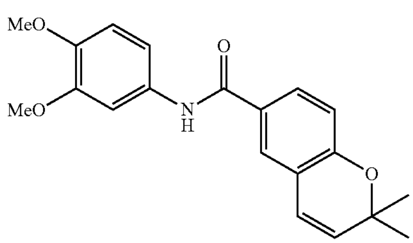 [SMILES: COc1ccc(NC(=O)c2ccc3c(c2)C=CC(C)(C)O3)cc1OC] |

TABLE 1-continued

| Compound | Structure |
|---|---|
| Example 52 (Compound 98) | 3,4-dimethoxy-N-(5-methoxy-2,2-dimethyl-2H-chromen-6-yl)benzamide |
| Example 53 (Compound 99) | (S)-2-(3,4-dimethoxyphenyl)-1-(2,2-dimethyl-2H-chromen-6-yl)propan-1-one |
| Example 54 (Compound 100) | (R)-2-(3,4-dimethoxyphenyl)-1-(2,2-dimethyl-2H-chromen-6-yl)propan-1-one |
| Example 55 (Compound 101) | 7-(allyloxy)-2,3-dimethoxy-10,10-dimethyl-6a,7,10,14a-tetrahydro-6H-chromeno[3',4':5,6]pyrano[3,2-g]chromene |
| Example 56 (SH-125) | 2-(3,4-difluorophenyl)-1-(5-methoxy-2,2-dimethyl-2H-chromen-6-yl)ethan-1-one |

TABLE 1-continued

| Compound | Structure |
| --- | --- |
| Example 57 (SH-126) | 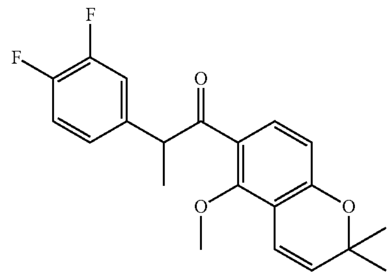 [SMILES: COc1c(C(=O)C(C)c2ccc(F)c(F)c2)ccc2c1C=CC(C)(C)O2] |
| Example 58 (SH-127) | 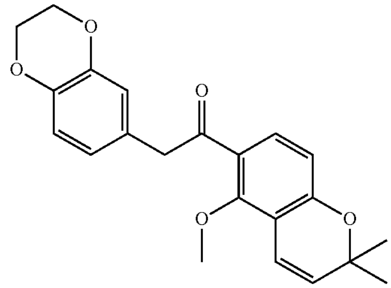 [SMILES: COc1c(C(=O)Cc2ccc3c(c2)OCCO3)ccc2c1C=CC(C)(C)O2] |
| Example 59 (SH-128) | 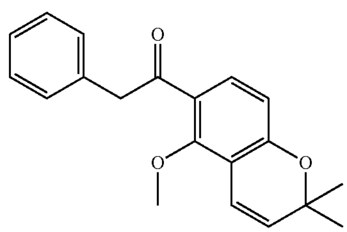 [SMILES: COc1c(C(=O)Cc2ccccc2)ccc2c1C=CC(C)(C)O2] |
| Example 60 (SH-132) | 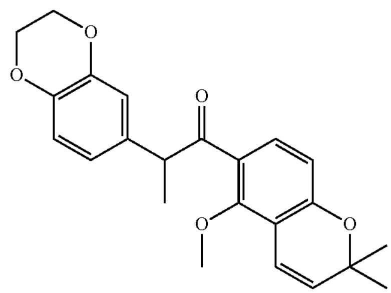 [SMILES: COc1c(C(=O)C(C)c2ccc3c(c2)OCCO3)ccc2c1C=CC(C)(C)O2] |
| Example 61 (SH-134) | 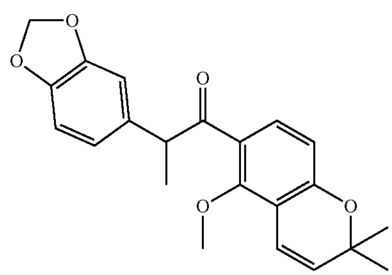 [SMILES: COc1c(C(=O)C(C)c2ccc3c(c2)OCO3)ccc2c1C=CC(C)(C)O2] |

TABLE 1-continued

| Compound | Structure |
|---|---|
| Example 62 (SH-181) | 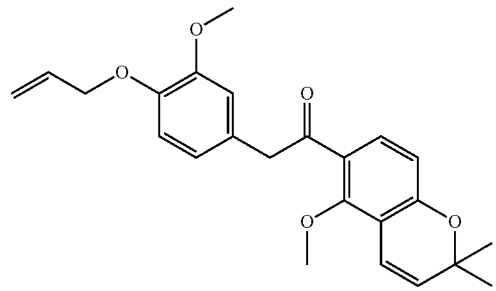 [SMILES: C=CCOc1ccc(CC(=O)c2ccc3c(c2OC)C=CC(C)(C)O3)cc1OC] |
| Example 63 (SH-182) | 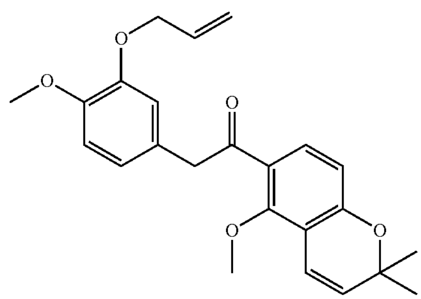 |
| Example 64 (SH-183) | 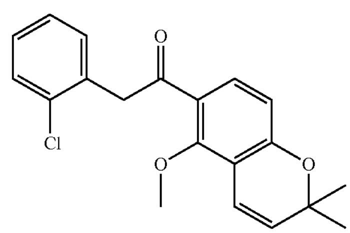 [SMILES: COc1c(C(=O)Cc2ccccc2Cl)ccc2c1C=CC(C)(C)O2] |
| Example 65 (SH-184) | 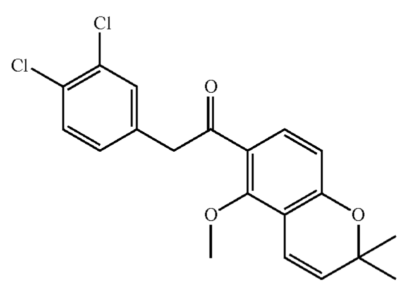 [SMILES: COc1c(C(=O)Cc2ccc(Cl)c(Cl)c2)ccc2c1C=CC(C)(C)O2] |
| Example 66 (SH-198) | 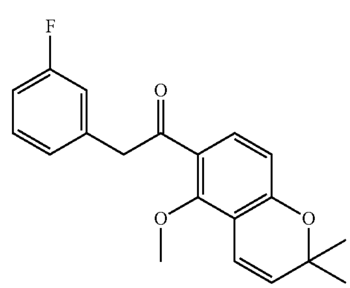 [SMILES: COc1c(C(=O)Cc2cccc(F)c2)ccc2c1C=CC(C)(C)O2] |

TABLE 1-continued
| Compound | Structure |
|---|---|
| Example 67 (SH-199) | 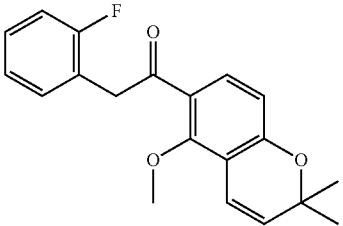 [SMILES: COc1c(C(=O)Cc2ccccc2F)ccc2c1C=CC(C)(C)O2] |
| Example 68 (SH-200) | 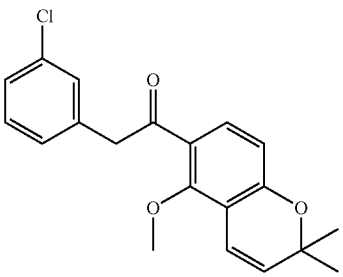 |
| Example 69 (SH-208) | 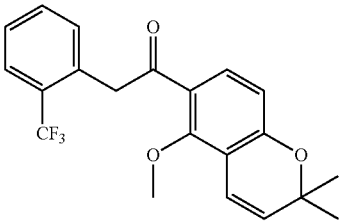 |
| Example 70 (SH-209) | 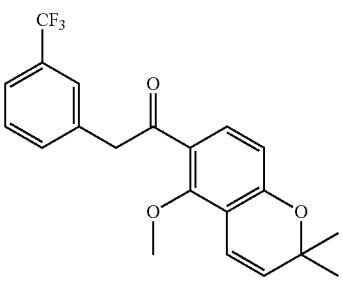 |
| Example 71 (SH-213) | 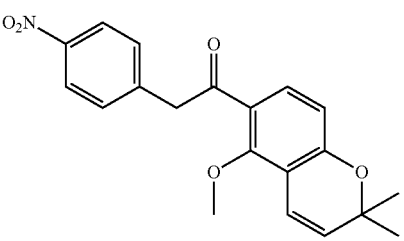 [SMILES: COc1c(C(=O)Cc2ccc([N+](=O)[O-])cc2)ccc2c1C=CC(C)(C)O2] |
| Example 72 (SH-214) | 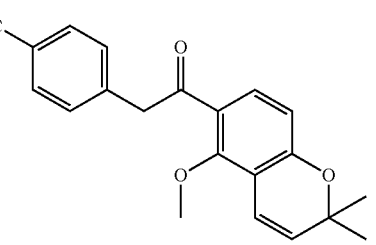 |

TABLE 1-continued

| Compound | Structure |
|---|---|
| Example 73 (SH-215) | 1-(5-methoxy-2,2-dimethyl-2H-chromen-6-yl)-2-(4-fluorophenyl)ethan-1-one |
| Example 74 (SH-216) | 2-(4-chlorophenyl)-1-(5-methoxy-2,2-dimethyl-2H-chromen-6-yl)ethan-1-one |
| Example 75 (SH-217) | 1-(5-methoxy-2,2-dimethyl-2H-chromen-6-yl)-2-(4-(trifluoromethyl)phenyl)ethan-1-one |
| Example 76 (SH-218) | 1-(5-methoxy-2,2-dimethyl-2H-chromen-6-yl)-2-(3-methoxyphenyl)ethan-1-one |
| Example 77 (SH-219) | 1-(5-methoxy-2,2-dimethyl-2H-chromen-6-yl)-2-(4-methoxyphenyl)ethan-1-one |
| Example 78 (SH-220) | 1-(5-methoxy-2,2-dimethyl-2H-chromen-6-yl)-2-(3-(trifluoromethoxy)phenyl)ethan-1-one |

TABLE 1-continued

| Compound | Structure |
| --- | --- |
| Example 79 (SH-221) | 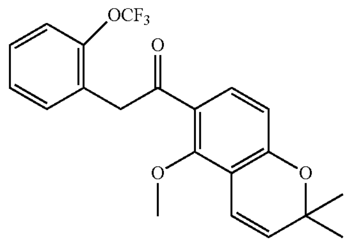 [SMILES: COc1c(C(=O)Cc2ccccc2OC(F)(F)F)ccc2c1C=CC(C)(C)O2] |
| Example 80 (SH-222) | 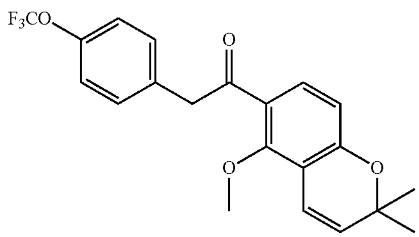 [SMILES: COc1c(C(=O)Cc2ccc(OC(F)(F)F)cc2)ccc2c1C=CC(C)(C)O2] |
| Example 81 (SH-225) | 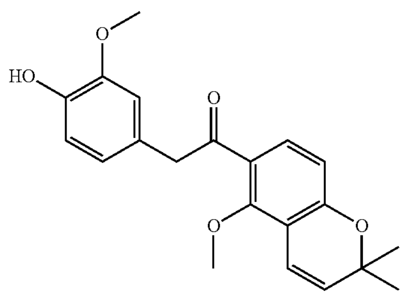 [SMILES: COc1cc(CC(=O)c2ccc3c(c2OC)C=CC(C)(C)O3)ccc1O] |
| Example 82 (SH-226) | 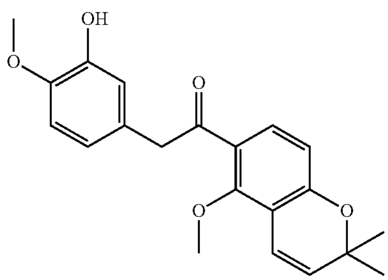 [SMILES: COc1ccc(CC(=O)c2ccc3c(c2OC)C=CC(C)(C)O3)cc1O] |
| Example 83 (SH-227) | 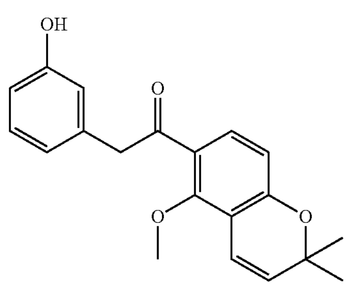 [SMILES: COc1c(C(=O)Cc2cccc(O)c2)ccc2c1C=CC(C)(C)O2] |
| Example 84 (SH-228) | 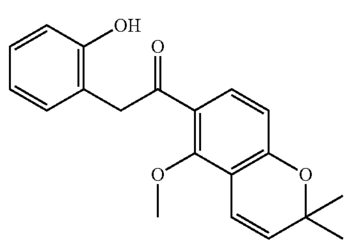 [SMILES: COc1c(C(=O)Cc2ccccc2O)ccc2c1C=CC(C)(C)O2] |

TABLE 1-continued

| Compound | Structure |
|---|---|
| Example 85 (SH-229) | 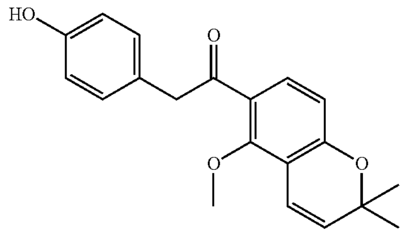 |
| Example 86 (SH-250) | 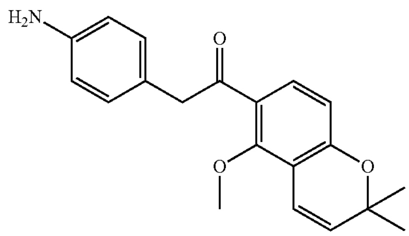 |
| Example 87 (SH-255) | 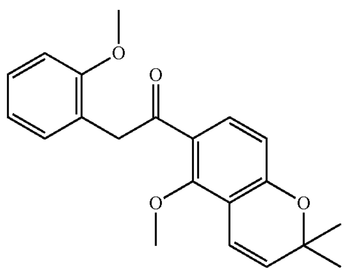 [SMILES: COc1ccccc1CC(=O)c1ccc2c(c1OC)C=CC(C)(C)O2] |
| Example 88 (SH-258) | 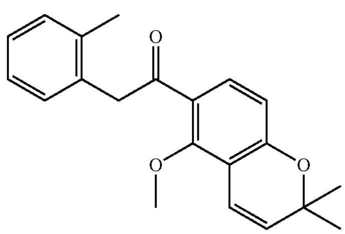 [SMILES: COc1c(C(=O)Cc2ccccc2C)ccc2c1C=CC(C)(C)O2] |
| Example 89 (SH-259) | 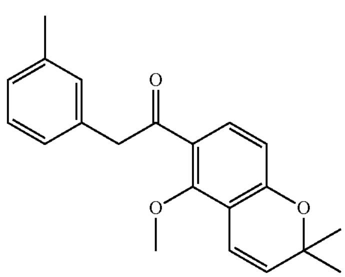 [SMILES: COc1c(C(=O)Cc2cccc(C)c2)ccc2c1C=CC(C)(C)O2] |
| Example 90 (SH-260) | 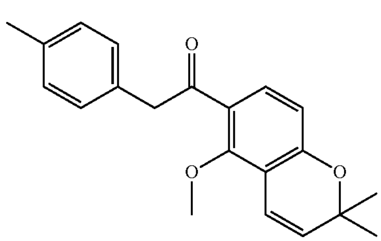 |

TABLE 1-continued

| Compound | Structure |
| --- | --- |
| Example 91 (SH-261) | 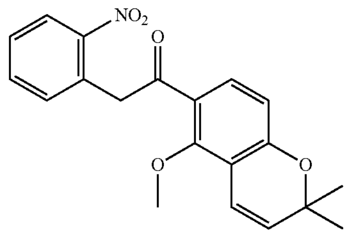 [SMILES: COc1c(C(=O)Cc2ccccc2[N+](=O)[O-])ccc2c1C=CC(C)(C)O2] |
| Example 92 (SH-277) | 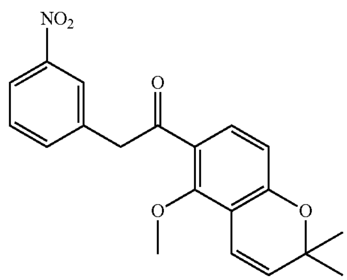 [SMILES: COc1c(C(=O)Cc2cccc([N+](=O)[O-])c2)ccc2c1C=CC(C)(C)O2] |
| Example 93 (SH-294) | 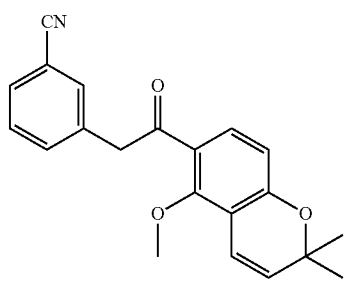 [SMILES: COc1c(C(=O)Cc2cccc(C#N)c2)ccc2c1C=CC(C)(C)O2] |
| Example 94 (SH-295) | 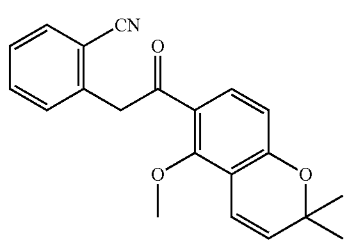 [SMILES: COc1c(C(=O)Cc2ccccc2C#N)ccc2c1C=CC(C)(C)O2] |
| Example 95 (SH-124) | 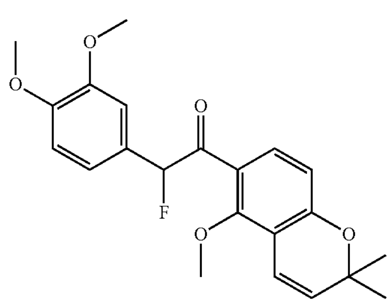 [SMILES: COc1ccc(C(F)C(=O)c2ccc3c(c2OC)C=CC(C)(C)O3)cc1OC] |

TABLE 1-continued

| Compound | Structure |
|---|---|
| Example 96 (SH-137) | 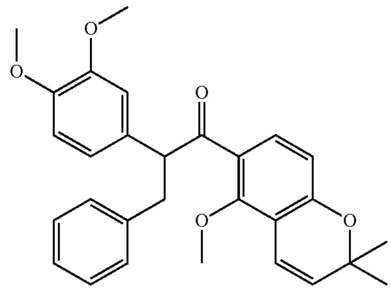 [SMILES: COc1ccc(C(Cc2ccccc2)C(=O)c2ccc3c(c2OC)C=CC(C)(C)O3)cc1OC] |
| Example 97 (SH-185) | 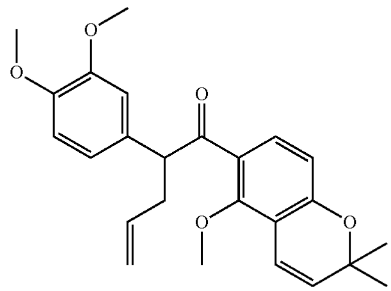 [SMILES: C=CCC(C(=O)c1ccc2c(c1OC)C=CC(C)(C)O2)c1ccc(OC)c(OC)c1] |
| Example 98 (SH-190) | 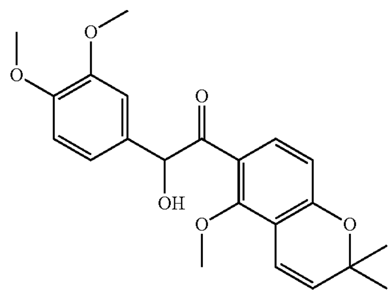 [SMILES: COc1ccc(C(O)C(=O)c2ccc3c(c2OC)C=CC(C)(C)O3)cc1OC] |

The present invention not only includes the compounds represented by formula 1 and formula 2 or the pharmaceutically acceptable salt but also includes every possible solvate, hydrate, or prodrug constructed from the same by the conventional method.

The compounds represented by formula 1 and formula 2 of the present invention can be used as a form of a pharmaceutically acceptable salt, in which the salt is preferably acid addition salt formed by pharmaceutically acceptable free acids. The acid addition salt can be obtained from inorganic acids such as hydrochloric acid, nitric acid, phosphoric acid, sulfuric acid, hydrobromic acid, hydroiodic acid, nitrous acid and phosphorous acid, or non-toxic organic acids such as aliphatic mono/dicarboxylate, phenyl-substituted alkanoate, hydroxy alkanoate, alkandioate, aromatic acids and aliphatic/aromatic sulfonic acids. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate and mandelate.

The acid addition salt in this invention can be prepared by the conventional method known to those in the art. For example, the compounds represented by formula 1 and formula 2 of the present invention are dissolved in acid aqueous solution. Then, the salt is obtained by precipitating the solution by using water-miscible organic solvent such as methanol, ethanol, acetone, or acetonitrile. The salt can be obtained by another way. The equal amount of each compound represented by formula 1 or formula 2 of the present invention and acid or alcohol in water are heated, followed by evaporating/drying the mixture to give the acid addition salt or suction-filtering the precipitated salt to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The compound of the present invention can be produced by the method informed in the following references [(a) Caboni, P.; Sherer, T.; Zhang, N.; Taylor, G.; Na, H.; Greenamyre, J.; Casida, J. Rotenone, deguelin, their metabolites, and the rat model of Parkinson's disease. *Chem. Res. Toxicol* 2004, 17, 1540-1548; (b) Anzeveno, P. Rotenoid interconversion. Synthesis of deguelin from rotenone. *J. Org. Chem.* 1979, 44, 2578-2580], but not always limited thereto. Besides, any informed method or even uninformed method can be used as long as it can synthesize the compound of the present invention.

The compound synthesized by the method of the present invention proceeds to high performance liquid chromatography (HPLC) for the separation/purification and then the molecular structure thereof can be identified by nuclear magnetic resonance (NMR).

The present invention also provides a pharmaceutical composition for preventing or treating cancer comprising the compound of formula 1 and/or the compound of formula 2 or the pharmaceutically acceptable salt thereof as an active ingredient.

The compound represented by formula 1 and/or formula 2 or the pharmaceutically acceptable salt thereof of the present invention suppresses the expression of Hsp90, by which it can inhibit the accumulation of HIF-1α, the Hsp90 client protein, and the activity of VEGF. The inhibition of HIF-1α activity indicates all the activity to inhibit the accumulation of HIF-1α or the expression of HIF-1α target gene.

In this invention, the inhibitory effect of the compound represented by formula 1 and/or formula 2 on the accumulation of HIF-1α was investigated. As a result, the compound of the invention was confirmed to inhibit HIF-1α accumulation dose-dependently without affecting the generation of tublin, the comparative control, under hypoxic condition.

The compound represented by formula 1 and/or formula 2 of the present invention was also confirmed to inhibit the expression of VEGF (vascular endothelial growth factor A) dose-dependently that has been known to be an important factor for cancer growth and metastasis, among the HIF-1α target genes (see FIGS. 2~4).

Therefore, the compound represented by formula 1 and/or formula 2 of the present invention can be used as an anticancer agent treating various cancers including colorectal cancer, liver cancer, stomach cancer, breast cancer, colon cancer, bone cancer, pancreatic cancer, head/neck cancer, uterine cancer, ovarian cancer, rectal cancer, esophageal cancer, small bowel cancer, anal cancer, colon cancer, fallopian tube carcinoma, endometrial carcinoma, uterine cervical carcinoma, vaginal carcinoma, Hodgkin's disease, prostate cancer, bladder cancer, kidney cancer, ureter cancer, renal cell carcinoma, renal pelvic carcinoma, and central nervous system tumor since the compound can suppress the expression of Hsp90 and accordingly inhibit the accumulation of HIF-1α, the Hsp90 client protein, and the activity of VEGF.

In addition, the present invention provides a pharmaceutical composition having the therapeutic effect on diabetic retinopathy or arthritis by inhibiting Hsp90 comprising the compound of formula 1 and/or the compound of formula 2 or the pharmaceutically acceptable salt thereof as an active ingredient.

Hsp90 can be a target of the study to develop a therapeutic agent for the disease particularly whose aggravation is related to the activation of angiogenesis. Angiogenesis factors like VEGF induced by HIF-1α, the Hsp90 client protein, activated under hypoxic condition are involved in the progress of such diseases as diabetic retinopathy and rheumatoid arthritis. Thus, the composition capable of inhibiting HIF-1α activated under hypoxic condition in disease tissue can be used as a therapeutic agent for diabetic retinopathy or arthritis.

The compound of formula 1 and/or formula 2 of the present invention was confirmed to be excellent in inhibiting angiogenesis in Zebra fish embryo (see FIGS. 2~4).

Therefore, the compound of the present invention can selectively inhibit the expression of VEGF (vascular endothelial growth factor A), the angiogenesis factor, so that it can be effectively used as an active ingredient of a pharmaceutical composition to treat diabetic retinopathy or arthritis aggravated with the increase of VEGF expression induced by HIF-1α under hypoxic condition.

The present invention also provides a treatment method for cancer, diabetic retinopathy, or rheumatoid arthritis containing the step of administering the compound represented by formula 1 and/or formula 2 of the invention or the pharmaceutically acceptable salt thereof to a subject with cancer, diabetic retinopathy, or rheumatoid arthritis.

The pharmaceutical composition of the present invention can be administered orally or parenterally and be used in general forms of pharmaceutical formulation, but not always limited thereto. The formulations for oral administration are exemplified by tablets, pills, hard/soft capsules, solutions, suspensions, emulsions, syrups, granules, and elixirs, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavors, and sweeteners can be additionally included thereto.

The pharmaceutical composition comprising the compound represented by formula 1 and/or formula 2 of the present invention can be administered by parenterally and the parenteral administration includes subcutaneous injection, intravenous injection, intramuscular injection and intrathoracic injection. To prepare the composition as a formulation for parenteral administration, the compound represented by formula 1 and/or formula 2 or the pharmaceutically acceptable salt thereof of the present invention are mixed with a stabilizer or a buffering agent to produce a solution or suspension, which is then formulated as ampoules or vials. The composition herein can be sterilized and additionally contains preservatives, stabilizers, wettable powders or emulsifiers, salt and/or buffers for the regulation of osmotic pressure, and other therapeutically useful materials, and the composition can be formulated by the conventional mixing, granulating or coating method. The effective dosage of the pharmaceutical composition comprising the compound represented by formula and/or formula 2 as an active ingredient of the present invention is 0.1~500 mg/kg (weight) per day, preferably 0.5~100 mg/kg (weight) per day for a mammal including human, which can be administered orally or parenterally several times a day or preferably once a day or a couple of times a day.

The pharmaceutical composition of the present invention can be administered alone or treated together with surgical operation, radiotherapy, hormone therapy, chemo-therapy and biological regulators.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Manufacturing Example 1: Preparation of Methyl 2-(3,4-dimethoxyphenyl)acetate (32)

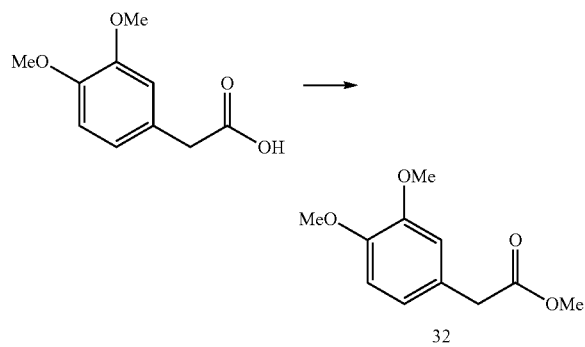

carboxylic acid (1 equivalent) and anhydrous DMF (catalytic amount) were dissolved in anhydrous $CH_2Cl_2$ (0.1 M). After lowering the temperature of the mixture to 0° C., oxalic acid (3 equivalent) was added drop by drop to the mixture. After stirring the mixture at room temperature for 30 minutes, anhydrous methanol (50 equivalent) was added drop by drop, followed by stirring again for 10 minutes. Then, the mixture was treated with water. The water layer was extracted with $CH_2Cl_2$ and the organic layer was dried over $MgSO_4$, followed by filtering. After concentrating the mixture under reduced pressure, the residue was purified by flash column chromatography (EtOAc:n-hexane=1:3) to give the compound 32.

$^1$H NMR (CDCl$_3$, 300 MHz) δ 6.79 (s, 3H), 3.86 (s, 3H), 3.84 (s, 3H), 3.67 (s, 3H), 3.55 (s, 2H).

Manufacturing Example 2: Preparation of Methyl 2-(3,4-dimethoxyphenyl)-3-(4-methoxybenzyloxy) propanoate (33)

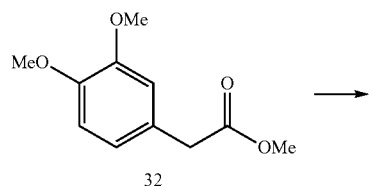

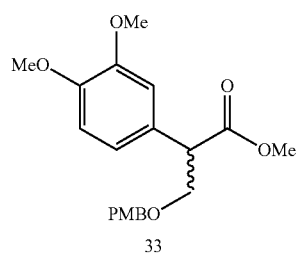

The compound 32 (500 mg, 2.38 mmol) prepared in Manufacturing Example 1 and paraformaldehyde paraformaldehyde (76 mg, 2.50 mmol) were dissolved in anhydrous DMSO (5.0 mL), which was then treated with sodium methoxide (6.8 mg, 0.12 mmol). The mixture was stirred at room temperature for 24 hours, which was poured into ice water (10 mL), followed by stirring. The mixture was neutralized with 2 N—HCl solution, which was poured into water, followed by extraction with EtOAc (×3). The organic layer was washed with saturated brine once and dried over $MgSO_4$, followed by filtering and concentrating under reduced pressure. Then, the residue was purified by silica gel resolution chromatography (EtOAc:n-hexane=1:1) to give the aldol product as a yellow solid (yield: 58%, 331 mg).

$^1$H NMR (CDCl$_3$, 300 MHz) δ6.74 (m, 3H), 4.05 (m, 1H), 3.81 (s, 3H), 3.79 (s, 3H), 3.73 (m, 2H), 3.65 (s, 3H).

p-methoxybenzyl 2,2,2-trichloroacetamidate (84 mg, 0.30 mmol) and CSA (catalytic amount) were added to anhydrous $CH_2Cl_2$ solution (1.0 mL) containing the aldol product (36 mg, 0.15 mmol) prepared above at room temperature. The reaction mixture was stirred under argon atmosphere overnight, followed by filtering. The resultant filter cake was washed with $CH_2Cl_2$. The filtrate was extracted with saturated $NaHCO_3$ solution and brine. The organic layer was dried over $MgSO_4$, filtered, and then evaporated. Then, the residue was purified by flash column chromatography (EtOAc:n-hexane=1:3) to give the compound 33 of Manufacturing Example 2 as a white solid (yield: 100%, 54 mg).

$^1$H NMR (CDCl$_3$, 500 MHz) δ7.19 (d, 2H, J=8.5 Hz), 6.84 (d, 2H, J=8.5 Hz), 6.78 (m, 3H), 4.46 (AB quartet, 2H, J=33.4, 11.7 Hz), 3.98 (m, 1H), 3.83 (s, 6H), 3.80 (m, 2H), 3.77 (s, 3H), 3.67 (s, 3H).

Manufacturing Example 3: Preparation of 2-(3,4-Dimethoxyphenyl)-3-(4-methoxybenzyloxy)propanal (34)

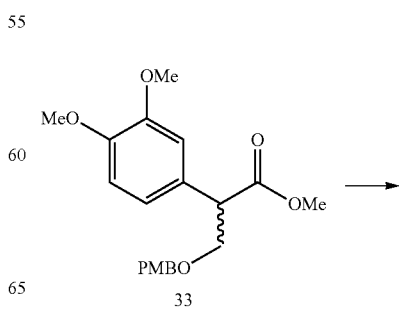

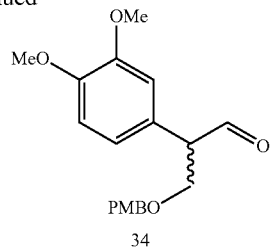

34

The compound 33 (20 mg, 0.055 mmol) prepared in Manufacturing Example 2 was dissolved in anhydrous THF (1.0 mL), which was treated with methanol (0.06 mmol, 1.1 equivalent) and then cooled down to −78° C. DIBAL-H (0.16 mL, 0.16 mmol) was slowly added thereto. While monitoring the reaction mixture with TLC, the mixture was stirred at −78° C. until the reaction was completed. Rochelle aqueous solution was carefully added thereto for 15 minutes. The mixture of the two layers was stirred strongly at 0° C. for 1 hour, which was added to water. The water layer was extracted with EtOAc (×2) and the organic layer was extracted with anhydrous NaSO$_4$, filtered and concentrated under reduced pressure. Then, the obtained residue was purified by flash column chromatography (EtOAc:n-hexane=1:4~1:1) to give the primary alcohol (yield: 88%, 16 mg).

$^1$H NMR (CDCl$_3$, 500 MHz) δ 7.21 (d, 2H, J=8.5 Hz), 6.85 (d, 2H, J=8.5 Hz), 6.77 (d, 1H, J=8.6 Hz), 6.73 (m, 2H), 4.46 (s, 2H), 3.93 (m, 1H), 3.83 (s. 6H), 3.81 (m, 1H), 3.78 (s, 3H), 3.72 (m, 2H), 3.10 (quin, 1H, J=6.5 Hz); HRMS (FAB) Calcd for C$_9$H$_{24}$O$_5$(M+H$^+$): 332.1624, Found: 332.1628.

Dess-Martin periodinane (2.0 equivalent) was added to CH$_2$Cl$_2$ (0.03 M) solution containing the primary alcohol (1.0 equivalent) obtained above, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:3) to give the compound 34 of Manufacturing Example 3 (yield: 71%, 11 mg).

$^1$H NMR (CDCl$_3$, 300 MHz) δ9.66 (d, 1H, J=1.65 Hz), 7.14 (d, 1H, J=8.4 Hz), 6.78 (m, 3H), 6.66 (m. 2H), 4.40 (d, 2H, J=3.5 Hz), 3.99 (dd, 1H, J=8.6, 6.9 Hz), 3.80 (s, 3H), 3.77 (s, 3H), 3.73 (s, 3H), 3.70 (m, 2H).

Manufacturing Example 4: Preparation of (S)-2-(3,4-Dimethoxyphenyl)-1-(5-methoxy-2,2-dimethyl-2H-chromen-6-yl)-3-(4-methoxybenzyl oxy)propan-1-one (35)

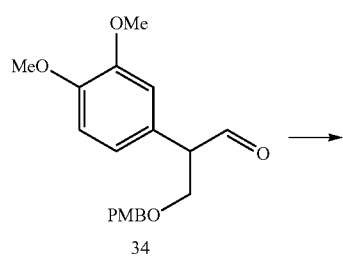

34

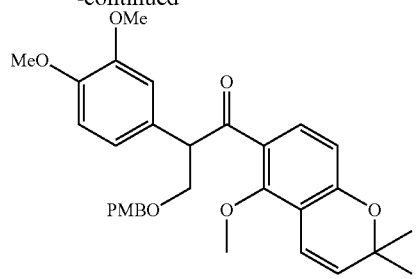

35 n-BuLi (1.4 equivalent) was added to anhydrous THF solution containing aryl bromide (1.5 equivalent) drop by drop at −78° C., which was stirred at −78° C. to generate aryl anions. The mixture was stirred at −78° C. for 20 minutes, to which aldehyde (1.0 equivalent) was added, followed by stirring for 30 minutes with raising the reaction temperature to room temperature. The reaction mixture was treated with saturated NH$_4$Cl aqueous solution, followed by extraction with EtOAc. The extract was washed with brine and then dried over MgSO$_4$. The residue obtained after evaporating the solvent was purified by flash column chromatography (EtOAc:n-hexane=1:2) to give the secondary alcohol (yield: 72%, 34 mg).

HRMS (FAB) Calcd for C$_{31}$H$_{36}$O$_7$ (M+H$^+$): 543.2359, Found: 543.2365.

Dess-Martin periodinane (3.0 equivalent) was added to CH$_2$Cl$_2$ (0.03 M) solution containing the secondary alcohol (1.0 equivalent) obtained above, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:3) to give the compound 35 of Manufacturing Example 4 (yield: 84%, 26 mg).

$^1$H NMR (CDCl$_3$, 300 MHz) δ7.34 (d, 1H, J=8.6 Hz), 7.11 (d, 2H, J=8.6 Hz), 6.73 (m, 5H), 6.50 (d, 1H, J=10.0 Hz), 6.45 (d, 1H, J=8.2 Hz), 5.57 (d, 1H, J=9.9 Hz), 4.83 (dd, 1H, J=8.9, 5.1 Hz), 4.39 (q, 2H, J=11.5 Hz), 4.12 (t, 1H, J=9.1 Hz), 3.75 (s, 6H), 3.71 (s, 3H), 3.57 (dd, 1H, J=9.1, 5.1 Hz), 3.52 (s, 3H), 1.34 (s, 6H);

HRMS (FAB) Calcd for C$_{31}$H$_{35}$O$_7$(M+H$^+$): 519.2383, Found: 519.2373.

Manufacturing Example 5: Preparation of (S)-2-(3,4-Dimethoxyphenyl)-3-hydroxy-1-(5-hydroxy-2,2-dimethyl-2H-chromen-6-yl)propan-1-one (36)

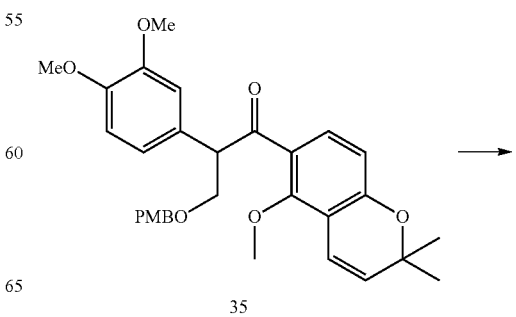

35

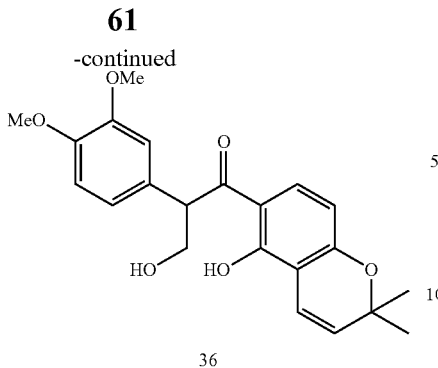

36

The compound 35 (23 mg, 0.044 mmol) prepared in Manufacturing Example 4 and CH$_2$Cl$_2$ (1.0 mL) were loaded in a 10 mL round-bottom flask, which was dried by heating. The mixture was cooled down to −78° C., to which boron trichloride (0.16 mL, 0.16 mmol, 1.0 M in CH$_2$Cl$_2$ solution) was added. After stirred for 1 hour, the reaction was terminated with saturated NH$_4$Cl aqueous solution. Then, the reaction mixture was extracted with CH$_2$Cl$_2$, dried over MgSO$_4$, and concentrated under reduced pressure. The residue was purified by flash column chromatography (EtOAc:n-hexane=1:2) to give the compound 36 of Manufacturing Example 5 as a light-yellow solid (yield: 75%, 12 mg).

$^1$H NMR (CDCl$_3$, 300 MHz) δ 7.40 (d, 1H, J=8.7 Hz), 6.76 (m, 3H), 6.53 (d, 1H, J=11.1 Hz), 6.49 (d, 1H, J=10.5 Hz), 5.63 (d, 1H, J=9.9 Hz), 4.75 (dd, 1H, J=8.7, 4.8 Hz), 3.81 (s, 3H), 3.80 (s, 3H), 3.77 (m, 2H), 1.39 (s, 3H), 1.38 (s, 3H);

HRMS (FAB) Calcd for C$_{22}$H$_{24}$O$_6$ (M$^+$): 384.1573, Found: 384.1570.

Manufacturing Example 6: Preparation of Methyl 2-(2-bromo-4,5-dimethoxyphenyl)acetate (38)

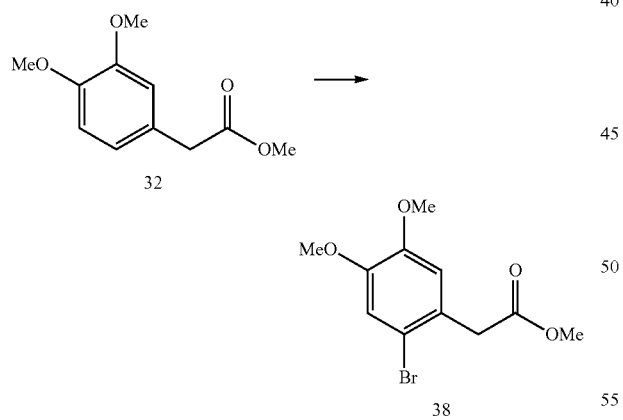

N-bromosuccinimide (449 mg, 2.50 mmol) was added to anhydrous THF (12.0 mL) solution containing the compound 32 (500 mg, 2.38 mmol) prepared in Manufacturing Example 1. The reaction mixture was stirred at −78° C. for 30 minutes. After raising the reaction temperature to room temperature, the mixture was filtered and concentrated under reduced pressure. The obtained residue was purified by flash column chromatography (EtOAc:n-hexane=1:3) to give the compound 38 of Manufacturing Example 6 as a light-yellow solid (yield: 96%, 660 mg).

$^1$H NMR (CDCl$_3$, 300 MHz) δ 6.96 (s, 1H), 6.72 (s, 1H), 3.79 (s, 6H), 3.66 (s, 2H), 3.65 (s, 3H).

Manufacturing Example 7: Preparation of Methyl 2-(2-bromo-4,5-dimethoxyphenyl)pent-4-enoate (39)

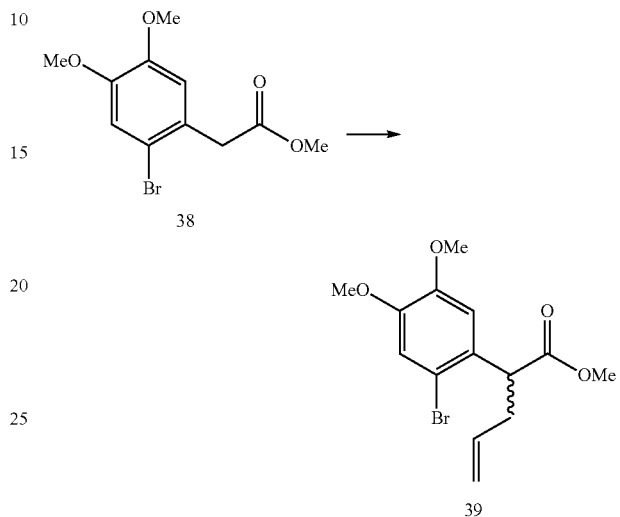

The compound 38 (150 mg, 0.52 mmol) obtained in Manufacturing Example 6 was dissolved in anhydrous THF (6.0 mL) at −78° C., to which LHMDS (0.63 mL, 0.93 mmol, 1.0 M in THF solution) was added drop by drop. After stirred for 20 minutes, the mixture was added with aryl bromide (0.044 mL, 0.52 mmol) drop by drop, followed by stirring again for 1 hour with raising the temperature to −40° C. The mixture was treated with saturated NH$_4$Cl aqueous solution (5.0 mL), to which water (5.0 mL) was added. The water layer was extracted with EtOAc (2×15 mL) and the organic layer was dried over MgSO$_4$, filtered, and concentrated under reduced pressure. The obtained residue was purified by flash column chromatography (EtOAc:n-hexane=1:8) to give the compound 39 of Manufacturing Example 7 (yield: 53%, 90 mg).

$^1$H NMR (CDCl$_3$, 300 MHz) δ 6.94 (s, 1H), 6.81 (s, 1H), 5.68 (m, 1H), 4.98 (m, 2H), 4.11 (dd, 1H, J=8.2, 7.2 Hz), 3.78 (s, 6H), 3.61 (s, 3H), 2.69 (m, 1H), 2.42 (m, 1H).

Manufacturing Example 8: Preparation of 1-(1-(Benzyloxy)pent-4-en-2-yl)-2-bromo-4,5-dimethoxybenzene (40)

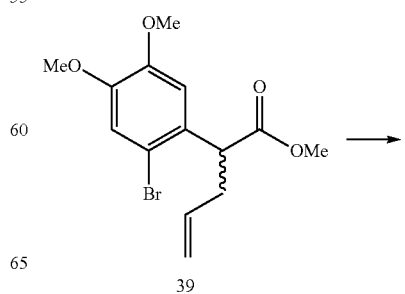

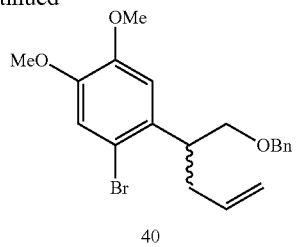

40

The compound 39 (84 mg, 0.25 mmol) prepared in Manufacturing Example 7 was dissolved in anhydrous THF (2.0 mL), and the mixture was cooled down to 0° C. Lithium aluminum hydride (10 mg, 0.25 mmol) was added thereto. The mixture was stirred at room temperature for 1 hour until the reaction was completed. Then, the reaction mixture was cooled down to 0° C. again, to which NaHCO$_3$ (saturated aqueous solution) was carefully added for 30 minutes. The mixture of two phases was stirred vigorously at 0° C. for 1 hour, to which water was added. The water layer was extracted with EtOAc (×2) and the organic layer was dried over MgSO$_4$, filtered, and concentrated under reduced pressure. The obtained residue was purified by flash column chromatography (EtOAc:n-hexane=1:6) to give the primary alcohol (yield: 88%).

$^1$H NMR (CDCl$_3$, 500 MHz) δ 7.01 (s, 1H), 6.73 (s, 1H), 5.73 (m, 1H), 5.03 (d, 1H, J=17.1 Hz), 4.97 (d, 1H, J=10.1 Hz), 3.84 (s, 3H), 3.83 (s, 3H), 3.77 (d, 2H, J=5.7 Hz), 3.41 (quin, 1H, J=7.1 Hz), 2.50 (quin, 1H, J=7.1 Hz), 2.37 (quin, 1H, J=7.1 Hz).

Sodium hydride (64 mg, 1.59 mmol, 60% in mineral oil) was added to anhydrous THF (7.0 mL) solution containing the primary alcohol (400 mg, 1.33 mmol) obtained above at 0° C., followed by stirring at room temperature for 30 minutes. Tetrabutyl ammonium bromide (23 mg, 0.066 mmol) and benzyl bromide (0.19 ml, 0.59 mmol) were added thereto, and the mixture was stirred at room temperature overnight. The mixture was treated with saturated NH$_4$Cl aqueous solution (5.0 mL), followed by extraction with EtOAc (10 mL×2). The extract was washed with brine, dried over MgSO$_4$, filtered, and concentrated under reduced pressure. The obtained residue was purified by flash column chromatography (EtOAc:n-hexane=1:8) to give the compound 40 of Manufacturing Example 8 as a colorless solid (yield: 86%, 448 mg).

$^1$H NMR (CDCl$_3$, 300 MHz) δ7.23 (m, 5H), 6.94 (s, 1H), 6.71 (s, 1H), 5.65 (m, 1H), 4.93 (m, 2H), 4.43 (s, 2H), 3.78 (s, 3H), 3.72 (s, 3H), 3.53 (m, 3H), 2.53 (m, 1H), 2.30 (m, 1H);

HRMS (FAB) Calcd for C$_{20}$H$_{23}$BrO$_3$ (M$^+$): 390.0831, Found: 390.0839.

Manufacturing Example 9: Preparation of 4-(Benzyloxy)-3-(2-bromo-4,5-dimethoxyphenyl)butan-1-ol (41)

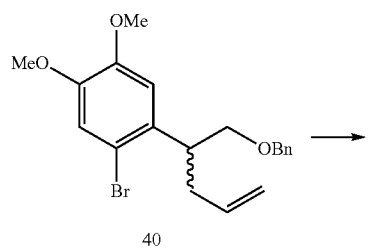

40

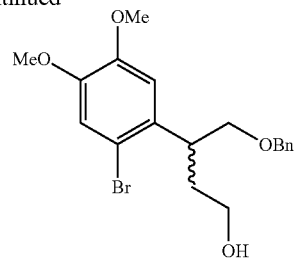

41

NMO (233 mg, 1.93 mmol) was added to the compound 40 (252 mg, 0.64 mmol) prepared in Manufacturing Example 8, which was dissolved in acetone:water (4:1, 25 mL) solution at 0° C. OsO$_4$ (0.32 mL, 0.032 mmol, 0.1 M in toluene solution) added thereto, followed by stirring at room temperature for 6 hours. The reaction mixture was extracted with EtOAc (3×15 mL). The extract was washed with saturated sodium sulfite solution and dried over MgSO$_4$. The solvent was removed under reduced pressure and the resultant non-purified product was dissolved in acetone:water (4:1, 25 mL) solution, followed by stirring at room temperature. NaIO$_4$ (413 mg, 1.93 mmol) was slowly added thereto. The mixture was stirred at room temperature for 30 minutes and then extracted with EtOAc (3×15 mL). The extract was washed with saturated sodium thiosulfate solution. The solvent was eliminated under reduced pressure and as a result, non-purified aldehyde was obtained. The non-purified aldehyde was used for the next step without being through purification process.

Sodium borohydride (49 mg, 1.29 mmol) was added to methanol (6.0 mL) containing the non-purified aldehyde (0.64 mmol) obtained above at −100° C. The temperature was maintained for 1 hour. The mixture was cooled down with saturated NH$_4$Cl aqueous solution, followed by extraction with EtOAc. The extract was dried over MgSO$_4$ and concentrated under reduced pressure. The obtained residue was purified by flash column chromatography (EtOAc:n-hexane=1:1) to give the compound 41 of Manufacturing Example 9 as a colorless solid (yield: 73%, 184 mg).

$^1$H NMR (CDCl$_3$, 300 MHz) δ 7.23 (m, 5H), 6.94 (s, 1H), 6.69 (s, 1H), 4.47 (s, 2H), 3.78 (s, 3H), 3.73 (s, 3H), 3.54 (m, 4H), 2.01 (m, 2H), 1.81 (m, 1H);

HRMS (FAB) Calcd for C$_9$H$_{23}$BrO$_4$ (M$^+$): 394.0780, Found: 394.0774.

Manufacturing Example 10: Preparation of 4-(Benzyloxymethyl)-6,7-dimethoxychroman (42)

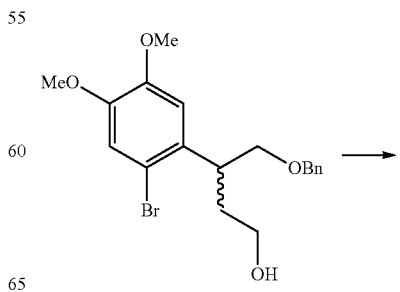

41

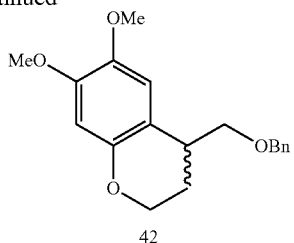

The compound 41 (379 mg, 0.96 mmol) obtained in Manufacturing Example 9 and sodium t-butoxide (124 mg, 1.25 mmol) were loaded in the heat dried 2-neck round-bottom flask containing toluene (10 mL) containing Pd$_2$(dba)$_3$ (13 mg, 0.0143 mmol) and 2-(di-t-butylphosphino)biphenyl (7.0 mg, 0.024 mmol) under argon atmosphere. For the reaction, the flask was heated at 50~55° C. overnight and then the temperature was cooled down to room temperature. The mixture was diluted with EtOAc (10 mL) and filtered using celite. The solvent was eliminated under reduced pressure and the obtained dark-yellow non-purified product was purified by flash column chromatography (EtOAc:n-hexane=1:6) to give the compound 42 of Manufacturing Example 10 as a light-yellow solid (yield: 75%, 226 mg).

$^1$H NMR (CDCl$_3$, 300 MHz) δ 7.24 (m, 5H), 6.61 (s, 1H), 6.30 (s, 1H), 4.48 (q, 2H, J=11.9 Hz), 4.03 (m, 2H), 3.73 (s, 3H), 3.70 (s, 3H), 3.61 (m, 1H), 3.49 (m, 1H), 2.98 (m, 1H), 1.95 (m, 2H);

HRMS (FAB) Calcd for C$_9$H$_{22}$O$_4$ (M$^+$): 314.1518, Found: 314.1518.

Manufacturing Example 11: Preparation of 6,7-Dimethoxychroman-4-carbaldehyde (43)

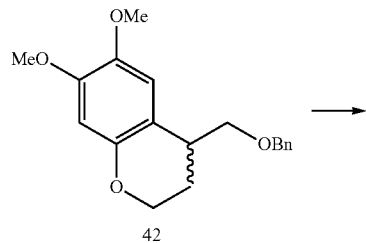

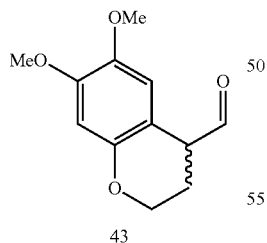

The methanol mixture (5 mL) containing the compound 42 (191 mg, 0.61 mmol) obtained in Manufacturing Example 10 and 20% Pd(OH)$_2$/C (38 mg) was stirred at room temperature for 5 hours under hydrogen atmosphere. The mixture was filtered using celite, and the filtrate was washed with methanol (10 mL). The methanol was evaporated and the obtained residue was purified by flash column chromatography (EtOAc:n-hexane=1:1) to give the primary alcohol (yield: 100%, 158 mg).

$^1$H NMR (CDCl$_3$, 300 MHz) δ6.61 (s, 1H), 6.33 (s, 1H), 4.08 (m, 2H), 3.78 (m, 2H), 3.74 (s, 6H), 2.85 (m, 1H), 1.98 (m, 2H); LRMS (FAB) m/z 225 (M+H$^+$).

Dess-Martin periodinane (3.0 equivalent) was added to CH$_2$Cl$_2$ (0.03 M) solution containing the primary alcohol (1.0 equivalent) obtained above, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:2) to give the compound 43 of Manufacturing Example 11 (yield: 60%, 15 mg).

$^1$H NMR (CDCl$_3$, 300 MHz) δ9.67 (d, 1H, J=1.8 Hz), 6.58 (s, 1H), 6.42 (s, 1H), 4.13 (m, 3H), 3.81 (s, 6H), 2.32 (m, 1H), 2.06 (m, 1H).

Manufacturing Example 12: Preparation of (6,7-Dimethoxychroman-4-yl) (2,2-dimethyl-2H-chromen-6-yl)methanol (44)

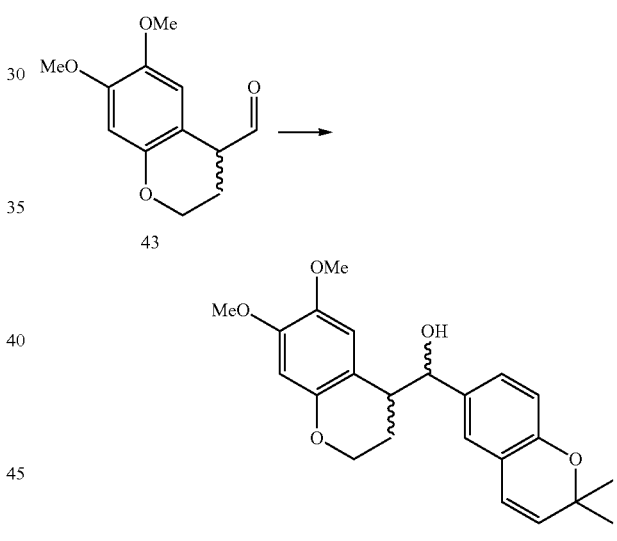

n-BuLi (1.4 equivalent) was added to anhydrous THF solution containing 6-bromo-2,2-dimethyl-2H-chromene (1.5 equivalent) drop by drop at −78° C., which was stirred at −78° C. to generate aryl anions. After stirred at −78° C. for 20 minutes, the mixture was added with the compound 43 (1.0 equivalent) obtained in Manufacturing Example 11. The mixture was stirred again for 30 more minutes to increase the reaction temperature to room temperature. The reaction mixture was treated with saturated NH$_4$Cl aqueous solution, followed by extraction with EtOAc. The extract was washed with brine and then dried over MgSO$_4$. The residue obtained after evaporating the solvent was purified by flash column chromatography (EtOAc:n-hexane=1:4) to give the compound 44 of Manufacturing Example 12 (yield: 75%, 18 mg).

HRMS (FAB) Calcd for C$_{23}$H$_{26}$O$_5$ (M+H$^+$): 382.1780, Found: 382.1793.

Manufacturing Example 13: Preparation of 2-(3,4-Dimethoxyphenyl) acetaldehyde (52)

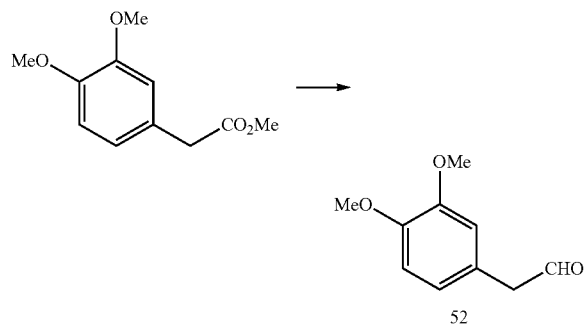

Anhydrous diethyl ether solution containing methyl 3',4'-dimethoxyphenyl acetate (1.94 g, 9.24 mmol) was stirred, during which DIBAL-H (11.1 mL, 1 M in THF solution) was added thereto drop by drop with maintaining the temperature at −78° C. The mixture was stirred at the same temperature for 1 hour. Rochelle aqueous solution was carefully added thereto for 15 minutes. The mixture of the two phases was stirred vigorously at 0° C. for 1 hour, which was added to water. The water layer was extracted with EtOAc (×2) and the organic layer was dried over MgSO$_4$, filtered and concentrated under reduced pressure. Then, the obtained residue was purified by flash column chromatography (EtOAc:n-hexane=1:2) to give the compound 52 of Manufacturing Example 13 (yield: 68%, 1.13 g).

$^1$H NMR (CDCl$_3$, 300 MHz) δ 9.66 (t, 1H, J=2.5 Hz), 6.80 (d, 1H, J=8.0 Hz), 6.68 (m, 1H), 6.64 (d, 1H, J=1.8 Hz), 3.81 (s. 6H), 3.56 (d, 2H, J=2.5 Hz).

Manufacturing Example 14: Preparation of 2-(3,4-Dimethoxyphenyl)propanal (55)

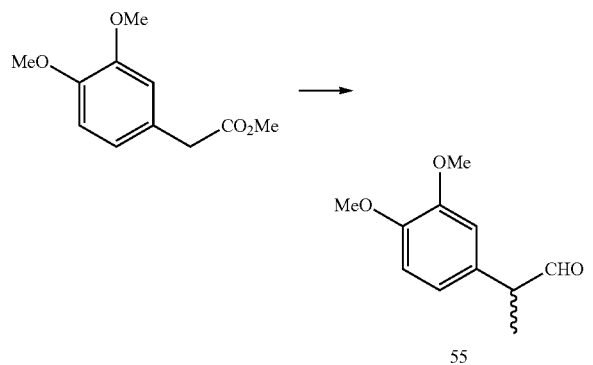

LDA (18.1 mL, 36.21 mmol, 2 M in THF solution) was added drop by drop to anhydrous THF solution (5 mL) containing methyl 3',4'-dimethoxyphenyl acetate (4.76 g, 22.63 mmol) under argon atmosphere at −78° C., followed by stirring for 30 minutes. Then, methyl iodide (2.82 mL, 45.26 mmol) was added thereto, followed by stirring for 1 hour. 2 N—HCl aqueous solution was added to the above reaction mixture, leading to acidization, and then the mixture was extracted with EtOAc. The organic layer was washed with brine, dried over MgSO$_4$, and concentrated under reduced pressure. The obtained residue was purified by silica gel column chromatography (EtOAc:n-hexane=1:4) to give 2-(3,4-dimethoxyphenyl)propanoate as a colorless oil (yield: 79%, 4.01 g).

$^1$H NMR (CDCl$_3$, 500 MHz) δ 6.80 (m, 3H), 3.85 (s, 3H), 3.83 (s, 3H), 3.64 (q, 1H, J=7.1 Hz), 3.63 (s, 3H), 1.46 (d, 3H, J=7.1 Hz);

$^{13}$C NMR (CDCl$_3$, 125 MHz) δ 175.7, 148.9, 148.1, 133.0, 119.5, 111.2, 110.6, 55.8, 55.8, 51.9, 44.9, 18.6.

Anhydrous THF solution containing the 2-(3,4-dimethoxyphenyl)propanoate obtained above was stirred, during which DIBAL-H (16.0 mL, 1 M in THF solution) was added drop by drop with maintaining the temperature at −78° C. The mixture was stirred again for 1 hour at the same temperature. Rochelle aqueous solution was carefully added thereto for 15 minutes. The mixture of the two phases was stirred vigorously at 0° C. for 1 hour, which was added to water. The water layer was extracted with EtOAc (×2) and the organic layer was dried over MgSO$_4$, filtered and concentrated under reduced pressure. Then, the obtained residue was purified by flash column chromatography (EtOAc:n-hexane=1:2) to give the compound 55 of Manufacturing Example 14 (yield: 61%, 1.58 g).

$^1$H NMR (CDCl$_3$, 300 MHz) δ 9.63 (d, 1H, J=1.5 Hz), 6.86 (d, 1H, J=8.2 Hz), 6.74 (m, 1H), 6.66 (d, 1H, J=2.0 Hz), 3.85 (s. 6H), 3.56 (q, 1H, J=6.9 Hz), 1.40 (d, 3H, J=6.9 Hz).

Manufacturing Example 15: Preparation of 2-(3,4-Dimethoxyphenyl)propanoic Acid (64)

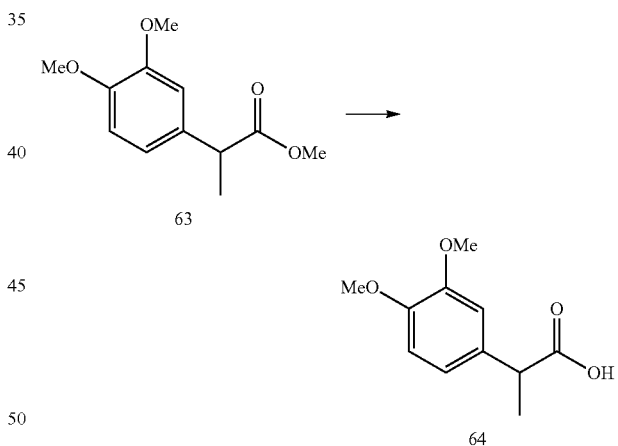

Monohydrate (230 mg, 5.35 mmol) was added to THF/water solution (2/1, 9.0 mL) containing the compound 63 (400 mg, 1.78 mmol) at room temperature, followed by stirring for 5 hours. Upon completion of the reaction, the reaction mixture was extracted with EtOAc (×2). The organic layer was alkalization with 2 N—NaOH aqueous solution, and the water layer was acidization with 2 N—HCl aqueous solution. The water layer was extracted with EtOAc (×2) and the organic layer was washed with brine, dried over MgSO$_4$, filtered and concentrated under reduced pressure. The obtained product was used in Manufacturing Examples 16 and 17.

$^1$H NMR (CDCl$_3$, 300 MHz) δ 6.83 (m, 3H), 3.85 (s, 3H), 3.84 (s, 3H), 3.66 (q, 1H, J=7.3 Hz), 1.48 (d, 3H, J=7.3 Hz).

Manufacturing Example 16~17: Preparation of (S)-2-(3,4-Dimethoxyphenyl)-N—((R)-2-hydroxy-1-phenylethyl) propanamide (65) and (R)-2-(3,4-Dimethoxyphenyl)-N—((R)-2-hydroxy-1-phenylethyl) propanamide (66)

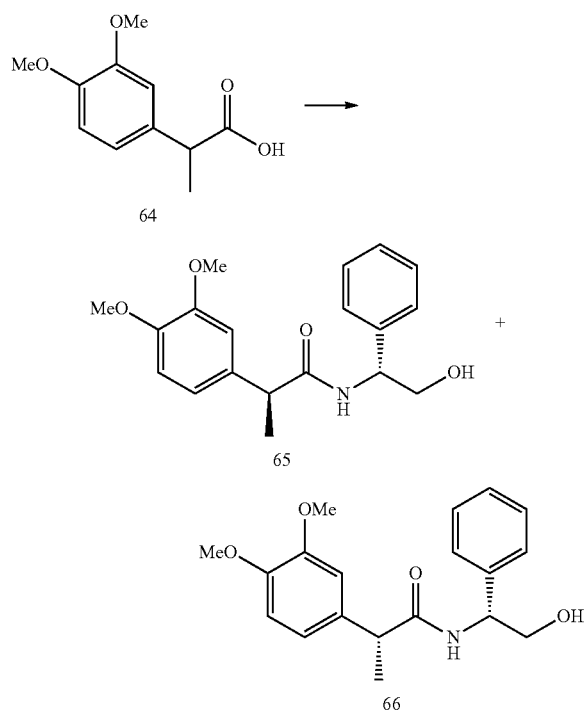

N-(3-dimethylaminopropyl)-N'-ethylcarbodiimide hydrochloride (EDCI) (287 mg, 1.47 mmol), (R)-(−)-2-phenylglycinol (207 mg, 1.47 mmol) and HOBt (230 mg, 1.47 mmol) were added to CH$_2$Cl$_2$ solution (10 mL) containing the compound 64 (282 mg, 1.34 mmol) prepared in Manufacturing Example 15. Finally, diisopropylethylamine (0.26 mL, 1.47 mmol) was added thereto drop by drop at 0° C. The reaction mixture was stirred at room temperature overnight. The reaction was terminated with saturated NH$_4$Cl aqueous solution and the mixture was diluted with CH$_2$Cl$_2$. The organic layer was washed with water, dried over MgSO$_4$, filtered, and concentrated under reduced pressure. Then, the obtained residue was purified by flash column chromatography (EtOAc:CH$_2$Cl$_2$:n-hexane=3:2:1) to give the compound 65 (yield: 42%, 187 mg) of Manufacturing Example 16 and the compound 66 (yield: 42%, 186 mg) of Manufacturing Example 17 as light-yellow solids. and (yield: 61%, 1.58 g).

(S)-Diastereomer (65): $^1$H NMR (CDCl$_3$, 300 MHz) δ 7.26 (m, 3H), 7.03 (m, 2H), 6.81 (m, 2H), 6.73 (s, 1H), 6.05 (m, 1H), 5.02 (m, 1H), 3.86 (s, 3H), 3.80 (m, 2H), 3.78 (s, 3H), 3.58 (q, 1H, J=7.1 Hz) 1.48 (d, 3H, J=7.1 Hz);

(R)-Diastereomer (66): $^1$H-NMR (CDCl$_3$, 300 MHz) δ 7.23 (m, 3H), 7.10 (m, 2H), 6.78 (m, 3H), 5.97 (m, 1H), 4.96 (m, 1H), 3.82 (s, 3H), 3.80 (s, 3H), 3.72 (d, 2H, J=5.0 Hz), 3.50 (q, 1H, J=7.1 Hz) 1.46 (d, 3H, J=7.1 Hz).

Manufacturing Example 18: Preparation of (S)-2-(3,4-Dimethoxyphenyl) propanoic Acid (67)

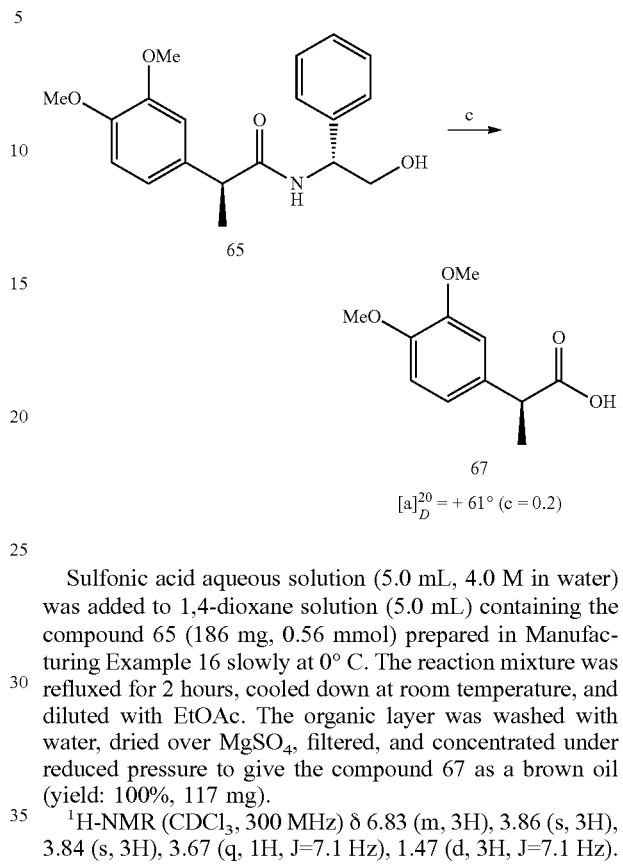

$[\alpha]_D^{20} = +61°$ (c = 0.2)

Sulfonic acid aqueous solution (5.0 mL, 4.0 M in water) was added to 1,4-dioxane solution (5.0 mL) containing the compound 65 (186 mg, 0.56 mmol) prepared in Manufacturing Example 16 slowly at 0° C. The reaction mixture was refluxed for 2 hours, cooled down at room temperature, and diluted with EtOAc. The organic layer was washed with water, dried over MgSO$_4$, filtered, and concentrated under reduced pressure to give the compound 67 as a brown oil (yield: 100%, 117 mg).

$^1$H-NMR (CDCl$_3$, 300 MHz) δ 6.83 (m, 3H), 3.86 (s, 3H), 3.84 (s, 3H), 3.67 (q, 1H, J=7.1 Hz), 1.47 (d, 3H, J=7.1 Hz).

Manufacturing Example 19: Preparation of (S)-2-(3,4-Dimethoxyphenyl) propanal (68)

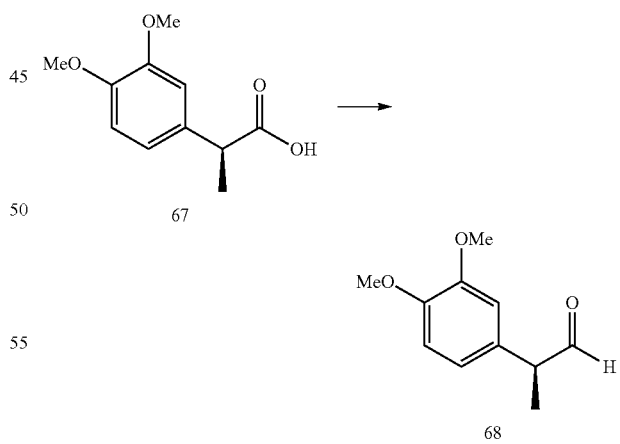

Anhydrous diethyl ether solution (8.0 mL) containing the compound 67 (115 mg, 0.55 mmol) prepared in Manufacturing Example 17 was cooled down at 0° C., to which BH$_3$.SMe$_2$ complex (1.5 mL, 3.00 mmol) was added drop by drop. The mixture was stirred for 1 hour at 0° C., and then stirred again for 3 more hours at room temperature. The reaction was terminated by adding water drop by drop at 0°

C. When hydrogen gas bubbles were no more observed, 2 N—NaOH aqueous solution was added thereto drop by drop. The water layer was extracted with ether (×2) and the ether layer was washed with brine, dried over MgSO$_4$, filtered, and concentrated under reduced pressure. Then, the obtained residue was purified by flash column chromatography (EtOAc:n-hexane=1:2) to give the primary alcohol as a light-yellow solid (yield: 85%, 104 mg).

$^1$H-NMR (CDCl$_3$, 500 MHz) δ 6.78 (m, 3H), 3.87 (s, 3H), 3.85 (s, 3H), 3.66 (m, 2H), 2.88 (sex, 1H, J=6.9 Hz), 1.24 (d, 3H, J=6.9 Hz).

Dess-Martin periodinane (3.0 equivalent) was added to CH$_2$Cl$_2$ (0.03 M) solution containing the primary alcohol (1.0 equivalent) obtained above, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:3) to give the compound 68 of Manufacturing Example 19 (yield: 81%, 21 mg).

$^1$H-NMR (CDCl$_3$, 300 MHz) 59.63 (d, 1H, J=1.5 Hz), 6.86 (d, 1H, J=8.2 Hz), 6.74 (dd, 1H, J=8.2, 2.0 Hz), 6.66 (d, 1H, J=2.0 Hz), 3.86 (s, 6H), 3.55 (q, 1H, J=7.1 Hz), 1.40 (d, 3H, J=7.1 Hz).

Manufacturing Example 20: Preparation of (R)-2-(3,4-Dimethoxyphenyl) propanoic Acid (70)

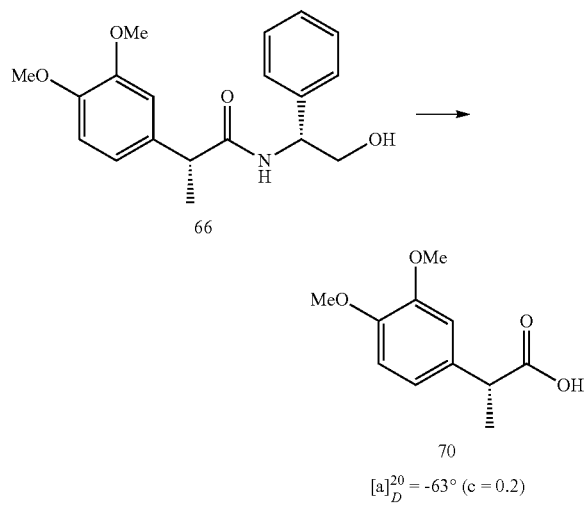

Sulfonic acid aqueous solution (5.6 mL, 4.0 M in water) was added to 1,4-dioxane solution (5.6 mL) containing the compound 66 (217 mg, 0.66 mmol) prepared in Manufacturing Example 17 slowly at 0° C. The reaction mixture was refluxed for 2 hours, cooled down at room temperature, and diluted with EtOAc. The organic layer was washed with water, dried over MgSO$_4$, filtered, and concentrated under reduced pressure to give the compound 70 as a brown oil (yield: 100%, 138 mg).

$^1$H-NMR (CDCl$_3$, 300 MHz) δ 6.83 (m, 3H), 3.86 (s, 3H), 3.84 (s, 3H), 3.67 (q, 1H, J=7.1 Hz), 1.47 (d, 3H, J=7.1 Hz).

Manufacturing Example 21: Preparation of (R)-2-(3,4-Dimethoxyphenyl) propanal (71)

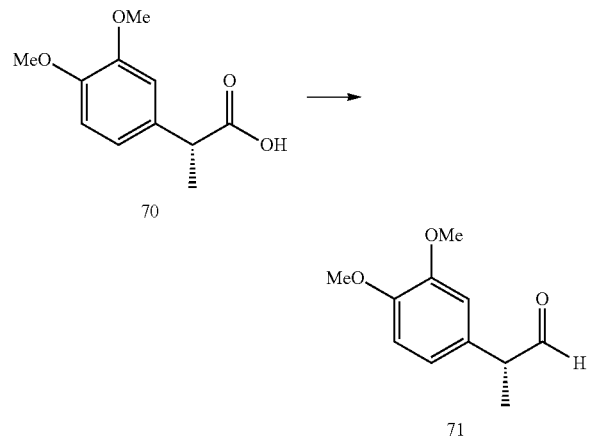

Anhydrous diethyl ether solution (10.0 mL) containing the compound 70 (115 mg, 0.55 mmol) prepared in Manufacturing Example 20 was cooled down at 0° C., to which BH$_3$.SMe$_2$ complex (1.8 mL, 3.61 mmol) was added drop by drop. The mixture was stirred for 1 hour at 0° C., and then stirred again for 3 more hours at room temperature. The reaction was terminated by adding water drop by drop at 0° C. When hydrogen gas bubbles were no more observed, 2 N—NaOH aqueous solution was added thereto drop by drop. The water layer was extracted with ether (×2) and the ether layer was washed with brine, dried over MgSO$_4$, filtered, and concentrated under reduced pressure. Then, the obtained residue was purified by flash column chromatography (EtOAc:n-hexane=1:2) to give the primary alcohol as a light-yellow solid (yield: 81%, 104 mg).

$^1$H-NMR (CDCl$_3$, 500 MHz) δ 6.78 (m, 3H), 3.87 (s, 3H), 3.85 (s, 3H), 3.66 (m, 2H), 2.88 (sex, 1H, J=6.9 Hz), 1.24 (d, 3H, J=6.9 Hz).

Dess-Martin periodinane (3.0 equivalent) was added to CH$_2$Cl$_2$ (0.03 M) solution containing the primary alcohol (1.0 equivalent) obtained above, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:3) to give the compound 71 of Manufacturing Example 21 (yield: 79%, 16 mg).

$^1$H-NMR (CDCl$_3$, 300 MHz) δ 9.63 (d, 1H, J=1.5 Hz), 6.86 (d, 1H, J=8.2 Hz), 6.74 (dd, 1H, J=8.2, 2.0 Hz), 6.66 (d, 1H, J=2.0 Hz), 3.86 (s, 6H), 3.55 (q, 1H, J=7.1 Hz), 1.40 (d, 3H, J=7.1 Hz).

Manufacturing Example 22: Preparation of 4-Nitrobenzene-1,3-diol (46)

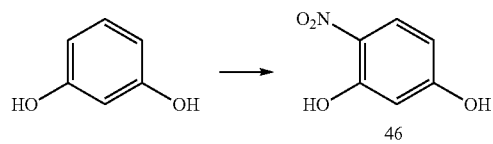 [SMILES: Oc1cccc(O)c1 ; O=[N+]([O-])c1ccc(O)cc1O]

Resorcinol (5.0 g, 44.96 mmol) was dissolved in chloroform:acetic acid (2:1, 270 mL) mixed solution, to which acetic acid solution (70 mL) containing nitric acid (3.6 mL) was slowly added, followed by stirring for 1 hour. The reaction was terminated by adding water (100 mL), followed by extraction with $CH_2Cl_2$ (100 mL×3) and drying over $MgSO_4$. The residue obtained after filtering under reduced pressure was purified by flash column chromatography (EtOAc:n-hexane=1:4  EtOAc:n-hexane:$CH_2Cl_2$=1:4:2) to give the compound 46 as a yellow solid (yield: 52%, 3.6 g).

$^1$H NMR ($CD_3OD$, 300 MHz) δ 7.99 (d, 1H, J=9.1 Hz), 6.43 (m, 2H).

Manufacturing Example 23: Preparation of 5-(2-Methylbut-3-yn-2-yloxy)-2-nitrophenol (47)

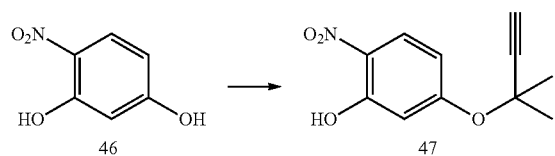 [SMILES: O=[N+]([O-])c1ccc(O)cc1O ; C#CC(C)(C)Oc1ccc([N+](=O)[O-])c(O)c1]

DBU (0.63 mL, 4.19 mmol) was added to acetonitrile solution (18 mL) containing 2-methyl-3-butin-2-ol (0.36 mL, 3.70 mmol) at 0° C., to which trifluoroacetanhydride (0.58 mL, 4.19 mmol) was added drop by drop for 30 minutes. The obtained yellow solution was stirred at 0° C. for 40 minutes. Acetonitrile solution (18 mL) containing the compound 46 (500 mg, 3.22 mmol) prepared in Manufacturing Example 22 in another flak was treated with DBU (0.63 mL, 4.19 mmol) at 0° C., to which $CuCl_2$ (8.65 mg, 0.064 mmol) was added. The yellow solution prepared above (2-methyl-3-butin-2-yl trifluoroacetate) was added to this mixture drop by drop for 40 minutes at 0° C. The reaction mixture was stirred at 0° C. overnight. The resultant residue obtained by concentration under reduced pressure was poured in water. The water layer was extracted with ethyl acetate and the organic layer was washed with 1 N—HCl, 1 N—KOH, and brine stepwise. The organic layer was then dried over $MgSO_4$ and concentrated under reduced pressure to give the compound 47 (Yield: 45%, 320 mg).

$^1$H NMR ($CDCl_3$, 300 MHz) δ 7.90 (d, 1H, J=9.4 Hz), 6.70 (d, 1H, J=10.0 Hz), 6.38 (d, 1H, J=9.4 Hz), 5.63 (d, 1H, J=10.0 Hz), 1.45 (s, 6H);

HRMS (FAB) Calcd for $C_{11}H_{12}NO_4$ (M+H$^+$): 206.1181, Found: 206.1186.

Manufacturing Example 24: Preparation of 2,2-Dimethyl-6-nitro-2H-chromen-5-ol (48)

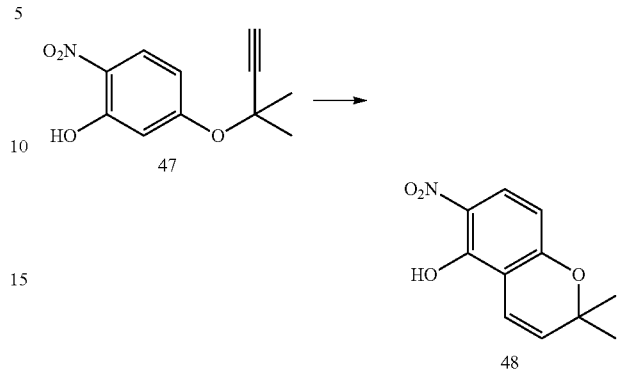

While monitoring N,N-diethylaniline solution (28 mL) containing O-alkylated phenol (310 mg, 1.40 mmol) with TLC, the solution was heated at 130° C. until the reaction was completed under nitrogen atmosphere. The reaction mixture was poured in ice water, followed by extraction with EtOAc. The organic layer was washed with 2 N—HCl aqueous solution, N-sodium hydroxide aqueous solution, and water stepwise, dried over $MgSO_4$, and concentrated under reduced pressure. Then, the obtained residue was purified by flash column chromatography (EtOAc:n-hexane=1:15) to give the compound of Manufacturing Example 24 as a light-yellow solid (yield: 91%, 281 mg).

$^1$H NMR ($CDCl_3$, 300 MHz) δ 7.90 (d, 1H, J=9.4 Hz), 6.70 (d, 1H, J=10.0 Hz), 6.38 (d, 1H, J=9.4 Hz), 5.63 (d, 1H, J=10.0 Hz), 1.45 (s, 6H);

HRMS (FAB) Calcd for $C_{12}H_{22}NO_4$ (M+H$^+$): 206.1181, Found: 206.1186.

Manufacturing Example 25: Preparation of 5-Methoxy-2,2-dimethyl-6-nitro-2H-chromene (49)

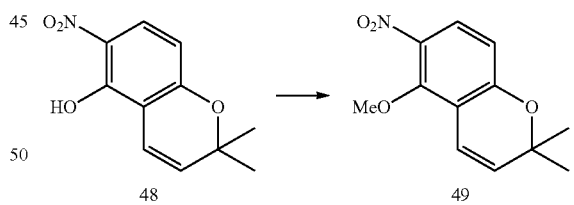

Anhydrous acetone (7.0 mL) containing the compound 48 (130 mg, 0.59 mmol) obtained in Manufacturing Example 24, potassium carbonate (244 mg, 1.76 mmol) and iodomethane (0.11 mL, 1.76) was heated at 55° C. overnight. The mixture was concentrated and then treated with water, followed by extraction with EtOAc (×3). The extract was washed with water, dried over $MgSO_4$, and concentrated under reduced pressure to give the compound 49.

$^1$H NMR ($CDCl_3$, 300 MHz) δ 7.77 (d, 1H, J=8.9 Hz), 6.59 (m, 2H), 5.72 (d, 1H, J=10.0 Hz), 3.89 (s, 3H), 1.44 (s, 6H);

HRMS (FAB) Calcd for $C_{12}H_{24}NO_4$ (M+H$^+$): 236.0923, Found: 236.0924.

Manufacturing Example 26: Preparation of 5-Methoxy-2,2-dimethyl-2H-chromen-6-amine (50)

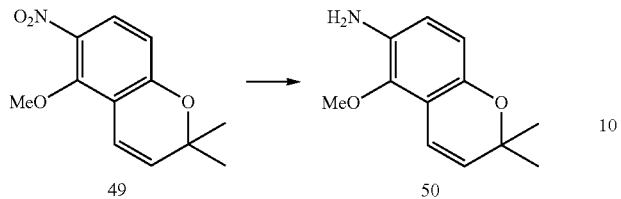

Boiling ethanol (2.0 mL) containing the compound 49 (136 mg, 0.663 mmol) prepared in Manufacturing Example 25 and tin (II) chloride dihydrate (740 mg, 3.21 mmol) was stirred for 1 hour under nitrogen atmosphere. Ethanol was eliminated by vacuum evaporation and the residue was extracted with ethyl acetate (×3). The organic layer was treated with 2 N—NaOH solution (10 mL) and then treated with water (2×10 mL). The organic layer was washed with brine, dried over $MgSO_4$, and concentrated under reduced pressure. Then, the obtained residue was purified by flash column chromatography (EtOAc:n-hexane=1:15) to give the compound 50 of Manufacturing Example 26 as a yellow solid (yield: 79%, 100 mg).

$^1$H NMR ($CDCl_3$, 300 MHz) δ 6.54 (m, 2H), 6.43 (d, 1H, J=8.4 Hz), 5.63 (d, 1H, J=9.9 Hz), 3.78 (s, 3H), 3.46 (br, 2H), 1.37 (s, 6H);
HRMS (FAB) Calcd for $C_{22}H_{25}NO_2$ ($M^+$): 205.1103, Found: 205.1104.

Manufacturing Example 27: Preparation of 6-Bromo-5-methoxy-2,2-dimethyl-2H-chromene (51)

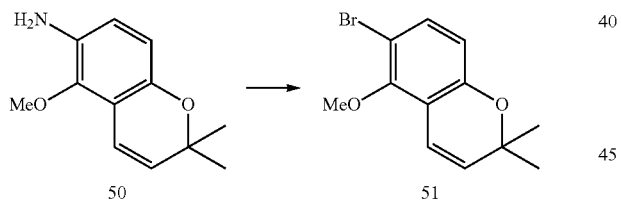

Water (5.0 mL) containing the compound 50 (260 mg, 1.27 mmol) obtained in Manufacturing Example 26 was cooled down to 0° C., to which HBr (1.6 mL, 48% in water) was slowly added. The reaction mixture was stirred vigorously for 10 minutes at 0° C. The slurry containing $NaNO_2$ and HBr was slowly added to water (1.0 mL) containing sodium nitrite. The temperature of the reaction mixture was maintained under 5° C. Water (5.0 mL) containing Cu(I)Br (190 mg, 1.30 mmol) was loaded in a separatory funnel, which was then heated at 60° C. Aniline solution was added thereto drop by drop, during which the temperature was maintained at 60° C. Upon completion of the reaction, the reaction mixture was cooled down to room temperature, followed by extraction with EtOAc (×2). The organic layer was washed with brine, dried over $MgSO_4$, and concentrated under reduced pressure. Then, the obtained residue was purified by flash column chromatography (EtOAc:n-hexane=1:12) to give the compound of Manufacturing Example 27 as a light-yellow oil (yield: 90%, 365 mg).

$^1$H NMR ($CDCl_3$, 500 MHz) δ 7.16 (d, 1H, J=8.6 Hz), 6.52 (d, 1H, J=10.0 Hz), 6.42 (d, 1H, J=8.6 Hz), 5.59 (d, 1H, J=10.0 Hz), 3.74 (s, 3H), 1.35 (s, 6H);
$^{13}$C NMR ($CDCl_3$, 125 MHz) δ153.3, 152.7, 132.1, 131.2, 116.9, 116.6, 113.9, 107.3, 76.1, 61.5, 30.9, 27.7.

Manufacturing Example 28: Preparation of 1,2-Dimethoxy-4-(phenylsulfonylmethyl)benzene (105)

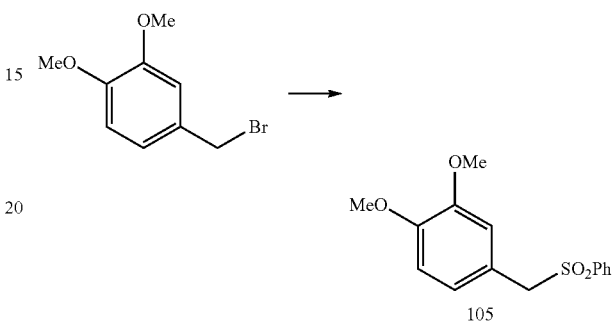

4-(bromoethyl)-1,2-dimethoxybenzene (100 mg, 0.43 mmol) and benzenesulfonic acid sodium salt dihydrate (87 mg, 0.52 mmol) were added to anhydrous DMF solution (1.5 mL). The mixture was stirred at 80° C. for 12 hours and then cooled down at room temperature. Upon completion of the conventional synthesis using water and EtOAc, the solvent was evaporated. Then, the obtained residue was purified by flash column chromatography (EtOAc:n-hexane:$CH_2Cl_2$=1:1:1) to give the compound 105 of Manufacturing Example 28 as a colorless oil (yield: 93%, 118 mg).

$^1$H NMR ($CDCl_3$, 300 MHz) δ7.56 (m, 3H), 7.39 (m, 1H), 6.67 (d, 1H, J=8.2 Hz), 6.55 (dd, 2H, J=8.1, 2.0 Hz), 6.47 (d, 1H, J=2.0 Hz), 4.18 (s, 2H), 3.79 (s, 3H), 3.65 (s, 3H).

Manufacturing Example 29: Preparation of 5-Hydroxy-2,2-dimethyl-2H-chromene-6-carbaldehyde (110)

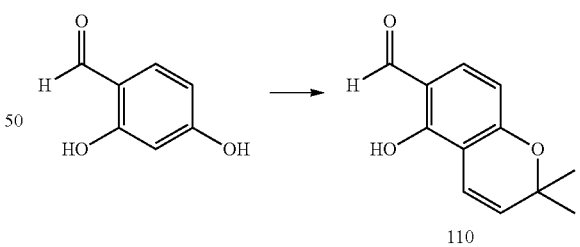

Pyridine (0.01 M) solution containing 3-methyl-but-2-enyl (2.0 equivalent) was added to anhydrous acetone solution (0.01 M) containing 2,4-dihydroxyaldehyde (1 equivalent) drop by droop at 120° C. for 5.5 hours, followed by heating for 18 hours. After cooling down at room temperature, the solvent was eliminated under reduced pressure using a rotary evaporator. Pyridine was eliminated by azeotropic distillation along with toluene. The obtained non-purified product was purified by flash column chromatography (EtOAc:n-hexane=1:8) to give the compound 119 as a colorless solid (yield: 32%, 1.12 g).

¹H-NMR (CDCl₃, 300 MHz) δ11.61 (s, 1H), 9.62 (s, 1H), 7.25 (d, 1H, J=8.6 Hz), 6.39 (d, 1H, J=8.6 Hz), 5.58 (d, 1H, J=10.0 Hz), 1.42 (s, 6H).

Manufacturing Example 30: Preparation of 5-(Methoxymethoxy)-2,2-dimethyl-2H-chromene-6-carbaldehyde (108)

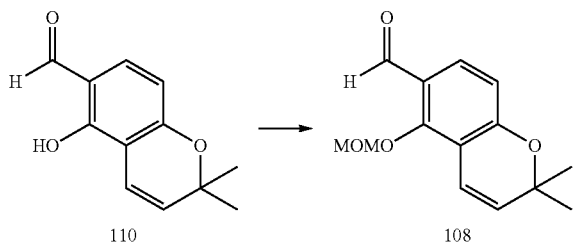

Chloromethylmethyl ether (0.11 mL, 1.47 mmol) was added to acetone solution (5 mL) containing the compound 110 (200 mg, 0.98 mmol) obtained in Manufacturing Example and potassium carbonate (406 mg, 2.94 mmol) at room temperature. The mixture was refluxed for 3 hours, followed by concentration under reduced pressure. The resultant non-purified residue was extracted with EtOAc and the organic layer was washed with brine. The extract was dried over anhydrous MgSO₄ and concentrated under reduced pressure. The obtained non-purified residue was purified by flash column chromatography (EtOAc:n-hexane=1:10) to give the compound 108 of Manufacturing Example 30 as a light-yellow solid (yield: 100%, 231 mg).

¹H NMR (CDCl₃, 300 MHz) δ 10.07 (s, 1H), 7.59 (d, J=8.6 Hz, 1H), 6.61 (d, J=8.6 Hz, 1H), 6.53 (d, J=10.0 Hz, 1H), 5.63 (d, J=10.0 Hz, 1H), 5.02 (s, 2H), 3.52 (s, 3H).

Manufacturing Example 31: Preparation of 2-(3,4-Dimethoxyphenyl)-1-(5-hydroxy-2,2-dimethyl-2H-chromen-6-yl)-2-(phenylsulfonyl)ethanone (106)

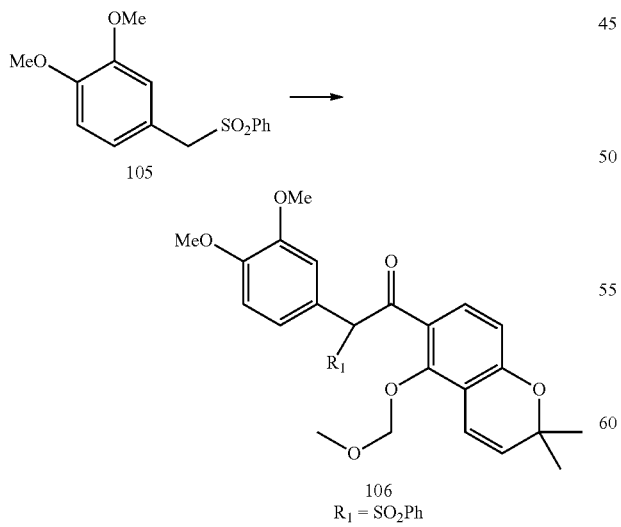

n-BuLi (0.26 mL, 0.444 mmol, 1.6 M in hexane) was added to anhydrous THF solution (5.0 mL) containing the compound 105 (119 mg, 0.407 mmol) prepared in Manufacturing Example 28 at −78° C., which was stirred at the same temperature for 1 hour. Anhydrous THF (3.0 mL) containing the compound 108 (121 mg, 0.448 mmol) obtained in Manufacturing Example 30 was added slowly to the above reaction mixture at −78° C. One hour later, water was added to the reaction mixture to terminate the reaction, followed by extraction with EtOAc (×3). The extract was washed with brine, dried over anhydrous MgSO₄, and concentrated under reduced pressure. The obtained intermediate residue (secondary alcohol) was used for the next step without being through purification process.

Dess-Martin periodinane (286 mg, 0.660 mmol) was added to anhydrous CH₂Cl₂ (5.0 mL) solution containing the secondary alcohol (183 mg, 0.339 mmol) obtained above, followed by stirring for 1 hour. The reaction mixture was treated with saturated sodium carbonate solution:saturated sodium thiosulfate solution (1:1, 4 mL), followed by stirring for 30 minutes. The reaction mixture was poured in water, followed by extraction with CH₂Cl₂ (×3). The organic layer was dried over MgSO₄, filtered and concentrated under reduced pressure. Then, the obtained residue was purified by flash column chromatography (EtOAc:n-hexane=1:2) to give the compound 106 of Manufacturing Example 31 (yield: 63%, 137 mg).

¹H NMR (CDCl₃, 300 MHz) δ 7.95 (dd, 1H, J=20.0, 7.9 Hz), 7.58 (m, 3H), 7.34 (m, 3H), 6.81 (dd, 1H, J=8.4, 2.2 Hz), 6.74 (d, 1H, J=2.2 Hz), 6.70 (d, 1H, J=8.4 Hz), 6.60 (d, 1H, J=10.0 Hz), 5.85 (s, 1H), 5.50 (d, 1H, J=10.0 Hz), 3.78 (s, 3H), 3.63 (s, 3H), 1.37 (s, 3H), 1.33 (s, 3H).

Manufacturing Example 32: Preparation of 2-(3,4-Dimethoxyphenyl)-1-(5-hydroxy-2,2-dimethyl-2H-chromen-6-yl)ethanone (107)

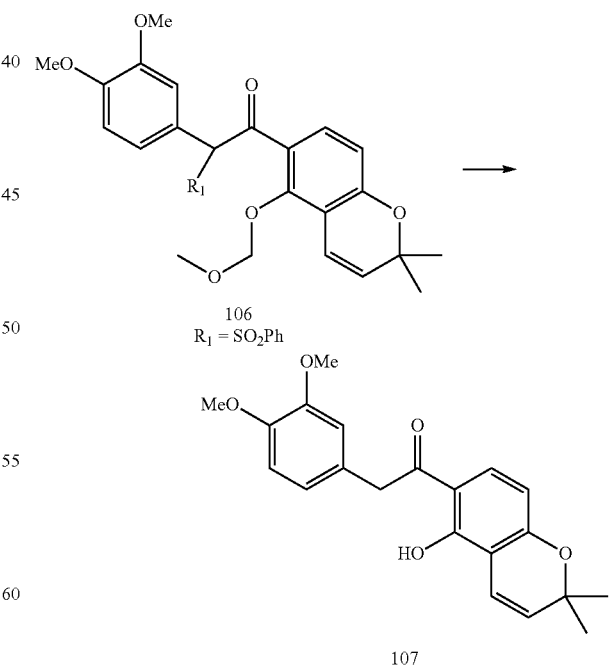

SmI₂ (0.81 mL, 0.081 mmol, 0.1 M in THF) was added to anhydrous THF (1.0 mL) containing the compound 106 (10 mg, 0.0202 mmol) prepared in Manufacturing Example 31 at −20° C. The reaction mixture was stirred at −20° C. for 10 minutes and then the reaction was terminated with saturated ammonium chloride aqueous solution (2.0 mL). The mixture was filtered by celite pad, followed by extraction with EtOAc (4.0 mL×3). The organic layer was dried over 20% sodium thiosulfate saturated aqueous solution, filtered and concentrated under reduced pressure. Then, the obtained residue was purified by flash column chromatography (EtOAc:n-hexane=1:3) to give the compound 107 of Manufacturing Example 32 as a light-yellow solid (yield: 87%, 77 mg).

$^1$H NMR (CDCl$_3$, 300 MHz) δ 12.88 (s, 1H), 7.58 (d, 1H, J=8.8 Hz), 7.74 (s, 1H), 6.71 (s, 1H), 6.63 (d, 1H, J=10.0 Hz), 6.25 (d, 1H, J=8.8 Hz), 5.50 (d, 1H, J=10.0 Hz), 4.15 (s, 2H), 3.79 (s, 6H), 1.37 (s, 6H).

Manufacturing Example 33: Preparation of 1,2-Dimethoxy-4-(prop-2-ynyloxy)benzene (115)

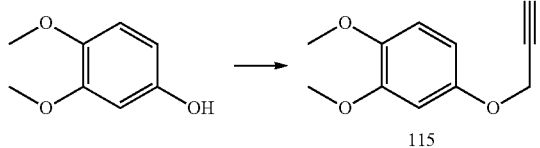

Propargyl bromide (225 mg, 1.51 mmol) and potassium carbonate (211 mg, 1.51 mmol) were added to DMF (0.2 M) solution containing 3,4-dimethoxyphenol, which was stirred at room temperature for 12 hours. The reaction was terminated with saturated ammonium chloride aqueous solution, followed by extraction with diethyl ether. The organic layer was washed with water (×2) and brine, dried over anhydrous MgSO$_4$, and concentrated under reduced pressure. Then, the obtained residue was purified by flash column chromatography (n-hexane:CH$_2$Cl$_2$=1:1) to give the compound 115 of Manufacturing Example 33 as a light-yellow oil (yield: 100%, 241 mg).

$^1$H NMR (CDCl$_3$, 300 MHz) δ 6.79 (d, 1H, J=8.8 Hz), 6.60 (d, 1H, J=2.7 Hz), 6.49 (dd, 1H, J=8.8, 2.7 Hz), 4.65 (d, 2H, J=2.4 Hz), 3.86 (s, 3H), 3.84 (s, 3H), 2.52 (t, 1H, J=2.4 Hz).

Manufacturing Example 34: Preparation of 4-(3-Bromoprop-2-ynyloxy)-1,2-dimethoxybenzene (116)

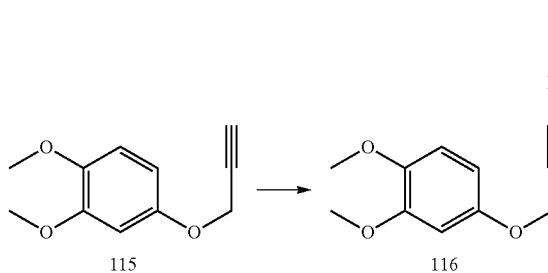

Cold bromine (1.12 mmol, 0.03 mL) was added to saturated sodium hydroxide aqueous solution (0.5 mL, 5.0 M), to which dimethoxyethane (1.0 mL) containing the compound 115 (108 mg, 0.56 mmol) obtained in Manufacturing Example 33 was added. Next, the flask was filled with nitrogen gas, which was stirred vigorously at room temperature for 5 hours. Ice water was poured in the reaction mixture, followed by extraction with n-hexane (5.0 mL). The extract was washed with water, dried over anhydrous sodium sulfate, and concentrated under reduced pressure. Then, the obtained residue was purified by flash column chromatography (EtOAc:n-hexane=1:5) to give the compound 116 of Manufacturing Example 34 as a light-yellow oil (yield: 86%, 130 mg).

$^1$H NMR (CDCl$_3$, 300 MHz) δ 6.79 (d, 1H, J=8.6 Hz, 1H), 6.58 (d, 1H, J=2.9 Hz), 6.47 (dd, 1H, J=8.6, 2.9 Hz), 4.66 (s, 2H), 3.86 (s, 3H), 3.84 (s, 3H).

Manufacturing Example 35: Preparation of 4-Bromo-6,7-dimethoxy-2H-chromene (118)

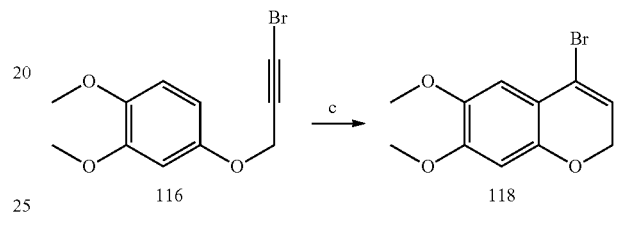

The compound 116 (130 mg, 0.48 mmol) prepared in Manufacturing Example 34 was added to N,N-diethylaniline (7.0 mL). While monitoring with TLC, the reaction mixture was heated at 210° C. until the reaction was completed under nitrogen atmosphere. The reaction mixture was poured in ice water, followed by extraction with EtOAc (10 mL). The organic layer was washed with 2 N—HCl aqueous solution, 2 N—NaOH aqueous solution, and water stepwise, dried over anhydrous sodium sulfate, and concentrated under reduced pressure. Then, the obtained residue was purified by flash column chromatography (EtOAc:n-hexane=1:8) to give the compound 118 of Manufacturing Example 35 as a light-yellow solid (yield: 77%, 100 mg).

$^1$H NMR (CDCl$_3$, 300 MHz) δ 6.73 (s, 1H), 6.42 (s, 1H), 6.01 (t, 1H, J=4.2 Hz), 4.72 (d, 2H, J=4.2 Hz), 3.88 (s, 3H), 3.86 (s, 3H).

Manufacturing Example 36: Preparation of 4-Bromo-6,7-dimethoxy-2,2-dimethyl-2H-chromene (119)

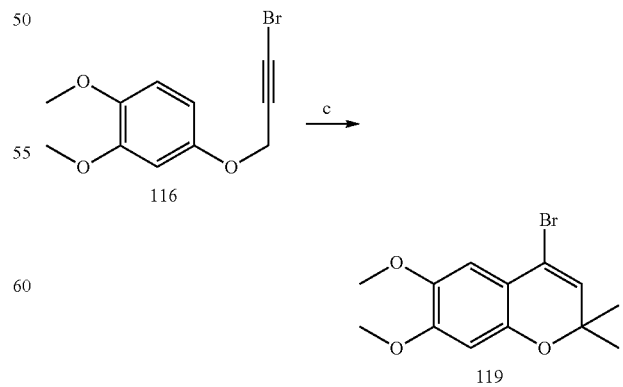

Anhydrous trichloroethylene solution (1.5 mL) containing 2,2-dimethylchromanone (100 mg, 0.41 mmol) was added to anhydrous trichloroethylene solution (1.5 mL) containing anhydrous DMF (0.05 mL, 0.62 mmol) and phosphorous oxibromide (188 mg, 0.62 mmol) at 0° C. While monitoring with TLC, the reaction mixture was heated at 60° C. until the reaction was completed. By concentrating the reaction mixture under reduced pressure, an orange gum was obtained. The gum was extracted with CH$_2$Cl$_2$ (×5), and the extract was washed with brine. The organic layer was dried over anhydrous sodium sulfate, and concentrated under reduced pressure. Then, the obtained residue was purified by flash column chromatography (EtOAc:n-hexane=1:5) to give the compound 119 of Manufacturing Example 36 as a yellow solid (yield: 91%, 9 mg).

$^1$H NMR (CDCl$_3$, 300 MHz) δ 6.95 (s, 1H), 6.38 (s, 1H), 5.82 (s, 1H), 3.85 (s, 3H), 3.83 (s, 3H), 1.41 (s, 6H).

Manufacturing Example 37: Preparation of 2,2-dimethyl-2H-chromene-6-carbaldehyde (120)

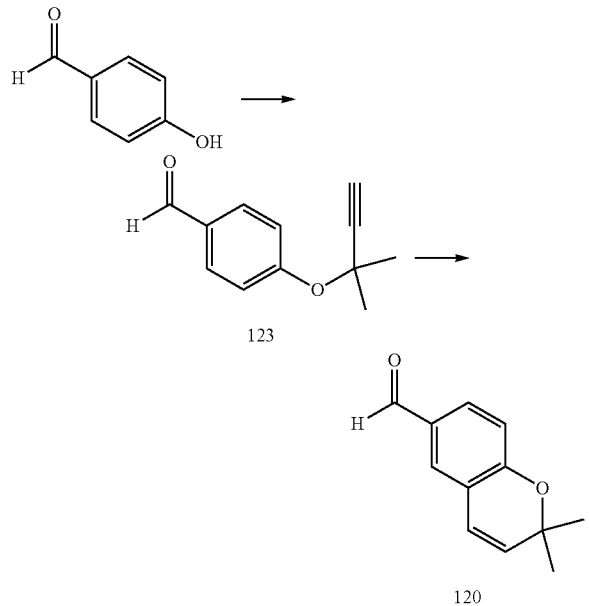

DMF (1.0 M) suspension containing phenol (1 equivalent), potassium carbonate (2 equivalent), potassium iodide (1.7 equivalent) and copper (I) iodide (0.02 equivalent) was prepared at room temperature, to which 3-chloro-3-methyl-1-butin (1.8 equivalent) was added. The reaction mixture was heated at 65° C. for 2 hours and then cooled down at room temperature. Diethyl ether was added to the mixture, which was washed with 10% sodium hydroxide (×3) and brine. The extract was dried over anhydrous MgSO$_4$, and concentrated under reduced pressure. Then, the obtained residue was purified by silica gel column chromatography (EtOAc:n-hexane) to give o-alkylated phenol.

While monitoring N,N-diethylaniline solution (0.05 M) containing O-alkylated phenol (1 equivalent) with TLC, the solution was heated at 190° C. until the reaction was completed under nitrogen atmosphere. The reaction mixture was poured in ice water, followed by extraction with EtOAc. The organic layer was washed with 2 N—HCl aqueous solution, N—NaOH aqueous solution, and water stepwise, dried over anhydrous sodium sulfate, and concentrated under reduced pressure. Then, the obtained non-purified residue was purified by flash column chromatography (EtOAc:n-hexane) to give the compound 120 (yield: 46%, 326 mg).

$^1$H NMR (CDCl$_3$, 300 MHz) δ 9.80 (s, 1H), 7.15 (dd, 1H, J=8.2, 2.0 Hz), 7.49 (d, 1H, J=2.0 Hz), 6.84 (d, 1H, J=8.4 Hz), 6.35 (d, 1H, J=9.8 Hz), 5.67 (d, 1H, J=9.8 Hz), 1.45 (s, 6H);

HRMS (FAB) Calcd for C$_2$H$_3$rO$_2$(M+H$^+$): 189.0916, Found: 189.0916.

Manufacturing Example 38: Preparation of 5-(Methoxy)-2,2-dimethyl-2H-chromene-6-carbaldehyde (121)

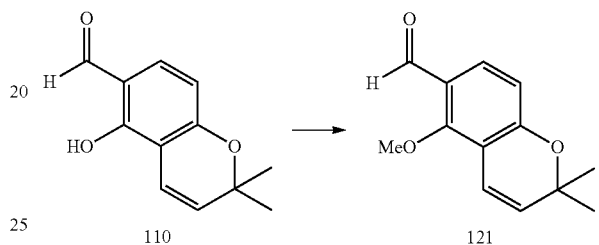

Iodomethane (0.11 mL, 1.47 mmol) was added to acetone solution (5 mL) containing the compound 110 (200 mg, 0.98 mmol) prepared in Manufacturing Example 29 and potassium carbonate (406 mg, 2.94 mmol) at room temperature. The mixture was refluxed for 3 hours, and then concentrated under reduced pressure. The obtained non-purified residue was extracted with EtOAc. The organic layer was washed with brine. The extract was dried over anhydrous MgSO$_4$, and concentrated under reduced pressure. Then, the obtained residue was purified by flash column chromatography (EtOAc:n-hexane=1:10) to give the compound 121 as a light-yellow solid (yield: 91%, 231 mg).

$^1$H NMR (CDCl$_3$, 300 MHz) δ 10.07 (s, 1H), 7.59 (d, J=8.6 Hz, 1H), 6.61 (d, J=8.6 Hz, 1H), 6.53 (d, J=10.0 Hz, 1H), 5.63 (d, J=10.0 Hz, 1H), 5.02 (s, 2H), 3.52 (s, 3H).

Manufacturing Example 39: Preparation of 6-Bromo-2,2-dimethyl-2H-chromene (131)

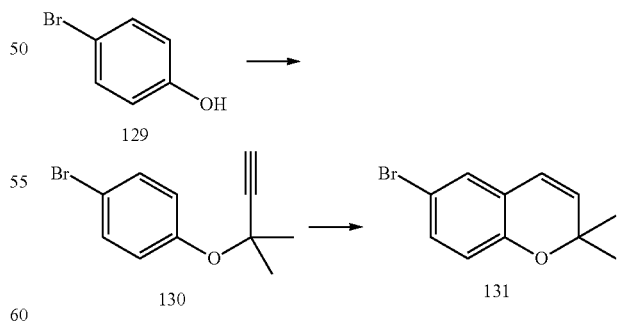

DBU (1.3 equivalent) was injected in acetonitrile (0.02 M) solution containing 2-methyl-3-butin-2-ol (1.15 equivalent) by using a syringe at 0° C. for 30 minutes. The resultant yellow solution was stirred at 0° C. for 40 minutes. In another flask, 4-bromophenol (1 equivalent) was added to acetonitrile (0.03 M) at 0° C., which was then treated with DBU (1.3 equivalent). CuCl$_2$.H$_2$O (0.02 equivalent) was added thereto. The yellow solution prepared above (2-methyl-3-butin-2-yl trifluoroacetate) was added to the mixture at 0° C. drop by drop by using a cannula for 40 minutes. The reaction mixture was stirred at 0° C. for 5 hours and then concentrated under reduced pressure. The obtained residue was poured in water. The water layer was extracted with hexane, and the organic layer was washed with 1 N—HCl, 1 N—KOH (×2), and brine stepwise. The organic layer was dried over anhydrous MgSO$_4$ and concentrated under reduced pressure to give o-alkylated phenol (1.0 equivalent). This product was used for the next step.

While monitoring N,N-diethylaniline solution (0.05 M) containing O-alkylated phenol (1.0 equivalent) with TLC, the solution was heated at 190° C. until the reaction was completed under nitrogen atmosphere. The reaction mixture was poured in ice water, followed by extraction with EtOAc. The organic layer was washed with 2 N—HCl aqueous solution, 2 N—NaOH aqueous solution, and water stepwise, dried over anhydrous sodium sulfate, and concentrated under reduced pressure. Then, the obtained non-purified residue was purified by flash column chromatography (EtOAc:n-hexane=1:20) to give the compound 131 as a light-yellow oil (yield: 68%, 464 mg).

$^1$H NMR (CDCl$_3$, 300 MHz) δ 7.15 (d, 1H, J=8.4 Hz), 7.06 (d, 1H, J=2.3 Hz), 6.63 (d, 1H, J=8.4 Hz), 6.23 (d, 1H, J=9.9 Hz), 5.62 (d, 1H, J=9.9 Hz), 1.39 (s, 6H).

Manufacturing Example 40: Preparation of (3,4-Dimethoxyphenyl) (2,2-dimethyl-2H-chromen-6-yl) methanol (132)

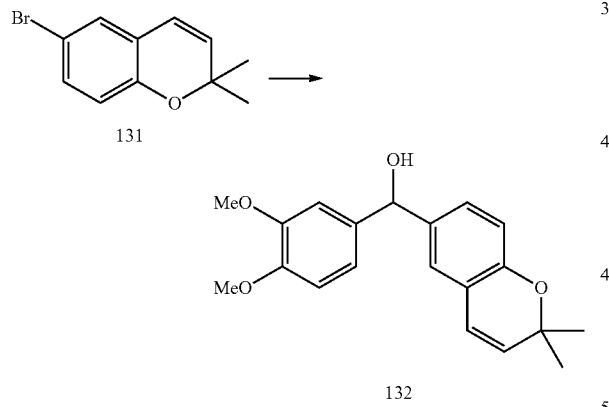

n-BuLi (0.17 mL, 0.28 mmol, 1.6 M in n-hexane solution) was added to anhydrous THF solution (3.0 mL) containing the compound 131 (60 mg, 0.25 mmol) obtained in Manufacturing Example 39 at −78° C., which was stirred for 30 minutes. Then, anhydrous THF (1.0 mL) containing 3,4-dimethoxybenzaldehyde (83 mg, 0.50 mmol) was added to the mixture drop by drop, followed by stirring for 30 minutes, during which the temperature was maintained at −78° C. Saturated ammonium chloride aqueous solution was added thereto to terminate the reaction, followed by extraction with EtOAc (×2). The extract was washed with brine. The organic layer was dried over anhydrous MgSO$_4$, and concentrated under reduced pressure. Then, the obtained residue was purified by flash column chromatography (EtOAc:n-hexane=1:4) to give the compound 132 as a white solid (yield: 66%, 108 mg).

$^1$H NMR (CDCl$_3$, 300 MHz) δ 7.06 (d, 1H, J=8.2 Hz), 7.85 (m, 4H), 6.71 (d, 1H, J=8.2 Hz), 6.26 (d, 1H, J=9.8 Hz), 5.70 (s, 1H), 5.58 (d, 1H, J=9.8 Hz), 3.84 (s, 3H), 3.83 (s, 3H), 2.09 (d, 1H, J=3.2 Hz), 1.39 (s, 6H).

Manufacturing Example 41: Preparation of 1-(5-hydroxy-2,2-dimethyl-2H-chromen-6-yl)ethanone (112)

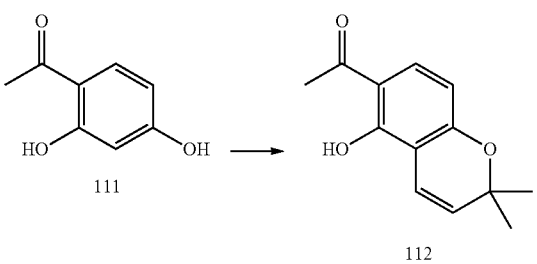 [SMILES: CC(=O)c1ccc(O)cc1O ; CC(=O)c1ccc2c(c1O)C=CC(C)(C)O2]

n-BuLi (1.4 equivalent) was added to anhydrous THF solution containing aryl bromide (1.5 equivalent) drop by drop at −78° C., which was stirred at −78° C. to generate aryl anions. The mixture was stirred at −78° C. for 20 minutes, to which 2',4'-dihydroxyacetophenone (1.0 equivalent) was added, followed by stirring for 30 minutes with raising the reaction temperature to room temperature. The reaction mixture was treated with saturated NH$_4$Cl aqueous solution, followed by extraction with EtOAc. The extract was washed with brine and then dried over MgSO$_4$. The residue obtained after evaporating the solvent was purified by flash column chromatography (EtOAc:n-hexane=1:15~1:10) to give the compound 112 as a light-yellow solid (yield: 32%, 460 mg).

$^1$H-NMR (CDCl$_3$, 300 MHz) δ 12.94 (s, 1H), 7.50 (d, 1H, J=8.7 Hz), 6.79 (d, 1H, J=10.0 Hz), 6.31 (d, 1H, J=8.7 Hz), 5.56 (d, 1H, J=8.7 Hz), 1.42 (s, 6H).

Manufacturing Example 42: Preparation of 1-(2,2-Dimethyl-2H-chromen-6-yl)ethanone (134)

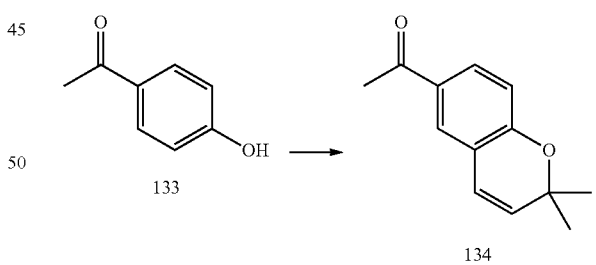

DMF (1.0 M) suspension containing compound 133 (1 equivalent), potassium carbonate (2 equivalent), potassium iodide (1.7 equivalent) and copper (I) iodide (0.02 equivalent) was prepared at room temperature, to which 3-chloro-3-methyl-1-butin (1.8 equivalent) was added. The reaction mixture was heated at 65° C. for 2 hours and then cooled down at room temperature. Diethyl ether was added to the mixture, which was washed with 10% sodium hydroxide (×3) and brine. The extract was dried over anhydrous MgSO$_4$, and concentrated under reduced pressure. Then, the obtained residue was purified by silica gel column chromatography to give o-alkylated phenol.

While monitoring N,N-diethylaniline solution (0.05 M) containing o-alkylated phenol (1 equivalent) with TLC, the solution was heated at 190° C. until the reaction was completed under nitrogen atmosphere. The reaction mixture was poured in ice water, followed by extraction with EtOAc. The organic layer was washed with 2 N—HCl aqueous solution, N—NaOH aqueous solution, and water stepwise, dried over anhydrous sodium sulfate, and concentrated under reduced pressure. Then, the obtained non-purified residue was purified by flash column chromatography (EtOAc:n-hexane=1:15) to give the compound 134 as a colorless oil (yield: 65%, 248 mg).

$^1$H NMR (CDCl$_3$, 300 MHz) δ 7.32 (dd, 1H, J=8.4, 2.1 Hz), 6.60 (d, 1H, J=2.4 Hz), 6.77 (d, 1H, J=8.4 Hz), 6.34 (d, 1H, J=9.9 Hz), 5.65 (d, 1H, J=9.9 Hz), 2.51 (s, 3H), 1.43 (s, 6H); LRMS (FAB) m/z 203 (M+H$^+$).

Manufacturing Example 43: Preparation of (7S, 7aR,13aS)-9,10-Dimethoxy-3,3-dimethyl-7,7a,13, 13a-tetrahydro-3H-chromeno[3,4-b]pyrano[2,3-h]chromen-7-ol (14)

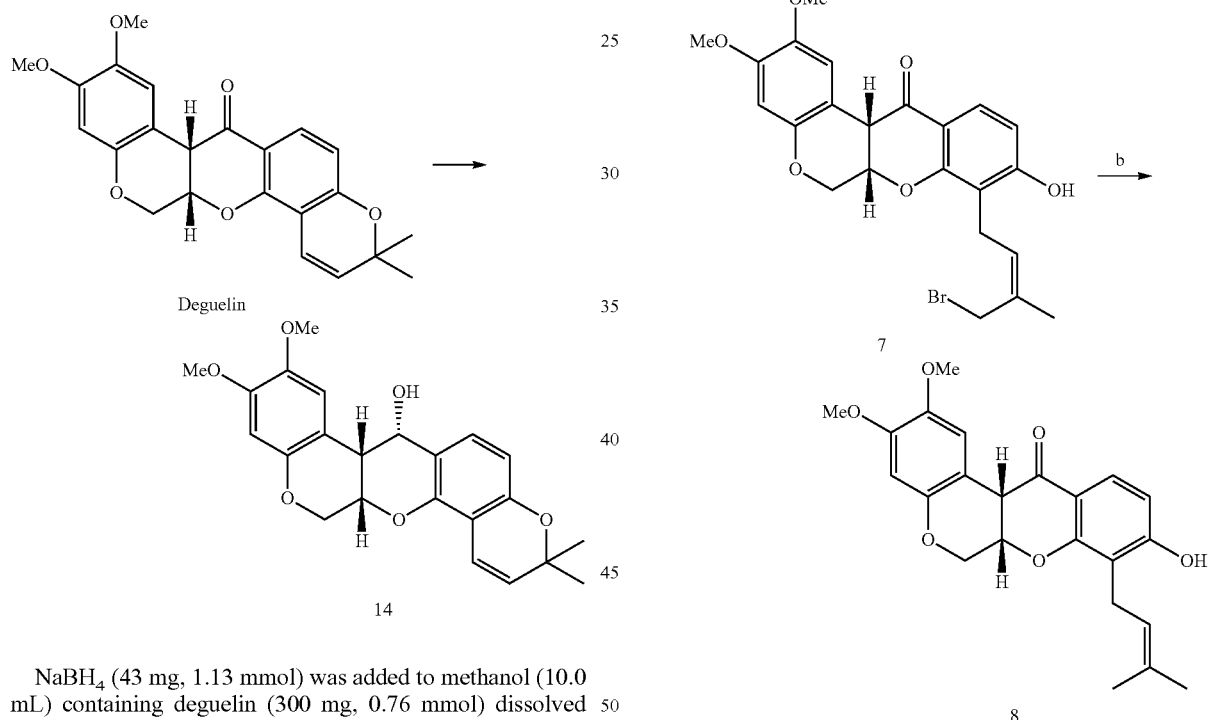

14

NaBH$_4$ (43 mg, 1.13 mmol) was added to methanol (10.0 mL) containing deguelin (300 mg, 0.76 mmol) dissolved therein at 0° C., followed by stirring for 30 minutes. The mixture was cooled down with water. The mixture was extracted with diethyl ether. The organic layer was washed with brine, dried over MgSO$_4$, and concentrated. Then, the obtained residue was purified by flash column chromatography (EtOAc:n-hexane=1:1) to give the compound 14 of Manufacturing Example 43 as a white solid (yield: 100%, 300 mg).

$^1$H-NMR (CDCl$_3$, 400 MHz) δ 6.99 (d, 1H, J=8.2 Hz), 6.68 (s, 1H), 6.64 (d, 1H, J=10.0 Hz), 6.47 (s, 1H), 6.41 (d, 1H, J=8.2 Hz), 5.56 (d, 1H, J=10.0 Hz), 4.80 (m, 2H), 4.57 (d, 1H, J=10.0 Hz), 4.21 (m, 1H), 3.84 (s, 3H), 3.82 (s, 3H), 3.36 (t, 1H, J=4.9 Hz), 1.41 (s, 3H), 1.39 (s, 3H);

$^{13}$C-NMR (CDCl$_3$, 100 MHz) δ 154.3, 149.6, 149.4, 147.9, 143.8, 130.0, 129.1, 116.4, 113.6, 111.3, 109.8, 109.5, 108.7, 100.7, 76.0, 69.1, 66.3, 65.0, 56.5, 55.8, 37.9, 27.8, 27.7;

HRMS (FAB) Calcd for C$_{23}$H$_{24}$O$_6$ (M+H$^+$): 396.1560, Found: 396.1562.

Example 1: Preparation of (6aS,12aS)-9-Hydroxy-2,3-dimethoxy-8-(3-methyl-2-butenyl)-6a,12a-dihydrochromeno[3,4-b]chromen-12(6H)-one (8)

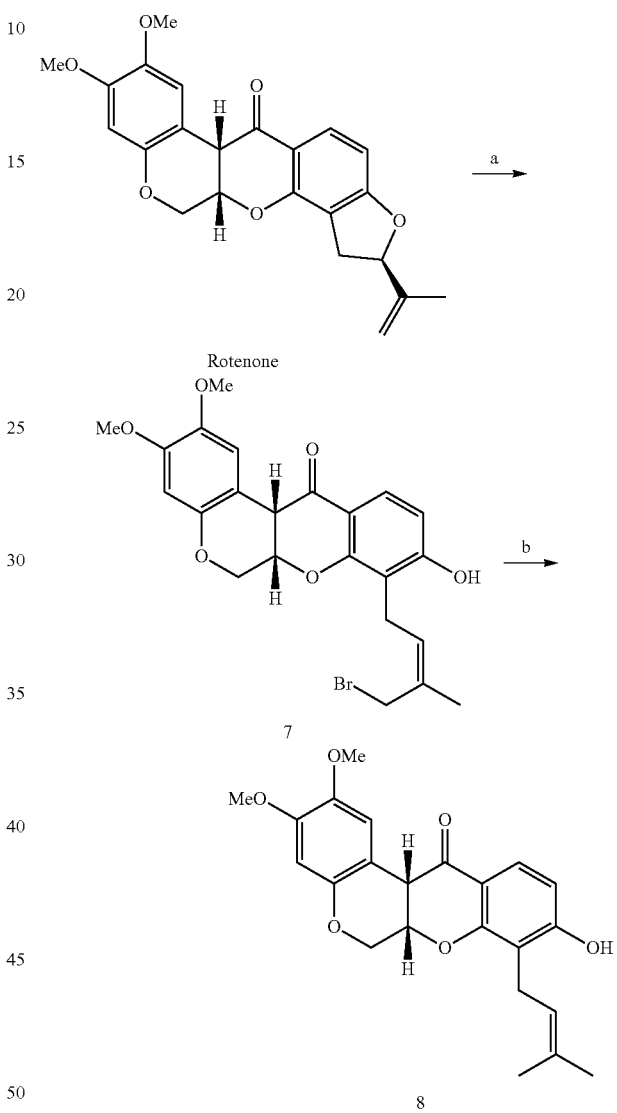

BBr$_3$ (0.53 mL, 0.53 mmol, 1.0 M in CH$_2$Cl$_2$ solution) was added to anhydrous CH$_2$Cl$_2$ solution (5.0 mL) containing rotenone (Sigma-Aldrich, 200 mg, 0.50 mmol) dissolved therein at −10° C. under argon atmosphere. The reaction mixture was well mixed for 5 minutes. Methanol (1.0 mL) was added to the mixture and the solvent was eliminated under reduced pressure. The mixture was filtered and the non-purified residue (compound 7) obtained thereby was used for the next step without being additionally purified.

Compound 7 and NaBH$_3$CN (69 mg, 1.1 mmol) were added to hexamethylphosphoamide (HMPA) solution, which was then heated at 70° C. for 3 hours with stirring. The mixture was poured in water. The extract of the mixture was washed with brine, dried over MgSO$_4$, and concentrated under reduced pressure. Then, the obtained residue was purified by flash column chromatography (EtOAc:n-hexane=1:2) to give the compound 8 of Example 1 as a light-yellow solid (yield: 50%, 55 mg).

$^1$H-NMR (CDCl$_3$, 500 MHz) δ 7.68 (d, 1H, J=8.7 Hz), 6.76 (s, 1H), 6.50 (d, 1H, J=8.7 Hz), 6.41 (s, 1H), 5.19 (m, 1H), 4.87 (t, 1H, J=2.97 Hz), 4.60 (dd, 1H, J=11.9, 3.1 Hz), 4.14 (d, 1H, J=11.9 Hz), 3.80 (m, 1H), 3.75 (s, 3H), 3.70 (s, 3H), 3.34 (m 2H), 1.74 (s, 3H), 1.65 (s, 3H);

$^{13}$C-NMR (CDCl$_3$, 125 MHz) δ190.4, 162.1, 160.1, 149.3, 147.5, 143.6, 134.0, 126.9, 121.1, 114.8, 112.5, 110.7, 110.5, 108.5, 104.7, 100.8, 72.0, 66.2, 56.2, 55.7, 44.1, 25.7, 22.0, 17.7;

HRMS (FAB) Calcd for C$_{23}$H$_{24}$O$_6$ (M$^+$): 396.1573, Found: 396.1575.

Example 2~4: Preparation of (7aS,13aS)-9-Hydroxy-13,13a-dihydro-10-methoxy-3,3-dimethyl-3H-chromeno[3,4-b]pyrano[2, 3-h]chromen-7 (7aH)-one (9)

(7aS,13aS)-10-Hydroxy-13,13a-dihydro-9-methoxy-3,3-dimethyl-3H-chromeno[3,4-b]pyrano[2,3-h]chromen-7(7aH)-one (10); and (7aS,13aS)-13,13a-Dihydro-9,10-dihydroxy-3,3-dimethyl-3H-chromeno[3,4-b]pyrano[2,3-h]chromen-7(7aH)-one (11)

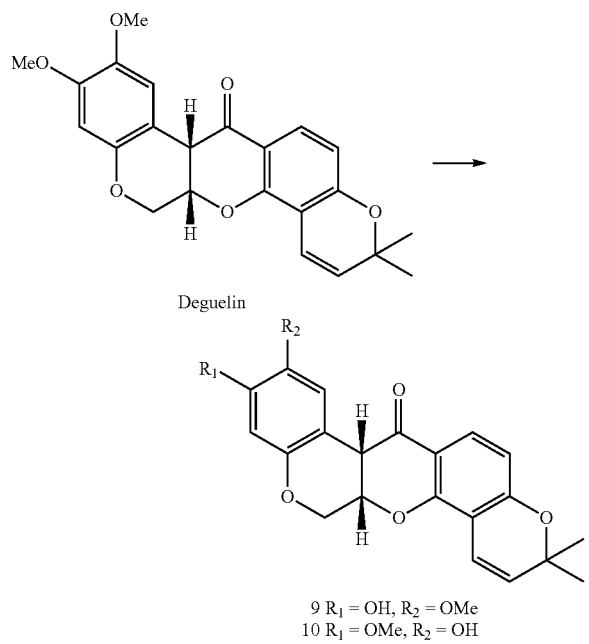

9 R$_1$ = OH, R$_2$ = OMe
10 R$_1$ = OMe, R$_2$ = OH
11 R$_1$, R$_2$ = OH

BBr$_3$ (0.25 mL, 0.25 mmol, 1.0 M in CH$_2$Cl$_2$ solution) was added to anhydrous CH$_2$Cl$_2$ solution (7.0 mL) containing deguelin (100 mg, 0.25 mmol) of Comparative Example 1 dissolved therein at −78° C. under argon atmosphere, followed by stirring for 1 hour. The mixture stood until the temperature thereof reached 0° C. The mixture was additionally stirred for 30 more minutes and then cooled down with water, followed by extraction with CH$_2$Cl$_2$. The extract was washed with brine. The organic layer was dried over MgSO$_4$, filtered, and concentrated under reduced pressure. Then, the obtained residue was purified by flash column chromatography (EtOAc:n-hexane:CH$_2$Cl$_2$=1:3:1~1:2:1) to give the compound 9 of Example 2 as a light-yellow solid (yield: 16%, 16 mg).

$^1$H-NMR (acetone-d$_6$, 400 MHz) δ 7.64 (d, 1H, J=8.7 Hz), 7.60 (s, 1H), 6.67 (s, 1H), 6.59 (d, 1H, J=10.1 Hz), 6.40 (d, 1H, J=8.7 Hz), 6.30 (s, 1H), 5.66 (d, 1H, J=10.1 Hz), 5.06 (m, 1H), 4.57 (dd, 1H, J=12.2, 2.9 Hz), 4.22 (d, 1H, J=12.2 Hz), 3.85 (d, 1H, J=4.0 Hz), 3.62 (s, 3H), 1.39 (s, 3H), 1.30 (s, 3H);

$^{13}$C-NMR (acetone-d$_6$, 100 MHz) δ190.2, 160.8, 158.2, 149.6, 148.6, 143.7, 130.4, 129.4, 116.6, 114.3, 112.2, 112.1, 110.3, 105.8, 105.2, 78.8, 74.0, 67.3, 57.3, 45.4, 29.0, 28.6;

HRMS (FAB) Calcd for C$_{22}$H$_{21}$O$_6$ (M+H$^+$): 381.1321, Found: 381.1327.

The compound 10 of Example 3 was also obtained as a light-yellow solid (yield: 14%, 14 mg).

$^1$H-NMR (acetone-d$_6$, 300 MHz) δ7.64 (d, 1H, J=8.6 Hz), 7.07 (s, 1H), 6.60 (s, 1H), 6.59 (d, 1H, J=10.1 Hz), 6.39 (d, 1H, J=8.6 Hz), 6.38 (s, 1H), 5.67 (d, 1H, J=10.1 Hz), 5.06 (m, 1H), 4.59 (dd, 1H, J=12.2, 2.9 Hz), 4.23 (d, 1H, J=12.2 Hz), 3.82 (d, 1H, J=4.0 Hz), 3.71 (s, 3H), 1.39 (s, 3H), 1.30 (s, 3H);

$^{13}$C-NMR (acetone-d$_6$, 75 MHz) δ190.0, 160.8, 158.2, 149.1, 148.2, 142.1, 130.4, 129.4, 116.6, 114.5, 114.3, 112.1, 110.3, 107.2, 102.1, 78.8, 73.9, 67.4, 56.6, 45.4, 29.0, 28.6;

HRMS (FAB) Calcd for C$_{22}$H$_{21}$O$_6$ (M+H$^+$): 381.1338, Found: 381.1335.

Further, the compound 11 of Example 4 was prepared as a light-yellow solid (yield: 33%, 32 mg).

$^1$H-NMR (acetone-d$_6$, 400 MHz) δ7.75 (s, 1H), 7.63 (d, 1H, J=8.7 Hz), 7.38 (s, 1H), 6.59 (s, 1H), 6.58 (d, 1H, J=10.1 Hz), 6.39 (d, 1H, J=8.7 Hz), 6.29 (s, 1H), 5.65 (d, 1H, J=10.1 Hz), 5.03 (m, 1H), 4.55 (dd, 1H, J=12.2, 2.9 Hz), 4.20 (d, 1H, J=12.2 Hz), 3.79 (d, 1H, J=4.0 Hz), 1.38 (s, 3H), 1.30 (s, 3H);

$^{13}$C-NMR (acetone-d$_6$, 100 MHz) δ190.1, 160.8, 158.2, 148.4, 146.9, 140.7, 130.4, 129.3, 116.6, 114.9, 114.2, 112.1, 110.3, 106.2, 105.1, 78.8, 74.0, 67.2, 45.4, 29.0, 28.6;

HRMS (FAB) Calcd for C$_{22}$H$_{29}$O$_6$ (M+H$^+$): 367.1182, Found: 367.1179.

Example 5: Preparation of 9,10-Dimethoxy-3,3-dimethyl-3H-chromeno[3,4-b]pyrano[2,3-h]chromen-7-(13H)-one (12)

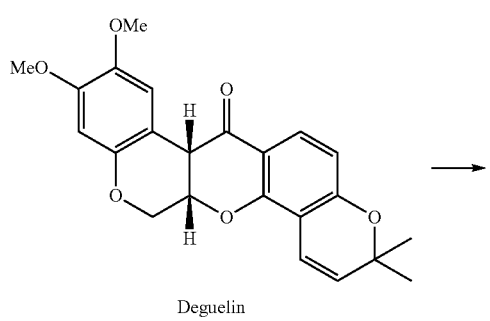

Deguelin

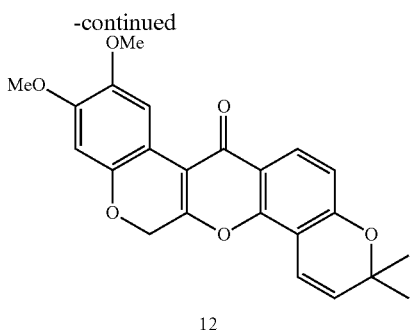

12

Sodium acetate (21 mg, 0.25 mmol) and $I_2$ (290 mg, 1.14 mmol) were added to ethyl alcohol (2.0 mL) containing deguelin (50 mg, 0.13 mmol) of Comparative Example 1 dissolved therein at room temperature. The mixture was refluxed for 12 hours, cooled down at room temperature, and extracted with EtOAc. The organic layer of the extract was washed with brine, dried over $MgSO_4$, and concentrated under reduced pressure. Then, the obtained residue was crystallized in EtOAc:n-hexane=1:1 solution to give the compound 12 of Example 5 as a light-yellow solid (yield: 35%, 17 mg).

$^1$H-NMR ($CDCl_3$, 500 MHz) δ 8.42 (s, 1H), 8.01 (d, 1H, J=8.7 Hz), 6.84 (d, 1H, J=8.7 Hz), 6.73 (d, 1H, J=10.0 Hz), 6.52 (s, 1H), 5.70 (d, 1H, J=8.7 Hz), 4.99 (s, 2H), 3.93 (s, 3H), 3.84 (s, 3H), 1.47 (s, 6H);

$^{13}$C-NMR ($CDCl_3$, 125 MHz) δ 174.2, 157.1, 156.1, 151.0, 148.9, 146.2, 144.0, 130.5, 126.4, 118.4, 115.3, 114.6, 111.7, 110.5, 109.9, 109.0, 100.3, 77.7, 64.8, 56.2, 55.8, 28.1, 28.1;

HRMS (FAB) Calcd for $C_{23}H_{20}O_6$ ($M^+$): 392.1260, Found: 392.1263.

Example 7: Preparation of (7aS,13aS)-9,10-Dimethoxy-3,3-dimethyl-7,7a,13,13a-tetrahydro-3H-chromeno[3,4-b]pyrano[2,3-h]chromene (13)

Sodium hydride (16 mg, 0.40 mmol) was added to anhydrous THF solution (2.0 mL) containing the compound 14 (40 mg, 0.10 mmol) prepared in Manufacturing Example 43 dissolved therein at 0° C. under argon atmosphere, followed by stirring for 30 minutes. Carbon disulfide (0.063 mL, 1.00 mmol) was added thereto at 0° C. Iodomethane (0.064 mL, 1.00 mmol) was added to the mixture at 0° C. and the temperature of the reaction mixture was raised to room temperature. After confirming the termination of the reaction by TLC, the mixture was cooled down with methanol (1.0 mL). The solvent was eliminated under reduced pressure, followed by extraction with EtOAc. The extract was washed with brine. The organic layer of the extract was dried over $MgSO_4$, filtered, and concentrated. The obtained non-purified residue was purified by flash column chromatography (EtOAc:n-hexane=1:6) to give the intermediate compound (yield: 71%, 35 mg). The intermediate compound (21 mg, 0.043 mmol) was dissolved in anhydrous toluene (1.0 mL), to which tri-n-butyltin hydride (0.024 mL, 0.086 mmol) and AIBN (catalytic amount) were added. While monitoring with TLC, the reaction mixture was refluxed until the reaction was completed. The solvent was eliminated under reduced pressure. Then, the obtained residue was purified by flash column chromatography (EtOAc:n-hexane=1:6) to give the compound 13 of Example 7 as a light-yellow oil (yield: 69%, 11 mg).

$^1$H-NMR ($CDCl_3$, 300 MHz) δ 6.75 (d, 1H, J=8.2 Hz), 6.63 (d, 1H, J=10.0 Hz), 6.62 (s, 1H), 6.38 (s, 1H), 6.31 (d, 1H, J=8.2 Hz), 5.52 (d, 1H, J=10.0 Hz), 5.53 (d, 1H, J=10.0 Hz), 4.67 (q, 1H, J=4.7 Hz), 4.24 (d, 1H, J=5.4 Hz), 3.79 (s, 6H), 3.26 (m, 1H), 2.99 (m, 2H), 1.38 (s, 3H), 1.37 (s, 3H);

$^{13}$C-NMR ($CDCl_3$, 75 MHz) δ 152.2, 148.9, 148.7, 147.7, 143.5, 128.9, 128.5, 116.7, 113.0, 111.4, 111.2, 109.7, 108.8, 100.6, 75.6, 69.7, 65.6, 56.6, 55.8, 31.6, 29.4, 27.8, 27.6;

HRMS (FAB) Calcd for $C_{23}H_{24}O_5$ ($M^+$): 380.1624, Found: 380.1631.

Example 9: Preparation of (7S,7aR,3aS)-9,10-Dimethoxy-3,3-dimethyl-7-ethoxy-7,7a,13,13a-tetrahydro-3H-chromeno[3,4-b]pyrano[2,3-h]chromene (16)

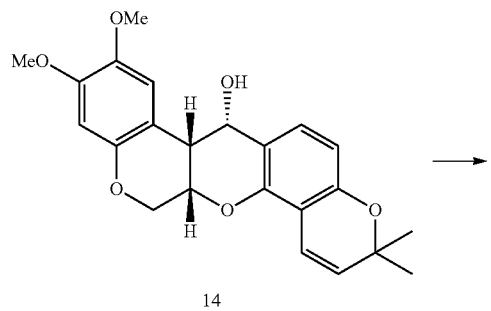

14

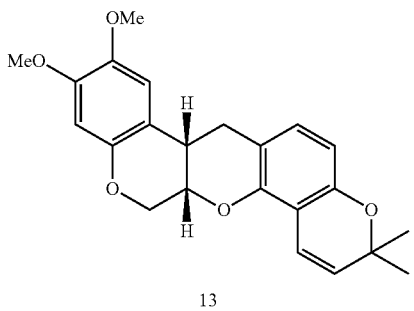

13

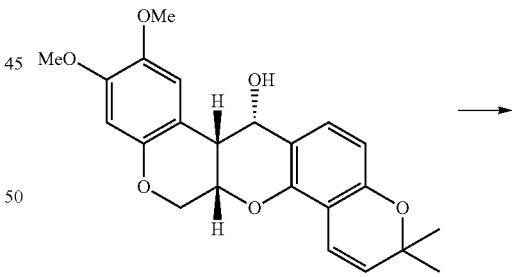

14

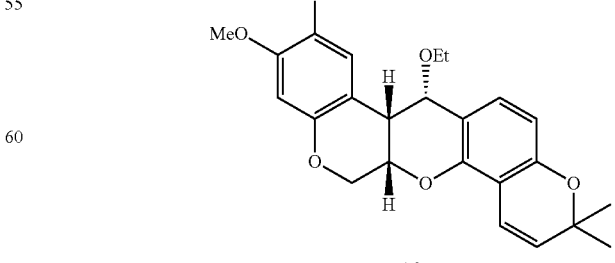

16

Iodoethane (1.5 equivalent) was added to anhydrous THF solution containing the compound 14 (1 equivalent) prepared in Example 7 at 0° C., to which t-BuOK solution (1 M in THF solution, 1 equivalent) was added drop by drop at 0° C. While monitoring with TLC, the reaction mixture was stirred at 0° C. until the reaction was completed. The mixture was cooled down with saturated NH$_4$Cl aqueous solution, followed by extraction with EtOAc. The organic layer of the extract was dried over MgSO$_4$, filtered, and concentrated under reduced pressure. Then, the obtained residue was purified by flash column chromatography (EtOAc:n-hexane=1:3) to give the compound 16 of Example 9 as a colorless solid (yield: 71%, 23 mg).

$^1$H-NMR (CDCl$_3$, 300 MHz) δ 6.95 (d, 1H, J=8.0 Hz), 6.84 (s, 1H), 6.63 (d, 1H, J=9.9 Hz), 6.39 (s, 1H), 6.35 (d, 1H, J=8.3 Hz), 5.53 (d, 1H, J=9.9 Hz), 4.75 (m, 1H), 4.58 (t, 1H, J=9.7 Hz), 4.53 (d, 1H, J=3.8 Hz), 4.20 (dd, 1H, J=9.9, 4.2 Hz), 3.80 (s, 3H), 3.80 (s, 3H), 3.42 (m, 2H), 3.29 (m, 1H), 1.39 (s, 3H), 1.38 (s, 3H), 1.00 (t, 3H, J=6.8 Hz);

$^{13}$C-NMR (CDCl$_3$, 75 MHz) δ 153.9, 149.1, 148.9, 148.4, 143.3, 128.9, 128.6, 116.6, 114.4, 111.7, 110.1, 109.8, 108.5, 100.3, 75.8, 75.0, 70.1, 66.0, 64.9, 56.5, 55.7, 36.8, 29.6, 27.8, 27.8;

HRMS (FAB) Calcd for C$_{25}$H$_{28}$O$_6$ (M$^+$): 424.1886, Found: 424.1894.

Example 10: Preparation of (7S,7aR,3aS)-9,10-Dimethoxy-3,3-dimethyl-7-propoxy-7,7a,13,13a-tetrahydro-3H-chromeno[3,4-b]pyrano[2,3-h]chromene (17)

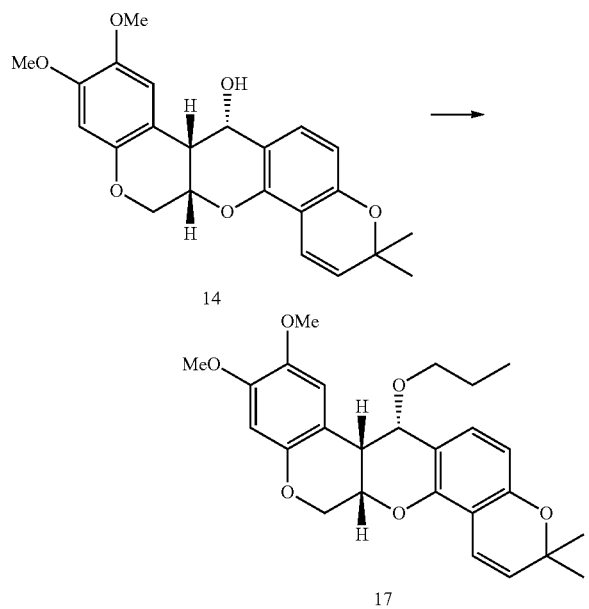

Iodopropane (1.5 equivalent) was added to anhydrous THF solution containing the compound 14 (1 equivalent) prepared in Example 7 at 0° C., to which t-BuOK solution (1 M in THF solution, 1 equivalent) was added drop by drop at 0° C. While monitoring with TLC, the reaction mixture was stirred at 0° C. until the reaction was completed. The mixture was cooled down with saturated NH$_4$Cl aqueous solution, followed by extraction with EtOAc. The organic layer of the extract was dried over MgSO$_4$, filtered, and concentrated under reduced pressure. Then, the obtained residue was purified by flash column chromatography (EtOAc:n-hexane=1:5) to give the compound 17 of Example 10 as a colorless solid (yield: 68%, 15 mg).

$^1$H-NMR (CDCl$_3$, 500 MHz) δ 6.94 (d, 1H, J=8.2 Hz), 6.83 (s, 1H), 6.63 (d, 1H, J=9.9 Hz) 6.39 (s, 1H), 6.34 (d, 1H, J=8.2 Hz), 5.53 (d, 1H, J=9.9 Hz), 4.77 (m, 1H), 4.57 (t, 1H, J=9.9 Hz), 4.50 (d, 1H, J=3.7 Hz), 4.21 (dd, 1H, J=9.9, 4.2 Hz), 3.80 (s, 6H), 3.39 (m, 2H), 3.18 (m, 1H), 1.39 (s, 8H), 0.69 (t, 3H, J=7.3 Hz);

$^{13}$C-NMR (CDCl$_3$, 125 MHz) δ 153.9, 149.1, 148.9, 148.3, 143.3, 128.9, 128.7, 116.6, 114.3, 111.7, 110.2, 109.8, 108.4, 100.3, 75.8, 75.3, 71.3, 70.1, 65.9, 56.5, 55.8, 36.8, 29.6, 27.9, 27.8, 22.9;

HRMS (FAB) Calcd for C$_{26}$H$_{31}$O$_6$ (M+H$^+$): 439.2121, Found: 439.2120.

Example 11: Preparation of (7S,7aR,3aS)-7-Benzyloxy-9,10-dimethoxy-3,3-dimethyl-7,7a,13,13a-tetrahydro-3H-chromeno[3,4-b]pyrano[2,3-h]chromene (18)

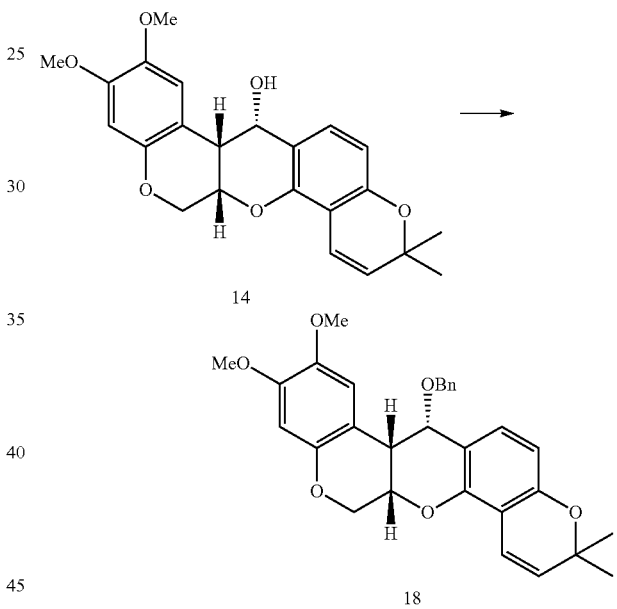

Benzylbromide (1.5 equivalent) was added to anhydrous THF solution containing the compound 14 (1 equivalent) prepared in Example 7 at 0° C., to which t-BuOK solution (1 M in THF solution, 1 equivalent) was added drop by drop at 0° C. While monitoring with TLC, the reaction mixture was stirred at 0° C. until the reaction was completed. The mixture was cooled down with saturated NH$_4$Cl aqueous solution, followed by extraction with EtOAc. The organic layer of the extract was dried over MgSO$_4$, filtered, and concentrated under reduced pressure. Then, the obtained residue was purified by flash column chromatography (EtOAc:n-hexane=1:6) to give the compound 18 of Example 11 as a colorless solid (yield: 88%, 22 mg).

$^1$H-NMR (CDCl$_3$, 500 MHz) δ 7.22 (m, 3H), 7.00 (m, 2H), 6.87 (d, 1H, J=8.2 Hz), 6.66 (d, 1H, J=9.9 Hz), 6.62 (s, 1H), 6.45 (s, 1H), 6.37 (d, 1H, J=8.2 Hz), 5.56 (d, 1H, J=9.9 Hz), 4.81 (m, 1H), 4.62 (t, 1H, J=9.9 Hz), 4.54 (d, 1H, J=3.2 Hz), 4.48 (AB quartet, 2H, J=85.0, 12.5 Hz), 4.25 (dd, 1H, J=14.2, 4.6 Hz), 3.84 (s, 3H), 3.72 (s, 3H), 3.36 (m, 1H), 1.42 (s, 3H), 1.40 (s, 3H);

$^{13}$C-NMR (CDCl$_3$, 125 MHz) δ 154.2, 149.1, 148.9, 148.7, 143.4, 137.9, 129.2, 129.0, 128.1, 127.6, 127.4, 127.2, 116.5, 113.8, 111.3, 110.1, 110.0, 108.4, 100.4, 75.9, 72.8, 69.9, 69.8, 65.8, 64.9, 56.2, 55.8, 37.3, 27.9, 27.8;

HRMS (FAB) Calcd for C$_{30}$H$_{30}$O$_6$ (M$^+$): 486.2042, Found: 486.2050.

Example 12: Preparation of (7S,7aS,13aS)-9,10-Dimethoxy-3,3-dimethyl-7-(tetrahydro-2H-pyran-2-yloxy)-7,7a,13,13a-tetrahydro-3H-chromeno[3,4-b]pyrano[2,3-h]chromene (19)

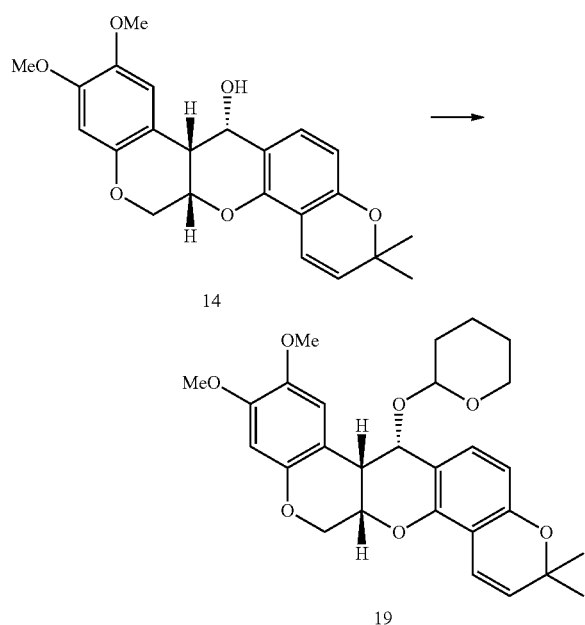

p-toluenesulfonate (5.8 mg, 0.023 mmol) was added to CH$_2$Cl$_2$ (1.0 mL) containing the compound 14 (30 mg, 0.076 mmol) prepared in Example 7 and DHP (13 mg, 0.15 mmol) dissolved therein, followed by stirring at room temperature for 1 hour. The reaction mixture was cooled down with water (0.5 mL), followed by extraction with EtOAc. The organic layer of the extract was dried over MgSO$_4$, filtered, and concentrated under reduced pressure. Then, the obtained residue was purified by flash column chromatography (EtOAc:n-hexane=1:4) to give the compound 19 of Example 12 as a colorless oil (yield: 50%, diastereomer mixture, 18 mg).

$^1$H-NMR (CDCl$_3$, 500 MHz) δ 7.06 (d, 1H, J=8.2 Hz), 6.91 (d, 1H, J=8.2 Hz), 6.84 (s, 1H), 6.72 (s, 1H), 6.63 (t, 1H, J=9.9 Hz), 6.42 (s, 1H), 6.69 (s, 1H), 6.37 (d, 1H, J=8.4 Hz), 6.33 (d, 1H, J=8.2 Hz), 5.54 (t, 1H, J=9.3 Hz), 4.85 (m, 4H), 4.75 (m, 1H), 4.63 (t, 1H, J=10.0 Hz), 4.55 (t, 1H, J=10.0 Hz), 4.33 (m, 1H), 4.21 (m, 2H), 3.81 (s, 3H), 3.80 (s, 3H), 3.79 (s, 3H), 3.78 (s, 3H), 3.70 (m, 1H), 3.40 (m, 3H), 3.29 (m, 1H), 3.11 (m, 1H), 1.71-1.19 (m, 12H), 1.40 (s, 12H);

$^{13}$C-NMR (CDCl$_3$, 125 MHz) δ 154.2, 153.7, 149.2, 149.1, 149.0, 148.9, 148.7, 148.7, 148.2, 148.2, 143.3, 143.2, 116.5, 116.4, 113.4, 113.1, 111.8, 111.7, 110.2, 110.0, 109.6, 109.6, 109.3, 109.3, 109.1, 108.2, 100.3, 100.2, 99.1, 93.2, 75.9, 75.8, 72.4, 69.8, 69.4, 69.1, 65.8, 65.2, 61.6, 60.4, 56.4, 56.5, 55.8, 55.8, 37.2, 36.8, 30.3, 30.2, 28.0, 27.9, 27.8, 27.7, 25.4, 25.3, 18.7, 18.1;

HRMS (FAB) Calcd for C$_{28}$H$_{32}$O$_7$ (M$^+$): 480.2148, Found: 480.2155.

Example 13: Preparation of (7S,7aS,13aS)-9,10-Dimethoxy-3,3-dimethyl-7,7a,13,13a-tetrahydro-3H-chromeno[3,4-b]pyrano[2,3-h]chromen-7-yl acetate (20)

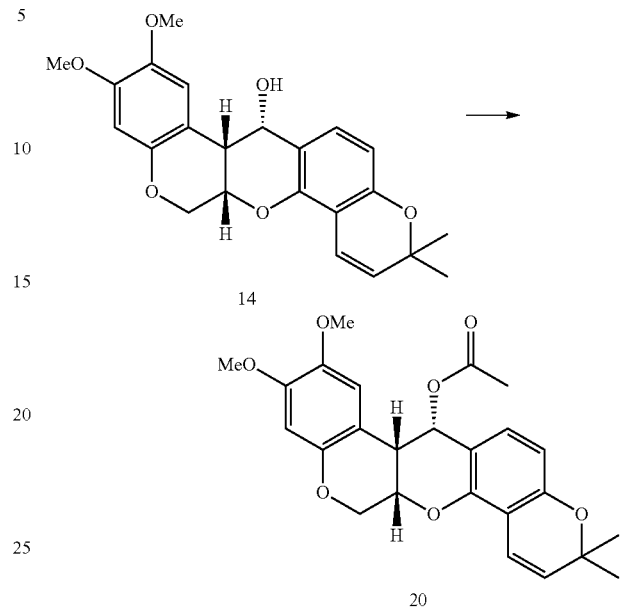

Et$_3$N (0.012 mL, 0.086 mmol) and acetic anhydride (0.06 mL, 0.64 mmol) were added to CH$_2$Cl$_2$ solution (1.0 mL) containing the compound 14 (30 mg, 0.076 mmol) prepared in Example 7 and DMAP (catalytic amount) dissolved therein at 0° C. under argon atmosphere. The reaction mixture was stirred at room temperature for 10 minutes. The reaction mixture was cooled down with saturated NH$_4$Cl aqueous solution, followed by extraction with CH$_2$Cl$_2$. The organic layer of the extract was washed with brine, dried over MgSO$_4$, and concentrated. Then, the obtained residue was purified by flash column chromatography (EtOAc:n-hexane=1:5) to give the compound 20 of Example 13 as a white solid (yield: 82%, 27 mg).

$^1$H-NMR (CDCl$_3$, 500 MHz) δ 7.01 (d, 1H, J=8.3 Hz), 6.63 (s, 1H), 6.63 (d, 1H, J=9.9 Hz), 6.38 (s, 1H), 6.38 (d, 1H, J=7.5 Hz), 6.24 (d, 1H, J=4.4 Hz), 5.56 (d, 1H, J=9.9 Hz), 4.86 (m, 1H), 4.43 (t, 1H, J=10.2 Hz), 4.24 (m, 1H), 3.81 (s, 6H), 3.49 (m, 1H), 1.71 (s, 3H), 1.40 (s, 6H);

$^{13}$C-NMR (CDCl$_3$, 125 MHz) δ170.0, 154.6, 149.3, 148.6, 148.5, 143.4, 130.5, 129.1, 116.2, 111.7, 110.9, 109.7, 109.6, 108.6, 100.1, 76.1, 69.0, 66.7, 64.5, 56.4, 55.8, 36.4, 27.9, 27.8, 20.8;

HRMS (FAB) Calcd for C$_{25}$H$_{26}$O$_7$ (M$^+$): 438.1679, Found: 438.1681.

Example 15: Preparation of (13aS)-9,10-Dimethoxy-3,3-dimethyl-13,13a-dihydro-3H-chromeno[3,4-b]pyrano[2,3-h]chromene (22)

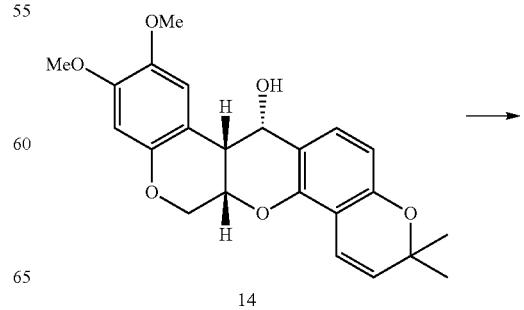

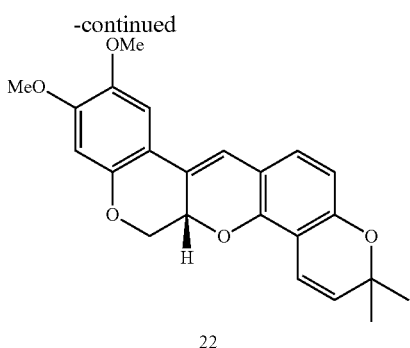

22

Acetic acid solution (1.0 mL) containing the compound (3 mg, 7.6 μmol) prepared in Example 7 dissolved therein was stirred at 100° C. for 2 hours, which was then treated with water (2.0 mL). The mixture was extracted with diethyl ether, and the water layer was extracted again with diethyl ether. The organic layer was washed with brine, dried over MgSO$_4$, filtered, and concentrated under reduced pressure. Then, the obtained residue was purified by flash column chromatography (EtOAc:n-hexane=1:7) to give the compound 22 of Example 15 as a colorless oil (yield: 70%, 2 mg).

$^1$H-NMR (CDCl$_3$, 400 MHz) δ 6.98 (s, 1H), 6.81 (d, 1H, J=8.2 Hz), 6.60 (d, 1H, J=10.0 Hz), 6.55 (s, 1H), 6.40 (s, 1H), 6.36 (d, 1H, J=8.2 Hz), 5.59 (d, 1H, J=10.0 Hz), 5.27 (m, 1H), 4.57 (dd, 1H, J=10.0, 5.4 Hz), 4.13 (t, 1H, J=10.0 Hz), 3.88 (s, 3H), 3.83 (s, 3H), 1.42 (s, 3H), 1.38 (s, 3H);

$^{13}$C-NMR (CDCl$_3$, 100 MHz) δ 153.3, 150.3, 149.2, 148.2, 144.7, 129.7, 126.4, 123.7, 116.6, 116.2, 111.8, 110.6, 109.8, 109.6, 105.2, 100.9, 76.1, 71.1, 67.9, 56.3, 55.9, 28.0, 27.6;

HRMS (FAB) Calcd for C$_{23}$H$_{22}$O$_5$ (M$^+$): 378.1467, Found: 378.1474.

Example 16: Preparation of (7aR,13aS)-9,10-Dimethoxy-3,3-dimethyl-13,13a-dihydro-3H-chromeno[3,4-b]pyrano[2,3-h]chromen-7(7aH)-one oxime (23)

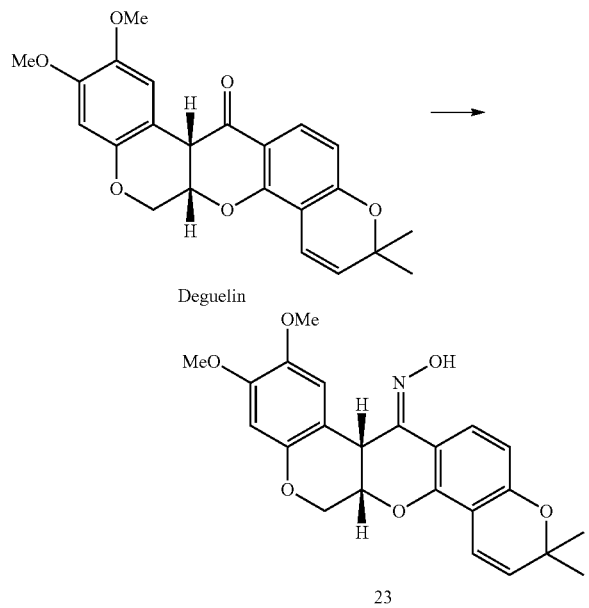

Hydroxylamine hydrochloride (14 mg, 0.19 mmol) was added to anhydrous pyridine (1.0 mL) containing deguelin (25 mg, 0.063 mmol) prepared in Comparative Example 1. The reaction temperature was increased to 70° C. While monitoring with TLC, the reaction mixture was stirred until the reaction was completed. The mixture was cooled down with water (0.5 mL), followed by extraction with CH$_2$Cl$_2$. The organic layer of the extract was washed with 2 N—HCl aqueous solution, water, and brine stepwise. The solvent was eliminated under reduced pressure and the residue was dried over MgSO$_4$, filtered, and concentrated. Then, the obtained residue was purified by flash column chromatography (EtOAc:n-hexane=1:2) to give the compound 23 of Example 16 as a white solid (26 mg).

$^1$H-NMR (CDCl$_3$, 500 MHz) δ 8.26 (br, 1H), 7.59 (d, 1H, J=8.7 Hz), 6.62 (m, 2H), 6.41 (s, 1H), 6.37 (d, 1H, J=8.7 Hz), 5.49 (d, 1H, J=10.0 Hz), 4.84 (d, 1H, J=3.2 Hz), 4.61 (dd, 1H, J=12.0, 2.4 Hz), 4.48 (m, 1H), 4.24 (d, 1H, J=12.0 Hz), 3.79 (s, 3H), 3.72 (s, 3H), 1.39 (s, 3H), 1.34 (s, 3H);

$^{13}$C-NMR (CDCl$_3$, 125 MHz) δ155.7, 151.6, 151.3, 149.3, 147.7, 143.6, 128.6, 124.5, 116.2, 112.2, 110.7, 109.8, 108.2, 106.2, 100.6, 76.5, 69.6, 66.8, 56.4, 55.8, 31.6, 28.1, 27.8;

HRMS (FAB) Calcd for C$_{23}$H$_{23}$NO$_6$ (M$^+$): 409.1525, Found: 409.1513.

Example 17: Preparation of (7aR,13aS)-9,10-Dimethoxy-3,3-dimethyl-13,13a-dihydro-3H-chromeno[3,4-b]pyrano[2,3-h]chromen-7(7aH)-one O-methyloxime (24)

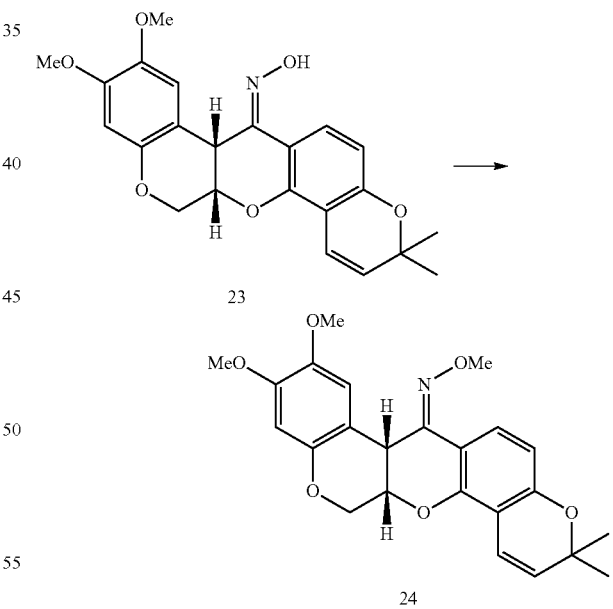

Iodomethane (1.5 equivalent) was added to anhydrous THF solution containing the compound 23 (1 equivalent) prepared in Example 16 at 0° C., to which t-BuOK solution (1 M in THF solution, 1 equivalent) was added drop by drop at 0° C. While monitoring with TLC, the reaction mixture was stirred at 0° C. until the reaction was completed. The mixture was cooled down with saturated NH$_4$Cl aqueous solution, followed by extraction with EtOAc. The organic layer of the extract was dried over MgSO$_4$, filtered, and concentrated under reduced pressure. Then, the obtained residue was purified by flash column chromatography (EtOAc:n-hexane=1:4) to give the compound 24 of Example 17 as a white solid (yield: 57%, 12 mg).

¹H-NMR (CDCl₃, 500 MHz) δ 7.68 (d, 1H, J=8.7 Hz), 6.61 (d, 1H, J=10.0 Hz), 6.51 (s, 1H), 6.38 (m, 2H), 5.48 (d, 1H, J=10.0 Hz), 4.71 (d, 1H, J=3.3 Hz), 4.59 (dd, 1H, J=12.0, 2.4 Hz), 4.45 (m, 1H), 4.21 (d, 1H, J=12.0 Hz), 4.03 (s, 3H), 3.77 (s, 3H), 3.73 (s, 3H), 1.39 (s, 3H), 1.33 (s, 3H);

¹³C-NMR (CDCl₃, 125 MHz) δ155.6, 151.2, 150.0, 149.2, 147.6, 143.5, 128.5, 124.7, 116.3, 111.9, 110.6, 109.7, 108.4, 106.3, 100.5, 76.5, 69.6, 66.9, 61.9, 56.3, 55.8, 32.3, 28.1, 27.8;

HRMS (FAB) Calcd for C₂₄H₂₅NO₆ (M⁺): 423.1682, Found: 423.1677.

Example 18: Preparation of (7aR,13aS)-9,10-Dimethoxy-3,3-dimethyl-13,13a-dihydro-3H-chromeno[3,4-b]pyrano[2,3-h]chromen-7(7aH)-one O-benzyloxime (25)

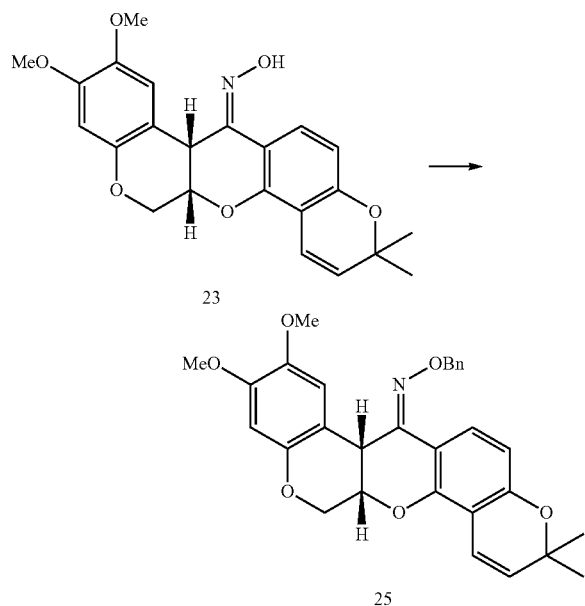

Benzylbromide (1.5 equivalent) was added to anhydrous THF solution containing the compound 23 (1 equivalent) prepared in Example 16 at 0° C., to which t-BuOK solution (1 M in THF solution, 1 equivalent) was added drop by drop at 0° C. While monitoring with TLC, the reaction mixture was stirred at 0° C. until the reaction was completed. The mixture was cooled down with saturated NH₄Cl aqueous solution, followed by extraction with EtOAc. The organic layer of the extract was dried over MgSO₄, filtered, and concentrated under reduced pressure. Then, the obtained residue was purified by flash column chromatography (EtOAc:n-hexane=1:5) to give the compound 25 of Example 18 as a white solid (yield: 33%, 11 mg).

¹H-NMR (CDCl₃, 500 MHz) δ 7.71 (d, 1H, J=8.7 Hz), 7.46 (d, 2H, J=7.1 Hz), 7.31 (m, 3H), 6.62 (d, 1H, J=10.0 Hz), 6.46 (s, 1H), 6.37 (m, 2H), 5.48 (d, 1H, J=10.0 Hz), 5.27 (AB quartet, 2H, J=50.7, 12.0 Hz), 4.76 (d, 1H, J=3.0 Hz), 4.58 (dd, 1H, J=12.0, 2.2 Hz), 4.44 (m, 1H), 4.20 (d, 1H, J=12.0 Hz), 3.78 (s, 3H), 3.48 (s, 3H), 1.40 (s, 3H), 1.33 (s, 3H);

¹³C-NMR (CDCl₃, 125 MHz) δ 155.6, 151.2, 150.1, 149.1, 147.5, 143.5, 137.5, 128.7, 128.7, 128.5, 128.4, 128.4, 128.1, 124.6, 116.3, 111.7, 110.6, 109.7, 108.5, 106.4, 100.5, 76.5, 76.5, 69.6, 66.8, 56.0, 55.7, 32.3, 28.1, 27.8;

HRMS (FAB) Calcd for C₃₀H₂₉NO₆ (M⁺): 499.1995, Found: 499.1999.

Example 20: Preparation of (7aS,13aS)-1,2-Dihydroxy-9,10-dimethoxy-3,3-dimethyl-2,3,13,13a-tetrahydro-1H-chromeno[3,4-b] pyrano[2,3-h]chromen-7(7aH)-one (27)

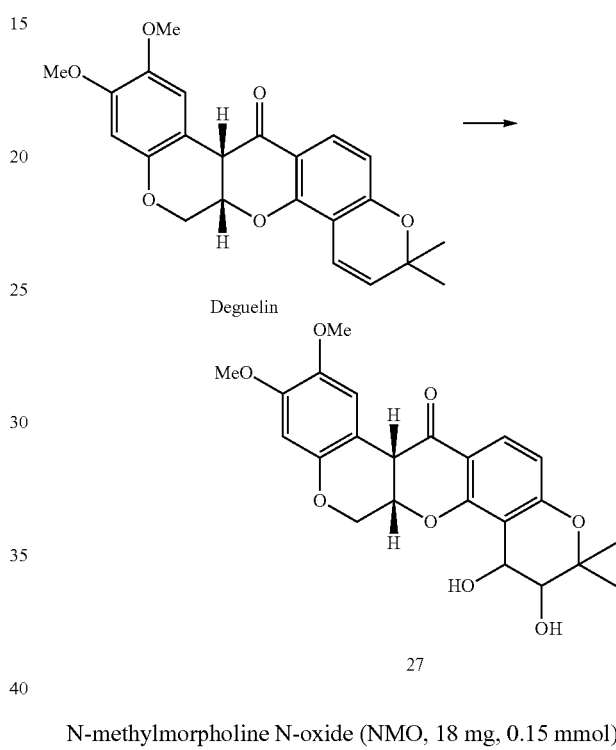

N-methylmorpholine N-oxide (NMO, 18 mg, 0.15 mmol) and OsO₄ (0.1 M in toluene, 0.020 mL, 0.002 mmol) were added to the mixed solution of acetone:water (4.0 mL, 4:1) containing deguelin (20 mg, 0.051 mmol) prepared in Comparative Example 1, followed by stirring at 0° C. for 10 minutes. The mixture was warmed up at room temperature, followed by stirring for 3 days. The mixture was cooled down with sulfite aqueous solution at 0° C., filtered with celite pad, and washed with EtOAc. The organic layer was extracted with EtOAc, dried over MgSO₄, filtered, and concentrated under reduced pressure. Then, the obtained residue was purified by flash column chromatography (EtOAc:n-hexane=2:1~EtOAc 100%) to give the compound 27 of Example 20 as a light-yellow solid (yield: 47%, diastereomer mixture, 10 mg).

(1)isomer A: ¹H-NMR (CDCl₃, 400 MHz) δ 7.76 (d, 1H, J=8.8 Hz), 6.48 (m, 3H), 4.98 (d, 1H, J=4.7 Hz), 4.46 (m, 3H), 4.42 (s, 1H), 3.80 (s, 3H), 3.76 (t, 1H, J=4.7 Hz), 3.71 (s, 3H), 3.45 (br, 1H), 3.34 (d, 1H, J=4.5 Hz), 1.40 (s, 3H), 1.31 (s, 3H); ¹³C-NMR (CDCl₃, 100 MHz) δ 190.7, 160.6, 160.4, 151.2, 148.2, 144.3, 128.7, 113.0, 110.5, 110.0, 109.1, 108.6, 101.1, 79.1, 76.3, 70.4, 67.3, 63.7, 61.9, 56.3, 55.9, 24.3, 22.5;

(2) isomer B: ¹H-NMR (CDCl₃, 400 MHz) δ 7.77 (d, 1H, J=8.8 Hz), 6.47 (m, 3H), 4.97 (d, 1H, J=4.7 Hz), 4.59 (m, 3H), 4.43 (s, 1H), 3.80 (s, 3H), 3.73 (m, 1H), 3.70 (s, 3H), 3.53 (br, 1H), 3.30 (d, 1H, J=4.5 Hz), 1.43 (s, 3H), 1.27 (s, 3H); $^{13}$C-NMR (CDCl$_3$, 100 MHz) δ 190.8, 160.8, 160.6, 151.2, 148.2, 144.1, 128.8, 113.2, 110.8, 109.7, 109.2, 108.4, 101.0, 79.0, 76.7, 70.3, 67.2, 63.8, 62.0, 56.3, 55.8, 24.5, 22.5.

Example 21: Preparation of 2,3,9-Trimethoxy-8-(3-methyl-but-2-enyl)-6a,12a-dihydro-6H-chromeno[3,4-b]chromen-12-one (28)

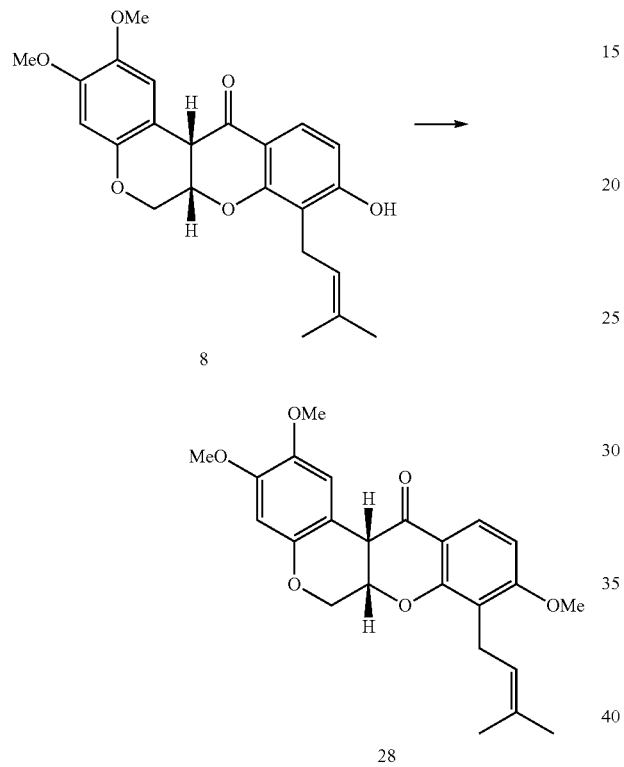

Cesium carbonate (1.5 equivalent) was added to anhydrous acetonitrile solution containing the compound 8 (1 equivalent) prepared in Example 1 and iodomethane (2 equivalent). While monitoring with TLC, the reaction mixture was stirred at 0° C. until the reaction was completed. The mixture was cooled down with water, followed by extraction with EtOAc. The organic layer of the extract was washed with brine, dried over MgSO$_4$, and concentrated under reduced pressure. Then, the obtained residue was purified by flash column chromatography (EtOAc:n-hexane=1:4) to give the compound 28 of Example 21 as a white solid (yield: 41%, 16 mg).

$^1$H-NMR (CDCl$_3$, 500 MHz) δ 7.80 (d, 1H, J=8.8 Hz), 6.74 (s, 1H), 6.56 (d, 1H, J=8.9 Hz), 6.41 (s, 1H), 5.11 (m, 1H), 4.87 (m, 1H), 4.58 (dd, 1H, J=11.9, 3.3 Hz), 4.15 (d, 1H, J=11.9 Hz), 3.83 (s, 3H), 3.81 (d, 1H, J=4.1 Hz), 3.77 (s, 3H), 3.74 (s, 3H), 3.28 (m, 2H), 1.74 (s, 3H), 1.61 (s, 3H);

$^{13}$C-NMR (CDCl$_3$, 125 MHz) δ 190.0, 163.6, 159.2, 149.3, 147.4, 143.6, 131.8, 126.9, 121.6, 117.4, 113.1, 110.3, 105.1, 104.6, 100.7, 71.8, 66.2, 56.2, 55.8, 55.8, 44.3, 25.7, 21.9, 17.6;

HRMS (FAB) Calcd for C$_{24}$H$_{26}$O$_6$ (M$^+$): 410.1732, Found: 410.1735.

Example 22: Preparation of 9-Allyloxy-2,3-dimethoxy-8-(3-methyl-but-2-enyl)-6a,12a-dihydro-6H-chromeno[3,4-b]chromen-12-one (29)

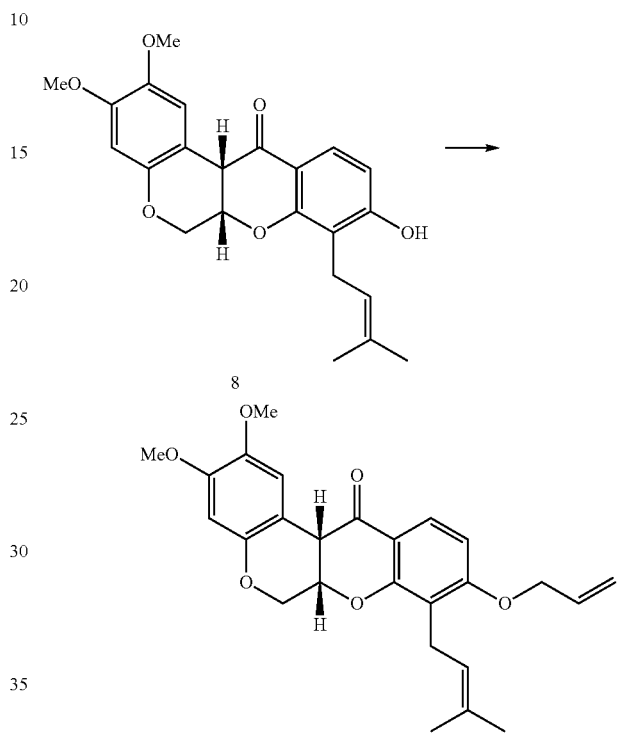

Cesium carbonate (1.5 equivalent) was added to anhydrous acetonitrile solution containing the compound 8 (1 equivalent) prepared in Example 1 and aryliodide (2 equivalent). While monitoring with TLC, the reaction mixture was stirred at 0° C. until the reaction was completed. The mixture was cooled down with water, followed by extraction with EtOAc. The organic layer of the extract was washed with brine, dried over MgSO$_4$, and concentrated under reduced pressure. Then, the obtained residue was purified by flash column chromatography (EtOAc:n-hexane=1:6) to give the compound 29 of Example 22 as a light-yellow solid (yield: 39%, 12 mg).

$^1$H-NMR (CDCl$_3$, 400 MHz) δ 7.78 (d, 1H, J=8.9 Hz), 6.75 (s, 1H), 6.53 (d, 1H, J=8.9 Hz), 6.42 (s, 1H), 5.98 (m, 1H), 5.30 (m, 2H), 5.15 (m, 1H), 4.88 (m, 1H), 4.58 (m, 3H), 4.16 (d, 1H, J=11.8 Hz), 3.81 (d, 1H, J=2.0 Hz), 3.78 (s, 3H), 3.74 (s, 3H), 3.33 (m, 2H), 1.74 (s, 3H), 1.62 (s, 3H);

$^{13}$C-NMR (CDCl$_3$, 100 MHz) δ 190.0, 162.6, 159.4, 149.4, 147.5, 143.7, 132.5, 131.7, 126.8, 121.6, 117.8, 117.6, 113.2, 110.5, 106.2, 104.7, 100.8, 72.0, 69.0, 66.3, 56.3, 55.8, 44.4, 25.7, 22.1, 17.8;

HRMS (FAB) Calcd for C$_{26}$H$_{28}$O$_6$ (M$^+$): 436.1886, Found: 436.1883.

Example 23: Preparation of 9-Benzyloxy-2,3-dimethoxy-8-(3-methyl-but-2-enyl)-6a,12a-dihydro-6H-chromeno[3,4-b]chromen-12-one (30)

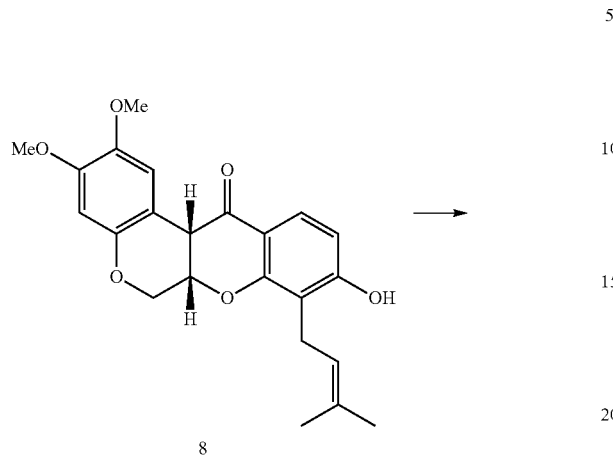

Cesium carbonate (1.5 equivalent) was added to anhydrous acetonitrile solution containing the compound 8 (1 equivalent) prepared in Example 1 and benzylbromide (2 equivalent). While monitoring with TLC, the reaction mixture was stirred at 0° C. until the reaction was completed. The mixture was cooled down with water, followed by extraction with EtOAc. The organic layer of the extract was washed with brine, dried over MgSO$_4$, and concentrated under reduced pressure. Then, the obtained residue was purified by flash column chromatography (EtOAc:n-hexane=1:6) to give the compound 30 of Example 23 as a white solid (yield: 25%, 12 mg).

$^1$H-NMR (CDCl$_3$, 400 MHz) δ 7.78 (d, 1H, J=8.8 Hz), 7.31 (m, 5H), 6.74 (s, 1H), 6.60 (d, 1H, J=8.8 Hz), 6.41 (s, 1H), 5.15 (m, 3H), 4.48 (m, 1H), 4.61 (dd, 1H, J=11.9, 3.0 Hz), 4.16 (d, 1H, J=11.9 Hz), 3.81 (d, 1H, J=4.1 Hz), 3.78 (s, 3H), 3.73 (s, 3H), 3.35 (m, 2H), 1.66 (s, 3H), 1.61 (s, 3H);

$^{13}$C-NMR (CDCl$_3$, 75 MHz) δ 190.0, 162.7, 159.3, 149.4, 147.5, 143.6, 136.3, 131.8, 129.7, 128.6, 128.0, 127.1, 126.9, 122.8, 121.7, 117.9, 113.4, 110.5, 106.3, 104.7, 100.8, 72.0, 70.3, 66.3, 56.3, 55.8, 44.4, 25.7, 22.2, 17.7;

HRMS (FAB) Calcd for C$_{30}$H$_{30}$O$_6$ (M+H$^+$): 487.2121, Found: 487.2113.

Example 24: Preparation of Acetic Acid 2,3-dimethoxy-8-(3-methyl-but-2-enyl)-12-oxo-6,6a,12,12a-tetrahydrochromeno[3,4-b]chromen-9-yl ester (31)

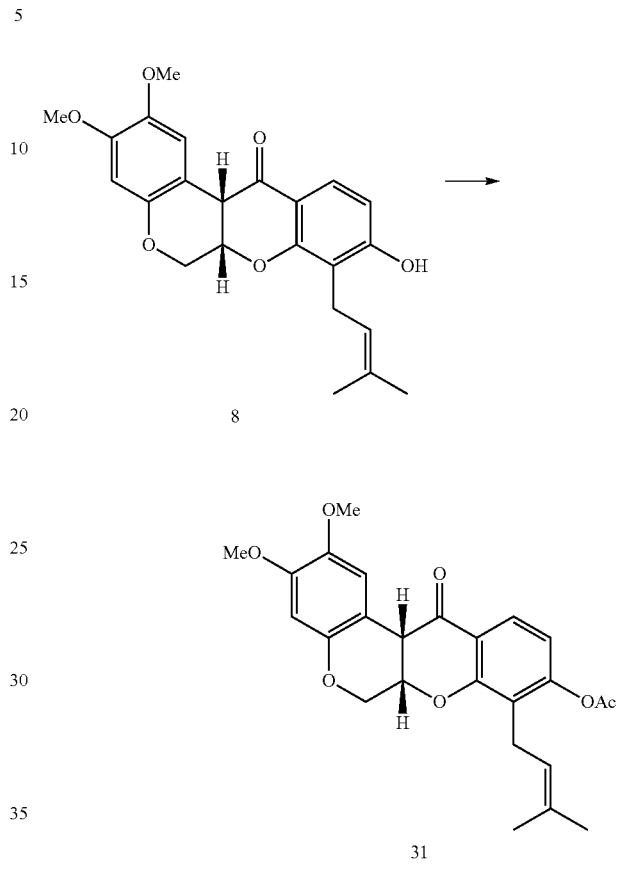

Triethylamine (0.01 mL, 0.07 mmol) and acetic anhydride (0.05 mL, 0.53 mmol) were added to CH$_2$Cl$_2$ solution (1.0 mL) containing the compound 8 (25 mg, 0.063 mmol) prepared in Example 1 and DMAP (catalytic amount) at 0° C. under argon atmosphere. The mixture was stirred at room temperature for 10 minutes. The mixture was cooled down with saturated NH$_4$Cl aqueous solution, followed by extraction with CH$_2$Cl$_2$. The organic layer of the extract was washed with brine, dried over MgSO$_4$, and concentrated under reduced pressure. Then, the obtained residue was purified by flash column chromatography (EtOAc:n-hexane=1:4) to give the compound 31 of Example 24 as a light-yellow oil (yield: 44%, 14 mg).

$^1$H-NMR (CDCl$_3$, 400 MHz) δ 7.80 (d, 1H, J=8.6 Hz), 6.70 (d, 1H, J=8.6 Hz), 6.68 (s, 1H), 6.42 (s, 1H), 5.02 (m, 1H), 4.93 (m, 1H), 4.60 (dd, 1H, J=12.0, 3.2 Hz), 4.17 (d, 1H, J=12.0 Hz), 3.87 (d, 1H, J=4.0 Hz), 3.78 (s, 3H), 3.74 (s, 3H), 3.24 (m, 2H), 2.27 (s, 3H), 1.72 (s, 3H), 1.62 (s, 3H);

$^{13}$C-NMR (CDCl$_3$, 75 MHz) δ 190.1, 168.6, 159.8, 154.9, 149.7, 147.6, 143.9, 132.5, 125.9, 123.0, 120.7, 116.4, 110.5, 104.0, 100.9, 72.3, 66.1, 56.3, 55.8, 44.4, 29.6, 25.6, 23.0, 20.8, 17.7;

HRMS (FAB) Calcd for C$_{25}$H$_{26}$O$_7$ (M$^+$): 438.1679, Found: 438.1681.

Example 25: Preparation of (3S)-3-(3,4-Dimethoxyphenyl)-8,8-dimethyl-2,3-dihydro-4H,8H-pyrano[2,3-f]chromen-4-one (37)

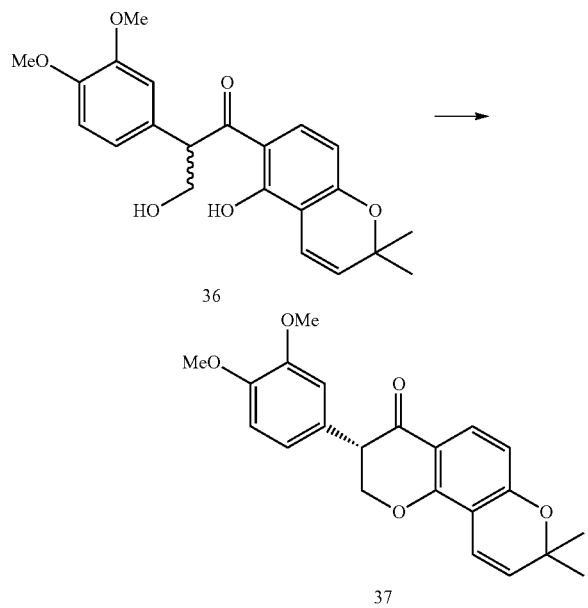

Anhydrous THF solution (0.5 mL) containing triphenylphosphine (65 mg, 0.25 mmol) and diisoppropylazodicarboxylate (0.024 mL, 0.12 mmol) was added to anhydrous THF (1.0 mL) containing the compound 36 (10 mg, 0.026 mmol) prepared in Manufacturing Example 5 under nitrogen atmosphere. While monitoring with TLC, the reaction mixture was stirred until the reaction was completed. The reaction mixture was concentrated under reduced pressure and the obtained residue was purified by flash column chromatography (EtOAc:n-hexane=1:4) to give the compound 37 of Example 25 as a white solid (yield: 58%, 5.5 mg).

$^1$H NMR (CDCl$_3$, 500 MHz) δ 7.74 (d, 1H, J=8.7 Hz), 6.82 (s, 2H), 6.77 (s, 1H), 6.61 (d, 1H, J=10.0 Hz), 6.47 (d, 1H, J=8.7 Hz), 5.58 (d, 1H, J=10.0 Hz), 4.63 (m, 2H), 3.83 (s, 3H), 3.83 (s, 3H), 1.44 (s, 6H);

$^{13}$C NMR (CDCl$_3$, 125 MHz) δ 190.9, 159.5, 157.6, 149.1, 148.5, 128.9, 128.6, 127.8, 120.6, 115.6, 114.7, 111.8, 111.4, 111.2, 109.1, 77.5, 55.8, 51.3, 29.6, 28.2, 28.2, 21.7;

HRMS (FAB) Calcd for C$_{22}$H$_{23}$O$_5$ (M+H$^+$): 367.1545, Found: 367.1552.

Example 26: Preparation of (6,7-Dimethoxychroman-4-yl) (2,2-dimethyl-2H-chromen-6-yl)methanone (45)

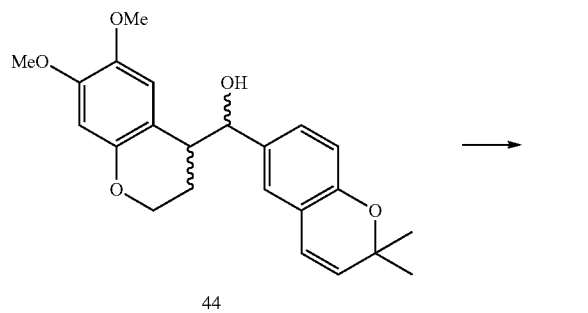

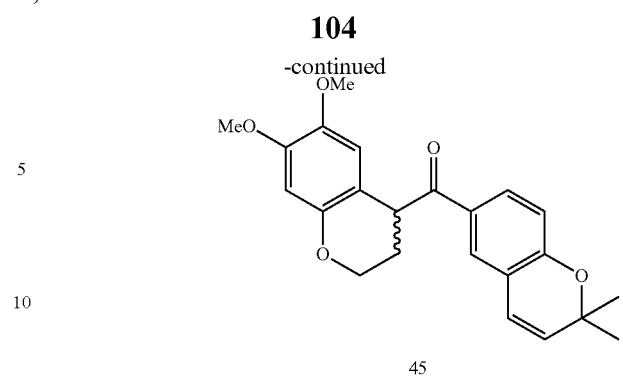

Dess-Martin periodinane (3.0 equivalent) was added to CH$_2$Cl$_2$ (0.03 M) solution containing the compound 44 (1.0 equivalent) obtained in Manufacturing Example 12, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:6) to give the compound 45 of Example 26 (yield: 55%, 9.9 mg).

$^1$H NMR (CDCl$_3$, 500 MHz) δ 7.79 (dd, 1H, J=8.5, 2.1 Hz), 7.66 (d, 1H, J=1.9 Hz), 6.81 (d, 1H, J=8.4 Hz), 6.42 (s, 1H), 6.34 (m, 2H), 5.66 (d, 1H, J=9.9 Hz), 4.61 (t, 1H, J=5.8 Hz), 4.17 (m, 2H), 3.81 (s, 3H), 3.65 (s, 3H), 2.21 (m, 2H), 1.45 (s, 6H);

$^{13}$C NMR (CDCl$_3$, 125 MHz) δ 199.6, 157.7, 149.4, 149.2, 143.3, 131.3, 130.5, 129.0, 127.4, 121.5, 120.9, 116.3, 112.4, 110.6, 101.1, 77.7, 63.4, 56.4, 55.8, 41.6, 28.4, 28.4, 26.5;

HRMS (FAB) Calcd for C$_{23}$H$_{24}$O$_5$ (M$^+$): 380.1624, Found: 380.1621.

Example 27: Preparation of 2-(3,4-Dimethoxyphenyl)-1-(2,2-dimethyl-2H-chromen-6-yl)ethanone (53)

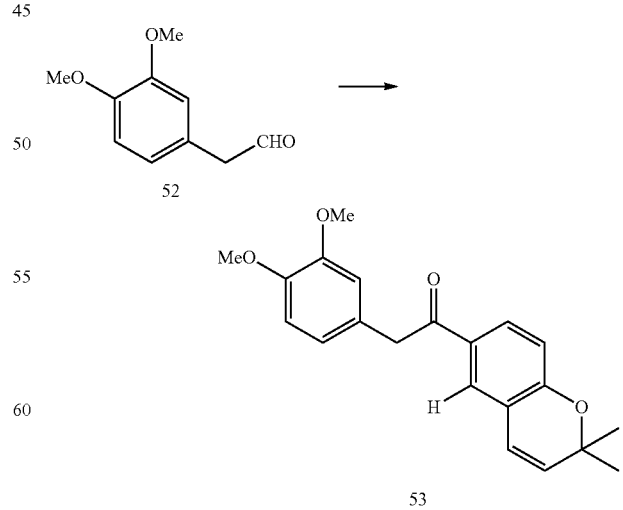

n-BuLi (1.4 equivalent) was added to anhydrous THF solution containing aryl bromide 6-bromo-2,2-dimethyl-2H- chromene (1.5 equivalent) drop by drop at −78° C., which was stirred at −78° C. to generate aryl anions. The mixture was stirred at −78° C. for 20 minutes, to which the compound 52 (1.0 equivalent) prepared in Manufacturing Example 13 was added, followed by stirring for 30 minutes with raising the reaction temperature to room temperature. The reaction mixture was treated with saturated $NH_4Cl$ aqueous solution, followed by extraction with EtOAc. The extract was washed with brine and then dried over $MgSO_4$. The residue obtained after evaporating the solvent was purified by flash column chromatography (EtOAc:n-hexane=1:2) to give the secondary alcohol.

Dess-Martin periodinane (3.0 equivalent) was added to $CH_2Cl_2$ (0.03 M) solution containing the secondary alcohol (1.0 equivalent) obtained above, followed by stirring for 1 hour. The reaction mixture was diluted with $CH_2Cl_2$, to which sodium thiosulfate (10%) was added. The mixture was stirred at room temperature for 10 minutes until the two layers were separated. The obtained organic layer was washed with saturated $NaHCO_3$ aqueous solution and dried over $MgSO_4$. The organic layer was filtered and concentrated under reduced pressure. Then, the obtained residue was purified by flash column chromatography (EtOAc:n-hexane=1:3) to give the compound 53 of Example 27 as a light-yellow solid (yield: 46%, 37 mg).

$^1$H NMR ($CDCl_3$, 400 MHz) δ 7.76 (dd, 1H, J=8.4, 2.2 Hz), 7.62 (d, 1H, J=2.2 Hz), 6.76 (m, 4H), 6.29 (d, 1H, J=9.8 Hz), 5.61 (d, 1H, J=9.8 Hz), 4.10 (s, 2H), 3.80 (s, 3H), 3.79 (s, 3H), 1.40 (s, 6H);
$^{13}$C NMR ($CDCl_3$, 100 MHz) δ 196.3, 157.3, 148.8, 147.7, 131.0, 130.4, 129.4, 127.3, 127.1, 121.5, 121.4, 120.6, 116.0, 112.3, 111.2, 77.4, 55.7, 55.7, 44.5, 28.2 28.2;
HRMS (FAB) Calcd for $C_{22}H_{23}O_4$ ($M+H^+$): 339.1596, Found: 339.1595.

Example 28: Preparation of 2-(3,4-Dimethoxyphenyl)-1-(5-methoxy-2,2-dimethyl-2H-chromen-6-yl) ethanone (54)

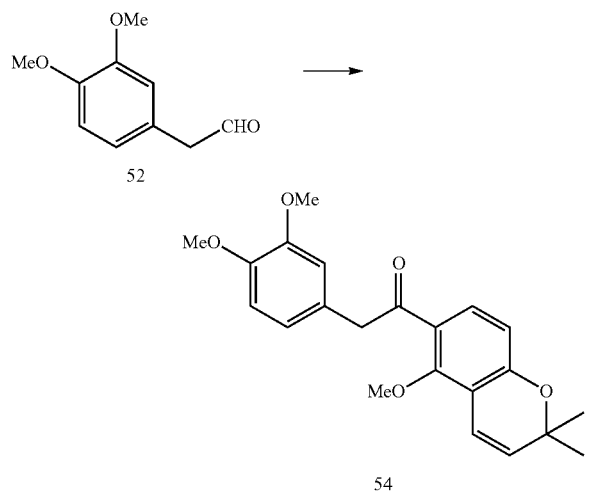

n-BuLi (1.4 equivalent) was added to anhydrous THF solution containing the compound 51 (1.5 equivalent) prepared in Manufacturing Example 27 drop by drop at −78° C., which was stirred at −78° C. to generate aryl anions. The mixture was stirred at −78° C. for 20 minutes, to which the compound 52 (1.0 equivalent) prepared in Manufacturing Example 13 was added, followed by stirring for 30 minutes with raising the reaction temperature to room temperature. The reaction mixture was treated with saturated $NH_4Cl$ aqueous solution, followed by extraction with EtOAc. The extract was washed with brine and then dried over $MgSO_4$. The residue obtained after evaporating the solvent was purified by flash column chromatography (EtOAc:n-hexane=1:2) to give the secondary alcohol.

Dess-Martin periodinane (3.0 equivalent) was added to $CH_2Cl_2$ (0.03 M) solution containing the secondary alcohol (1.0 equivalent) obtained above, followed by stirring for 1 hour. The reaction mixture was diluted with $CH_2Cl_2$, to which sodium thiosulfate (10%) was added. The mixture was stirred at room temperature for 10 minutes until the two layers were separated. The obtained organic layer was washed with saturated $NaHCO_3$ aqueous solution and dried over $MgSO_4$. The organic layer was filtered and concentrated under reduced pressure. Then, the obtained residue was purified by flash column chromatography (EtOAc:n-hexane=1:4) to give the compound 54 of Example 28 as a light-yellow solid (yield: 48%, 80 mg).

$^1$H NMR ($CDCl_3$, 300 MHz) δ 7.43 (d, 1H, J=8.4 Hz), 6.72 (s, 3H), 6.54 (d, 1H, J=9.9 Hz), 6.52 (d, 1H, J=8.4 Hz), 5.62 (d, 1H, J=9.9 Hz), 4.12 (s, 2H), 3.77 (s, 6H), 3.69 (s, 3H), 1.37 (s, 6H);
$^{13}$C NMR ($CDCl_3$, 75 MHz) δ 198.7, 157.7, 156.3, 148.8, 147.8, 131.1, 130.5, 127.6, 124.8, 121.7, 116.5, 114.8, 112.8, 112.6, 111.2, 63.2, 55.8, 55.8, 50.3, 50.2, 28.1, 28.0;
HRMS (FAB) Calcd for $C_{22}H_{25}O_5$ ($M+H^+$): 369.1702, Found: 369.1705.

Example 29: Preparation of 2-(3,4-Dimethoxyphenyl)-1-(5-methoxy-2,2-dimethyl-2H-chromen-6-yl) propan-1-one (56)

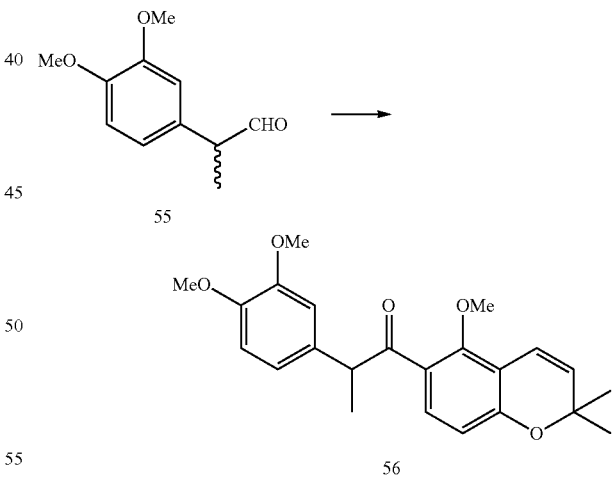

n-BuLi (1.4 equivalent) was added to anhydrous THF solution containing the compound 51 (1.5 equivalent) prepared in Manufacturing Example 27 drop by drop at −78° C., which was stirred at −78° C. to generate aryl anions. The mixture was stirred at −78° C. for 20 minutes, to which the compound 55 (1.0 equivalent) prepared in Manufacturing Example 14 was added, followed by stirring for 30 minutes with raising the reaction temperature to room temperature. The reaction mixture was treated with saturated $NH_4Cl$ aqueous solution, followed by extraction with EtOAc. The extract was washed with brine and then dried over MgSO$_4$. The residue obtained after evaporating the solvent was purified by flash column chromatography (EtOAc:n-hexane=1:2) to give the secondary alcohol.

Dess-Martin periodinane (3.0 equivalent) was added to CH$_2$Cl$_2$ (0.03 M) solution containing the secondary alcohol (1.0 equivalent) obtained above, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:4) to give the compound 56 of Example 29 as a light-yellow solid (yield: 64%, 11 mg).

$^1$H NMR (CDCl$_3$, 500 MHz) δ 7.27 (d, 1H, J=8.5 Hz), 6.76 (m, 3H), 6.55 (d, 1H, J=10.0 Hz), 6.48 (d, 1H, J=8.5 Hz), 5.62 (d, 1H, J=10.0 Hz), 4.60 (q, 1H, J=6.9 Hz), 3.81 (s, 3H), 3.80 (s, 3H), 3.65 (s, 3H), 1.48 (d, 3H, J=6.9 Hz), 1.39 (s, 6H);

$^{13}$C NMR (CDCl$_3$, 75 MHz) δ 202.5, 157.1, 155.7, 149.0, 147.9, 133.8, 130.7, 130.5, 125.5, 120.2, 116.5, 112.3, 111.2, 77.2, 76.7, 63.3, 55.8, 55.7, 50.0, 43.1, 28.0, 28.0, 19.0;

HRMS (FAB) Calcd for C$_{23}$H$_{27}$O$_5$ (M+H$^+$): 383.1858, Found: 383.1853.

Example 30: Preparation of 2-(3,4-Dimethoxyphenyl)-1-(5-methoxy-2,2-dimethyl-2H-chromen-6-yl)-2-methylpropan-1-one (57)

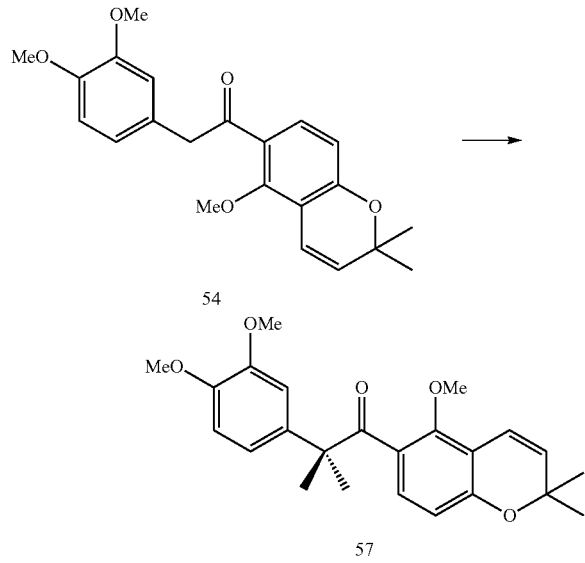

Anhydrous THF solution (1.0 mL) containing the compound 54 (15 mg, 0.041 mmol) obtained in Example 28 was stirred, to which sodium hydride (5.0 mg, 0.12 mmol, 60% in mineral oil) and iodomethane (0.02 mL, 0.16 mmol) were added at room temperature under argon atmosphere. Upon completion of the reaction, the mixture was extracted with EtOAc (2.0 mL×3). The organic layer of the extract was washed with brine, dried over MgSO$_4$, and concentrated under reduced pressure. Then, the obtained residue was purified by flash column chromatography (EtOAc:n-hexane=1:4) to give the compound 57 of Example 30 as a light-yellow solid (yield: 88%, 14 mg).

$^1$H NMR (CDCl$_3$, 400 MHz) δ 6.87 (m, 3H), 6.52 (d, 1H, J=9.9 Hz), 6.21 (q, 2H, J=5.4 Hz), 5.61 (d, 1H, J=9.9 Hz), 3.88 (s, 3H), 3.83 (s, 3H), 3.70 (s, 3H), 1.50 (s, 6H), 1.37 (s, 6H);

$^{13}$C NMR (CDCl$_3$, 100 MHz) δ 206.6, 155.1, 154.1, 148.9, 147.9, 136.2, 130.5, 127.8, 126.7, 118.2, 116.6, 115.0, 111.1, 111.0, 109.8, 77.2, 76.2, 63.6, 55.8, 55.8, 51.6, 27.9, 27.8, 26.3;

HRMS (FAB) Calcd for C$_{24}$H$_{29}$O$_5$ (M+H$^+$): 397.2015, Found: 397.2015.

Example 31: Preparation of 2-(3,4-Dimethoxyphenyl)-1-(5-methoxy-2,2-dimethyl-2H-chromen-6-yl)prop-2-en-1-one (58)

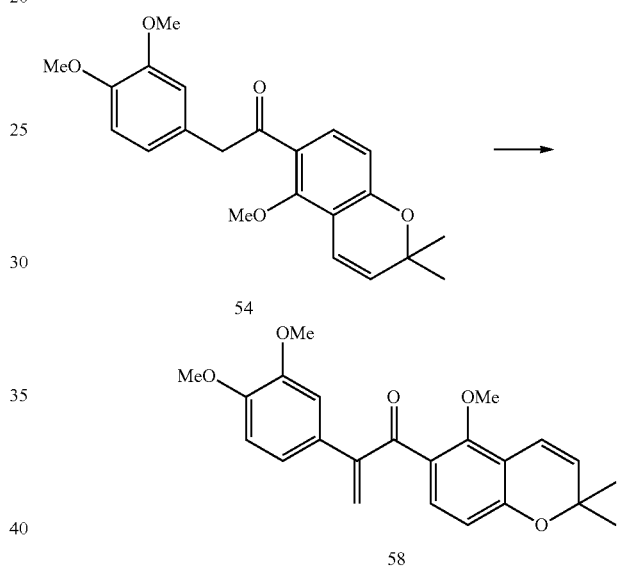

Potassium carbonate (15 mg, 0.11 mmol) was added to anhydrous DMF solution (1 mL) containing the compound 54 (20 mg, 0.054 mmol) prepared in Example 28 at room temperature under nitrogen atmosphere, followed by stirring at room temperature for 40 minutes. Then, paraformaldehyde (3 mg, 0.082 mmol) was added thereto. The mixture was stirred for 4 hours, followed by extraction with EtOAc (2.0 mL×2). The organic extract was washed with saturated NH$_4$Cl aqueous solution and brine, dried over MgSO$_4$, and concentrated under reduced pressure. The obtained residue was purified by flash column chromatography (EtOAc:n-hexane=1:4) to give the compound 58 of Example 31 as a colorless oil (yield: 87%, 18 mg).

$^1$H NMR (CDCl$_3$, 300 MHz) δ 7.30 (d, 1H, J=8.6 Hz), 6.95 (m, 2H), 6.78 (d, 1H, J=8.0 Hz), 6.51 (m, 2H), 5.90 (s, 1H), 5.60 (d, 1H, J=10.0 Hz), 5.55 (s, 1H), 3.81 (s, 3H), 3.80 (s, 3H), 3.70 (s, 3H), 1.38 (s, 6H);

$^{13}$C NMR (CDCl$_3$, 100 MHz) δ 196.5, 157.3, 156.2, 149.4, 149.1, 148.6, 131.7, 130.4, 129.7, 125.0, 121.7, 120.2, 116.5, 114.8, 111.8, 110.9, 110.7, 77.2, 76.8, 63.1, 55.8, 28.0, 27.9;

HRMS (FAB) Calcd for C$_{23}$H$_{25}$O$_5$ (M+H$^+$): 381.1702, Found: 381.1709.

Example 32: Preparation of 1-(3,4-Dimethoxyphenyl)cyclopropyl) (5-methoxy-2,2-dimethyl-2H-chromen-6-yl)methanone (59)

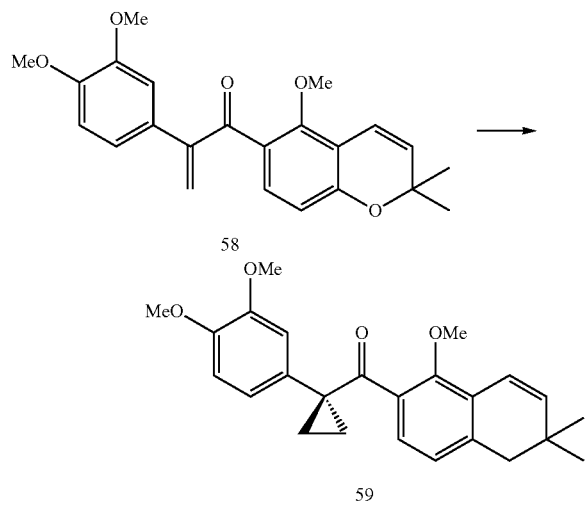

Sodium hydride (1.2 mg, 0.029 mmol, 60% in mineral oil) and trimethylsulfonium iodide (6.5 mg, 0.029 mmol) were added to anhydrous DMSO (0.5 mL) at room temperature under nitrogen atmosphere. The mixture was stirred for 40 minutes, to which anhydrous DMSO (0.5 mL) containing the compound 58 (10 mg, 0.026 mmol) prepared in Example 31 was added. The reaction mixture was stirred for 1 hour, cooled down with saturated NH$_4$Cl aqueous solution, and extracted with EtOAc (×3). The organic layer was washed with saturated NH$_4$Cl aqueous solution and brine, dried over MgSO$_4$, and concentrated under reduced pressure. The obtained residue was purified by flash column chromatography (EtOAc:n-hexane=1:4) to give the compound 59 of Example 32 as a light-yellow solid (yield: 91%, 9 mg).

$^1$H NMR (CDCl$_3$, 500 MHz) δ 6.98 (d, 1H, J=8.4 Hz), 6.78 (m, 2H), 6.67 (d, 1H, J=8.4 Hz), 6.48 (d, 1H, J=10.0 Hz), 6.35 (d, 1H, J=8.4 Hz), 5.58 (d, 1H, J=10.0 Hz), 3.78 (s, 3H), 3.75 (s, 3H), 3.73 (s, 3H), 1.67 (q, 2H, J=4.0 Hz), 1.35 (s, 6H), 1.28 (q, 2H, J=4.0 Hz);

$^{13}$C NMR (CDCl$_3$, 125 MHz) δ 203.6, 155.4, 153.9, 148.4, 147.8, 133.0, 130.4, 128.7, 126.3, 121.4, 116.5, 114.7, 113.6, 111.4, 110.6, 76.2, 63.1, 55.7, 55.7, 37.1, 27.8, 27.8, 17.7, 17.7;

HRMS (FAB) Calcd for C$_{24}$H$_{26}$O$_5$ (M$^+$): 394.1780, Found: 394.1774.

Example 33: Preparation of (S)-2-(3,4-Dimethoxyphenyl)-1-(5-methoxy-2,2-dimethyl-2H-chromen-6-yl)propan-1-one (69)

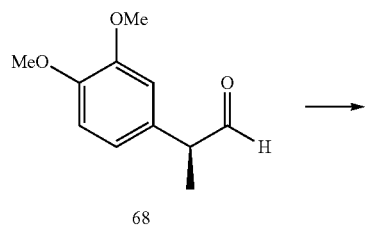

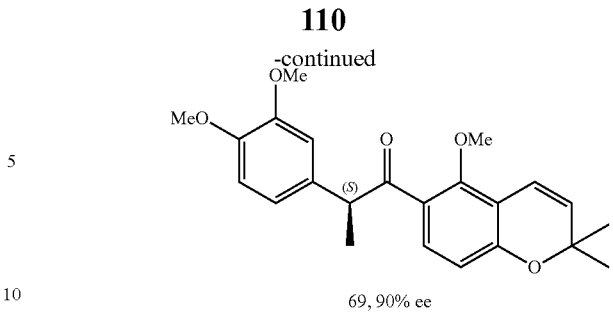

69, 90% ee

CeCl$_3$.7H$_2$O (189 mg, 0.52 mmol) was loaded in 1-neck flask, which was heated slowly until the temperature reached 135~140° C. under reduced pressure (0.1 Torr) with stirring for 2 hours. When the flask was hot, argon gas was injected. Then, the flask was cooled down in an ice water bath. The reaction mixture was stirred vigorously, during which THF (1.0 mL) was added at once. The ice water bath was removed and the suspension was stirred overnight at room temperature under argon atmosphere. The flask was cooled down to −78° C. n-BuLi (0.13 mL, 0.13 mmol) was added to anhydrous THF solution (1.0 mL) containing the compound 51 (61 mg, 0.23 mmol) prepared in Manufacturing Example 27 at −78° C., followed by stirring for 20 minutes. The generated aryl anions were added to the reaction mixture. After stirring the mixture at −78° C. for 1.5 hours, the compound 68 (20 mg, 0.10 mmol) prepared in Manufacturing Example 19 was added to the mixture, followed by stirring for 30 minutes. The reaction mixture was treated with saturated NH$_4$Cl aqueous solution. The generated product was extracted with EtOAc, washed with brine, NaHCO$_3$, and brine stepwise, and dried over anhydrous MgSO$_4$. The solvent was evaporated and the residue was purified by flash column chromatography (EtOAc:n-hexane=1:3) to give the secondary alcohol as a diastereomer mixture (yield: 80%, 32 mg).

isomer A: $^1$H-NMR (Acetone-d$_6$, 300 MHz) δ 7.22 (d, 1H, J=8.4 Hz), 6.73 (m, 3H), 6.50 (m, 2H), 5.69 (d, 1H, J=9.9 Hz), 4.95 (m, 1H), 3.70 (s, 6H), 3.61 (s, 3H), 3.07 (quin, 1H, J=6.8 Hz), 1.35 (s, 6H), 1.28 (d, 3H, J=6.9 Hz);

isomer B: $^1$H-NMR (Acetone-d$_6$, 500 MHz) δ 7.02 (d, 1H, J=8.4 Hz), 6.75 (m, 3H), 6.55 (d, 1H, J=10.0 Hz), 6.43 (d, 1H, J=8.5 Hz), 5.70 (d, 1H, J=9.9 Hz), 4.93 (dd, 1H, J=7.5, 4.0 Hz), 3.72 (s, 3H), 3.72 (s, 3H), 3.71 (s, 3H), 2.95 (quin, 1H, J=7.2 Hz), 1.34 (d, 6H, J=11.8 Hz), 1.06 (d, 3H, J=7.2 Hz).

The secondary alcohol (32 mg, 0.083 mmol) obtained above was dissolved in CH$_2$Cl$_2$ (2.0 mL), to which molecular sieve (41 mg) and N-methylmorpholine-N-oxide (NMO, 15 mg, 0.13 mmol) were added. The mixture was stirred for 10 minutes, to which tetrapropylammonium perruthenate (TPAP, 3 mg, 0.0083 mmol) was added. Upon completion of the reaction, the mixture was diluted with CH$_2$Cl$_2$ and washed with 10% sodium sulfite aqueous solution, brine, and lastly saturated copper (II) sulfate solution. The organic layer was dried over MgSO$_4$, filtered, and concentrated under reduced pressure. The obtained residue was purified by flash column chromatography (EtOAc:n-hexane=1:4) to give the compound 69 of Example 33 (yield: 84%, 27 mg).

$^1$H NMR (CDCl$_3$, 500 MHz) δ 7.27 (d, 1H, J=8.5 Hz), 6.76 (m, 3H), 6.55 (d, 1H, J=10.0 Hz), 6.48 (d, 1H, J=8.5 Hz), 5.62 (d, 1H, J=10.0 Hz), 4.60 (q, 1H, J=6.9 Hz), 3.81 (s, 3H), 3.80 (s, 3H), 3.65 (s, 3H), 1.48 (d, 3H, J=6.9 Hz), 1.39 (s, 6H);

$^{13}$C NMR (CDCl$_3$, 75 MHz) δ 202.5, 157.1, 155.7, 149.0, 147.9, 133.8, 130.7, 130.5, 125.5, 120.2, 116.5, 112.3, 111.2, 77.2, 76.7, 63.3, 55.8, 55.7, 50.0, 43.1, 28.0, 28.0, 19.0;

HRMS (FAB) Calcd for C$_{23}$H$_{27}$O$_5$ (M+H$^+$): 383.1858, Found: 383.1853.

Example 34: Preparation of (R)-2-(3,4-Dimethoxyphenyl)-1-(5-methoxy-2,2-dimethyl-2H-chromen-6-yl)propan-1-one (72)

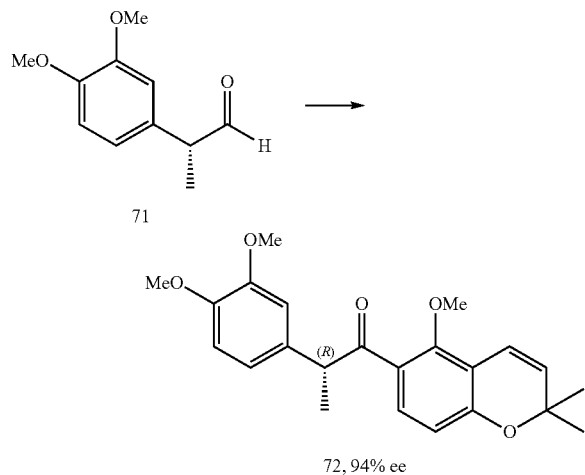

CeCl$_3$.7H$_2$O (125 mg, 0.34 mmol) was loaded in 1-neck flask, which was heated slowly until the temperature reached 135~140° C. under reduced pressure (0.1 Torr) with stirring for 2 hours. When the flask was hot, argon gas was injected. Then, the flask was cooled down in an ice water bath. The reaction mixture was stirred vigorously, during which THF (1.0 mL) was added at once. The ice water bath was removed and the suspension was stirred overnight at room temperature under argon atmosphere. The flask was cooled down to −78° C. n-BuLi (0.084 mL, 0.13 mmol) was added to anhydrous THF solution (1.0 mL) containing the compound 51 (36 mg, 0.14 mmol) prepared in Manufacturing Example 27 at −78° C., followed by stirring for 20 minutes. The generated aryl anions were added to the reaction mixture. After stirring the mixture at −78° C. for 1.5 hours, the compound 71 (13 mg, 0.067 mmol) prepared in Manufacturing Example 21 was added to the mixture, followed by stirring for 30 minutes. The reaction mixture was treated with saturated NH$_4$Cl aqueous solution. The generated product was extracted with EtOAc, washed with brine, NaHCO$_3$, and brine stepwise, and dried over anhydrous MgSO$_4$. The solvent was evaporated and the residue was purified by flash column chromatography (EtOAc:n-hexane=1:3) to give the secondary alcohol as a diastereomer mixture (yield: 48%, 12 mg).

isomer A: $^1$H-NMR (Acetone-d$_6$, 300 MHz) δ 7.22 (d, 1H, J=8.4 Hz), 6.73 (m, 3H), 6.50 (m, 2H), 5.69 (d, 1H, J=9.9 Hz), 4.95 (m, 1H), 3.70 (s, 6H), 3.61 (s, 3H), 3.07 (quin, 1H, J=6.8 Hz), 1.35 (s, 6H), 1.28 (d, 3H, J=6.9 Hz);

isomer B: $^1$H-NMR (Acetone-d$_6$, 500 MHz) δ 7.02 (d, 1H, J=8.4 Hz), 6.75 (m, 3H), 6.55 (d, 1H, J=10.0 Hz), 6.43 (d, 1H, J=8.5 Hz), 5.70 (d, 1H, J=9.9 Hz), 4.93 (dd, 1H, J=7.5, 4.0 Hz), 3.72 (s, 3H), 3.72 (s, 3H), 3.71 (s, 3H), 2.95 (quin, 1H, J=7.2 Hz), 1.34 (d, 6H, J=11.8 Hz), 1.06 (d, 3H, J=7.2 Hz).

The secondary alcohol (14 mg, 0.036 mmol) obtained above was dissolved in CH$_2$Cl$_2$ (1.0 mL), to which molecular sieve (18 mg) and N-methylmorpholine-N-oxide (NMO, 7.0 mg, 0.055 mmol) were added. The mixture was stirred for 10 minutes, to which tetrapropylammonium perruthenate (TPAP, 1.3 mg, 0.0036 mmol) was added. Upon completion of the reaction, the mixture was diluted with CH$_2$Cl$_2$ and washed with 10% sodium sulfite aqueous solution, brine, and lastly saturated copper (II) sulfate solution. The organic layer was dried over MgSO$_4$, filtered, and concentrated under reduced pressure. The obtained residue was purified by flash column chromatography (EtOAc:n-hexane=1:4) to give the compound 72 of Example 34 (yield: 71%, 10 mg).

$^1$H NMR (CDCl$_3$, 500 MHz) δ 7.27 (d, 1H, J=8.5 Hz), 6.76 (m, 3H), 6.55 (d, 1H, J=10.0 Hz), 6.48 (d, 1H, J=8.5 Hz), 5.62 (d, 1H, J=10.0 Hz), 4.60 (q, 1H, J=6.9 Hz), 3.81 (s, 3H), 3.80 (s, 3H), 3.65 (s, 3H), 1.48 (d, 3H, J=6.9 Hz), 1.39 (s, 6H);

$^{13}$C NMR (CDCl$_3$, 75 MHz) δ 202.5, 157.1, 155.7, 149.0, 147.9, 133.8, 130.7, 130.5, 125.5, 120.2, 116.5, 112.3, 111.2, 77.2, 76.7, 63.3, 55.8, 55.7, 50.0, 43.1, 28.0, 28.0, 19.0;

HRMS (FAB) Calcd for C$_{23}$H$_{27}$O$_5$ (M+H$^+$): 383.1858, Found: 383.1849.

Example 35: Preparation of 3-(3,4-Dimethoxyphenyl)-8,8-dimethyl-4H,8H-pyrano[2,3-f]chromen-4-one (80)

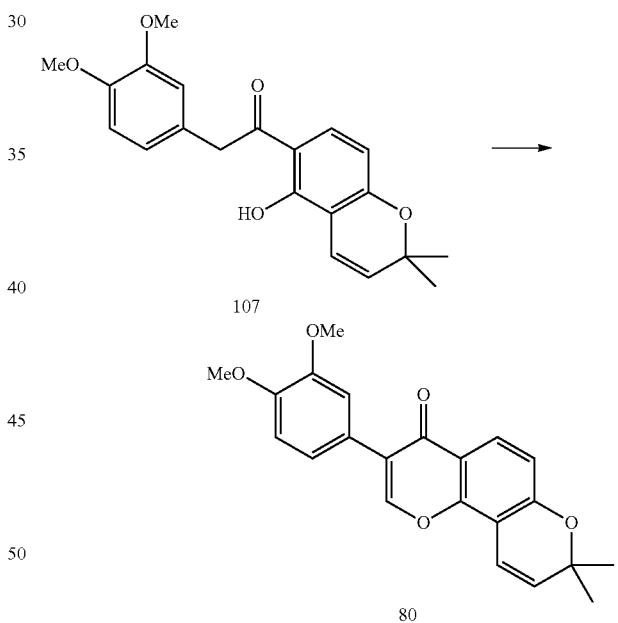

Dimethylaminodimethoxymethane (6.7 μl, 0.051 mmol) was added to anhydrous toluene solution (1.0 mL) containing the compound 107 (15 mg, 0.042 mmol) prepared in Manufacturing Example 32 at room temperature, followed by reflux for 2 hours. The solvent was eliminated under reduced pressure and the obtained residue was purified by flash column chromatography (EtOAc:n-hexane=1:3) to give the compound 80 of Example 35 (yield: 100%, 20 mg).

$^1$H-NMR (CDCl$_3$, 300 MHz) δ 8.00 (d, 1H, J=8.8 Hz), 7.90 (s, 1H), 7.14 (d, 1H, J=2.0 Hz), 6.98 (dd, 1H, J=8.3, 2.0 Hz), 6.86 (d, 1H, J=8.3 Hz), 6.80 (d, 1H, J=9.0 Hz), 6.75 (d, 1H, J=10.0 Hz), 5.66 (d, 1H, J=10.0 Hz), 3.86 (s, 3H), 3.84 (s, 3H), 1.43 (s, 6H);

$^{13}$C-NMR (CDCl$_3$, 100 MHz) δ175.8, 157.2, 152.2, 151.8, 149.0, 148.7, 130.8, 126.6, 124.6, 124.6, 120.9, 118.2, 115.2, 114.8, 112.5, 111.1, 109.1, 77.6, 55.9, 55.8, 28.0, 28.0;

HRMS (FAB) Calcd for C$_{22}$H$_{21}$O$_5$ (M+H$^+$): 365.1389, Found: 365.1394.

Example 36: Preparation of 6,7-Dimethoxy-2H-chromen-4-yl(2,2-dimethyl-2H-chromen-6-yl)methanone (81)

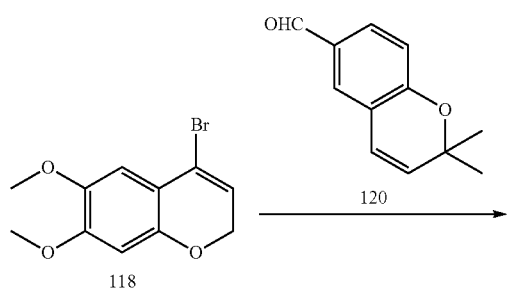

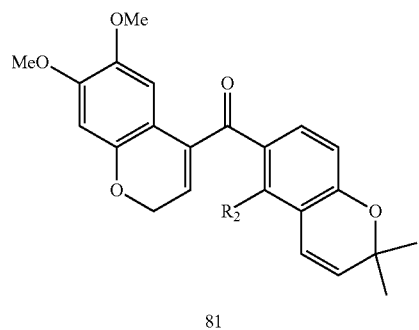

The compound 118 (49 mg, 0.179 mmol) prepared in Manufacturing Example 38 was added to anhydrous THF solution (2.0 mL) under nitrogen atmosphere, to which n-BuLi (0.12 mL, 0.20 mmol, 1.6 M in hexane) was added drop by drop at −78° C. The reaction mixture was stirred at −78° C. for 20 minutes, to which anhydrous THF solution (1.0 mL) containing the compound 120 (78 mg, 0.357 mmol) prepared in Manufacturing Example 37 was added drop by drop by using a cannula. The prepared light-yellow solution was stirred at −78° C. for 20 minutes, followed by extraction with EtOAc (×2). The organic layer was washed with brine, dried over anhydrous sodium sulfate, and concentrated under reduced pressure using a rotary evaporator. The obtained non-purified residue was purified by flash column chromatography (EtOAc:n-hexane=1:10) to give the intermediate secondary alcohol as a light-yellow solid (yield: 61%, 45 mg).

$^1$H NMR (CDCl$_3$, 300 MHz) δ7.15 (dd, 1H, J=8.3, 2.2 Hz), 7.03 (d, 1H, J=2.2 Hz), 6.75 (d, 1H, J=8.3 Hz), 6.62 (s, 1H), 6.41 (s, 1H), 6.26 (d, 1H, J=9.9 Hz), 5.83 (t, 1H, J=4.1 Hz), 5.59 (d, 1H, J=9.9 Hz), 5.52 (br, 1H), 4.77 (m, 2H), 3.79 (s, 3H), 3.62 (s, 3H), 1.39 (s, 6H).

Dess-Martin periodinane (3.0 equivalent) was added to CH$_2$Cl$_2$ (0.03 M) solution containing the secondary alcohol (1.0 equivalent) obtained above, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:5) to give the compound 81 (yield: 87%, 39 mg).

$^1$H NMR (CDCl$_3$, 300 MHz) δ 7.70 (dd, 1H, J=8.4, 2.2 Hz), 7.59 (d, 1H, J=2.2 Hz), 6.91 (s, 1H), 6.77 (d, 1H, J=8.4 Hz), 6.48 (s, 1H), 6.32 (d, 1H, J=9.9 Hz), 5.96 (t, 1H, J=4.0 Hz), 5.65 (d, 1H, J=9.9 Hz), 4.77 (d, 2H, J=4.0 Hz), 3.84 (s, 3H), 3.72 (s, 3H), 1.44 (s, 6H);

$^{13}$C NMR (CDCl$_3$, 100 MHz) δ 193.7, 157.8, 160.0, 148.4, 143.4, 134.7, 132.1, 131.2, 129.7, 128.5, 124.1, 121.4, 120.6, 116.1, 112.0, 108.3, 100.4, 77.7, 64.6, 56.1, 55.9, 28.3, 28.3;

HRMS (FAB) Calcd for C$_{23}$H$_{22}$O$_5$ (M+H$^+$): 378.1467, Found: 378.1475.

Example 37: Preparation of 6,7-Dimethoxy-2,2-dimethyl-2H-chromen-4-yl) (4-methoxy-2,2-dimethyl-2H-chromen-6-yl)methanone (82)

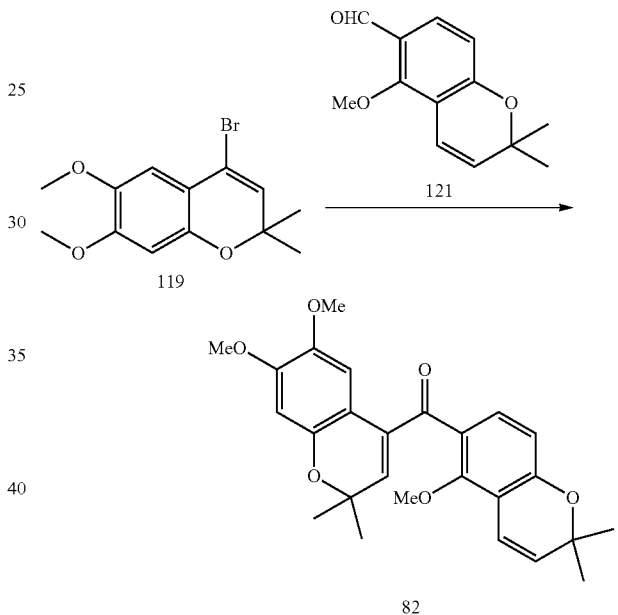

The compound 82 was prepared as a colorless solid by the same manner as described in Example 36 except that the compound 119 was used instead of the compound 118, the compound 121 was used instead of the compound 120, and flash column chromatography (EtOAc:n-hexane=1:4) was used for the purification (yield: 44%, 29 mg).

Secondary alcohol: $^1$H NMR (CDCl$_3$, 300 MHz) δ 7.01 (d, 1H, J=8.2 Hz), 6.59 (s, 1H), 6.56 (d, 1H, J=10.0 Hz), 6.50 (d, 1H, J=8.2 Hz), 6.38 (s, 1H), 5.91 (br, 1H), 5.74 (s, 1H), 5.63 (d, 1H, J=10.0 Hz), 3.88 (s, 3H), 3.77 (s, 3H), 3.62 (s, 3H), 1.45 (s, 3H), 1.43 (s, 3H), 1.39 (s, 6H);

Compound 82: $^1$H NMR (CDCl$_3$, 300 MHz) δ 7.31 (d, J=8.4 Hz, 1H), 7.21 (s, 1H), 6.60 (d, J=9.5 Hz, 1H), 6.57 (d, J=7.9 Hz, 1H), 6.45 (s, 1H), 5.88 (s, 1H), 5.65 (d, J=10 Hz, 1H), 3.83 (s, 3H), 3.75 (s, 3H), 3.72 (s, 3H), 1.43 (s, 6H), 1.42 (s, 6H); $^{13}$C NMR (CDCl$_3$, 75 MHz) δ 194.3, 157.4, 156.3, 150.1, 147.3, 143.1, 136.1, 133.2, 131.8, 130.4, 124.7, 116.5, 114.8, 111.8, 110.7, 108.8, 108.7, 101.1, 77.4, 76.8, 75.4, 63.1, 56.3, 56.8, 28.0, 26.6; HRMS (FAB) Calcd for C$_{26}$H$_{29}$O$_6$ (M+H$^+$): 437.1964, Found: 437.1973.

Example 38: Preparation of 6,7-Dimethoxy-2,2-dimethyl-2H-chromen-4-yl) (2,2-dimethyl-2H-chromen-6-yl)methanone (83)

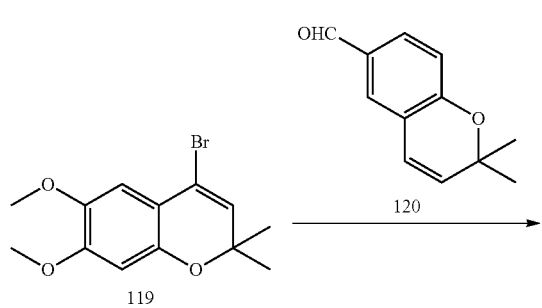

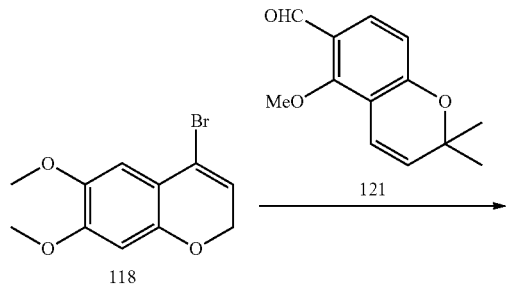

The compound 83 was prepared as a colorless solid by the same manner as described in Example 36 except that the compound 119 was used instead of the compound 118, and flash column chromatography (EtOAc:n-hexane=1:4) was used for the purification (yield: 51%, 35 mg).

Secondary alcohol: $^1$H NMR (CDCl$_3$, 300 MHz) δ 7.09 (dd, 1H, J=8.3 Hz), 6.98 (d, 1H, J=2.0 Hz), 6.50 (s, 1H), 6.35 (s, 1H), 6.21 (d, 1H, 0 J=9.9 Hz), 5.65 (s, 1H), 5.54 (d, 1H, J=9.9 Hz), 5.46 (br, 1H), 3.73 (s, 3H), 3.54 (s, 3H), 1.39 (s, 6H), 1.34 (s, 6H);

Compound 83: $^1$H NMR (CDCl$_3$, 300 MHz) δ 7.68 (dd, 1H, J=8.4, 2.2 Hz), 7.57 (d, 1H, J=2.2 Hz), 6.86 (s, 1H), 6.76 (d, 1H, J=8.4 Hz), 6.46 (s, 1H), 6.32 (d, 1H, J=9.9 Hz), 5.74 (s, 1H), 5.65 (d, 1H, J=9.9 Hz), 3.84 (s, 3H), 3.71 (s, 3H), 1.47 (s, 6H), 1.44 (s, 6H); $^{13}$C NMR (CDCl$_3$, 75 MHz) δ 194.0, 157.8, 150.4, 147.3, 143.2, 132.5, 132.3, 132.1, 131.2, 130.1, 128.5, 121.6, 120.7, 116.1, 108.7, 101.2, 77.7, 77.2, 75.5, 56.4, 55.9, 50.3, 50.3, 28.4, 27.0; HRMS (FAB) Calcd for C$_{25}$H$_{26}$O$_5$ (M+H$^+$): 406.1780, Found: 406.1775.

Example 39: Preparation of 6,7-Dimethoxy-2H-chromen-4-yl) (4-methoxy-2,2-dimethyl-2H-chromen-6-yl)methanone (84)

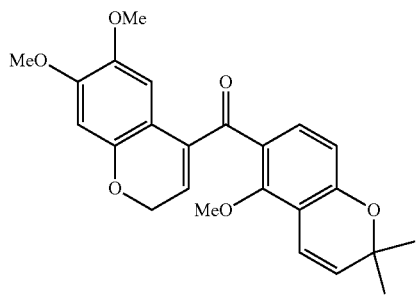

The compound 84 was prepared as a colorless solid by the same manner as described in Example 36 except that the compound 121 was used instead of the compound 120, and flash column chromatography (EtOAc:n-hexane=1:5) was used for the purification (yield: 41%, 22 mg).

Secondary alcohol: $^1$H NMR (CDCl$_3$, 300 MHz) δ 7.01 (d, 1H, J=8.3 Hz), 6.60 (s, 1H), 6.48 (s, 1H), 6.34 (s, 1H), 5.83 (m, 2H), 5.59 (d, 1H, J=9.9 Hz), 4.73 (d, 1H, J=3.8 Hz), 3.81 (s, 3H), 3.73 (s, 3H), 3.60 (s, 3H), 1.34 (s, 6H);

Compound 84: $^1$H NMR (CDCl$_3$, 300 MHz) δ 7.31 (d, J=8.6 Hz, 1H), 7.27 (s, 1H), 6.59 (d, J=10.1 Hz, 1H), 6.56 (d, J=8.0 Hz, 1H), 6.47 (s, 1H), 6.11 (t, J=4.0 Hz, 1H), 5.65 (d, J=10 Hz, 1H), 4.78 (d, J=4.2 Hz, 2H), 3.84 (s, 3H), 3.77 (s, 3H), 3.72 (s, 3H), 1.43 (s, 6H); $^{13}$C NMR (CDCl$_3$, 100 MHz) δ 193.3, 157.3, 156.1, 149.8, 148.6, 143.3, 135.4, 131.6, 130.5, 128.2, 124.3, 116.4, 114.8, 111.8, 111.7, 108.5, 100.3, 77.2, 64.7, 63.1, 56.1, 55.8, 27.9, 27.9; LRMS (FAB) m/z 409 (M+H$^+$).

Example 40: Preparation of 2-(3,4-Dimethoxyphenyl)-1-(5-methoxy-2,2-dimethyl-2H-chromen-6-yl)-2-(phenylsulfonyl)ethanone (86)

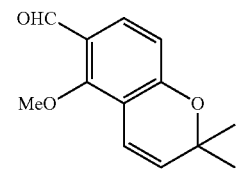

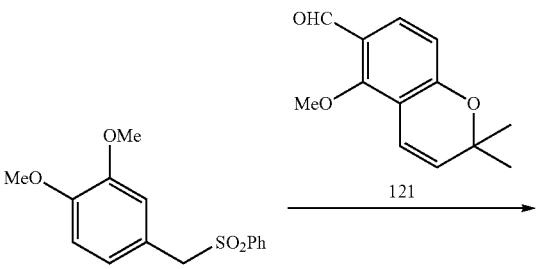

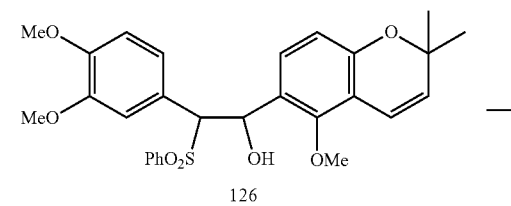

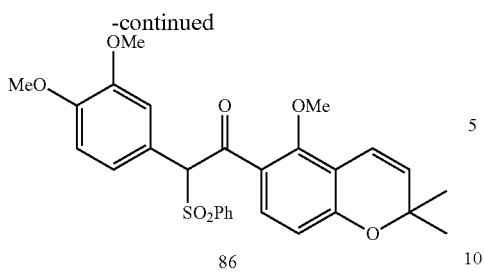

86

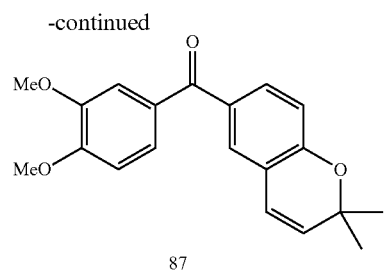

87 n-BuLi (0.26 mL, 0.444 mmol, 1.6 M in hexane) was added drop by drop to anhydrous THF solution (5.0 mL) containing the compound 105 (0.407 mmol) prepared in Manufacturing Example 28 at −78° C., which was stirred at the same temperature for 1 hour. Anhydrous THF (3.0 mL) containing the compound 121 (0.448 mmol) obtained in Manufacturing Example 38 was added slowly to the above reaction mixture at −78° C. One hour later, water was added to the reaction mixture to terminate the reaction, followed by extraction with EtOAc (×3). The extract was washed with brine, dried over anhydrous sodium sulfate, and concentrated under reduced pressure. The obtained non-purified residue (compound 126) was used for the next step without being through purification process.

Dess-Martin periodinane (286 mg, 0.660 mmol) was added to anhydrous $CH_2Cl_2$ (5.0 mL) solution containing the compound 126 (183 mg, 0.339 mmol) obtained above, followed by stirring for 1 hour. The reaction mixture was treated with saturated sodium carbonate solution:saturated sodium thiosulfate solution (1:1, 4 mL), followed by stirring for minutes. The reaction mixture was poured in water, followed by extraction with $CH_2Cl_2$ (×3). The organic layer was dried over $MgSO_4$, filtered and concentrated under reduced pressure. Then, the obtained residue was purified by flash column chromatography (EtOAc:n-hexane=1:2) to give the compound 86 (yield: 63%, 137 mg).

$^1$H NMR (CDCl$_3$, 300 MHz) δ 7.53 (m, 3H), 7.35 (m, 3H), 6.80 (m, 2H), 6.68 (d, J=8.2 Hz, 1H), 6.50 (d, J=8.6 Hz, 1H), 6.45 (d, J=10.1 Hz, 1H), 6.35 (s, 1H), 5.61 (d, J=10.1 Hz, 1H), 3.79 (s, 3H), 3.61 (s, 3H), 3.53 (s, 3H), 1.38 (s, 3H), 1.35 (s, 3H);

$^{13}$C NMR (CDCl$_3$, 100 MHz) δ 206.6, 155.1, 154.1, 148.9, 147.9, 136.2, 130.5, 127.8, 126.7, 118.2, 116.6, 115.0, 111.1, 111.0, 109.8, 77.2, 76.2, 63.6, 55.8, 55.8, 51.6, 27.9, 27.8, 26.3;

HRMS (FAB) Calcd for $C_{24}H_{29}O_5$ (M+H$^+$): 397.2015, Found: 397.2015.

Example 41: Preparation of (3,4-Dimethoxyphenyl) (2,2-dimethyl-2H-chromen-6-yl)methanone (87)

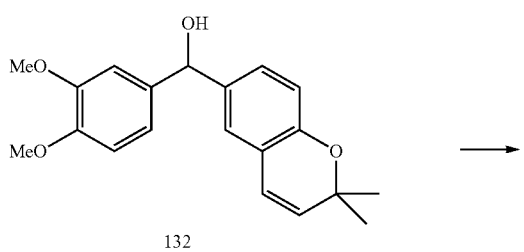

132

Dess-Martin periodinane (3.0 equivalent) was added to $CH_2Cl_2$ (0.03 M) solution containing the compound 132 (1.0 equivalent) obtained in Manufacturing Example 40, followed by stirring for 1 hour. The reaction mixture was diluted with $CH_2Cl_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:8) to give the compound 87 as a colorless solid (yield: 81%, 86 mg).

$^1$H NMR (CDCl$_3$, 300 MHz) δ 7.56 (d, 1H, J=8.4, 2.2 Hz), 7.47 (d, 1H, J=2.2 Hz), 7.41 (d, 1H, J=1.8 Hz), 7.34 (d, 1H, J=8.2, 2.0 Hz), 6.88 (d, 1H, J=8.4 Hz), 6.79 (d, 1H, J=8.4 Hz), 6.34 (d, 1H, J=9.9 Hz), 5.65 (d, 1H, J=9.9 Hz), 3.94 (s, 3H), 3.92 (s, 3H), 1.45 (s, 6H);

$^{13}$C NMR (CDCl$_3$, 100 MHz) δ 194.3, 156.7, 152.5, 148.8, 131.8, 131.1, 130.7, 130.7, 128.5, 124.7, 121.6, 120.5, 115.7, 112.1, 109.7, 77.4, 56.0, 28.3, 28.2;

LRMS (FAB) m/z 325 (M+H$^+$).

Example 42: Preparation of (E)-1-(3,4-Dimethoxyphenyl)-3-(2,2-dimethyl-2H-chromen-6-yl)prop-2-en-1-one (88)

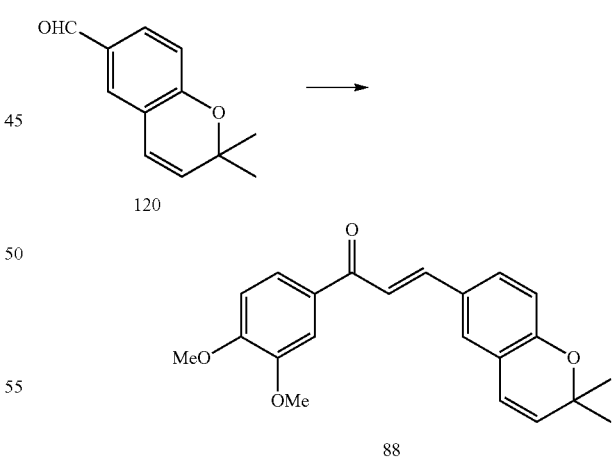

Potassium hydroxide aqueous solution (1.5 equivalent) was added to ethyl alcohol (0.1 M) containing the compound 120 (2.0 equivalent) obtained in Manufacturing Example 37 and 3',4'-dimethoxyphenylacetophenone (1.0 equivalent) at room temperature, followed by reflux for 5 hours. The mixture was cooled down to room temperature. The solvent was eliminated under reduced pressure using a rotary evaporator and the obtained non-purified residue was extracted with EtOAc (×2). The organic layer was washed with brine, dried over anhydrous MgSO$_4$, and concentrated under reduced pressure using a rotary evaporator. The obtained residue was purified by flash column chromatography (EtOAc:n-hexane=1:5) to give the compound 88 as a light-yellow solid (yield: 59%, 29 mg).

$^1$H NMR (CDCl$_3$, 300 MHz) δ 7.62 (m, 3H), 7.35 (m, 2H), 7.21 (d, 1H, J=2.0 Hz), 6.86 (d, 1H, J=8.4 Hz), 6.74 (d, 1H, J=8.4 Hz), 6.29 (d, 1H, J=9.9 Hz), 5.61 (d, 1H, J=9.7 Hz), 3.90 (s, 3H), 3.90 (s, 3H), 1.39 (s, 6H);

$^{13}$C NMR (CDCl$_3$, 100 MHz) δ 188.6, 155.3, 153.0, 149.1, 143.9, 131.6, 131.3, 129.7, 127.7, 123.2, 121.6, 121.3, 119.1, 116.8, 116.0, 110.7, 109.9, 77.1, 56.1, 56.0, 28.2, 28.1.

Example 43: Preparation of (E)-3-(3,4-Dimethoxyphenyl)-1-(5-hydroxy-2,2-dimethyl-2H-chromen-6-yl)prop-2-en-1-one (89)

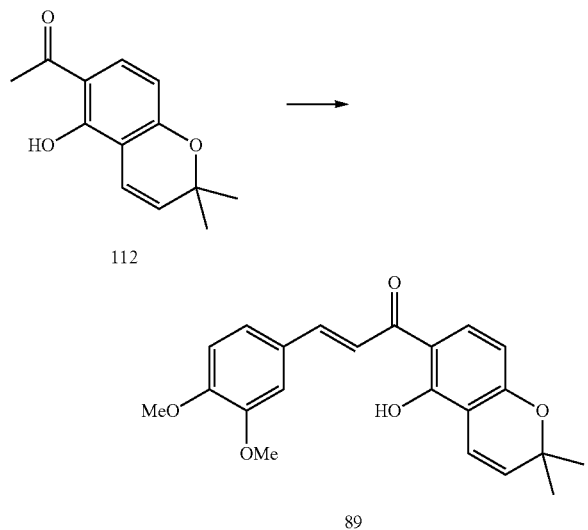

Potassium hydroxide aqueous solution (1.0 mL, 0.5 mM) was added to ethyl alcohol (4.0 mL) containing the compound 112 (100 mg, 0.46 mmol) obtained in Manufacturing Example and 3,4-dimethoxybenzaldehyde (154 mg, 0.92 mmol) at room temperature, followed by reflux for 5 hours. The mixture was cooled down to room temperature and concentrated under reduced pressure. The non-purified residue was extracted with EtOAc (10 mL) and water (5.0 mL). The organic layer was washed with brine, dried over anhydrous MgSO$_4$, and concentrated under reduced pressure. The obtained residue was purified by flash column chromatography (EtOAc:n-hexane=1:4) to give the compound 89 as a white solid (yield: 57%, 95 mg).

$^1$H-NMR (CDCl$_3$, 400 MHz) δ 13.77 (s, 1H), 7.78 (d, 1H, J=15.3 Hz), 7.68 (d, 1H, J=8.8 Hz), 7.37 (d, 1H, J=15.3 Hz), 7.18 (d, 1H, J=8.1 Hz), 7.10 (s, 1H), 6.84 (d, 1H, J=8.3 Hz), 6.71 (d, 1H, J=10.0 Hz), 6.33 (d, 1H, J=8.8 Hz), 5.54 (d, 1H, J=10.0 Hz), 3.90 (s, 3H), 3.88 (s, 3H), 1.42 (s, 6H);

$^{13}$C-NMR (CDCl$_3$, 100 MHz) δ 191.7, 160.8, 159.5, 151.4, 149.1, 144.3, 130.4, 127.9, 127.6, 123.2, 117.8, 115.8, 113.9, 111.0, 110.2, 110.0, 109.3, 108.8, 108.0, 77.6, 55.8, 28.2.

Example 44: Preparation of (E)-3-(3,4-Dimethoxyphenyl)-1-(2,2-dimethyl-2H-chromen-6-yl)prop-2-en-1-one (90)

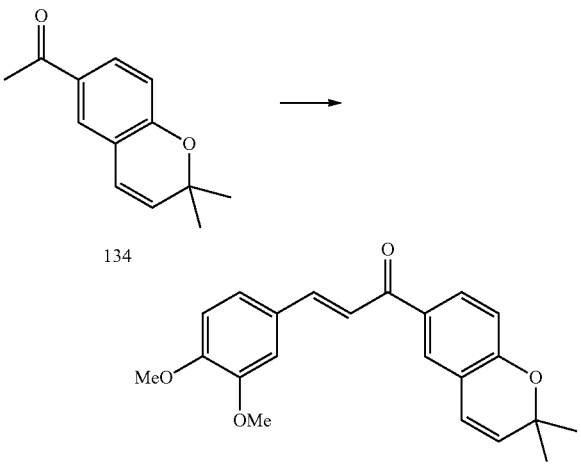

Potassium hydroxide aqueous solution (1.5 equivalent) was added to ethyl alcohol (0.1 M) containing the compound 134 (2.0 equivalent) obtained in Manufacturing Example 42 and 3,4-dimethoxybenzaldehyde (1.0 equivalent) at room temperature, followed by reflux for 5 hours. The mixture was cooled down to room temperature. The solvent was eliminated under reduced pressure using a rotary evaporator and the obtained non-purified residue was extracted with EtOAc (×2). The organic layer was washed with brine, dried over anhydrous MgSO$_4$, and concentrated under reduced pressure using a rotary evaporator. The obtained residue was purified by flash column chromatography (EtOAc:n-hexane=1:4) to give the compound 90 as a light-yellow solid (yield: 57%, 23 mg).

$^1$H NMR (CDCl$_3$, 300 MHz) δ 7.87 (dd, 1H, J=8.4, 2.0 Hz), 7.77 (m, 2H), 7.41 (d, 1H, J=15.5 Hz), 7.24 (m, 2H), 6.92 (d, 1H, J=8.4 Hz), 6.87 (d, 1H, J=8.4 Hz), 6.43 (d, 1H, J=9.9 Hz), 5.71 (d, 1H, J=9.9 Hz), 3.98 (s, 3H), 3.95 (s, 3H), 1.49 (s, 6H);

$^{13}$C NMR (CDCl$_3$, 100 MHz) δ 190.7, 188.5, 157.1, 151.1, 149.1, 143.9, 131.2, 131.0, 130.1, 127.9, 127.0, 122.8, 121.6, 120.7, 119.6, 116.0, 111.0, 110.0, 77.4, 55.8, 28.2, 28.1;

HRMS (FAB) Calcd for C$_{22}$H$_{23}$O$_4$ (M+H$^+$): 351.1596, Found: 351.1590.

Example 45: Preparation of (E)-1-(5-hydroxy-2,2-dimethyl-2H-chromen-6-yl)-3-(2,4,5-trimethoxyphenyl)prop-2-en-1-one (91)

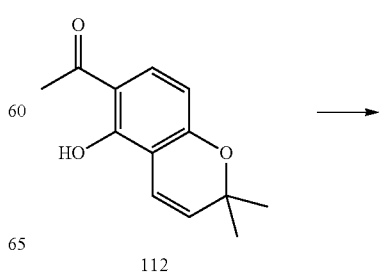

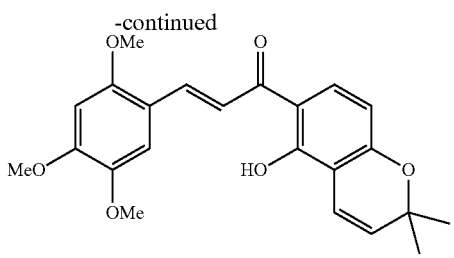

91

The compound 91 was prepared by the same manner as described in Example 43 except that 2,4,5-trimethoxybenzaldehyde was used instead of 3,4-dimethoxybenzaldehyde (yield: 61%, 29 mg).

$^1$HNMR (CDCl$_3$, 300 MHz) δ 7.87 (dd, 1H, J=8.4, 2.0 Hz), 7.77 (m, 2H), 7.41 (d, 1H, J=15.5 Hz), 7.24 (m, 2H), 6.92 (d, 1H, J=8.4 Hz), 6.87 (d, 1H, J=8.4 Hz), 6.43 (d, 1H, J=9.9 Hz), 5.71 (d, 1H, J=9.9 Hz), 3.98 (s, 3H), 3.95 (s, 3H), 1.49 (s, 6H);

$^{13}$C-NMR(CDCl$_3$, 100 MHz) δ 190.7, 188.5, 157.1, 151.1, 149.1, 143.9, 131.2, 131.0, 130.1, 127.9, 127.0, 122.8, 121.6, 120.7, 119.6, 116.0, 111.0, 110.0, 77.4, 55.8, 28.2, 28.1;

HRMS (FAB) Calcd for C$_{22}$H$_{23}$O$_4$(M+H$^+$): 351.1596, Found: 351.1590.

Example 46: Preparation of (E)-3-(3,4-Dimethoxyphenyl)-1-(5-methoxy-2,2-dimethyl-2H-chromen-6-yl)prop-2-en-1-one (92)

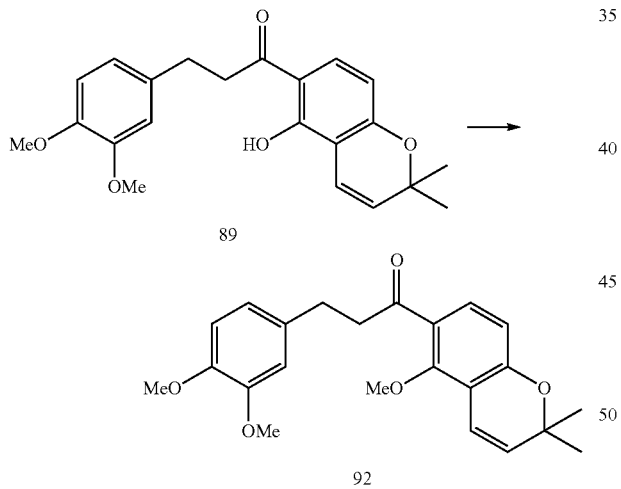

Acetone (0.25 M) mixture containing phenol (1 equivalent), potassium carbonate (3 equivalent) and iodomethane (1.5 equivalent) was refluxed for 4 hours, which was further stirred at room temperature overnight. The mixture was concentrated, treated with water, and extracted with CH$_2$Cl$_2$ (×3). The extract was washed with water and dried over anhydrous MgSO$_4$. The solvent was eliminated under reduced pressure and the obtained non-purified residue was purified by flash column chromatography (EtOAc:n-hexane=1:5) to give the compound 92 as a light-yellow solid (yield: 81%, 18 mg).

$^1$H NMR (CDCl$_3$, 300 MHz) δ 7.60 (d, 1H, J=14.5 Hz), 7.46 (d, 1H, J=8.4 Hz), 7.30 (d, 1H, J=14.5 Hz), 7.12 (m, 2H), 6.82 (d, 1H, J=8.4 Hz), 6.58 (m, 2H), 6.63 (d, 1H, J=10.0 Hz), 3.86 (s, 3H), 3.85 (s, 3H), 1.39 (s, 6H);

HRMS (FAB) Calcd for C$_{23}$H$_{25}$O$_5$ (M+H$^+$): 381.1702, Found: 381.1698.

Example 47: Preparation of (E)-1-(5-methoxy-2,2-dimethyl-2H-chromen-6-yl)-3-(2,4,5-trimethoxyphenyl)prop-2-en-1-one (93)

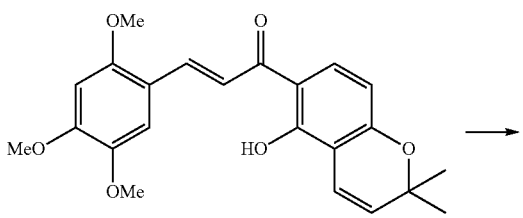

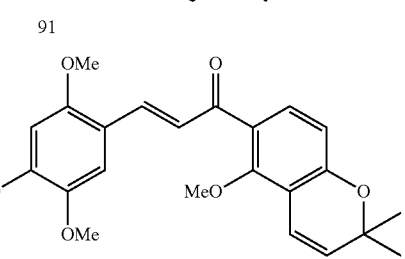

93

The compound 93 was prepared by the same manner as described in Example 46 except that the compound 91 was used instead of the compound 89 (yield: 75%, 20 mg).

$^1$H NMR (CDCl$_3$, 300 MHz) δ 7.96 (d, 1H, J=15.9 Hz), 7.44 (d, 1H, J=8.4 Hz), 7.32 (d, 1H, J=15.9 Hz), 7.05 (s, 1H), 6.57 (m, 1H), 6.44 (s, 1H), 5.62 (d, 1H, J=9.8 Hz), 3.87 (s, 3H), 3.81 (s, 3H), 3.81 (s, 3H), 3.69 (s, 3H), 1.39 (s, 6H);

$^{13}$C-NMR(CDCl$_3$, 100 MHz) δ 191.5, 156.9, 156.0, 154.4, 152.3, 143.2, 138.6, 131.1, 130.4, 126.0, 124.1, 116.6, 115.7, 114.7, 112.4, 110.9, 96.9, 76.7, 63.2, 56.5, 56.4, 56.3, 28.0, 28.0;

HRMS (FAB) Calcd for C$_{24}$H$_{27}$O$_6$ (M+H$^+$): 411.1808, Found: 411.1813.

Example 48: Preparation of 2-(3,4-Dimethoxyphenyl)-8,8-dimethyl-4H,8H-pyrano[2,3-f]chromen-4-one (94)

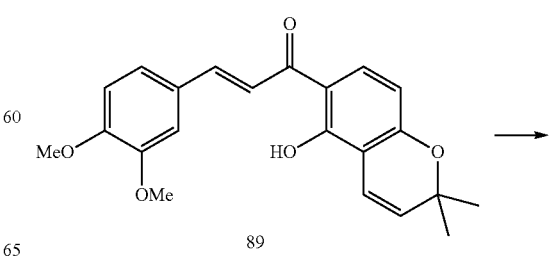

89

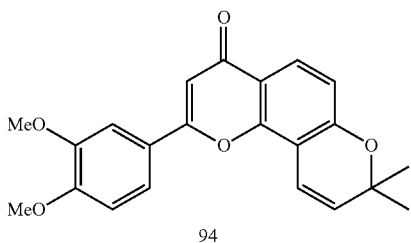

94

Iodide (catalytic amount) was added to anhydrous DMSO (5.0 mL) containing the compound 89 (50 mg, 0.14 mmol) prepared in Example 43 at room temperature. While monitoring with TLC, the reaction mixture was refluxed until the reaction was completed. The mixture was cooled down to room temperature. Then, the mixture was poured in 20% sodium thiosulfate aqueous solution (10 mL), followed by extraction with EtOAc (10 mL). The organic layer was washed with water and brine, dried over anhydrous sodium sulfate, and concentrated under reduced pressure using a rotary evaporator. Then, the obtained residue was purified by flash column chromatography ($CH_2Cl_2$:MeOH=1:10) to give the compound 94 as a white solid (yield: 28%, 14 mg).

$^1$H-NMR (CDCl$_3$, 300 MHz) δ 7.92 (d, 1H, J=8.6 Hz), 7.48 (dd, 1H, J=8.4, 2.0 Hz), 7.29 (d, 1H, J=2.0 Hz), 6.93 (d, 1H, J=8.4 Hz), 6.81 (m, 2H), 6.66 (s, 1H), 5.70 (d, 1H, J=9.8 Hz), 3.91 (s, 3H), 3.90 (s, 3H), 1.45 (s, 6H);

HRMS (FAB) Calcd for $C_{22}H_{21}O_5$ (M+H$^+$): 365.1389, Found: 365.1387.

Example 49: Preparation of 2-(3,4-Dimethoxyphenyl)-N-(5-methoxy-2,2-dimethyl-2H-chromen-6-yl)acet-amide (95)

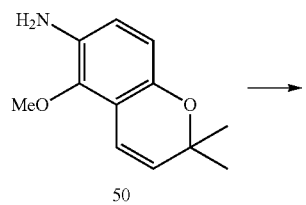

50

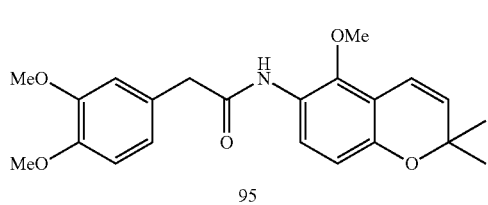

95

N,N-diisopropylethylamine (2.2 equivalent) was added to anhydrous dichloromethane (0.3 M) mixture containing 3',4'-dimethoxyphenylacetic acid (1.0 equivalent), PyBOP (1.0 equivalent) and the compound 50 (1.2 equivalent) obtained in Manufacturing Example 26. The mixture was stirred overnight under nitrogen atmosphere. The solvent was evaporated and the obtained residue was dissolved in EtOAc. The reaction mixture was extracted with 5% HCl aqueous solution, washed with brine, and extracted again with saturated sodium hydrogen carbonate aqueous solution, dried over anhydrous MgSO$_4$, and filtered. The solvent was evaporated and the obtained brown oil residue was purified by flash column chromatography (EtOAc:n-hexane=1:2) to give the compound 95 as a yellow solid (yield: 91%, 31 mg).

$^1$H NMR (CDCl$_3$, 400 MHz) δ 7.93 (d, 1H, J=8.8 Hz), 7.52 (br, 1H), 6.82 (m, 3H), 6.49 (d, 1H, J=8.8 Hz), 6.37 (d, 1H, J=9.9 Hz), 5.57 (d, 1H, J=9.9 Hz), 3.82 (s, 3H), 3.81 (s, 3H), 3.62 (s, 2H), 3.35 (s, 3H), 1.31 (s, 6H);

$^{13}$C NMR (CDCl$_3$, 100 MHz) δ 168.8, 149.5, 149.3, 148.3, 144.8, 131.2, 127.0, 124.2, 121.5, 120.3, 116.2, 114.1, 112.3, 112.0, 111.5, 75.4, 61.4, 55.7, 55.7, 44.3, 27.3, 27.2;

HRMS (FAB) Calcd for $C_{22}H_{25}NO_5$ (M+H$^+$): 384.1811, Found: 384.1806.

Example 50: Preparation of N-(3,4-Dimethoxybenzyl)-2,2-dimethyl-2H-chromene-6-carboxamide (96)

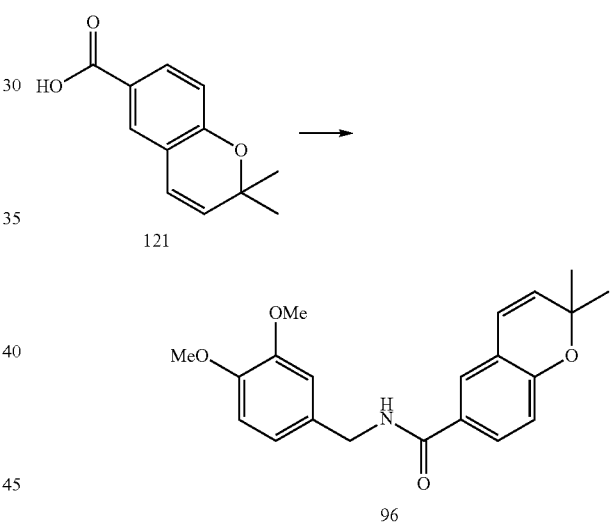

The compound 96 was prepared as a yellow solid by the same manner as described in Example 49 except that N,N-diisopropylethylamine (2.2 equivalent) was added to anhydrous dichloromethane (0.3 M) mixture containing 3,4-dimethoxybenzylamine (1.0 equivalent), PyBOP (1.0 equivalent) and the compound 121 (1.2 equivalent) prepared in Manufacturing Example 38 (yield: 79%, 41 mg).

$^1$H NMR (CDCl$_3$, 400 MHz) δ 7.51 (dd, 1H, J=8.3, 2.0 Hz), 7.43 (d, 1H, J=2.0 Hz), 6.80 (m, 3H), 6.71 (d, 1H, J=8.3 Hz), 6.46 (m, 2H), 5.60 (d, 1H, J=9.8 Hz), 4.49 (d, 1H, J=5.5 Hz), 3.81 (s, 3H), 3.80 (s, 3H), 1.39 (s, 6H);

$^{13}$C NMR (CDCl$_3$, 100 MHz) δ 166.7, 155.8, 149.0, 148.3, 131.2, 130.9, 127.8, 126.6, 125.5, 121.6, 120.8, 120.1, 116.0, 111.2, 111.1, 77.6, 55.8, 55.7, 43.8, 28.1, 28.1;

HRMS (FAB) Calcd for $C_{21}H_{23}NO_4$ (M+H$^+$): 354.1705, Found: 354.1703.

Example 51: Preparation of N-(3,4-Dimethoxyphenyl)-2,2-dimethyl-2H-chromene-6-carboxamide (97)

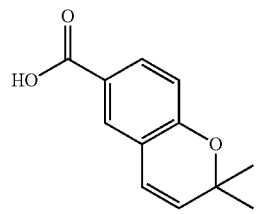

121

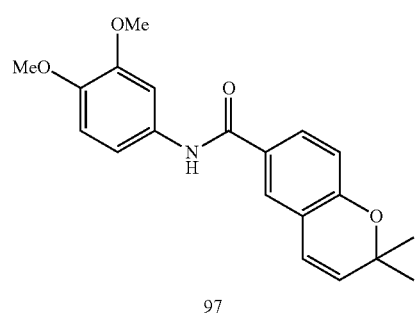

97

The compound 97 was prepared as a yellow solid by the same manner as described in Example 49 except that N,N-diisopropylethylamine (2.2 equivalent) was added to anhydrous dichloromethane (0.3 M) mixture containing 3,4-dimethoxyaniline (1.0 equivalent), PyBOP (1.0 equivalent) and the compound 121 (1.2 equivalent) prepared in Manufacturing Example 38, and flash column chromatography (EtOAc:n-hexane=1:3) was used for the purification (yield: 87%, 29 mg).

$^1$H NMR (CDCl$_3$, 400 MHz) δ 7.89 (s, 1H), 7.53 (dd, 1H, J=8.8, 2.2 Hz), 7.50 (d, 1H, J=2.3 Hz), 7.42 (d, 1H, J=2.2 Hz), 6.96 (dd, 1H, J=8.6, 2.3 Hz), 6.76 (m, 2H), 6.28 (d, 1H, J=9.8 Hz), 5.63 (d, 1H, J=9.8 Hz), 3.82 (s, 6H), 1.42 (s, 6H);

$^{13}$C NMR (CDCl$_3$, 100 MHz) δ 184.5, 165.2, 156.0, 148.9, 145.7, 131.7, 131.4, 127.9, 127.0, 125.6, 121.5, 121.0, 116.2, 112.1, 111.2, 105.9, 77.2, 56.0, 56.0, 55.7, 28.1, 28.1;

HRMS (FAB) Calcd for C$_{20}$H$_{21}$NO$_4$ (M+H$^+$): 340.1549, Found: 340.1542.

Example 52: Preparation of N-(2,2-Dimethyl-2H-chromen-6-yl)-3,4-dimethoxybenzamide (98)

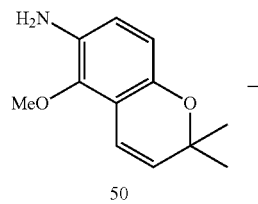

50

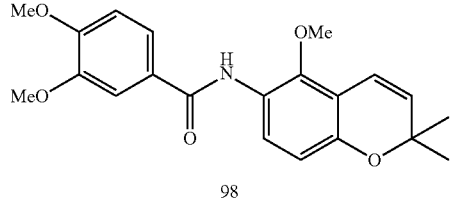

98

N,N-diisopropylethylamine (2.2 equivalent) was added to anhydrous dichloromethane (0.3 M) mixture containing 3',4'-dimethoxybenzoic acid (1.0 equivalent), PyBOP (1.0 equivalent) and the compound 50 (1.2 equivalent) obtained in Manufacturing Example 26. The mixture was stirred overnight under nitrogen atmosphere. The solvent was evaporated and the obtained residue was dissolved in EtOAc. The reaction mixture was extracted with 5% HCl aqueous solution, washed with brine, and extracted again with saturated sodium hydrogen carbonate aqueous solution, dried over anhydrous MgSO$_4$, and filtered. The solvent was evaporated and the obtained brown oil residue was purified by flash column chromatography (EtOAc:n-hexane=1:2) to give the compound 98 as a yellow solid (yield: 60%, 17 mg).

$^1$H NMR (CDCl$_3$, 500 MHz) δ 8.16 (s, 1H), 8.08 (d, 1H, J=8.8 Hz), 7.49 (s, 1H), 7.36 (dd, 1H, J=7.8. 1.8 Hz), 6.89 (d, 1H, J=7.8 Hz), 6.61 (d, 1H, J=8.8 Hz), 6.53 (d, 1H, J=9.9 Hz), 6.57 (d, 1H, J=9.9 Hz), 3.93 (s, 3H), 3.91 (s, 3H), 3.78 (s, 1H), 1.40 (s, 6H);

$^{13}$C NMR (CDCl$_3$, 125 MHz) δ 164.7, 151.9, 149.8, 149.1, 145.4, 131.4, 127.7, 124.6, 121.2, 119.1, 116.5, 114.3, 112.4, 110.7, 110.3, 75.6, 62.0, 56.0, 27.5, 27.5;

LRMS (FAB) m/z 370 (M+H$^+$).

Example 53: Preparation of (R)-2-(3,4-Dimethoxyphenyl)-1-(2,2-dimethyl-2H-chromen-6-yl)propan-1-one (99)

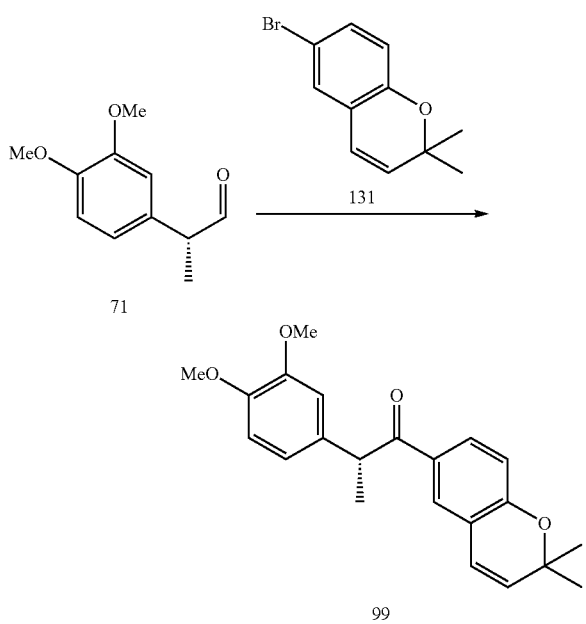

n-BuLi (1.4 equivalent) was added to anhydrous THF solution containing the compound 131 (aryl bromide, 1.5 equivalent) drop by drop at −78° C., which was stirred at −78° C. to generate aryl anions. The mixture was stirred at −78° C. for 20 minutes, to which the compound 71 (1.0 equivalent) prepared in Manufacturing Example 21 was added, followed by stirring for 30 minutes. The reaction mixture was treated with saturated NH$_4$Cl aqueous solution, followed by extraction with EtOAc. The extract was washed with brine and then dried over MgSO$_4$. The residue obtained after evaporating the solvent was purified by flash column chromatography (EtOAc:n-hexane=1:4) to give the secondary alcohol (yield: 48%, 19 mg).

Dess-Martin periodinane (3.0 equivalent) was added to CH$_2$Cl$_2$ (0.03 M) solution containing the secondary alcohol (1.0 equivalent) obtained above, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:5) to give the compound 99 (yield: 85%, 16 mg).

$^1$H NMR (CDCl$_3$, 500 MHz) δ 7.73 (dd, 1H, J=8.4, 1.7 Hz), 7.60 (d, 1H, J=1.6 Hz), 6.78 (m, 3H), 6.68 (d, 1H, J=8.5 Hz), 6.27 (d, 1H, J=9.9 Hz), 5.59 (d, 1H, J=9.9 Hz), 4.54 (q, 1H, J=6.8 Hz), 3.82 (s, 3H), 3.80 (s, 3H), 1.46 (d, 3H, J=6.8 Hz), 1.39 (s, 6H);

$^{13}$C NMR (CDCl$_3$, 125 MHz) δ 198.9, 157.1, 149.2, 147.8, 134.3, 130.9, 130.5, 129.4, 127.3, 121.6, 120.5, 119.9, 115.9, 111.4, 110.5, 77.4, 55.8, 55.7, 46.8, 28.3, 28.3, 19.5;

HRMS (FAB) Calcd for C$_{22}$H$_{24}$O$_4$ (M+H$^+$): 353.1753, Found: 353.1760.

Example 54: Preparation of (S)-2-(3,4-Dimethoxyphenyl)-1-(2,2-dimethyl-2H-chromen-6-yl)propan-1-one (100)

n-BuLi (1.4 equivalent) was added to anhydrous THF solution containing the compound 131 (aryl bromide, 1.5 equivalent) drop by drop at −78° C., which was stirred at −78° C. to generate aryl anions. The mixture was stirred at −78° C. for 20 minutes, to which the compound 68 (1.0 equivalent) prepared in Manufacturing Example 19 was added, followed by stirring for 30 minutes. The reaction mixture was treated with saturated NH$_4$Cl aqueous solution, followed by extraction with EtOAc. The extract was washed with brine and then dried over MgSO$_4$. The residue obtained after evaporating the solvent was purified by flash column chromatography (EtOAc:n-hexane=1:4) to give the secondary alcohol (yield: 59%, 13 mg).

Dess-Martin periodinane (3.0 equivalent) was added to CH$_2$Cl$_2$ (0.03 M) solution containing the secondary alcohol (1.0 equivalent) obtained above, followed by stirring for 1 hour. The reaction mixture was diluted with CH$_2$Cl$_2$, to which sodium thiosulfate (10%) was added. The mixture was stirred at room temperature for 10 minutes until the two layers were separated. The obtained organic layer was washed with saturated NaHCO$_3$ aqueous solution and dried over MgSO$_4$. The organic layer was filtered and concentrated under reduced pressure. Then, the obtained residue was purified by flash column chromatography (EtOAc:n-hexane=1:5) to give the compound 100 (yield: 85%, 9.8 mg, 76% ee).

$^1$H NMR (CDCl$_3$, 500 MHz) δ 7.74 (dd, 1H, J=8.4, 1.7 Hz), 7.60 (d, 1H, J=1.6 Hz), 6.78 (m, 3H), 6.68 (d, 1H, J=8.5 Hz), 6.28 (d, 1H, J=9.9 Hz), 5.59 (d, 1H, J=9.9 Hz), 4.54 (q, 1H, J=6.8 Hz), 3.82 (s, 3H), 3.80 (s, 3H), 1.46 (d, 3H, J=6.8 Hz), 1.40 (s, 32H), 1.39 (s, 3H);

$^{13}$C NMR (CDCl$_3$, 125 MHz) δ 198.9, 157.1, 149.2, 147.8, 134.3, 130.9, 130.5, 129.4, 127.4, 121.7, 120.5, 119.9, 116.0, 111.4, 110.5, 77.5, 55.8, 55.7, 46.8, 28.3, 28.3, 19.6;

HRMS (FAB) Calcd for C$_{22}$H$_{24}$O$_4$ (M+H$^+$): 353.1753, Found: 353.1759.

Example 55: Preparation of (7S,7aR,3aS)-9,10-Dimethoxy-3,3-dimethyl-7-(prop-2-en-oxy)-7,7a,13,13a-tetrahydro-3H-chromeno[3,4-b]pyrano[2,3-h]chromene (101)

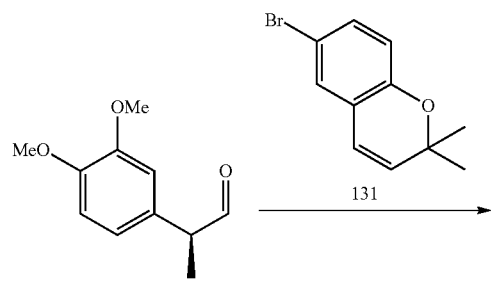

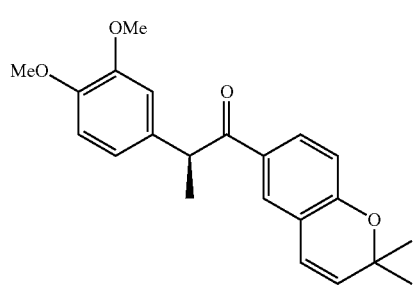

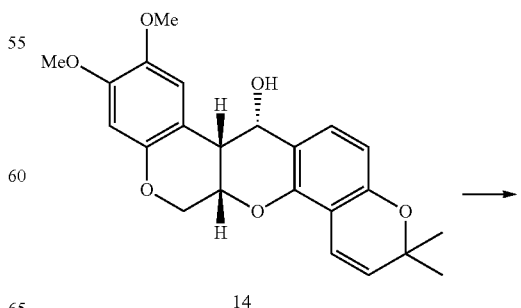

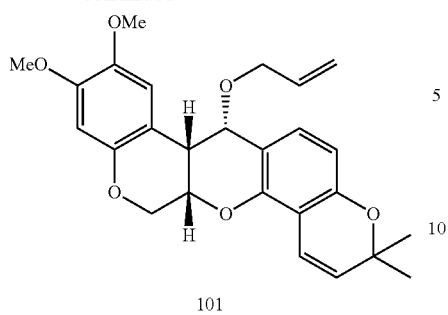

101

3-iodopropene (1.5 equivalent) was added to anhydrous THF solution containing the compound 14 (1 equivalent) prepared in Example 7 at 0° C., to which t-BuOK solution (1 M in THF solution, 1 equivalent) was added drop by drop at 0° C. While monitoring with TLC, the reaction mixture was stirred at 0° C. until the reaction was completed. The mixture was cooled down with saturated NH$_4$Cl aqueous solution, followed by extraction with EtOAc. The organic layer of the extract was dried over MgSO$_4$, filtered, and concentrated under reduced pressure. Then, the obtained residue was purified by flash column chromatography (EtOAc:n-hexane=1:5) to give the compound 101 as a colorless solid (yield: 68%, 15 mg).

$^1$H NMR (CDCl$_3$, 500 MHz) δ 7.93 (d, 1H, J=8.2 Hz), 6.79 (s, 1H), 6.64 (d, 1H, J=9.9 Hz), 6.41 (s, 1H), 6.36 (d, 1H, J=8.2 Hz), 5.66 (m, 1H), 5.54 (d, 1H, J=9.9 Hz), 5.56 (m, 2H), 4.78 (quin, 1H, J=5.3 Hz), 4.57 (m, 2H), 4.23 (dd, 1H, J=9.4, 3.8 Hz) 3.90 (m, 1H), 3.81 (s, 3H), 1.39 (s, 3H);

$^{13}$C NMR (CDCl$_3$, 125 MHz) δ 154.1, 149.1, 149.0, 148.5, 143.4, 134.7, 129.0, 128.9, 116.5, 116.4, 113.9, 111.6, 109.9, 109.9, 108.5, 100.3, 75.9, 73.8, 70.0, 69.6, 65.8, 56.5, 55.7, 37.0, 27.9, 27.8.

Example 56: Preparation of 2-(3,4-difluorophenyl)-1-(5-methoxy-2,2-dimethyl-2H-chromen-6-yl)ethanone

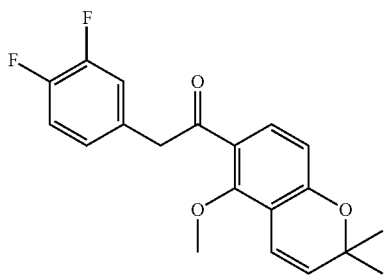

The subject compound is prepared through the same method in said example 28, except using 2-(3,4-Difluoro)acetaldehyde instead of using 2-(3,4-Dimethoxyphenyl)acetaldehyde (Manufacturing Example 13) (yield: 77%, 8.7 mg).

$^1$H NMR (CDCl$_3$, 300 MHz) δ7.49 (d, 1H), J=4.3 Hz), 7.00 (m, 3H), 6.58 (m, 2H), 5.68 (d, 2H, J=4.9 Hz), 4.20 (s, 2H), 3.76 (s, 3H), 1.44 (s, 6H).

Example 57: Preparation of 2-(3,4-difluorophenyl)-1-(5-methoxy-2,2-dimethyl-2H-chromen-6-yl)propan-1-one The subject compound is prepared through the same method in said example 29, except using 2-(3,4-Difluoro)propanal instead of using 2-(3,4-Dimethoxyphenyl)propanal (Manufacturing Example 14) (yield: 76%, 6.7 mg).

$^1$H NMR (CDCl$_3$, 300 MHz) δ7.31 (d, 1H, J=8.6 Hz), 7.05 (m, 3H), 6.54 (m, 2H), 5.65 (d, 1H, J=10.1 Hz), 4.66 (q, 1H, J=7.1 Hz), 3.66 (s, 3H), 1.46 (d, 3H, J=7.0 Hz), 1.41 (s, 6H).

Example 58: Preparation of 2-(2,3-dihydrobenzo[b][1,4]dioxin-6-yl)-1-(5-methoxy-2,2-dimethyl-2H-chromen-6-yl)ethanone The subject compound is prepared through the same method in said example 28, except using 2-(2,3-dihydrobenzo[b][1,4]dioxin-6-yl)acetaldehyde instead of using 2-(3,4-Dimethoxyphenyl)acetaldehyde (Manufacturing Example 13) (yield: 74%, 9.4 mg).

$^1$H NMR (CDCl$_3$, 300 MHz) δ7.48 (d, 1H, J=8.6 Hz), 6.73 (m, 3H), 6.58 (m, 2H), 5.66 (d, 1H, J=10.1 Hz), 4.21 (s, 4H), 4.12 (s, 2H), 1.43 (s, 6H).

Example 59: Preparation of 1-(5-methoxy-2,2-dimethyl-2H-chromen-6-yl)-2-phenylethanone

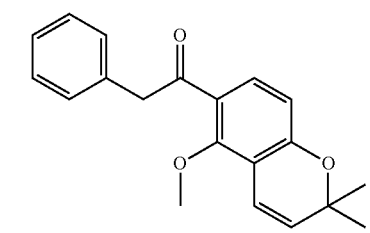 [SMILES: COc1c(C(=O)Cc2ccccc2)ccc2c1C=CC(C)(C)O2]

The subject compound is prepared through the same method in said example 28, except using 2-phenylacetaldehyde instead of using 2-(3,4-Dimethoxyphenyl)acetaldehyde (Manufacturing Example 13) (yield: 75%, 6.2 mg).

¹H NMR (CDCl₃, 300 MHz) δ7.49 (d, 1H, J=8.6 Hz), 7.27 (m, 5H), 6.58 (m, 2H), 5.66 (d, 1H, J=10.1 Hz), 4.24 (s, 2H), 3.74 (s, 3H), 1.43 (s, 6H).

Example 60: Preparation of 2-(2,3-dihydrobenzo[b][1,4]dioxin-6-yl)-1-(5-methoxy-2,2-dimethyl-2H-chromen-6-yl)propan-1-one

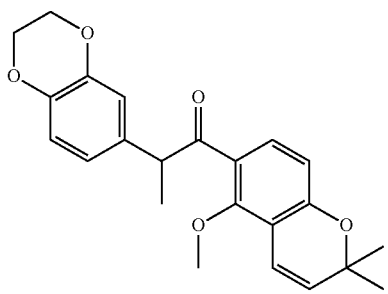 [SMILES: COc1c(C(=O)C(C)c2ccc3c(c2)OCCO3)ccc2c1C=CC(C)(C)O2]

The subject compound is prepared through the same method in said example 29, except using 2-(2,3-dihydrobenzo[b][1,4]dioxin-6-yl)acetaldehyde instead of using 2-(3,4-Dimethoxyphenyl)propanal (Manufacturing Example 14) (yield: 66%, 7.8 mg).

¹H NMR (CDCl₃, 300 MHz) δ7.31 (d, 1H, J=8.4 Hz), 6.76 (s, 2H), 6.72 (s, 2H), 6.53 (m, 2H), 5.63 (d, 1H, J=10.1 Hz), 4.56 (q, 1H, J=7.0 Hz), 4.18 (s, 4H), 3.67 (s, 3H), 1.44 (d, 3H, J=7.0 Hz), 1.40 (s, 6H);

¹³C NMR (CDCl₃, 600 MHz) δ 202.1, 157.1, 155.9, 143.4, 142.3, 134.6, 130.9, 130.4, 125.4, 121.0, 117.2, 116.7, 116.1, 114.8, 112.4, 76.7, 64.3, 64.3, 63.3, 49.6, 28.0, 28.0, 19.1.

Example 61: Preparation of 2-(benzo[d][1,3]dioxol-5-yl)-1-(5-methoxy-2,2-dimethyl-2H-chromen-6-yl)propan-1-one

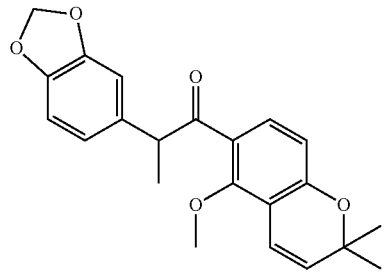 [SMILES: COc1c(C(=O)C(C)c2ccc3c(c2)OCO3)ccc2c1C=CC(C)(C)O2]

The subject compound is prepared through the same method in said example 29, except using 2-(benzo[d][1,3]dioxol-5-yl)acetaldehyde instead of using 2-(3,4-Dimethoxyphenyl)propanal (Manufacturing Example 14) (yield: 61%, 3.7 mg).

¹H NMR (CDCl₃, 300 MHz) δ7.30 (d, 1H, J=8.4 Hz), 6.76 (s, 1H), 6.68 (m, 2H), 6.73 (m, 2H), 5.88 (s, 2H), 5.63 (d, 1H, J=10.1 Hz), 4.59 (q, 1H, J=6.9 Hz), 3.67 (s, 3H), 1.45 (d, 3H, J=7.0 Hz), 1.40 (s, 6H);

¹³C NMR (CDCl₃, 400 MHz) δ202.2, 157.2, 155.8, 147.7, 146.3, 135.1, 130.9, 130.5, 125.1, 121.2, 116.5, 114.8, 112.4, 108.4, 108.3, 100.9, 63.4, 50.0, 29.7, 28.0, 28.0, 19.2.

Example 62: Preparation of 2-(4-(allyloxy)-3-methoxyphenyl)-1-(5-methoxy-2,2-dimethyl-2H-chromen-6-yl)ethanone

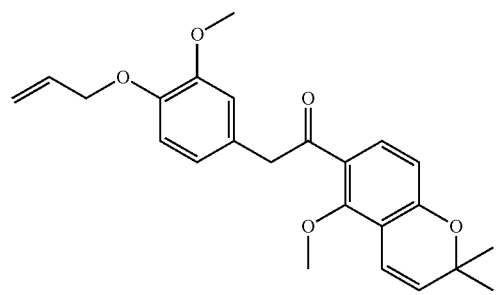 [SMILES: C=CCOc1ccc(CC(=O)c2ccc3c(c2OC)C=CC(C)(C)O3)cc1OC]

The subject compound is prepared through the same method in said example 28, except using 2-(4-(allyloxy)-3-methoxyphenyl)acetaldehyde instead of using 2-(3,4-Dimethoxyphenyl)acetaldehyde (Manufacturing Example 13) (yield: 53%, 4.0 mg).

¹H-NMR (CDCl₃, 300 MHz) δ 7.47 (d, 1H, J=8.6 Hz), 6.80-6.71 (m, 3H), 6.58 (d, 1H, J=9.9 Hz), 6.56 (d, 1H, J=8.6 Hz), 6.04 (m, 1H), 5.66 (m, 1H, J=10.0 Hz), 5.35 (m, 1H), 5.23 (m, 1H), 4.55 (m, 2H), 4.16 (s, 2H), 3.81 (s, 3H), 3.73 (s, 3H), 1.42 (s, 6H).

Example 63: Preparation of 2-(3-(allyloxy)-4-methoxyphenyl)-1-(5-methoxy-2,2-dimethyl-2H-chromen-6-yl)ethanone

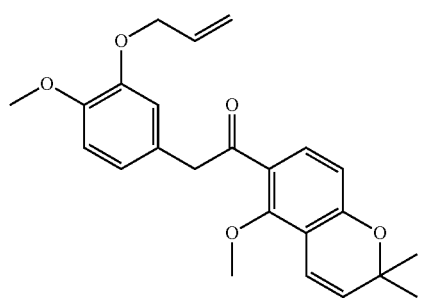

The subject compound is prepared through the same method in said example 28, except using 2-(3-(allyloxy)-4-methoxyphenyl)acetaldehyde instead of using 2-(3,4-Dimethoxyphenyl)acetaldehyde (Manufacturing Example 13) (yield: 37%, 2.9 mg).

¹H-NMR (CDCl₃, 300 MHz) δ 7.45 (d, 1H, J=7.9 Hz), 6.77 (s, 3H), 6.60-6.53 (m, 2H), 6.06 (m, 1H), 5.65 (d, 1H, J=10.0 Hz), 5.34 (ddt, 1H, J=17.1, 1.4, 1.4 Hz), 5.22 (ddt, 1H, J=10.4, 1.2, 1.2 Hz), 4.54 (ddd, 2H, J=5.3, 1.4, 1.4 Hz), 4.14 (s, 2H), 3.81 (s, 3H), 3.73 (s, 3H), 1.42 (s, 6H).

Example 64: Preparation of 2-(2-chlorophenyl)-1-(5-methoxy-2,2-dimethyl-2H-chromen-6-yl)ethanone

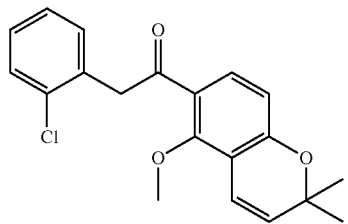 [SMILES: COc1c(C(=O)Cc2ccccc2Cl)ccc2c1C=CC(C)(C)O2]

The subject compound is prepared through the same method in said example 28, except using 2-(2-chlorophenyl)acetaldehyde instead of using 2-(3,4-Dimethoxyphenyl)acetaldehyde (Manufacturing Example 13) (yield: 76%, 5.5 mg).

$^1$H-NMR (CDCl$_3$, 600 MHz) δ 7.59 (d, 1H, J=8.7 Hz), 7.37 (m, 1H), 7.22-7.16 (m, 3H), 6.62 (m, 1H), 6.58 (m, 1H), 5.67 (d, 1H, J=10.0 Hz), 4.40 (s, 2H), 3.83 (s, 3H), 1.44 (s, 6H).

Example 65: Preparation of 2-(3,4-dichlorophenyl)-1-(5-methoxy-2,2-dimethyl-2H-chromen-6-yl)ethanone

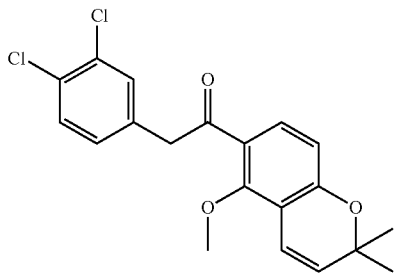 [SMILES: COc1c(C(=O)Cc2ccc(Cl)c(Cl)c2)ccc2c1C=CC(C)(C)O2]

The subject compound is prepared through the same method in said example 28, except using 2-(3,4-dichlorophenyl)acetaldehyde instead of using 2-(3,4-Dimethoxyphenyl)acetaldehyde (Manufacturing Example 13) (yield: 71%, 5.1 mg).

$^1$H-NMR (CDCl$_3$, 300 MHz) δ 7.49 (d, 1H, J=9.0 Hz), 7.35 (d, 1H, J=6.9 Hz), 7.33 (s, 1H), 7.07 (dd, 1H, J=8.4, 2.4 Hz), 6.60-6.56 (m, 2H), 5.68 (d, 1H, J=9.9 Hz), 4.19 (s, 2H), 3.76 (s, 3H), 1.43 (s, 6H);

$^{13}$C-NMR (CDCl$_3$, 75 MHz) δ 196.9, 158.2, 156.6, 135.3, 132.3, 131.6, 131.2, 130.8, 130.6, 130.2, 129.1, 124.4, 116.4, 114.8, 112.9, 77.1, 63.3, 47.5, 28.0, 28.0.

Example 66: Preparation of 2-(3-fluorophenyl)-1-(5-methoxy-2,2-dimethyl-2H-chromen-6-yl)ethanone

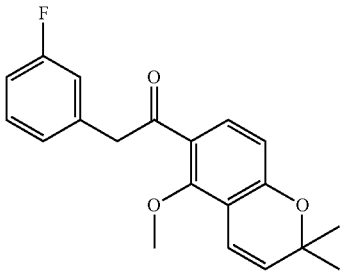 [SMILES: COc1c(C(=O)Cc2cccc(F)c2)ccc2c1C=CC(C)(C)O2]

The subject compound is prepared through the same method in said example 28, except using 2-(3-fluorophenyl)acetaldehyde instead of using 2-(3,4-Dimethoxyphenyl)acetaldehyde (Manufacturing Example 13) (yield: 76%, 6.8 mg).

$^1$H-NMR (CDCl$_3$, 300 MHz) δ 7.49 (d, 1H, J=8.4 Hz), 7.22 (m, 1H), 7.04-6.83 (m, 3H), 6.60 (s, 1H), 6.56 (s, 1H), 5.67 (d, 1H, J=10.2 Hz), 4.23 (s, 2H), 3.75 (s, 3H), 1.43 (s, 6H);

$^{13}$C-NMR (CDCl$_3$, 125 MHz) δ 197.5, 163.7 (d, JC-F=244.0 Hz), 158.0, 156.5, 137.5 (d, JC-F=7.7 Hz), 131.1, 130.5, 129.7 (d, JC-F=8.2 Hz), 125.3 (d, JC-F=2.8 Hz), 124.5, 116.6 (d, JC-F=21.3 Hz), 116.4, 114.8, 113.5 (d, JC-F=20.8 Hz), 112.7, 76.9, 63.2, 48.1 (d, JC-F=1.4 Hz), 28.0, 28.0.

Example 67: Preparation of 2-(2-fluorophenyl)-1-(5-methoxy-2,2-dimethyl-2H-chromen-6-yl)ethanone

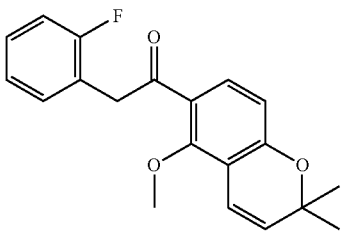 [SMILES: COc1c(C(=O)Cc2ccccc2F)ccc2c1C=CC(C)(C)O2]

The subject compound is prepared through the same method in said example 28, except using 2-(2-fluorophenyl)acetaldehyde instead of using 2-(3,4-Dimethoxyphenyl)acetaldehyde (Manufacturing Example 13) (yield: 79%, 10.1 mg).

$^1$H-NMR (CDCl$_3$, 600 MHz) δ 7.56 (d, 1H, J=8.7 Hz), 7.24-7.19 (m, 2H), 7.09-7.02 (m, 2H), 6.60 (d, 1H, J=2.2 Hz), 6.59 (d, 1H, J=4.1 Hz), 5.67 (d, 1H, J=10.0 Hz), 4.30 (s, 2H), 3.81 (s, 3H), 1.43 (s, 6H);

$^{13}$C-NMR (CDCl$_3$, 150 MHz) δ 196.5, 161.9 (d, JC-F=244 Hz), 157.9, 156.6, 131.8 (d, JC-F=4.3 Hz), 131.1, 130.5, 128.6 (d, JC-F=7.8 Hz), 124.5, 123.9 (d, JC-F=21.5 Hz), 122.6 (d, JC-F=15.8 Hz), 116.5, 115.16 (d, JC-F=21.5 Hz), 114.8, 112.7, 76.8, 63.1, 42.1, 27.9, 27.9.

Example 68: Preparation of 2-(3-chlorophenyl)-1-(5-methoxy-2,2-dimethyl-2H-chromen-6-yl)ethanone

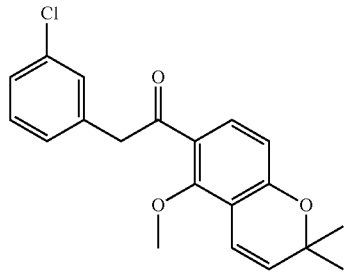 [SMILES: COc1c(C(=O)Cc2cccc(Cl)c2)ccc2c1C=CC(C)(C)O2]

The subject compound is prepared through the same method in said example 28, except using 2-(3-chlorophenyl) acetaldehyde instead of using 2-(3,4-Dimethoxyphenyl)acetaldehyde (Manufacturing Example 13) (yield: 81%, 9.9 mg).

$^1$H-NMR (CDCl$_3$, 600 MHz) δ 7.50 (d, 1H, J=8.7 Hz), 7.22-7.18 (m, 3H), 7.12 (m, 1H), 6.59 (s, 1H), 6.57 (d, 1H, J=2.2 Hz), 5.67 (d, 1H, J=10.0 Hz), 4.21 (S, 2H), 3.75 (s, 3H), 1.43 (s, 6H);

$^{13}$C-NMR (CDCl$_3$, 125 MHz) δ 197.3, 158.0, 156.5, 137.0, 134.1, 131.1, 130.6, 129.7, 129.5, 127.8, 126.8, 124.5, 116.4, 114.8, 112.8, 76.9, 63.2, 48.0, 28.0, 28.0.

Example 69: Preparation of 1-(5-methoxy-2,2-dimethyl-2H-chromen-6-yl)-2-(2-(trifluoromethyl)phenyl)ethanone

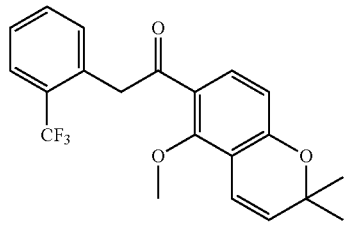

The subject compound is prepared through the same method in said example 28, except using 2-(2-(trifluoromethyl)phenyl)acetaldehyde instead of using 2-(3,4-Dimethoxyphenyl)acetaldehyde (Manufacturing Example 13) (yield: 77%, 5.6 mg).

$^1$H-NMR (CDCl$_3$, 500 MHz) δ 7.65 (d, 1H, J=7.7 Hz), 7.58 (d, 1H, J=8.6 Hz), 7.50 (t, 1H, J=7.4 Hz), 7.36 (t, 1H, J=7.6 Hz), 7.28 (d, 1H, J=7.6 Hz), 6.61 (t, 2H, J=8.0 Hz), 5.68 (d, 1H, J=10.0 Hz), 4.48 (s, 2H), 3.83 (s, 3H), 1.44 (s, 6H);

$^{13}$C-NMR (CDCl$_3$, 125 MHz) δ 196.2, 158.1, 156.7, 133.8 (d, JC-F=1.6 Hz), 133.0, 131.6, 131.1, 130.5, 129.0 (q, JC-F=29.5 Hz), 126.9, 125.9 (q, JC-F=10.9 Hz), 124.4 (q, JC-F=272 Hz), 124.3, 116.6, 114.8, 112.8, 76.9, 63.1, 46.0, 28.0, 28.0;

HR-MS (FAB) calcd for C21H20F3O3 (M+H$^+$) 377.1365; found 377.1372.

Example 70: Preparation of 1-(5-methoxy-2,2-dimethyl-2H-chromen-6-yl)-2-(3-(trifluoromethyl)phenyl)ethanone

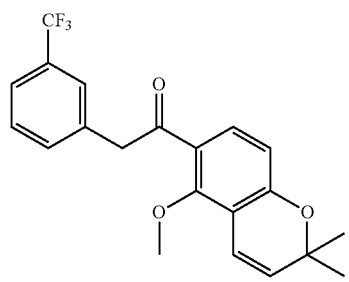 [SMILES: COc1c(C(=O)Cc2cccc(C(F)(F)F)c2)ccc2c1C=CC(C)(C)O2]

The subject compound is prepared through the same method in said example 28, except using 2-(3-(trifluoromethyl)phenyl)acetaldehyde instead of using 2-(3,4-Dimethoxyphenyl)acetaldehyde (Manufacturing Example 13) (yield: 76%, 7.9 mg).

$^1$H-NMR (CDCl$_3$, 500 MHz) δ 7.52-7.39 (m, 5H), 6.60-6.57 (m, 2H), 5.68 (d, 1H, J=10.0 Hz), 4.30 (s, 2H), 3.76 (s, 3H), 1.43 (s, 6H);

$^{13}$C-NMR (CDCl$_3$, 125 MHz) δ 197.2, 158.1, 156.6, 136.0, 133.1, 131.1, 130.7 (q, JC-F=31.9 Hz), 130.6, 128.7, 126.4 (q, JC-F=3.8 Hz), 124.5, 124.1 (q, JC-F=270 Hz), 123.5 (q, JC-F=3.7 Hz), 116.4, 114.8, 112.9, 77.2, 63.2, 48.2, 28.0, 28.0.

Example 71: Preparation of 1-(5-methoxy-2,2-dimethyl-2H-chromen-6-yl)-2-(4-nitrophenyl)ethanone

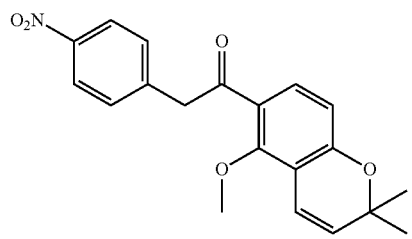

The subject compound is prepared through the same method in said example 28, except using 2-(4-nitrophenyl) acetaldehyde instead of using 2-(3,4-Dimethoxyphenyl)acetaldehyde (Manufacturing Example 13) (yield: 45%, 4.1 mg).

$^1$H-NMR (CDCl$_3$, 500 MHz) δ 8.14 (d, 2H, J=8.5 Hz), 7.51 (d, 1H, J=8.6 Hz), 7.39 (d, 2H, J=8.5 Hz), 6.59 (d, 1H, J=8.9 Hz), 6.57 (d, 1H, J=10.3 Hz), 5.68 (d, 1H, J=10.0 Hz), 4.35 (s, 2H), 3.77 (s, 3H), 1.43 (s, 6H);

$^{13}$C-NMR (CDCl$_3$, 125 MHz) δ 196.3, 158.4, 156.7, 146.8, 142.8, 131.2, 130.7, 130.6, 130.6, 124.1, 123.5, 123.5, 116.3, 114.8, 112.9, 77.0, 77.0, 63.3, 48.2, 28.0.

Example 72: Preparation of 4-(2-(5-methoxy-2,2-dimethyl-2H-chromen-6-yl)-2-oxoethyl)benzonitrile

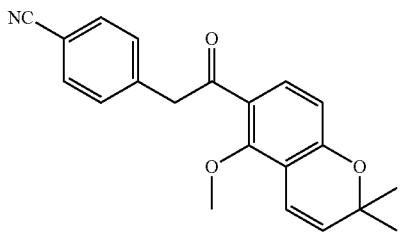 [SMILES: COc1c(C(=O)Cc2ccc(C#N)cc2)ccc2c1C=CC(C)(C)O2]

The subject compound is prepared through the same method in said example 28, except using 4-(2-oxoethyl)benzonitrile instead of using 2-(3,4-Dimethoxyphenyl)acetaldehyde (Manufacturing Example 13) (yield: 76%, 8.3 mg).

$^1$H-NMR (CDCl$_3$, 500 MHz) δ 7.58 (d, 2H, J=8.1 Hz), 7.50 (d, 1H, J=8.6 Hz), 7.34 (d, 2H, J=8.1 Hz), 6.59 (d, 1H, J=8.9 Hz), 6.57 (d, 1H, J=10.3 Hz), 5.68 (d, 1H, J=10.0 Hz), 4.30 (s, 2H), 3.76 (s, 3H), 1.43 (s, 6H);

$^{13}$C-NMR (CDCl$_3$, 125 MHz) δ 196.5, 158.3, 156.6, 140.7, 132.1, 132.1, 131.2, 130.7, 130.5, 130.5, 124.2, 118.9, 116.3, 114.8, 112.9, 110.6, 77.0, 63.3, 48.5, 28.0, 28.0.

Example 73: Preparation of 2-(4-fluorophenyl)-1-(5-methoxy-2,2-dimethyl-2H-chromen-6-yl)ethanone

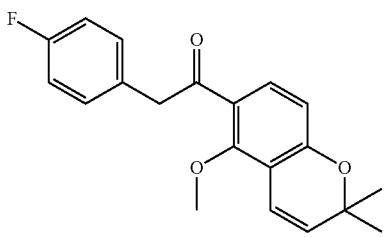 [SMILES: COc1c(C(=O)Cc2ccc(F)cc2)ccc2c1C=CC(C)(C)O2]

The subject compound is prepared through the same method in said example 28, except using 2-(4-fluorophenyl)acetaldehyde instead of using 2-(3,4-Dimethoxyphenyl)acetaldehyde (Manufacturing Example 13) (yield: 89%, 11.2 mg).

$^1$H-NMR (CDCl$_3$, 600 MHz) δ 7.48 (d, 1H, J=8.2 Hz), 7.19 (m, 2H), 6.97 (t, 2H, J=8.7 Hz), 6.59 (d, 1H, J=2.7 Hz), 6.57 (d, 1H, J=1.3 Hz), 5.67 (d, 1H, J=9.6 Hz), 4.21 (s, 2H), 3.75 (s, 3H), 1.43 (s, 6H).

Example 74: Preparation of 2-(4-chlorophenyl)-1-(5-W methoxy-2,2-dimethyl-2H-chromen-6-yl)ethanone

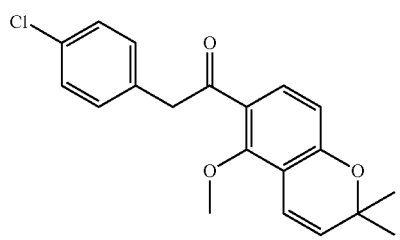 [SMILES: COc1c(C(=O)Cc2ccc(Cl)cc2)ccc2c1C=CC(C)(C)O2]

The subject compound is prepared through the same method in said example 28, except using 2-(4-chlorophenyl)acetaldehyde instead of using 2-(3,4-Dimethoxyphenyl)acetaldehyde (Manufacturing Example 13) (yield: 76%, 14.1 mg).

1H-NMR (CDCl3, 500 MHz) δ 7.48 (d, 1H, J=8.5 Hz), 7.25 (d, 2H, J=8.3 Hz), 7.16 (d, 2H, J=8.2 Hz), 6.58 (d, 2H, J=9.2 Hz), 5.67 (d, 1H, J=10.0 Hz), 4.21 (s, 2H), 3.75 (s, 3H), 1.43 (s, 6H);

13C-NMR (CDCl3, 125 MHz) δ 197.7, 157.9, 156.5, 133.5, 132.5, 131.1, 130.9, 130.9, 130.6, 128.5, 128.5, 124.5, 116.4, 114.8, 112.7, 76.9, 63.2, 47.8, 28.0, 28.0.

Example 75: Preparation of 1-(5-methoxy-2,2-dimethyl-2H-chromen-6-yl)-2-(4-(trifluoromethyl)phenyl)ethanone

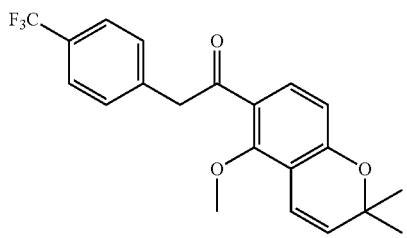 [SMILES: COc1c(C(=O)Cc2ccc(C(F)(F)F)cc2)ccc2c1C=CC(C)(C)O2]

The subject compound is prepared through the same method in said example 28, except using 2-(4-(trifluoromethyl)phenyl)acetaldehyde instead of using 2-(3,4-Dimethoxyphenyl)acetaldehyde (Manufacturing Example 13) (yield: 79%, 12.3 mg).

$^1$H-NMR (CDCl$_3$, 600 MHz) δ 7.55 (d, 2H, J=8.2 Hz), 7.51 (d, 1H, J=8.7 Hz), 7.35 (d, 2H, J=8.2 Hz), 6.59 (d, 1H, J=5.0 Hz), 6.58 (d, 1H, J=6.4 Hz), 5.68 (d, 1H, J=10.0 Hz), 4.30 (s, 2H), 3.74 (s, 3H), 1.43 (s, 6H).

Example 76: Preparation of 1-(5-methoxy-2,2-dimethyl-2H-chromen-6-yl)-2-(3-methoxyphenyl)ethanone

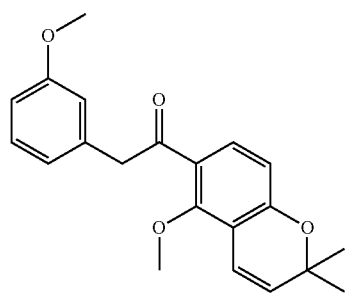 [SMILES: COc1cccc(CC(=O)c2ccc3c(c2OC)C=CC(C)(C)O3)c1]

The subject compound is prepared through the same method in said example 28, except using 2-(3-methoxyphenyl)acetaldehyde instead of using 2-(3,4-Dimethoxyphenyl)acetaldehyde (Manufacturing Example 13) (yield: 83%, 11.2 mg).

$^1$H-NMR (CDCl$_3$, 600 MHz) δ 7.48 (d, 1H, J=8.7 Hz), 7.18 (t, 1H, J=7.8 Hz), 6.82 (d, 1H, J=7.8 Hz), 6.79 (s, 1H), 6.75 (d, 1H, J=7.8 Hz), 6.58 (d, 1H, J=10.5 Hz), 6.57 (d, 1H, J=8.2 Hz), 5.66 (d, 1H, J=9.6 Hz), 4.21 (s, 2H), 3.75 (s, 3H), 3.74 (s, 3H), 1.42 (s, 6H);

¹³C-NMR (CDCl₃, 150 MHz) δ 198.1, 159.5, 157.7, 156.4, 136.5, 131.1, 130.4, 129.3, 124.7, 121.9, 116.5, 115.1, 114.7, 112.6, 112.2, 76.8, 63.1, 55.0, 48.6, 27.9, 27.9.

Example 77: Preparation of 1-(5-methoxy-2,2-dimethyl-2H-chromen-6-yl)-2-(4-methoxyphenyl)ethanone

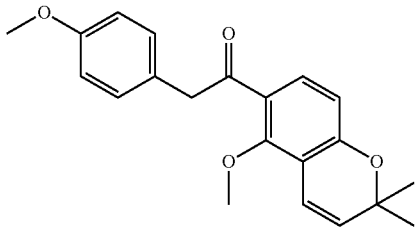

The subject compound is prepared through the same method in said example 28, except using 2-(4-methoxyphenyl)acetaldehyde instead of using 2-(3,4-Dimethoxyphenyl)acetaldehyde (Manufacturing Example 13) (yield: 88%, 13.3 mg).

¹H-NMR (CDCl₃, 500 MHz) δ 7.48 (d, 1H, J=8.5 Hz), 7.14 (d, 2H, J=8.3 Hz), 6.82 (d, 2H, J=8.3 Hz), 6.57 (t, 2H, J=10.6 Hz), 5.66 (d, 1H, J=9.9 Hz), 4.1 (s, 2H), 3.76 (s, 3H), 3.74 (s, 3H), 1.42 (s, 6H);

¹³C-NMR (CDCl₃, 125 MHz) δ 198.7, 158.3, 157.6, 156.3, 131.1, 130.5, 130.5, 130.5, 127.1, 124.8, 116.5, 114.8, 113.9, 113.9, 112.6, 76.8, 63.2, 55.1, 47.7, 28.0, 28.0.

Example 78: Preparation of 1-(5-methoxy-2,2-dimethyl-2H-chromen-6-yl)-2-(3-(trifluoromethoxy)phenyl)ethanone

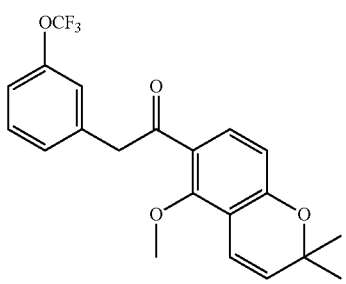

The subject compound is prepared through the same method in said example 28, except using 2-(3-(trifluoromethoxy)phenyl)acetaldehyde instead of using 2-(3,4-Dimethoxyphenyl)acetaldehyde (Manufacturing Example 13) (yield: 79%, 10.3 mg).

¹H-NMR (CDCl₃, 500 MHz) δ 7.50 (d, 1H, J=8.6 Hz), 7.30 (t, 1H, J=7.9 Hz), 7.17 (d, 1H, J=7.6 Hz), 7.11 (s, 1H), 7.07 (d, 1H, J=8.1 Hz), 6.59 (d, 1H, J=2.9 Hz), 6.58 (d, 1H, J=4.4 Hz), 5.67 (d, 1H, J=10.0 Hz), 4.26 (s, 2H), 3.74 (s, 3H), 1.43 (s, 6H);

¹³C-NMR (CDCl₃, 125 MHz) δ 197.2, 158.0, 156.5, 149.2 (d, JC-F=1.6 Hz), 137.3, 131.1, 130.6, 129.5, 128.1, 124.4, 122.2, 120.4 (q, JC-F=255.4 Hz), 119.0, 116.4, 114.8, 112.8, 76.9, 63.2, 48.1, 27.9, 27.9.

Example 79: Preparation of 1-(5-methoxy-2,2-dimethyl-2H-chromen-6-yl)-2-(2-(trifluoromethoxy)phenyl)ethanone

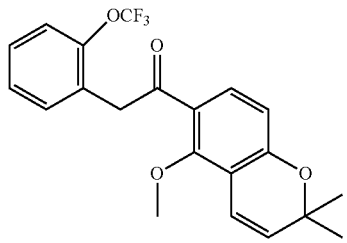 [SMILES: COc1c(C(=O)Cc2ccccc2OC(F)(F)F)ccc2c1C=CC(C)(C)O2]

The subject compound is prepared through the same method in said example 28, except using 2-(2-(trifluoromethoxy)phenyl)acetaldehyde instead of using 2-(3,4-Dimethoxyphenyl)acetaldehyde (Manufacturing Example 13) (yield: 83%, 7.3 mg).

¹H-NMR (CDCl₃, 600 MHz) δ 7.56 (d, 1H, J=8.7 Hz), 7.30-7.21 (m, 4H), 6.61 (d, 1H, J=5.5 Hz), 6.60 (d, 1H, J=7.8 Hz), 5.67 (d, 1H, J=10.0 Hz), 4.34 (s, 2H), 3.81 (s, 3H), 1.44 (s, 6H);

¹³C-NMR (CDCl₃, 150 MHz) δ 196.2, 158.0, 156.6, 147.8, 132.2, 131.0, 130.5, 128.3, 128.1, 126.6, 124.5, 120.5 (q, JC-F=256.3 Hz), 120.2, 116.5, 114.8, 112.7, 76.8, 63.1, 43.1, 27.9, 27.9.

Example 80: Preparation of 1-(5-methoxy-2,2-dimethyl-2H-chromen-6-yl)-2-(4-(trifluoromethoxy)phenyl)ethanone

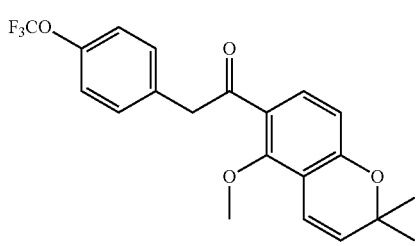 [SMILES: COc1c(C(=O)Cc2ccc(OC(F)(F)F)cc2)ccc2c1C=CC(C)(C)O2]

The subject compound is prepared through the same method in said example 28, except using 2-(4-(trifluoromethoxy)phenyl)acetaldehyde instead of using 2-(3,4-Dimethoxyphenyl)acetaldehyde (Manufacturing Example 13) (yield: 81%, 9.2 mg).

¹H-NMR (CDCl₃, 600 MHz) δ 7.50 (d, 1H, J=8.7 Hz), 7.26-7.24 (m, 2H), 7.13 (d, 2H, J=7.8 Hz), 6.59 (d, 1H, J=3.2 Hz), 6.58 (d, 1H, J=4.5 Hz), 5.67 (d, 1H, J=9.6 Hz), 4.24 (s, 2H), 3.75 (s, 3H), 1.43 (s, 6H);

¹³C-NMR (CDCl₃, 150 MHz) δ 197.6, 158.0, 156.5, 148.0, 133.8, 131.1, 131.0, 131.0, 130.6, 124.5, 120.8, 120.8, 120.4 (q, JC-F=255.6 Hz), 116.4, 114.8, 112.8, 76.9, 63.2, 47.7, 28.0, 28.0.

Example 81: Preparation of 2-(4-hydroxy-3-methoxyphenyl)-1-(5-methoxy-2,2-dimethyl-2H-chromen-6-yl) ethanone

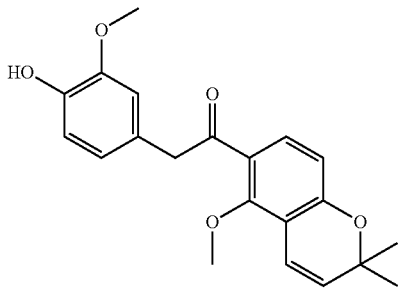 [SMILES: COc1cc(CC(=O)c2ccc3c(c2OC)C=CC(C)(C)O3)ccc1O]

The subject compound is prepared through the same method in said example 28, except using 2-(4-hydroxy-3-methoxyphenyl)acetaldehyde instead of using 2-(3,4-Dimethoxyphenyl)acetaldehyde (Manufacturing Example 13) (yield: 77%, 5.3 mg).

$^1$H-NMR (CDCl$_3$, 500 MHz) δ 7.47 (d, 1H, J=8.6 Hz), 6.81 (d, 1H, J=8.0 Hz), 6.76 (s, 1H), 6.71 (d, 1H, J=8.0 Hz), 6.57 (t, 2H, J=10.4 Hz), 5.66 (d, 1H, J=9.9 Hz), 5.53 (s, 1H), 4.15 (s, 2H), 3.82 (s, 3H), 3.74 (s, 3H) 1.42 (s, 6H);

$^{13}$C-NMR (CDCl$_3$, 125 MHz) δ 198.7, 157.7, 156.3, 146.4, 144.4, 131.1, 130.5, 126.8, 124.8, 122.4, 116.5, 114.8, 114.2, 112.6, 112.0, 76.8, 63.2, 55.8, 48.2, 28.0, 28.0.

Example 82: Preparation of 2-(3-hydroxy-4-methoxyphenyl)-1-(5-methoxy-2,2-dimethyl-2H-chromen-6-yl) ethanone

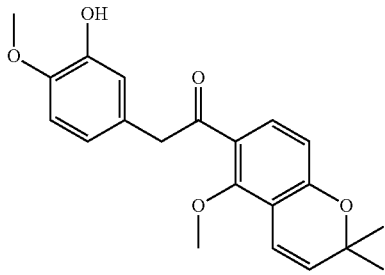

The subject compound is prepared through the same method in said example 28, except using 2-(3-hydroxy-4-methoxyphenyl)acetaldehyde instead of using 2-(3,4-Dimethoxyphenyl)acetaldehyde (Manufacturing Example 13) (yield: 74%, 6.4 mg).

$^1$H-NMR (CDCl$_3$, 600 MHz) δ 7.47 (d, 1H, J=8.2 Hz), 6.80 (d, 1H, J=2.3 Hz), 6.76 (d, 1H, J=8.2 Hz), 6.71 (dd, 1H, J=8.2, 2.2 Hz), 6.58 (d, 1H, J=10.5 Hz), 6.56 (d, 1H, J=8.7 Hz), 5.65 (d, 1H, J=9.5 Hz), 5.59 (s, 1H), 4.13 (s, 2H) 3.81 (s, 3H), 3.74 (s, 3H), 1.42 (s, 6H);

$^{13}$C-NMR (CDCl$_3$, 150 MHz) δ 198.5, 157.6, 156.3, 145.4, 145.4, 131.1, 130.4, 128.2, 124.8, 121.0, 116.5, 115.8, 114.8, 112.5, 110.6, 76.8, 63.1, 55.8, 47.9, 27.9, 27.9.

Example 83: Preparation of 2-(3-hydroxyphenyl)-1-(5-methoxy-2,2-dimethyl-2H-chromen-6-yl)ethanone

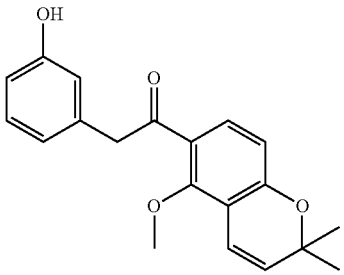 [SMILES: COc1c(C(=O)Cc2cccc(O)c2)ccc2c1C=CC(C)(C)O2]

The subject compound is prepared through the same method in said example 28, except using 2-(3-hydroxyphenyl)acetaldehyde instead of using 2-(3,4-Dimethoxyphenyl) acetaldehyde (Manufacturing Example 13) (yield: 51%, 3.7 mg).

$^1$H-NMR (CDCl$_3$, 500 MHz) δ 7.50 (d, 1H, J=8.6 Hz), 7.09 (t, 1H, J=7.7 Hz), 6.75-6.73 (m, 2H), 6.68 (d, 1H, J=7.8 Hz), 6.64 (s, 1H), 6.58 (d, 1H, J=3.5 Hz), 6.56 (s, 1H), 5.65 (d, 1H, J=10.0 Hz), 4.18 (s, 2H) 3.72 (s, 3H), 1.42 (s, 6H);

$^{13}$C-NMR (CDCl$_3$, 125 MHz) δ 199.1, 158.0, 156.6, 156.1, 136.2, 131.3, 130.5, 129.5, 124.4, 121.4, 116.5, 116.4, 114.8, 113.9, 112.6, 76.9, 63.1, 48.3, 27.9, 27.9.

Example 84: Preparation of 2-(2-hydroxyphenyl)-1-(5-methoxy-2,2-dimethyl-2H-chromen-6-yl)ethanone

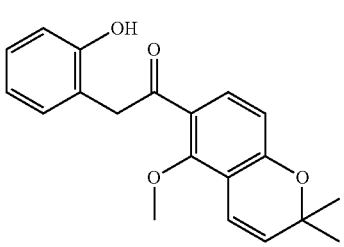 [SMILES: COc1c(C(=O)Cc2ccccc2O)ccc2c1C=CC(C)(C)O2]

The subject compound is prepared through the same method in said example 28, except using 2-(2-hydroxyphenyl)acetaldehyde instead of using 2-(3,4-Dimethoxyphenyl) acetaldehyde (Manufacturing Example 13) (yield: 49%, 2.4 mg).

$^1$H-NMR (MeOD, 500 MHz) δ 7.57 (d, 1H, J=8.6 Hz), 7.07-7.03 (m, 2H), 6.76-6.73 (m, 2H), 6.63 (d, 1H, J=10.0 Hz), 6.57 (d, 1H, J=8.6 Hz), 5.77 (d, 1H, J=10.0 Hz), 4.22 (s, 2H), 3.78 (s, 3H) 1.42 (s, 6H);

$^{13}$C-NMR (MeOD, 125 MHz) δ 202.1, 159.9, 158.6, 157.4, 133.1, 133.0, 132.6, 129.8, 126.9, 124.4, 121.2, 118.2, 117.0, 116.6, 114.1, 78.8, 64.4, 45.2, 29.0, 29.0.

Example 85: Preparation of 2-(4-hydroxyphenyl)-1-(5-methoxy-2,2-dimethyl-2H-chromen-6-yl)ethanone

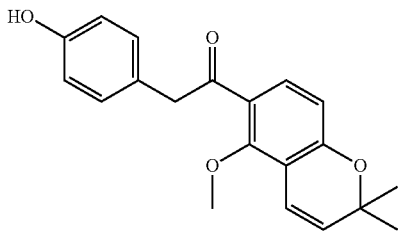

The subject compound is prepared through the same method in said example 28, except using 2-(4-hydroxyphenyl)acetaldehyde instead of using 2-(3,4-Dimethoxyphenyl)acetaldehyde (Manufacturing Example 13) (yield: 73%, 3.9 mg).

$^1$H-NMR (CDCl$_3$, 600 MHz) δ 7.49 (d, 1H, J=8.7 Hz), 7.05 (d, 2H, J=8.2 Hz), 6.70 (d, 2H, J=8.7 Hz), 6.58 (d, 1H, J=8.2 Hz), 6.57 (d, 1H, J=7.8 Hz), 5.79 (s, 1H), 5.66 (d, 1H, J=10.0 Hz), 4.16 (s, 2H) 3.74 (s, 3H), 1.42 (s, 6H);

$^{13}$C-NMR (CDCl$_3$, 150 MHz) δ 199.3, 157.8, 156.4, 154.6, 131.2, 130.6, 130.6, 130.5, 126.7, 124.7, 116.4, 115.4, 115.4, 114.8, 112.6, 76.9, 63.2, 47.7, 28.0, 28.0.

Example 86: Preparation of 2-(4-aminophenyl)-1-(5-methoxy-2,2-dimethyl-2H-chromen-6-yl)ethanone

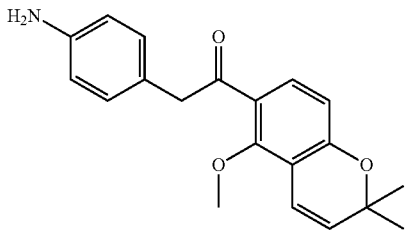

The subject compound is prepared through the same method in said example 28, except using 2-(4-aminophenyl)acetaldehyde instead of using 2-(3,4-Dimethoxyphenyl)acetaldehyde (Manufacturing Example 13) (yield: 21%, 1.7 mg).

$^1$H-NMR (CDCl$_3$, 300 MHz) δ 7.46 (d, 1H, J=8.4 Hz), 7.01 (d, 2H, J=8.4 Hz), 6.62-6.54 (m, 4H), 5.65 (d, 1H, J=10.2 Hz), 4.11 (s, 2H), 3.72 (s, 3H), 1.42 (s, 6H);

HR-MS (FAB) calcd for C20H21NO3 (M+H+) 324.1600; found 324.1603.

Example 87: Preparation of 1-(5-methoxy-2,2-dimethyl-2H-chromen-6-yl)-2-(2-methoxyphenyl)ethanone

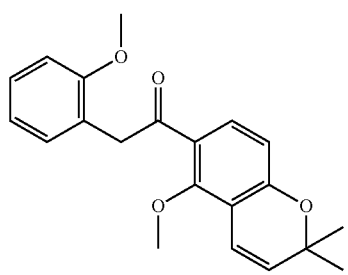 [SMILES: COc1ccccc1CC(=O)c1ccc2c(c1OC)C=CC(C)(C)O2]

The subject compound is prepared through the same method in said example 28, except using 2-(2-methoxyphenyl)acetaldehyde instead of using 2-(3,4-Dimethoxyphenyl)acetaldehyde (Manufacturing Example 13) (yield: 56%, 3.1 mg).

$^1$H-NMR (CDCl$_3$, 600 MHz) δ 7.54 (d, 1H, J=8.7 Hz), 7.22 (dd, 1H, J=8.2 Hz, 7.4 Hz), 7.14 (d, 1H, J=7.4 Hz), 6.90 (dd, 1H, J=8.7 Hz, 7.3 Hz), 6.84 (d, 1H, J=8.2 Hz), 6.60 (d, 1H, J=10.1 Hz), 6.58 (d, 1H, J=8.7 Hz), 5.65 (d, 1H, J=9.6 Hz), 4.23 (s, 2H) 3.81 (s, 3H), 3.74 (s, 3H), 1.43 (s, 6H).

Example 88: Preparation of 1-(5-methoxy-2,2-dimethyl-2H-chromen-6-yl)-2-o-tolylethanone

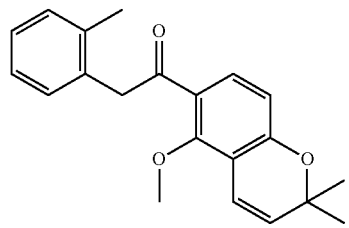 [SMILES: COc1c(C(=O)Cc2ccccc2C)ccc2c1C=CC(C)(C)O2]

The subject compound is prepared through the same method in said example 28, except using 2-o-tolylacetaldehyde instead of using 2-(3,4-Dimethoxyphenyl)acetaldehyde (Manufacturing Example 13) (yield: 59%, 4.1 mg).

$^1$H-NMR (CDCl$_3$, 500 MHz) δ 7.52 (d, 1H, J=8.6 Hz), 7.20 (m, 4H), 6.60 (d, 2H, J=8.7 Hz), 5.68 (d, 1H, J=10.0 Hz), 4.27 (s, 2H), 3.79 (s, 3H), 2.23 (s, 3H), 1.44 (s, 6H).

Example 89: Preparation of 1-(5-methoxy-2,2-dimethyl-2H-chromen-6-yl)-2-m-tolylethanone

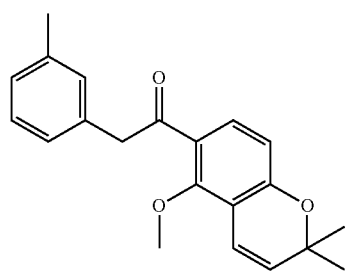 [SMILES: COc1c(C(=O)Cc2cccc(C)c2)ccc2c1C=CC(C)(C)O2]

The subject compound is prepared through the same method in said example 28, except using 2-m-tolylacetaldehyde instead of using 2-(3,4-Dimethoxyphenyl)acetaldehyde (Manufacturing Example 13) (yield: 74%, 8.3 mg).

$^1$H-NMR (CDCl$_3$, 400 MHz) δ 7.49 (d, 1H, J=8.6 Hz), 7.17 (t, 1H, J=7.5 Hz), 7.03 (dd, 3H, J=7.5 Hz, 6.8 Hz), 6.58 (dd, 2H, J=9.7 Hz, 8.4 Hz), 5.66 (d, 1H, J=10.0 Hz), 4.21 (s, 2H) 3.74 (s, 3H), 2.30 (s, 3H), 1.43 (s, 6H).

Example 90: Preparation of 1-(5-methoxy-2,2-dimethyl-2H-chromen-6-yl)-2-p-tolylethanone

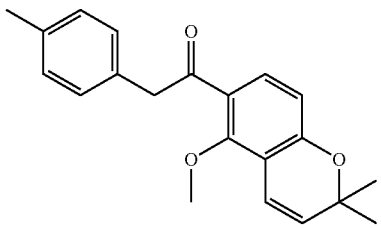

The subject compound is prepared through the same method in said example 28, except using 2-p-tolylacetaldehyde instead of using 2-(3,4-Dimethoxyphenyl)acetaldehyde (Manufacturing Example 13) (yield: 66%, 7.9 mg).

$^1$H-NMR (CDCl$_3$, 500 MHz) δ 7.48 (d, 1H, J=8.6 Hz), 7.11 (dd, 4H, J=15.4 Hz, 8.1 Hz), 6.59 (d, 1H, J=10.3 Hz), 6.57 (d, 1H, J=8.6 Hz), 5.66 (d, 1H, J=10.0 Hz), 4.20 (s, 2H) 3.74 (s, 3H), 2.29 (s, 3H), 1.43 (s, 6H).

Example 91: Preparation of 1-(5-methoxy-2,2-dimethyl-2H-chromen-6-yl)-2-(2-nitrophenyl)ethanone

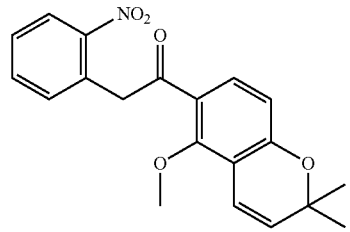 [SMILES: COc1c(C(=O)Cc2ccccc2[N+](=O)[O-])ccc2c1C=CC(C)(C)O2]

The subject compound is prepared through the same method in said example 28, except using 2-(2-nitrophenyl)acetaldehyde instead of using 2-(3,4-Dimethoxyphenyl)acetaldehyde (Manufacturing Example 13) (yield: 27%, 3.7 mg).

$^1$H-NMR (CDCl$_3$, 500 MHz) δ 8.10 (d, 1H, J=8.2 Hz), 7.60 (d, 1H, J=8.6 Hz), 7.56 (t, 1H, J=7.5 Hz), 7.43 (t, 1H, J=7.8 Hz), 7.30 (d, 1H, J=7.5 Hz), 6.61 (t, 2H, J=10.2 Hz), 5.68 (d, 1H, J=10.0 Hz), 4.68 (s, 2H) 3.85 (s, 3H), 1.44 (s, 6H).

Example 92: Preparation of 1-(5-methoxy-2,2-dimethyl-2H-chromen-6-yl)-2-(3-nitrophenyl)ethanone

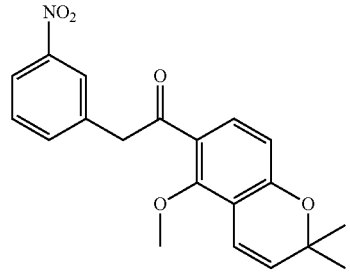 [SMILES: COc1c(C(=O)Cc2cccc([N+](=O)[O-])c2)ccc2c1C=CC(C)(C)O2]

The subject compound is prepared through the same method in said example 28, except using 2-(3-nitrophenyl)acetaldehyde instead of using 2-(3,4-Dimethoxyphenyl)acetaldehyde (Manufacturing Example 13) (yield: 43%, 5.4 mg).

$^1$H-NMR (CDCl$_3$, 600 MHz) δ 8.10 (m, 2H), 7.57 (d, 1H, J=7.7 Hz), 7.53 (d, 1H, J=8.7 Hz), 7.47 (t, 1H, J=8.0 Hz), 6.61 (d, 1H, J=8.6 Hz), 6.58 (d, 1H, J=9.6 Hz), 5.69 (d, 1H, J=10.0 Hz), 4.36 (s, 2H) 3.80 (s, 3H), 1.44 (s, 6H).

Example 93: Preparation of 3-(2-(5-methoxy-2,2-W dimethyl-2H-chromen-6-yl)-2-oxoethyl)benzonitrile

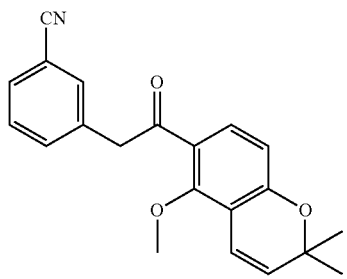 [SMILES: COc1c(C(=O)Cc2cccc(C#N)c2)ccc2c1C=CC(C)(C)O2]

The subject compound is prepared through the same method in said example 28, except using 3-(2-oxoethyl)benzonitrile instead of using 2-(3,4-Dimethoxyphenyl)acetaldehyde (Manufacturing Example 13) (yield: 88%, 12.7 mg).

$^1$H-NMR (CDCl$_3$, 600 MHz) δ 7.53 (s, 1H), 7.51 (d, 1H, J=7.8 Hz), 7.50 (d, 1H, J=8.7 Hz), 7.47 (d, 1H, J=7.8 Hz), 7.39 (t, 1H, J=7.6 Hz), 6.59 (d, 1H, J=9.2 Hz), 6.57 (d, 1H, J=10.0 Hz), 5.68 (d, 1H, J=9.7 Hz), 4.28 (s, 2H) 3.77 (s, 3H), 1.43 (s, 6H).

Example 94: Preparation of 2-(2-(5-methoxy-2,2-dimethyl-2H-chromen-6-yl)-2-oxoethyl)benzonitrile

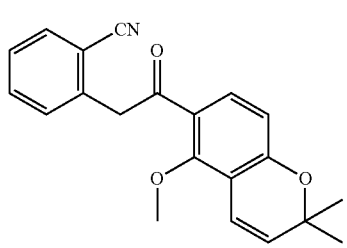

The subject compound is prepared through the same method in said example 28, except using 2-(2-oxoethyl)benzonitrile instead of using 2-(3,4-Dimethoxyphenyl)acetaldehyde (Manufacturing Example 13) (yield: 38%, 2.1 mg).

LR-MS (FAB) calcd for C21H19NO3 (M) 333.14; found 333.14.

Example 95: Preparation of 2-(3,4-dimethoxyphenyl)-2-fluoro-1-(5-methoxy-2,2-dimethyl-2H-chromen-6-yl)ethanone

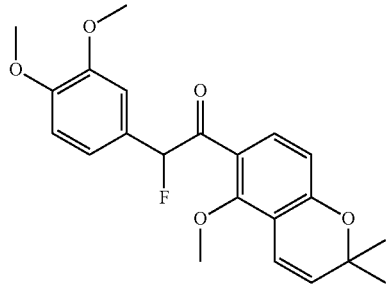

After dissolving the Example 28 compound (7.0 mg, 0.019 mmol) in anhydrous dichloromethane (0.2 mL), TMSOTf (6.9 μL, 0.038 mmol) and triethylamine (7.9 μL, 0.057 mmol) were added with stirring, reaction condition was monitored by TLC. After the reaction was terminated, complete the reaction using sodium bicarbonate aqueous solution, extract using dichloromethane, dry using MgSO$_4$, concentrate under reduced pressure and residue was obtained. After dissolving the residue in DMF (0.3 mL), adding Selectfluor® (7.1 mg, 0.019 mmol) and stirring for 15 minutes. Adding TBAF (1.0M in THF, 0.019 mL, 0.019 mmol), after 5 minutes, adding water gently and stirring 2 hours. Filtering Reaction mixture by Celite pad, extract using EtOAc, dry using MgSO$_4$, concentrate under reduced pressure, purified using flash column chromatography (EtOAc:n-hexane=1:6), than the subject compound obtained (yield 67%, 4.9 mg).

$^1$H NMR (CDCl$_3$, 400 MHz) δ7.42 (d, 1H, J=8.7 Hz), 6.95 (m, 1H), 6.92 (s, 1H), 6.78 (d, 1H, J=8.2 Hz), 6.58 (m, 2H), 6.51 (s, 1H), 5.65 (d, 1H, J=10.1 Hz), 3.82 (s, 3H), 3.82 (s, 3H), 3.69 (s, 3H), 1.41 (s, 6H).

Example 96: Preparation of 2-(3,4-dimethoxyphenyl)-1-(5-methoxy-2,2-dimethyl-2H-chromen-6-yl)-3-phenylpropan-1-one

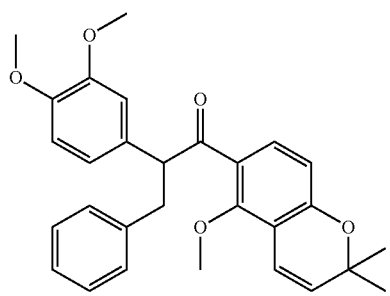 [SMILES: COc1ccc(C(Cc2ccccc2)C(=O)c2ccc3c(c2OC)C=CC(C)(C)O3)cc1OC]

The subject compound is prepared through the same method in below example 97, except using benzyl bromide instead of using allyl bromide (yield: 38%, 2.1 mg).

$^1$H NMR (CDCl$_3$, 300 MHz) δ 7.20-7.08 (m, 6H), 6.76-6.71 (m, 3H), 6.46 (dd, 2H), 5.60 (d, 1H), 4.79 (t, 1H), 3.80 (s, 3H), 3.77 (s, 3H), 3.52 (dd, 1H), 3.35 (s, 3H), 2.97 (dd, 1H), 1.37 (s, 6H).

Example 97: Preparation of 2-(3,4-dimethoxyphenyl)-1-(5-methoxy-2,2-dimethyl-2H-chromen-6-yl)pent-4-en-1-one

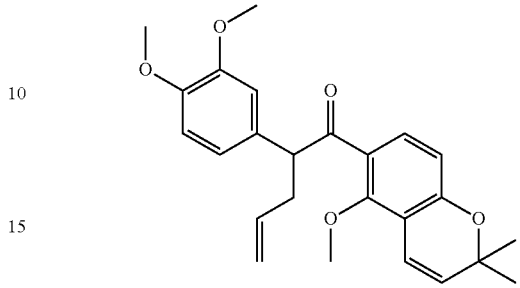

To a suspension of sodium hydride (60% in dispersion, 2.1 mg, 0.053 mmol) in dry THF (1 mL) was added a solution of Example 28 compound (19.4 mg, 0.053 mmol) in dry THF (1.0 mL) at 0° C. and stirred for 30 min. Allyl bromide (0.005 mL, 0.058 mmol) was added at 0° C. and the reaction temperature was allowed to raise to ambient temperature and stirred overnight. The reaction mixture was quenched with water and extracted with EtOAc. The organic layer was washed with brine, dried over MgSO$_4$, and concentrated under reduced pressure. The residue was purified by flash column chromatography on silica gel (EtOAc/n-Hexane=1:6) to afford 13.3 mg (61%) of subject compound as a colorless oil $^1$H-NMR (CDCl$_3$, 300 MHz) δ 7.30 (d, 1H, J=8.6 Hz), 6.80-6.71 (m, 3H), 6.54 (m, 1H), 6.48 (m, 1H), 5.74 (m, 1H), 5.62 (d, 1H, J=10.0 Hz), 5.04 (m, 1H), 4.94 (m, 1H), 4.55 (t, 1H, J=7.4 Hz), 3.81 (s, 3H), 3.80 (s, 3H), 3.59 (s, 3H), 2.88 (m, 1H), 2.49 (m, 1H), 1.39 (s, 3H), 1.39 (s, 3H).

Example 98: Preparation of 2-(3,4-dimethoxyphenyl)-2-hydroxy-1-(5-methoxy-2,2-dimethyl-2H-chromen-6-yl)ethanone

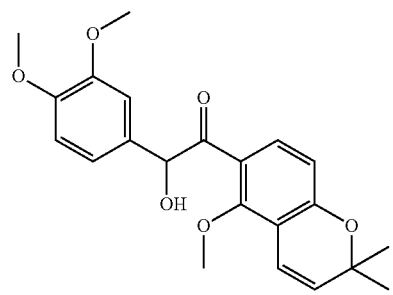

SH-42 (Example 28) and N-Bromosuccinimide (NBS) were dissolved by DMSO at rt under air and warmed up to 60° C. After over night stirring, the solvent was removed. The residue was extracted with DCM and purified by flash column chromatography to afford yellow oil product (51%, 5.2 mg).

$^{13}$C-NMR (CDCl$_3$, 400 MHz) δ 199.4, 158.4, 156.4, 148.9, 148.7, 131.6, 131.2, 130.6, 121.3, 119.7, 116.1, 114.7, 112.7, 111.0, 110.0, 77.1, 77.1, 66.3, 55.7, 28.1, 28.0;

HR-MS (FAB) calcd for C22H25O6 (M+H+) 385.1651; found 385.1654.

Comparative Example 1: Preparation of (7aS, 13aS)-9,10-Dimethoxy-3,3-dimethyl-13,13a-dihydro-3H-chromeno[3,4-b]pyrano[2,3-h]chromen-7(7aH)-one (Deguelin)

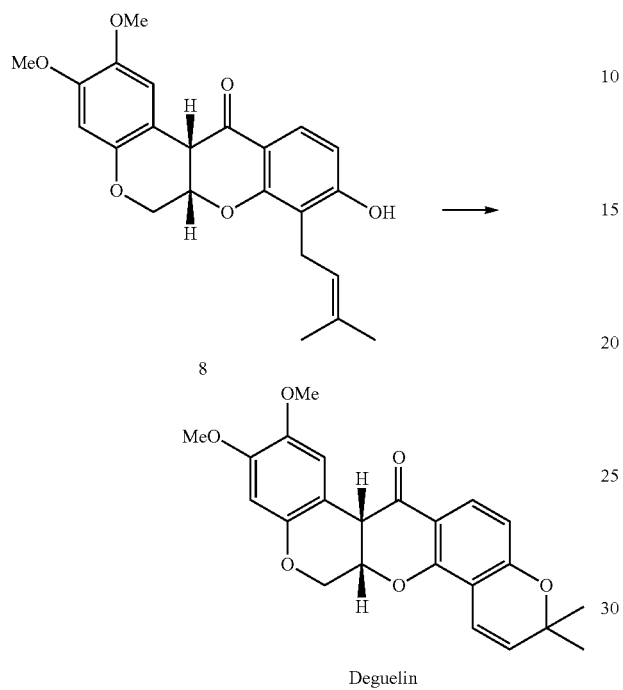

Phenylselenyl chloride (68 mg, 0.35 mmol) was added to anhydrous $CH_2Cl_2$ solution (4.0 mL) containing the compound 8 (128 mg, 0.32 mmol) prepared in Example 1 at −30° C. under argon atmosphere, followed by stirring for 10 minutes with maintaining the temperature at −30° C. The temperature was raised to room temperature with stirring for 2 hours, and then additional stirring was performed for 1 more hour. The solvent was eliminated from the reaction mixture under reduced pressure and the obtained residue was dissolved in THF (4.0 mL), to which hydrogen peroxide (30% in water, 0.06 mL) was added 0° C. The reaction mixture was stirred until the temperature of the mixture reached to room temperature, during which the reaction was monitored with TLC. EtOAc (8.0 mL) and water (4.0 mL) were added thereto. The organic layer was separated, washed with 5% $NaHCO_3$ aqueous solution and brine, dried over $MgSO_4$, filtered, and then concentrated. The obtained non-purified residue was purified by flash column chromatography (EtOAc:n-hexane=1:2) to give deguelin as a light-yellow solid (yield: 61%, 78 mg).

$^1$H-NMR ($CDCl_3$, 400 MHz) δ 7.72 (d, 1H, J=8.7 Hz), 6.77 (s, 1H), 6.62 (d, 1H, J=10.0 Hz), 6.43 (s, 1H), 6.43 (d, 1H, J=8.7 Hz), 5.53 (d, 1H, J=10.0 Hz), 4.89 (m, 1H), 4.61 (dd, 1H, J=12.0, 3.1 Hz), 4.17 (d, 1H, J=12.0 Hz), 3.82 (d, 1H, J=4.1 Hz), 3.78 (s, 3H), 3.75 (s, 3H), 1.43 (s, 3H), 1.36 (s, 3H);

$^{13}$C-NMR ($CDCl_3$, 100 MHz) δ 189.2, 160.0, 156.9, 149.4, 147.4, 143.8, 128.6, 128.5, 115.7, 112.7, 111.4, 110.4, 109.1, 104.7, 100.9, 77.6, 72.4, 66.2, 56.3, 55.8, 44.3, 28.4, 28.1;

HRMS (FAB) Calcd for $C_{23}H_{23}O_6$ (M+H$^+$): 395.1495, Found: 395.1495.

Experimental Example 1: Evaluation of Cancer Cell Growth Inhibition

To investigate the inhibitory effect of the compounds of Examples of the present invention on cancer cell growth, the following experiment was performed. Particularly, H1299 NSCLC (non-small cell lung cancer) cells were distributed in a 96-well plate at the density of $5 \times 10^3$ cells/well, followed by culture in a 37° C., 5% $CO_2$ incubator for 24 hours. The compound of each example was dissolved in DMSO (10 nM, 100 nM, 1 μM, 10 μM), which was treated to each well. 48 hours later, cell growth was measured by using MTS reagent (3-(4,5-dimethylthiazole-2-yl)-5-(3-carboxymethoxyphenyl)-2-(4-sulfophenyl)-2H-tetrazolium).

The experiment was performed in triplicate and the standard error of the analysis result was corrected. The results are presented in Table 2.

TABLE 2

| Compound | IC$_{50}$ (μM) |
| --- | --- |
| Comparative Example 1 (Deguelin) | 0.11 |
| Example 1 (Compound 8) | NA |
| Example 2 (Compound 9) | 9.8 |
| Example 3 (Compound 10) | 0.87 |
| Example 4 (Compound 11) | 0.97 |
| Example 5 (Compound 12) | 10.1 |
| Example 7 (Compound 13) | 4.2 |
| Example 9 (Compound 16) | 9.8 |
| Example 10 (Compound 17) | 10.5 |
| Example 11 (Compound 18) | NA |
| Example 12 (Compound 19) | NA |
| Example 13 (Compound 20) | 0.68 |
| Example 15 (Compound 22) | NA |
| Example 16 (Compound 23) | 0.3 |
| Example 17 (Compound 24) | 4.3 |
| Example 18 (Compound 25) | NA |
| Example 20 (Compound 27) | NA |
| Example 21 (Compound 28) | 5.2 |
| Example 22 (Compound 29) | NA |
| Example 23 (Compound 30) | NA |
| Example 24 (Compound 31) | NA |
| Example 25 (Compound 37) | 4.5 |
| Example 26 (Compound 45) | 3.8 |
| Example 27 (Compound 53) | 1.0 |
| Example 28 (Compound 54) | 0.14 |
| Example 29 (Compound 56) | 0.73 |
| Example 30 (Compound 57) | 3.2 |

TABLE 2-continued

| Compound | IC$_{50}$ (µM) |
| --- | --- |
| Example 32 (Compound 59) | 102 |
| Example 33 (Compound 69) | 0.49 |
| Example 34 (Compound 72) | 1.3 |

As shown in Table 2, when the compounds of the present invention were treated to H1299 NSCLC cells, the mean value of cell growth IC$_{50}$ was approximately 3~5 µM. In particular, IC$_{50}$ of the compound 54 of Example 28 was 0.14 µm, indicating that the compound had similar cancer cell growth inhibiting effect to the conventional anticancer agent deguelin of Comparative Example 1.

Therefore, the compounds of the present invention can be effectively used as an anticancer agent since they have excellent cancer cell growth inhibiting effect.

Experimental Example 2: Evaluation of HIF-1α Inhibiting Effect

The inhibitory effect of the compounds of the invention that had confirmed previously to have a strong cell growth inhibitory activity in Experimental Example 1 on the accumulation of HIF-1α was investigated in the lung cancer cell line H1299 NSCLC. Particularly, to confirm whether or not the compounds prepared in Examples of the present invention could inhibit HIF-1α generation induced under hypoxic condition dose-dependently, the compounds prepared in Examples and deguelin prepared in Comparative Example 1 were treated to the cells at different concentrations and then HIF-1α generation was investigated by Western blotting.

First, H1299 NSCLC (non-small cell lung cancer) cells were distributed in a 96-well plate at the density of 5×10$^3$ cells/well, followed by culture for 24 hours. The cells were pre-treated under hypoxic condition (oxygen 1%, nitrogen 94%, carbon dioxide 5%) for 12 hours to induce the accumulation of HIF-1α. The compound of formula 1 was dissolved in DMSO, which was treated to H1299 NSCLC cells at the concentrations of 0~10 µM. The cells were cultured under hypoxic condition for 16 hours. Then, the nucleus extract was prepared by using RIPA buffer. At this time, to compare the HIF-1 target gene expression according to hypoxia, the control group was cultured under 20% oxygen condition. 30 µg of the nucleus extract was separated by SDS-PAGE (sodium dodecyl sulfate-polyacrylamide gel electrophoresis), which was transferred onto polyvinylidene fluoride membrane. HIF-1α was quantified by using HIF-1α antibody (BD Pharmingen) and HRP (horseradish peroxidase) conjugated secondary antibody. Tublin was used as the internal control gene. The results are presented in FIG. 1.

FIG. 1 is a diagram illustrating the result of Western blotting performed to measure the activity of the compounds of the present invention to inhibit the accumulation of HIF-1α.

As shown in FIG. 1, the compounds prepared in Examples of the present invention were confirmed to inhibit HIF-1α generation dose-dependently without damaging tublin generation under hypoxic condition.

Therefore, it was confirmed that the compounds of the present invention inhibit the accumulation of HIF-1α characterized by aggravating cancer, so that they can be effectively used as an active ingredient of an anticancer agent.

Experimental Example 3: Evaluation of Angiogenesis Inhibiting Effect

To investigate the inhibitory effect of the compounds of the present invention on VEGF (Vascular endothelial growth factor A), the angiogenesis factor, angiogenesis in the transgenic zebra fish was examined.

After cross-breeding zebra fish, the generated zebra fish embryos (Albino; Tg(fli1:EGFP)$^{b4;y1}$, Zebra fish International Resource Center, University of Oregon, Eugene) were cultured in 28.5° C. amniotic fluid (Artificial sea salt was dissolved in distilled water at the concentration of 0.2 g/L.) for 6 hours. 10 zebra fish embryos cultured above were grouped together, which were distributed in a 24-well plate, followed by culture along with 500 µl of the amniotic fluid. The compound of each example was treated thereto at the concentrations of 50 nM, 250 nM, and 1.25 µM. 48 hours later, during which the experiment was kept going on, the amniotic fluid (including each compound) was replaced. 72 hours later, angiogenesis in the subintestinal vessel plexus (SIV) of each embryo was examined and photographed under DM5000B fluorescent microscope (Leica Microsystems, Wetzlar GmbH, Germany).

FIG. 2 is a photograph illustrating the effect of the compound 53 of the present invention on angiogenesis.

FIG. 3 is a photograph illustrating the effect of the compound 69 of the present invention on angiogenesis.

FIG. 4 is a photograph illustrating the effect of the compound 72 of the present invention on angiogenesis.

As shown in FIGS. 2, 3, and 4, when the embryo was treated with the compound of the present invention, angiogenesis was reduced by the compound dose-dependently, compared with the other embryo non-treated with the compound.

Therefore, the compounds of the present invention can inhibit angiogenesis, that is they can inhibit the activity of VEGF, the angiogenesis factor, so that they can be effectively used as an active ingredient of an anticancer agent.

Experimental Example 4: Evaluation of Angiogenesis Inhibiting Effect

Following experiment was performed to investigate the angiogenesis inhibiting effect of deguelin and the compound of each example under hypoxic condition by inhibiting VEGF generation.

Preparation Stage: Preparation of Cell Culture Fluid

First, HCT116, the human colorectal cancer cell line, was cultured in a hypoxic chamber (1% O$_2$) as the in vitro hypoxic model. The cells were treated with deguelin, compound 69 (Example 33) and compound 54 (Example 28) at the concentrations of 1~100 nM, followed by culture for 8 hours. Next, the culture fluid was collected and proceeded to centrifugation at 4° C. for 10 minutes (6,000×g). Cell culture fluid was obtained from the supernatant (conditioned media (CM)). The obtained cell culture fluid was treated to human umbilical vein endothelial cells (HUVECs) which were cultured separately. Then changes of angiogenesis were investigated by the following experiments.

<4-1> Evaluation of Vascular Endothelial Cell Proliferation Inhibiting Effect

The cell culture fluid prepared in the above preparation stage was treated to umbilical vein endothelial cells (HUVECs) for 18 hours. Cell proliferation was confirmed by [$^3$H]-thymidine incorporation assay. The result is presented in FIG. 5.

FIG. 5 is a graph illustrating the inhibitory effect of the compound of the present invention on the proliferation of vascular endothelial cells.

As shown in FIG. 5, compared with the control (deguelin), the compound 69 of Example 33 and the compound of Example 28 inhibited the proliferation of vascular endothelial cells dose-dependently, and the inhibition effect was greater than that of deguelin.

<4-2> Evaluation of Vascular Endothelial Cell Migration Inhibiting Effect

The cell culture fluid obtained in the above preparation stage was loaded in the lower chamber of trans-well plate (6.5 mm diameter filter) and umbilical vein endothelial cells (HUVECs) were plated carefully in the upper chamber, followed by culture at 37° C. for 4 hours. The cells migrated down the filter were confirmed by H&E staining. The results are presented in FIG. 6 and FIG. 7.

FIG. 6 is a diagram illustrating the inhibitory effect of the compound of the present invention on the migration of vascular endothelial cells.

FIG. 7 is a graph illustrating the inhibitory effect of the compound of the present invention on the migration of vascular endothelial cells.

As shown in FIG. 6 and FIG. 7, the cell culture fluid treated with the compound 69 (Example 33) and the compound 54 (Example 28) at the concentration of 100 nM showed the inhibitory effect on the migration of vascular endothelial cells, and such effect was greater than that of the control, deguelin. In the meantime, the inhibitory effect of the above compounds on vascular endothelial cell migration was dose-dependent.

<4-3> Evaluation of Vascular Endothelial Cell Tube Formation Inhibiting Effect

Umbilical vein endothelial cells (HUVECs) were treated with the cell culture fluid obtained in the above preparation stage. 30 hours later, tube formation was observed. As a result, tube formation was induced by the control deguelin and the compounds of the present invention. The results are presented in FIG. 8.

FIG. 8 is a diagram illustrating the inhibitory effect of the compound of the present invention on the tube formation of vascular endothelial cells.

As shown in FIG. 8, the inhibitory effect of the compound 69 (Example 33) and the compound 54 (Example 28) on the tube formation was greater than that of the control deguelin.

Therefore, it was confirmed that the compounds of the present invention have excellent anti-angiogenesis effect, compared with that of the conventional anticancer agent deguelin, so that they can be effectively used as an active ingredient of an anticancer agent.

Experimental Example 5: Cytotoxicity Test

To investigate the cytotoxicity of the control deguelin, the compound 69 (Example 33), and the compound 54 (Example 28) to the normal cells, it was examined how these compounds affect the proliferation of human bronchial epithelial cells (HBEC-1 and BEAS-2B).

Particularly, HBEC-1 and BEAS-2B cells were seeded on a 96-well culture plate (5,000 cells/well), followed by culture for 24 hours. The plate was treated with 0.1% DMSO (comparative control (CT)), 1 μM of deguelin (control), or μM of the compound 69 (Example 33) and the compound 54 (Example 28) (experimental group), followed by further culture for 3 days. Cytotoxicity was evaluated by MTT assay. The results are presented in FIG. 9.

FIG. 9 is a graph illustrating the cell survival rate (%) obtained by MTT assay performed to investigate the cytotoxicity of the compound of the present invention.

As shown in FIG. 9, when deguelin was treated, the cell survival rate was approximately 60%. In the meantime, when the compound 69 of Example 33 and the compound 54 of Example 28 were treated, the cell survival rate was approximately 80%. The above results indicate that the compounds of the present invention have the cancer cell specific cytotoxicity.

Therefore, it was confirmed that the compounds of the present invention have significantly lower cytotoxicity to normal cells than the conventional anticancer agent deguelin, so that they can be effectively used as an active ingredient of an anticancer agent.

Experimental Example 6: HIF-1α Inhibitory Activity Assessment

HRE-A549 cells stably transfected with hypoxia-response element-luciferase construct were incubated in Dulbecco's modified Eagle's medium. Following overnight serum deprivation, the cells were treated with or without Deguelin or example compounds. After 1 h incubation, the cells were incubated in hypoxia-chamber for 24 h at 37° C. Luciferase activity was measured by adding luciferase assay reagent (Promega, Madison, Wis.). The results are presented in Table 3.

TABLE 3

| Compound | IC$_{50}$ (μM) | S.E. | P value |
|---|---|---|---|
| Comparative Example 1 (Deguelin) | 0.1658 | 0.1581 | 0.30 |
| Example 28 | 2.1514 | 0.5267 | 0.00 |
| Example 67 | 0.0788 | 0.0316 | 0.02 |
| Example 64 | 0.3335 | 0.0793 | 0.00 |
| Example 66 | 0.3626 | 0.1583 | 0.03 |
| Example 75 | 0.6042 | 0.4506 | 0.19 |
| Example 68 | 0.611 | 0.208 | 0.01 |
| Example 85 | 0.791 | 0.4953 | 0.13 |
| Example 76 | 0.8295 | 0.2031 | 0.00 |
| Example 59 | 0.8833 | 0.3257 | 0.01 |
| Example 84 | 0.9432 | 0.4183 | 0.04 |
| Example 73 | 1.026 | 0.2938 | 0.00 |
| Example 72 | 1.2449 | 0.5212 | 0.03 |
| Example 74 | 1.2705 | 0.127 | <0.0001 |
| Example 56 | 1.2794 | 0.4038 | 0.00 |
| Example 58 | 1.3344 | 0.3492 | 0.00 |
| Example 83 | 1.4454 | 0.8825 | 0.12 |
| Example 69 | 2.1371 | 0.7549 | 0.01 |

$^a$All compounds were purified by column chromatography and recrystallization (>95%).

As shown in the above table 3,

Example compounds of the present invention may inhibit HIF-1α at significantly low concentration. In particular, Example 67 compound of the present invention may effectively inhibit HIF-1α at 2 times lower concentration when compared to Comparative Example 1 (Deguelin).

Experimental Example 7: Retinal Neovascularization Inhibitory Activity Assessment Oxygen-induced retinopathy (OIR) OIR was induced in newborn mice. Briefly, newborn mice were placed in hyperoxia (75±0.5% O$_2$) from postnatal day (P) 7 to P12 and returned to normoxia. At P14, we intravitreally injected 1 μl of PBS or each example compound (1 μM) into the right eyes of the mice (n=6). At P17, the enucleated eyes were processed for further analyses. For qualitative analyses, FITC-dextran (500 kDa) was perfused intravenously 1 h before the sacrifice. The retinal flat mounts were observed via the fluorescence microscope. For quantitative analyses, the eyes were prepared for hematoxylin and eosin (H&E) staining and the slides were observed via the light microscope. The results are presented in FIG. 10.

As shown in the FIG. 10,

Example compounds of the present invention may inhibit retinal neovascularization at significantly low concentration.

Experimental Example 8: Anchorage-Dependent and Anchorage-Independent Colony Formation Assay <8-1> Cell Culture H1299, H460, H292, and BEAS-2B cells were purchased from the ATCC. The other NSCLC cells were kindly provided by Dr. John V. Heymach (MD Anderson Cancer Center, Houston, Tex.). HUVECs were purchased from Invitrogen. Human bronchial epithelial (HBE) cells were kindly provided by Dr. John Minna (The University of Texas Southwestern Medical Center, Dallas, Tex.). Human retinal pigment epithelial (RPE) cells were kindly provided by Dr. Jeong Hun Kim (College of Medicine, Seoul National University, Seoul, Republic of Korea). HT-22 cells were provided by Dr. Dong Gyu Jo (College of Pharmacy, Sungkyunkwan University, Suwon, Republic of Korea). Cell lines were authenticated and validated at the Korean Cell Line Bank using AmplFLSTR identifier PCR Amplification Kit (Applied Biosystems; cat. No. 4322288) in 2013. Cells passed for fewer than 6 months after receipt or resuscitation of validated cells were used in this study.

HT-22 and RPE cells were cultured in DMEM supplemented with 10% fetal bovine serum (FBS) and antibiotics. Other cancer cells were cultured in RPMI 1640 medium supplemented with 10% FBS and antibiotics. BEAS-2B and HBE cells were maintained in KSFM (Invitrogen) supplemented with EGF and bovine pituitary extracts. HUVECs were cultured in endothelial cell basal medium [EBM-2 (Lonza Inc., Allendale, N.J., USA)] supplemented with EGM-2 SingleQuots (Lonza). HUVECs between passages 3 and 8 were used. Cells were incubated at 37° C. with 5% $CO_2$ in a humidified atmosphere.

Drug-resistant cells that have acquired resistance to paclitaxel (H226B/R and H460/R) and an IGF-1R TKI linsitinib (H292/R) were generated by continuous exposure to increasing concentrations of corresponding anticancer drugs for more than 6 months. H226B/K-Ras cells were generated by retroviral transduction of mutant K-Ras.

<8-2> Experiment Method

For the anchorage-dependent colony formation assay, cells were seeded onto 6-well plates at a density of 300 cells/well and then treated with increasing concentrations of example 28 compound ("SH" in FIG. 11) for 2 weeks. The colonies were fixed with 100% methanol, stained with 0.005% crystal violet solution at room temperature, and then washed with deionized water 3-5 times. The colonies were photographed and counted. The results are presented in FIG. 11.

FIG. 11, the effect of example 28 compound on the anchorage-dependent colony formation of lung cancer cells with or without anticancer drug resistance.

For the anchorage-independent colony formation assay, the cells were mixed with sterile 1% agar solution (final concentration of 0.4%) and then poured onto 1% base agar in 24-well plates. Example 28 compound ("SH" in FIG. 12), diluted in complete medium, was added to the agar after the top agar solidified. The cells embedded in the top agar were incubated for 2 weeks at 37° C. with 5% $CO_2$. After incubation, the colonies were stained with MTT solution and then photographed and counted. The results are presented in FIG. 12.

FIG. 12, the anchorage-independent growth of cells treated with increasing concentrations of example 28 compound was determined using a soft agar colony formation assay.

As shown in FIGS. 11 and 12,

Example 28 compound of present invention may exhibit remarkably superior anticancer effect with respect to various types of cancer cell having anticancer agent resistance as well as a general cancer cell.

Experimental Example 9: Tube Formation of Vascular Endothelial Cells

H1299 cells were treated with example 28 compound ("SH" in FIG. 13) or deguelin for 1 d and then further incubated under normoxic or hypoxic conditions for 4 h. After incubation, the drug-containing medium was discarded and fresh serum-free medium was added to cell and further incubated for 24 h. After incubation, the conditioned medium (CM) was collected.

Briefly, the HUVECs were diluted in complete medium and seeded onto CellBIND surface 96-well plates (Corning). The cells were treated with the CM. The morphological changes of the HUVECs were photographed and scored. The results are presented in FIG. 13.

FIG. 13, HUVECs were treated with the CM from H1299 cells treated with example 28 compound. *, P<0.05; , P<0.01; *, P<0.001, compared with vehicle-treated control.

As shown in FIG. 13,

HUVECs incubated with the conditioned medium (CM) derived from H1299 cells, which had been treated with example 28 compound under normoxic or hypoxic conditions, formed significantly fewer tubes than did those treated with CM from untreated H1299 cells.

Collectively, these results demonstrate the broad anticancer activities of example 28 compound.

Experimental Example 10: Reduced Toxicity Profile of Example 28 Compound Compared with Deguelin A concern on the use of deguelin as an anticancer drug is potential toxicities. In a previous study, deguelin caused parkinsonism-like syndrome, which was manifested by decreased tyrosine hydroxylase immunoreactivity in the rat brain. In addition, it was reported that Hsp90 inhibitors may induce ocular and liver toxicity. Although it is not clear whether therapeutic doses of deguelin would induce the side effects and whether the side effects can be relieved after drug withdrawal, the potential toxicities of deguelin can be a considerable obstacle to its clinical use. On the basis of this notion, applicant evaluated whether example 28 compound harbors less or no potential toxicity compared with deguelin.

We examined toxicity of example 28 compound at the cellular levels by testing the effects of example 28 compound on the viability of several normal cells, including human normal lung epithelial cells (HBE and BEAS-2B; FIG. 14), hippocampal cells (HT-22; FIG. 15), retinal pigment epithelial cells (FIG. 16), and vascular endothelial cells (HUVEC; FIG. 17). Compared with deguelin, example 28 compound showed significantly reduced cytotoxicity in the tested normal cells.

Also, Example 28 compound treatment showed minimal influence on the body weight of rats (FIG. 18). In contrast, the body weight in the deguelin-treated rats was significantly reduced compared with control.

Together, these results indicate the markedly improved safety profile of example 28 compound.

The Manufacturing Examples of the composition for the present invention are described hereinafter.

Manufacturing Example 1: Preparation of Powders

| Compound of formula 1 or formula 2 | 2 g |
| Lactose | 1 g |

Powders were prepared by mixing all the above components, which were filled in airtight packs according to the conventional method for preparing powders.

Manufacturing Example 2: Preparation of Tablets

| Compound of formula 1 or formula 2 | 100 mg |
| Corn starch | 100 mg |
| Lactose | 100 mg |
| Magnesium stearate | 2 mg |

Tablets were prepared by mixing all the above components by the conventional method for preparing tablets.

Manufacturing Example 3: Preparation of Capsules

| Compound of formula 1 or formula 2 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

Manufacturing Example 4: Preparation of Injectable Solutions

| Compound of formula 1 or formula 2 | 10 µg/ml |
| Weak HCl BP | until pH 3.5 |
| Injectable NaCl BP | up to 1 ml |

The compound of formula 1 or formula 2 of the present invention was dissolved in proper volume of injectable NaCl BP. pH of the prepared solution was regulated as 3.5 by using weak HCl BP. The volume was adjusted by using injectable NaCl BP. The solution was well mixed and filled in 5 ml type I transparent glass ampoules. The ampoules were sealed by melting the glass of opening, followed by autoclave at 120° C. for at least 15 minutes for sterilization.

INDUSTRIAL APPLICABILITY

The compounds represented by formula 1 and formula 2 of the present invention suppress the expression of Hsp90 so that they can inhibit the accumulation of HIF-1α, the Hsp90 client protein, and also efficiently inhibit the activation of VEGF. In addition, these compounds display low cytotoxicity, so that they can be effectively used as an active ingredient of an anti-cancer agent, a diabetic retinopathy treating agent, and an anti-arthritic agent.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

The invention claimed is:

1. A compound represented by formula 2 or a pharmaceutically acceptable salt thereof:

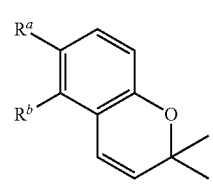

[Formula 2]

wherein, $R^a$ is

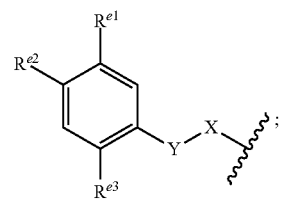

$R^b$ is $C_{1-3}$ alkoxy;

$R^{e1}$, $R^{e2}$ and $R^{e3}$ are independently —H, or $C_{1-3}$ alkoxy;

X is

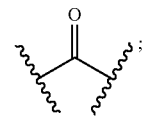

Y is methylene,

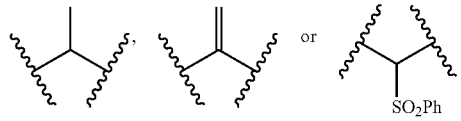

2. The compound represented by formula 2 or the pharmaceutically acceptable salt thereof according to claim 1, wherein:

$R^a$ is

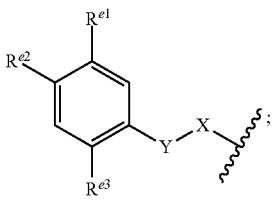

$R^b$ is $C_{1-2}$ alkoxy;
$R^{e1}$, $R^{e2}$ and $R^{e3}$ are independently —H, or $C_{1-2}$ alkoxy;
X is

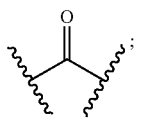 [SMILES: *C(*)=O]

and
Y is methylene,

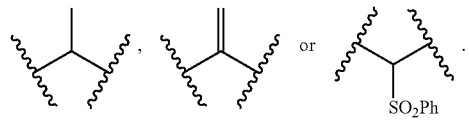

3. The compound represented by formula 2 or the pharmaceutically acceptable salt thereof according to claim 1, wherein:
$R^a$ is

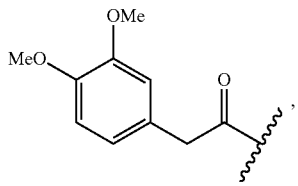

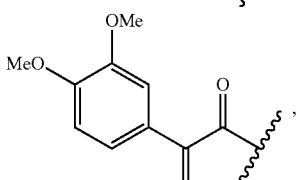

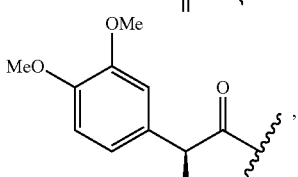

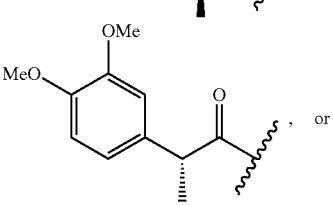

-continued

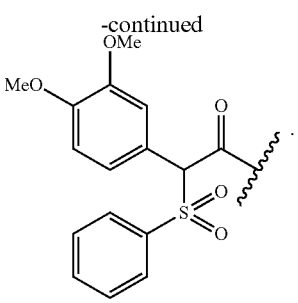

4. The compound represented by formula 2 or the pharmaceutically acceptable salt thereof according to claim 1, wherein:
$R^b$ is methoxy.

5. The compound represented by formula 2 or the pharmaceutically acceptable salt thereof according to claim 1, wherein the compound represented by formula 2 is selected from the group consisting of the following compounds:

2-(3,4-dimethoxyphenyl)-1-(5-methoxy-2,2-dimethyl-2H-chromen-6-yl)ethanone, 2-(3,4-dimethoxyphenyl)-1-(5-methoxy-2,2-dimethyl-2H-chromen-6-yl)propan-1-one 2-(3,4-dimethoxyphenyl)-1-(5-methoxy-2,2-dimethyl-2H-chromen-6-yl)-2-methylpropan-1-one, 2-(3,4-dimethoxyphenyl)-1-(5-methoxy-2,2-dimethyl-2H-chromen-6-yl)prop-2-en-1-one, (S)-2-(3,4-dimethoxyphenyl)-1-(5-methoxy-2,2-dimethyl-2H-chromen-6-yl)propan-1-one, (R)-2-(3,4-dimethoxyphenyl)-1-(5-methoxy-2,2-dimethyl-2H-chromen-6-yl)propan-1-one, 2-(3,4-dimethoxyphenyl)-1-(5-methoxy-2,2-dimethyl-2H-chromen-6-yl)-2-(phenylsulfonyl)ethanone.

6. A method of treating diabetic retinopathy comprising administering to a subject in need thereof an effective amount of the compound of claim 1 or the pharmaceutically acceptable salt thereof as an active ingredient.

7. A method of inhibiting retinal neovascularization comprising administering to a subject in need thereof an effective amount of the compound of claim 1 or the pharmaceutically acceptable salt thereof as an active ingredient.

8. A method of treating cancer comprising administering to a subject in need thereof an effective amount of the compound of claim 1 or the pharmaceutically acceptable salt thereof as an active ingredient.

9. A method of treating cancer according to claim 8, wherein the cancer is selected from the group consisting of the following solid tumors characterized by Hsp90 accumulation: colorectal cancer, liver cancer, stomach cancer, breast cancer, colon cancer, bone cancer, pancreatic cancer, head and neck cancer, uterine cancer, ovarian cancer, rectal cancer, esophageal cancer, small bowel cancer, anal cancer, colon cancer, fallopian tube carcinoma, endometrial carcinoma, uterine cervical carcinoma, vaginal carcinoma, Hodgkin's disease, prostate cancer, bladder cancer, kidney cancer, ureter cancer, renal cell carcinoma, renal pelvic carcinoma, and central nervous system tumor.

10. A compound represented by formula 2 or a pharmaceutically acceptable salt thereof:

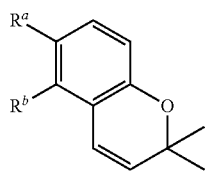

wherein, $R^a$ is

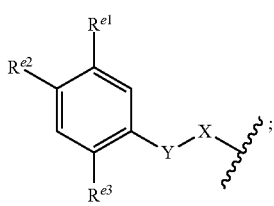

$R^b$ is $C_{1-3}$ alkoxy;

$R^{e1}$, $R^{e2}$ and $R^{e3}$ are independently —F, —Cl, —CF$_3$, or —CN; or $R^{e1}$ and $R^{e2}$ are linked together to form

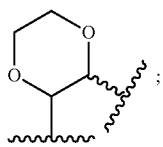

X is

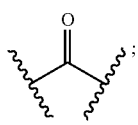

and

Y is methylene,

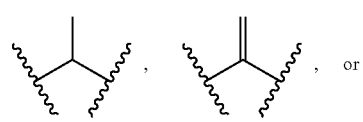

11. The compound represented by formula 2 or the pharmaceutically acceptable salt thereof according to claim 10, wherein:

$R^a$ is

[Formula 2]

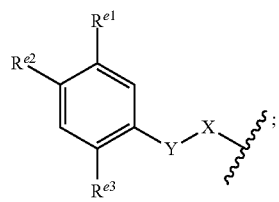

$R^b$ is $C_{1-2}$ alkoxy, $R^{e1}$, $R^{e2}$ and $R^{e3}$ are independently —F, —Cl, —CF$_3$, or —CN; or $R^{e1}$ and $R^{e2}$ are linked together to form

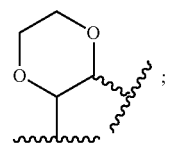

X is

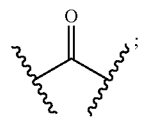 [SMILES: *C(*)=O]

and

Y is methylene,

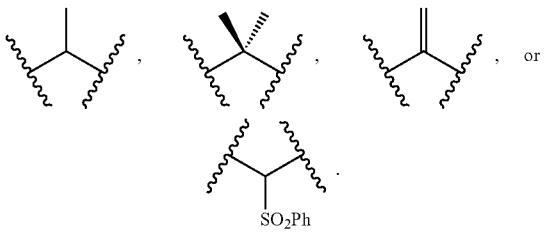

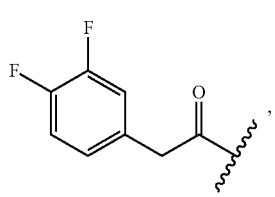

12. The compound represented by formula 2 or the pharmaceutically acceptable salt thereof according to claim 10, wherein:

$R^a$ is

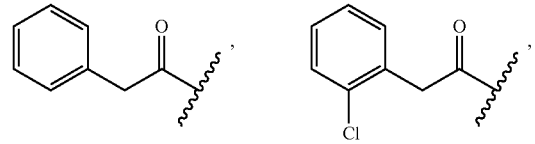

-continued

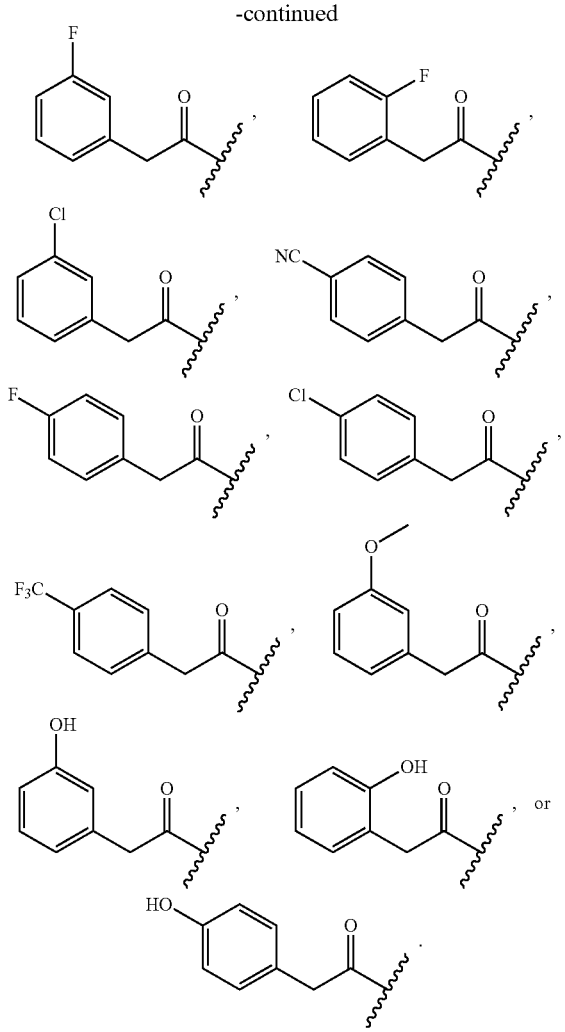

13. The compound represented by formula 2 or the pharmaceutically acceptable salt thereof according to claim 10, wherein $R^b$ is methoxy.

14. The compound represented by formula 2 or the pharmaceutically acceptable salt thereof according to claim 1, wherein the compound represented by formula 2 is selected from the group consisting of the following compounds:

2-(3,4-difluorophenyl)-1-(5-methoxy-2,2-dimethyl-2H-chromen-6-yl)ethanone, 2-(2,3-dihydrobenzo[b][1,4]dioxin-6-yl)-1-(5-methoxy-2,2-dimethyl-2H-chromen-6-yl)ethanone, 1-(5-methoxy-2,2-dimethyl-2H-chromen-6-yl)-2-phenylethanone, 2-(2-chlorophenyl)-1-(5-methoxy-2,2-dimethyl-2H-chromen-6-yl)ethanone, 2-(3-fluorophenyl)-1-(5-methoxy-2,2-dimethyl-2H-chromen-6-yl)ethanone, 2-(2-fluorophenyl)-1-(5-methoxy-2,2-dimethyl-2H-chromen-6-yl)ethanone, 2-(3-chlorophenyl)-1-(5-methoxy-2,2-dimethyl-2H-chromen-6-yl)ethanone, 4-(2-(5-methoxy-2,2-dimethyl-2H-chromen-6-yl)-2-oxoethyl)benzonitrile, 2-(4-fluorophenyl)-1-(5-methoxy-2,2-dimethyl-2H-chromen-6-yl)ethanone, 2-(4-chlorophenyl)-1-(5-methoxy-2,2-dimethyl-2H-chromen-6-yl)ethanone, 1-(5-methoxy-2,2-dimethyl-2H-chromen-6-yl)-2-(4-(trifluoromethyl)phenyl)ethanone, 1-(5-methoxy-2,2-dimethyl-2H-chromen-6-yl)-2-(3-methoxyphenyl)ethanone, 2-(3-hydroxyphenyl)-1-(5-methoxy-2,2-dimethyl-2H-chromen-6-yl)ethanone, 2-(2-hydroxyphenyl)-1-(5-methoxy-2,2-dimethyl-2H-chromen-6-yl)ethanone, and 2-(4-hydroxyphenyl)-1-(5-methoxy-2,2-dimethyl-2H-chromen-6-yl)ethanone.

15. A method of treating diabetic retinopathy comprising administering to a subject in need thereof an effective amount of the compound of claim 10 or the pharmaceutically acceptable salt thereof as an active ingredient.

16. A method of inhibiting retinal neovascularization comprising administering to a subject in need thereof an effective amount of the compound of claim 10 or the pharmaceutically acceptable salt thereof as an active ingredient.

17. A method of treating cancer comprising administering to a subject in need thereof an effective amount of the compound of claim 10 or the pharmaceutically acceptable salt thereof as an active ingredient.

18. A method of treating cancer according to claim 17, wherein the cancer is selected from the group consisting of the following solid tumors characterized by Hsp90 accumulation: colorectal cancer, liver cancer, stomach cancer, breast cancer, colon cancer, bone cancer, pancreatic cancer, head and neck cancer, uterine cancer, ovarian cancer, rectal cancer, esophageal cancer, small bowel cancer, anal cancer, colon cancer, fallopian tube carcinoma, endometrial carcinoma, uterine cervical carcinoma, vaginal carcinoma, Hodgkin's disease, prostate cancer, bladder cancer, kidney cancer, ureter cancer, renal cell carcinoma, renal pelvic carcinoma, and central nervous system tumor.

\* \* \* \* \*